US008906844B2

(12) United States Patent
Mezo et al.

(10) Patent No.: US 8,906,844 B2
(45) Date of Patent: Dec. 9, 2014

(54) IMMUNOMODULATORY PEPTIDES

(75) Inventors: Adam R. Mezo, Needham, MA (US); Kevin A. McDonnell, Waltham, MA (US)

(73) Assignee: Biogen Idec Hemophilia Inc., Cambridge, MA (US)

( * ) Notice: Subject to any disclaimer, the term of this patent is extended or adjusted under 35 U.S.C. 154(b) by 915 days.

(21) Appl. No.: 12/671,883

(22) PCT Filed: Aug. 1, 2008

(86) PCT No.: PCT/US2008/071960
§ 371 (c)(1),
(2), (4) Date: Jun. 17, 2010

(87) PCT Pub. No.: WO2009/020867
PCT Pub. Date: Feb. 12, 2009

(65) Prior Publication Data
US 2011/0230639 A1   Sep. 22, 2011

Related U.S. Application Data

(60) Provisional application No. 60/954,968, filed on Aug. 9, 2007.

(51) Int. Cl.
*A61K 38/16* (2006.01)
*C07K 14/00* (2006.01)
*C07K 7/08* (2006.01)
*C07K 14/735* (2006.01)
*A61K 38/00* (2006.01)

(52) U.S. Cl.
CPC .. *C07K 7/08* (2013.01); *A61K 38/00* (2013.01)
USPC ............ 514/1.1; 530/324; 530/327; 530/326; 530/325; 530/350; 514/21.1

(58) Field of Classification Search
CPC .. C07K 16/283; C07K 16/2803; C07K 16/28; C07K 14/00; C07K 14/001; C07K 14/70535; C07K 14/70503; C07K 14/705; C07K 1/00; C07K 4/00; C07K 2/00; C07K 7/08; C07K 7/04; A61K 38/03; A61K 38/16; A61K 38/1774; A61K 38/17
USPC ........................................................ 514/1.1
See application file for complete search history.

(56) References Cited

U.S. PATENT DOCUMENTS

| | | | |
|---|---|---|---|
| 3,941,763 A | 3/1976 | Sarantakis |
| 4,179,337 A | 12/1979 | Davis et al. |
| 4,215,051 A | 7/1980 | Schroeder et al. |
| 4,301,144 A | 11/1981 | Iwashita et al. |
| 4,496,689 A | 1/1985 | Mitra |
| 4,640,835 A | 2/1987 | Shimizu et al. |
| 4,670,417 A | 6/1987 | Iwasaki et al. |
| 4,671,958 A | 6/1987 | Rodwell et al. |
| 4,713,339 A | 12/1987 | Levinson et al. |
| 4,791,192 A | 12/1988 | Nakagawa et al. |
| 4,867,973 A | 9/1989 | Goers et al. |
| 5,252,714 A | 10/1993 | Harris et al. |
| 5,326,856 A | 7/1994 | Coughlin et al. |
| 5,449,761 A | 9/1995 | Belinka et al. |
| 5,623,053 A | 4/1997 | Gastinel et al. |
| 5,691,154 A | 11/1997 | Callstrom et al. |
| 5,846,728 A | 12/1998 | Haralambidis et al. |
| 5,888,512 A | 3/1999 | Clayberger et al. |
| 5,981,216 A | 11/1999 | Kenten et al. |
| 6,015,881 A | 1/2000 | Kang et al. |
| 6,030,613 A | 2/2000 | Blumberg et al. |
| 6,086,875 A | 7/2000 | Blumberg et al. |
| 6,121,022 A | 9/2000 | Presta et al. |
| 6,197,526 B1 | 3/2001 | Yu et al. |
| 6,212,022 B1 | 4/2001 | Kamikubo |
| 6,281,331 B1 | 8/2001 | Kang et al. |
| 6,469,136 B1 | 10/2002 | Bray et al. |
| 6,472,506 B1 | 10/2002 | Moreau et al. |
| 6,541,669 B1 | 4/2003 | Moran et al. |
| 6,660,843 B1 | 12/2003 | Feige et al. |
| 6,685,179 B2 | 2/2004 | Kita |
| 6,900,292 B2 | 5/2005 | Sun et al. |
| 6,992,234 B2 | 1/2006 | Roopenian |

(Continued)

FOREIGN PATENT DOCUMENTS

| | | |
|---|---|---|
| EP | 0 154 316 A2 | 9/1985 |
| EP | 0 394 827 A1 | 10/1990 |
| EP | 0 401 384 A1 | 12/1990 |
| WO | WO 92/16221 A1 | 10/1992 |
| WO | WO 95/34326 A1 | 12/1995 |
| WO | WO 97/12042 A2 | 4/1997 |
| WO | WO 97/43316 A1 | 11/1997 |
| WO | WO 98/23289 A1 | 6/1998 |
| WO | WO 00/24782 A2 | 5/2000 |
| WO | WO 01/83525 A2 | 11/2001 |

(Continued)

OTHER PUBLICATIONS

Advisory Action issued in U.S. Appl. No. 11/676,148, dated Sep. 11, 2009.
Advisory Action issued in U.S. Appl. No. 11/676,148, dated Aug. 18, 2009.

(Continued)

*Primary Examiner* — Karlheinz R Skowronek
*Assistant Examiner* — Catherine Mader
(74) *Attorney, Agent, or Firm* — Finnegan, Henderson, Farabow, Garrett & Dunner LLP.

(57) ABSTRACT

The invention relates to peptides derivatized with a hydrophilic polymer which, in some embodiments, bind to human FcRn and inhibit binding of the Fc portion of an IgG to an FcRn, thereby modulating serum IgG levels. The disclosed compositions and methods may be used in some embodiments, for example, in treating autoimmune diseases and inflammatory disorders. The invention also relates, in further embodiments, to methods of using and methods of making the peptides of the invention.

20 Claims, 21 Drawing Sheets

(56) References Cited

U.S. PATENT DOCUMENTS

| | | | |
|---|---|---|---|
| 7,141,676 B1 | 11/2006 | Wilbur et al. | |
| 7,176,185 B2 | 2/2007 | Hilfinger et al. | |
| 7,232,805 B2 | 6/2007 | Weinshenker et al. | |
| 8,101,186 B2* | 1/2012 | Mezo et al. | 424/185.1 |
| 2002/0138863 A1 | 9/2002 | Roopenian | |
| 2004/0241727 A1 | 12/2004 | Liew | |
| 2004/0241729 A1 | 12/2004 | Liew | |
| 2005/0009136 A1 | 1/2005 | Nixon et al. | |
| 2005/0027109 A1 | 2/2005 | Mezo et al. | |
| 2005/0079169 A1 | 4/2005 | Balthasar et al. | |
| 2005/0147610 A1 | 7/2005 | Ghayur et al. | |
| 2005/0260194 A1 | 11/2005 | Peters et al. | |
| 2006/0228348 A1 | 10/2006 | Stefano | |
| 2007/0092507 A1 | 4/2007 | Balthasar et al. | |
| 2007/0254831 A1 | 11/2007 | Mezo et al. | |
| 2010/0048488 A1 | 2/2010 | Mezo et al. | |
| 2011/0059889 A1* | 3/2011 | Mezo et al. | 514/6.9 |

FOREIGN PATENT DOCUMENTS

| | | |
|---|---|---|
| WO | WO 02/02641 A1 | 1/2002 |
| WO | WO 02/43658 A2 | 6/2002 |
| WO | WO 02/094981 A2 | 11/2002 |
| WO | WO 2004/016734 A2 | 2/2004 |
| WO | WO 2004/043403 A2 | 5/2004 |
| WO | WO 2004/100882 A2 | 11/2004 |
| WO | WO 2004/101739 A2 | 11/2004 |
| WO | WO 2004/108885 A2 | 12/2004 |
| WO | WO 2005/001025 A2 | 1/2005 |
| WO | WO 2006/000213 A2 | 1/2006 |
| WO | WO 2007/098420 A2 | 8/2007 |
| WO | WO 2009/020867 A2 | 2/2009 |
| WO | WO 2010/014909 A1 | 2/2010 |

OTHER PUBLICATIONS

Bain et al., "Site-Specific Incorporation of Non-Natural Residues into Peptides: Effect of Residue Structure on Suppression and Translation Efficiencies," *Tetrahedron* 47(14/15):2389-2400 (1991).
Baldassarre et al., "Production of Transgenic Goats by Pronuclear Microinjection of In Vitro Produced Zygotes Derived from Oocytes Recovered by Laparoscopy," *Theriogenology* 59:831-839 (2003).
Biernat et al., "Amino-Terminal Dimerization of Peptides on the Solid Support. Synthesis and Biological Activity of the Immunosuppressive HLA-DR Fragments Linked by Poly(ethylene glycol)s," *Bioconjugate Chem.* 17:1116-1124 (2006).
Bodanszky, "VII. Techniques for the Facilitation of Peptide Synthesis," *Principles of Peptide Synthesis*, 1$^{st}$ ed. Chapter 7 (1984).
Bodanszky, "VII. Techniques for the Facilitation of Peptide Synthesis," *Principles of Peptide Synthesis*, 2$^{nd}$ revised ed., Chapter 7 (1993).
Boder et al., "Yeast Surface Display for Screening Combinatorial Polypeptide Libraries," *Nature Biotechnol.* 15:553-557 (1997).
Brambell et al., "A Theoretical Model of γ-Globulin Catabolism," *Nature* 203:1352-1355 (1964).
Brinster et al., "Expression of a Microinjected Immunoglobulin Gene in the Spleen of Transgenic Mice," *Nature* 306:332-336 (1983).
Brinster et al., "Factors Affecting the Efficiency of Introducing Foreign DNA into Mice by Microinjecting Eggs," *Proc. Natl. Acad. Sci. USA* 82:4438-4442 (1985).
Brisson et al., "Expression of a Bacterial Gene in Plants by Using a Viral Vector," *Nature* 310:511-514 (1984).
Broglie et al., "Light-Regulated Expression of a Pea Ribulose-1,5-Bisphosphate Carboxylase Small Subunit Gene in Transformed Plant Cells," *Science* 224:838-843 (1984).
Burmeister et al., "Crystal Structure at 2.2 A Resolution of the MHC-Related Neonatal Fc Receptor," *Nature* 372:336-343 (1994).
Burmeister et al., "Crystal Structure of the Complex of Rat Neonatal Fc Receptor with Fc," *Nature* 372:379-383 (1994).
Chamow et al., "Modification of CD4 Immunoadhesin with Monomethoxypoly(ethylene glocol) Aldehyde via Reductive Alkylation," *Bioconjugate Chem.* 5:133-140 (1994).

Chaudhury et al., "The Major Histocompatibility Complex-Related Fc Receptor for IgG (FcRn) Binds Albumin and Prolongs Its Lifespan," *J. Exp. Med.* 197(3):315-322 (2003).
Christianson et al., "β2-Microglobulin-Deficient Mice are Protected from Hypergammaglobulinemia and Have Defective Antibody Responses Because of Increased IgG Catabolism," *J. Immunol.* 159(10):4781-4792 (1997).
Chuang et al., "Pharmaceutical Strategies Utilizing Recombinant Human Serum Albumin," *Pharm. Res.* 19(5):569-577 (2002).
Coruzzi et al., "Tissue-Specific and Light-Regulated Expression of a Pea Nuclear Gene Encoding the Small Subunit of Ribulose-1,5-Bisphosphate Carboxylase," *EMBO J.* 3(8):1671-1679 (1984).
Costagliola et al., "Genetic Immunization Against the Human Thyrotropin Receptor Causes Thyroiditis and Allows Production of Monoclonal Antibodies Recognizing the Native Receptor," *J. Immunol.*, 160:1458-1465 (1998).
Davis et al., "Preparation and Characterization of Antibodies with Specificity for the Amino-Terminal Tetrapeptide Sequence of the Platelet-Derived Connective Tissue Activating Peptide-III," *Biochem. Intl.* 10(3):395-404 (1985).
Dawson et al., "Chemical Synthesis, Characterization and Activity of RK-1, a Novel α-Defensin-Related Peptide," *J. Peptide Sci.* 6:19-25 (2000).
Dawson et al., "Synthesis of Native Proteins by Chemical Ligation," *Annu. Rev. Biochem.* 69:923-960 (2000).
Erickson et al., "Ch. 3 Solid-Phase Peptide Synthesis," *The Proteins* vol. II 3rd ed. Neurath and Hill, eds., Academic Press, NY, pp. 255-527 (1976).
Etzkorn et al., "Cyclic Hexapeptides and Chimeric Peptides as Mimics of Tendamistat," *J. Am. Chem. Soc.* 116:10412-10425 (1994).
Evans et al., "Design of Nonpeptidal Ligands for a Peptide Receptor: Cholecystokinin Antagonists," *J. Med. Chem.* 30:1229-1239 (1987).
Examiner's Answer to Appeal Brief in U.S. Appl. No. 11/676,148, dated Apr. 29, 2010.
Examiner's Response to Applicants' Reply Brief issued in U.S. Appl. No. 11/676,148, dated Sep. 17, 2010.
Fauchere, "Elements for the Rational Design of Peptide Drugs," *Adv. Drug Res.* 15:29-69 (1986).
Finn et al., "Ch. 2 The Synthesis of Peptides by Solution Methods with Emphasis on Peptide Hormones," *The Proteins* vol. II 3rd ed., Neurath and Hill, eds., Academic Press, NY, pp. 105-253 (1976).
Fountoulakis et al., "Interferon γ Receptor Extracellular Domain Expressed as IgG Fusion Protein in Chinese Hamster Ovary Cells," *J. Biol. Chem.* 270(8):3958-3964 (1995).
Francis, "Protein Modification and Fusion Proteins," *Focus on Growth Factors* 3(2):4-10 (1992).
Freidinger et al., "Protected Lactam-Bridged Dipeptides for Use as Conformational Constraints in Peptides," *J. Org. Chem.* 47:104-109 (1982).
Freidinger, "Design and Synthesis of Novel Bioactive Peptides and Peptidomimetics," *J. Med. Chem.* 46(26):5553-5566 (2003).
Gavilondo et al., "Antibody Engineering at the Millennium," *Biotechniques* 29(1):128-145 (2000).
Ghetie et al., "Abnormally Short Serum Half-Lives of IgG in β2-Microglobulin-Deficient Mice," *Eur. J. Immunol.* 26:690-696 (1996).
Greene, *Protective Groups in Organic Synthesis*, Ch. 5 Protection for The Carboxyl Group, pp. 152-192 (1991).
Grierson et al., Ch. 7-9, *Plant Molecular Biology*, 2d ed., Blackie, London (1988).
Gurley et al., "Upstream Sequences Required for Efficient Expression of a Soybean Heat Shock Gene," *Mol. Cell. Biol.* 6(2):559-565 (1986).
Gussow et al., "The Human β2-Microblobulin Gene," *J. Immunol.* 139(9):3132-3138 (1987).
Hanessian et al., "Design and Synthesis of Conformationally Constrained Amino Acids as Versatile Scaffolds and Peptide Mimetics," *Tetrahedron* 53(38):12789-12854 (1997).
Hansen et al., "Effects of Intravenous Immunoglobulin on Platelet Count and Antiplatelet Antibody Disposition in a Rat Model of Immune Thrombocytopenia," *Blood* 100(6):2087-2093 (2002).

(56) References Cited

OTHER PUBLICATIONS

Hansen et al., "Intravenous Immunoglobulin Mediates an Increase in Anti-Platelet Antibody Clearance via the FcRn Receptor," *Thromb. Haemost.* 88:898-899 (2002).

Haslam, Chapter 5, *Protective Groups in Organic Chemistry*, J.F.W. McOmie, Ed., Planum Press, NY (1973).

Houghten et al., "Generation and Use of Synthetic Peptide Combinatorial Libraries for Basic Research and Drug Discovery," *Nature* 354:84-86 (1991).

International Search Report and Written Opinion as issued in PCT/US2008/071960, as mailed on Apr. 1, 2009.

International Search Report and Written Opinion as issued in PCT/US2009/052417, as mailed on Jan. 5, 2010.

International Search Report and Written Opinion as issued in PCT/US2007/062349, as mailed on Dec. 3, 2007.

Interview Summary issued in U.S. Appl. No. 11/676,148, dated Aug. 10, 2009.

Israel et al., "Expression of the Neonatal Fc Receptor, FcRn, on Human Intestinal Epithelial Cells," *Immunology* 92(1):69-74 (1997).

Israel et al., "Requirement for a β2-Microglobulin-Associated Fc Receptor for Acquisition of Maternal IgG by Fetal and Neonatal Mice," *J. Immunol.* 154:6246-6251 (1995).

Johnson et al., "Amino-Terminal Dimerization of an Erythropoietin Mimetic Peptide Results in Increased Erythropoietic Activity," *Chem. Biol.* 4(12):939-950 (1997).

Junghans et al., "The Protection Receptor for IgG Catabolism is the β2-Microglobulin-Containing Neonatal Intestinal Transport Receptor," *Proc. Natl. Acad. Sci. USA* 93:5512-5516 (1996).

Junghans, "Finally! The Brambell Receptor (FcRB)). Mediator of Transmission of Immunity and Protection from Catabolism for IgG," *Immunol. Res.* 16(1):29-57 (1997).

Kato et al., "Mutational Analysis of Protein Solubility Enhancement Using Short Peptide Tags," *Biopolymers* 85(1):12-18 (2006).

Kelley et al., "Development and Validation of an Affinity Chromatography Step Using a Peptide Ligand for cGMP Production of Factor VIII," *Biotechnol. Bioeng.* 87(3):400-412 (2004).

Kim et al., "Development and Characterization of a Glucagon-Like Peptide 1-Albumin Conjugate. The Ability to Activate the Glucagon-Like Peptide 1 Receptor In Vivo," *Diabetes* 52:751-759 (2003).

Kinstler et al., "Mono-N-Terminal Poly(Ethylene Glycol)-Protein Conjugates," *Adv. Drug Del. Rev.* 54:477-485 (2002).

Knudsen et al., "Potent Derivatives of Glucagon-Like Peptide-1 with Pharmacokinetic Properties Suitable for Once Daily Administration," *J. Med. Chem.* 43:1664-1669 (2000).

Kobayashi et al., "FcRn-Mediated Transcytosis of Immunoglobulin G in Human Renal Proximal Tubular Epithelial Cells," *Am. J. Renal Physiol.* 282:F358-F365 (2002).

Kolonin et al., "Teratogenicity Induced by Targeting a Placental Immunoglobulin Transporter," *Proc. Natl. Acad. Sci. USA* 99(20):13055-13060 (2002).

Kyte et al., "A Simple Method for Displaying the Hydropathic Character of a Protein," *J. Mol. Biol.* 157:105-132 (1982).

Lam et al., "A New Type of Synthetic Peptide Library for Identifying Ligand-Binding Activity," *Nature* 354:82-84 (1991).

Lamb et al., "Ch. 2, Commercial Production of Radioisotopes for Nuclear Medicine," *Radiotracers for Medical Applications* vol. 1, Rayudu (Ed.), CRC Press, Inc., Boca Raton, pp. 17-62, 1983.

Leach et al., "Isolation from Human Placenta of the IgG Transporter, FcRn, and Localization to the Syncytiotrophoblast. Implications for Maternal-Fetal Antibody Transport," *J. Immunol.* 157:3317-3322 (1996).

Li et al., "Complete FcRn Dependence for Intravenous Ig Therapy in Autoimmune Skin Blistering Diseases," *J. Clin. Invest.* 115(12):3440-3450 (2005).

Liu et al., "β2-Microglobulin-Deficient Mice are Resistant to Bullous Pemphigoid," *J. Exp. Med.* 186(5):777-783 (1997).

Logan et al., "Adenovirus Tripartite Leader Sequence Enhances Translation of mRNAs Late After Infection," *Proc. Natl. Acad. Sci. USA* 81:3655-3659 (1984).

Low et al., "Inhibitors of the FcRn:IgG Protein-Protein Interaction," *AAPS J.* 11(3):432-434 (2009).

Mackett et al., "General Method for Production and Selection of Infectious Vaccinia Virus Recombinants Expressing Foreign Genes," *J. Virol.* 49(3):857-864 (1984).

Mackett et al., "Vaccinia Virus: A Selectable Eukaryotic Cloning and Expression Vector," *Proc. Natl. Acad. Sci. USA* 79:7415-7419 (1982).

Malassagne et al., "Hypodermin A, a New Inhibitor of Human Complement for the Prevention of Xenogeneic Hyperacute Rejection," *Xenotransplantation* 10(3):267-277 (2003).

Malik et al., "Polyethylene Glycol (PEG)-Modified Granulocyte-Macrophage Colony-Stimulating Factor (GM-CSF) with Conserved Biological Activity," *Exp. Hematol.* 20:1028-1035 (1992).

McDonnell et al., "Synthesis and Structure—Activity Relationships of Dimeric Peptide Antagonists of the Human Immunoglobulin G—Human Neonatal Fc Receptor (IgG-FcRn) Interaction," *J. Med. Chem.* 53(4):1587-1596 (2010).

McIntosh et al., "Characterization of Immunoglobulin Binding by Schistosomes," *Parasite Immunol.* 28(9):407-419 (2006).

McKnight et al., "Expression of the Chicken Transferrin Gene in Transgenic Mice," *Cell* 34:335-341 (1983).

Merrifield, "Ch. 16 Solid-Phase Peptide Synthesis," *Chemical Polypeptides*, Katsoyannis, ed., Plenum Press NY, London, pp. 335-361 (1973).

Merrifield, "Solid Phase Peptide Synthesis. I. The Synthesis of a Tetrapeptide," *J. Am. Chem. Soc.* 85:2149-2154 (1963).

Mezo et al., "Discovery and Development of Peptides that Inhibit FcRn for the Treatment of Autoimmune Disease," *Biopolymers* 88(4):602 (2007).

Mezo et al., "Pegylation of Peptides Targeting FcRn: Synthesis and Structure-Activity Relationships," *Biopolymers* 92(4):351 (2009).

Mezo et al., "Reduction of IgG in Nonhuman Primates by a Peptide Antagonist of the Neonatal Fc Receptor FcRn," *Proc. Natl. Acad. Sci. USA* 105(7):2337-2342 (2008).

Mezo et al., "Structure-Activity Relationships of a Peptide Inhibitor of the Human FcRn: Human IgG Interaction," *Bioorg. Med. Chem.* 16(12):6394-6405 (2008).

Mezo et al., "X-Ray Crystal Structures of Monomeric and Dimeric Peptide Inhibitors in Complex with the Human Neonatal Fc Receptor, FcRn," *J. Biol. Chem.* 285(36):27694-27701 (2010).

Monaghan et al., "Solid-Phase Synthesis of Peptide-Dendrimer Conjugates for an Investigation of Integrin Binding," ARKIVOC 46-53 (2001).

Neumann et al., "Gene Transfer into Mouse Lyoma Cells by Electroporation in High Electric Fields," *EMBO J.* 1(7):841-845 (1982).

NOF Corporation, DDS Development Dept., "World-Wide Leader in DDS (Drug Delivery Systems): PEG Derivatives, Phospholipids and Drug Delivery Materials for Pharmaceutical Products and Formulations," Catalogue Ver. 8 (2006).

Office Action issued in U.S. Appl. No. 11/676,148, dated May 28, 2009.

Office Action issued in U.S. Appl. No. 11/676,148, dated Nov. 13, 2008.

Panicali et al., "Construction of Poxviruses as Cloning Vectors: Insertion of the Thymidine Kinase Gene from Herpes Simplex Virus into the DNA of Infectious Vaccinia Virus," *Proc. Natl. Acad. Sci. USA* 79:4927-4931 (1982).

Peters et al., "A General Platform for the Non-Invasive Delivery and Extended Pharmacokinetic Profile of Peptide Drugs," *Biopolymers* 71(3):393 (2003).

Posnett et al., "A Novel Method for Producing Anti-Peptide Antibodies," *J. Biol. Chem.* 263(4):1719-1725 (1988).

Raghavan et al., "Investigation of the Interaction Between the Class I MHC-Related Fc Receptor and Its Immunoglobulin G Ligand," *Immunity* 1(4):303-315 (1994).

Ritchie et al., "Allelic Exclusion and Control of Endogenous Immunoglobulin Gene Rearrangement in K Transgenic Mice," *Nature* 312:517-520 (1984).

Rizo et al., "Constrained Peptides: Models of Bioactive Peptides and Protein Substructures," *Annu. Rev. Biochem.* 61:387-418 (1992).

(56) References Cited

OTHER PUBLICATIONS

Roberts et al., "RNA-Peptide Fusions for the In Vitro Selection of Peptides and Proteins," *Proc. Nat. Acad. Sci. USA* 94:12297-12302 (1997).

Robl et al., "Artificial Chromosome Vectors and Expression of Complex Proteins in Transgenic Animals," *Theriogenology* 59:107-113 (2003).

Rogers et al., "Gene Transfer in Plants: Production of Transformed Plants Using Ti Plasmid Vectors," *Methods for Plant Molecular Biology*, Academic Press NY, Section VIII, Weisbach and Weisbach, eds., pp. 423-463 (1988).

Roopenian et al., "The MHC Class I-Like IgG Receptor Controls Perinatal IgG Transport, IgG Homeostatis, and Fate of IgG-Fc-Coupled Drugs," *J. Immunol.* 170:3528-3533 (2003).

Rose, "Facile Synthesis of Homogeneous Artificial Proteins," *J. Am. Chem. Soc.* 116:30-33 (1994).

Ruther et al., "Easy Identification of cDNA Clones," *EMBO J.* 2(10):1791-1794 (1983).

Sanchez et al., "Stoichiometry of the Interaction Between the Major Histocompatibility Complex-Related Fc Receptor and Its Fc Ligand," *Biochemistry* 38:9471-9476 (1999).

Sato et al., "Therapeutic peptides: technological advances driving peptides into development," *Curr. Opin. Biotechnol.* 17(6):638-642 (2006).

Schlachetzki et al., "Expression of the Neonatal Fc Receptor (FcRn) at the Blood-Brain Barrier,"*J. Neurochem.* 81:203-206 (2002).

Search Report as issued in Turkish Application No. 2008/07263, as mailed on Nov. 24, 2009.

Simister et al., "An IgG-Transporting Fc Receptor Expressed in the Syncytiotrophoblast of Human Placenta," *Eur. J. Immunol.* 26:1527-1531 (1996).

Simonsen et al., "Isolation and Expression of an Altered Mouse Dihydrofolate Reductase cDNA," *Proc. Natl. Acad. Sci. USA* 80:2495-2499 (1983).

Smith et al., "Molecular Engineering of the *Autographa californica* Nuclear Polyhedrosis Virus Genome: Deletion Mutations Within the Polyhedrin Gene," *J. Virol.* 46(2):584-593 (1983).

Smith et al., "Phage Display," *Chem. Rev.* 97:391-410 (1997).

Story et al., "A Major Histocompatibility Complex Class I-Like Fc Receptor Cloned from Human Placenta: Possible Role in Transfer of Immunoglobulin G from Mother to Fetus," *J. Exp. Med.* 180:2377-2381 (1994).

Subasinghe et al., "Bicyclic Thiazolidine Lactam Peptidomimetics of the Dopamine Receptor Modulating Peptide Pro-Leu-Gly-Nh$_2$," *J. Med. Chem.* 36:2356-2361 (1993).

Takamatsu et al., "Expression of Bacterial Chloramphenicol Acetyltransferase Gene in Tobacco Plants Mediated by TMV-RNA," *EMBO J.* 6(2):307-311 (1987).

Thornton et al., "Prediction of Progress at Last," *Nature* 354:105-106 (1991).

Thumshirn et al., "Multimeric Cyclic RGD Peptides as Potential Tools for Tumor Targeting: Solid-Phase Peptide Synthesis and Chemoselective Oxime Ligation," *Chem. Eur. J.* 9:2717-2725 (2003).

Traunecker et al., "Soluble CD4 Molecules Neutralize Human Immunodeficiency Virus Type 1," *Nature* 331:84-86 (1988).

U.S. Appl. No. 11/676,148, filed Feb. 16, 2007, entitled "Peptides that Block the Binding of IgG to FcRn."

U.S. Appl. No. 12/533,474, filed Jul. 31, 2009, entitled "Immunomodulatory Peptides."

U.S. Appl. No. 12/641,844, filed Dec. 18, 2009, entitled "Peptides that Block the Binding of IgG to FcRn."

Vaccaro et al., "Divergent Activities of an Engineered Antibody in Murine and Human Systems have Implications for Therapeutic Antibodies," *Proc. Natl. Acad. Sci. USA* 103(49):18709-18714 (2006).

Veber et al., "The Design of Metabolically-Stable Peptide Analogs," *Trends Neurosci.* 392-396 (1985).

Vidarsson et al., "FcRn: an IgG Receptor on Phagocytes with a Novel Role in Phagocytosis," *Blood* 108(10):3573-3579 (2006).

Wagner et al., "Microinjection of a Rabbit β-Globin Gene into Zygotes and Its Subsequent Expression in Adult Mice and Their Offspring," *Proc. Natl. Acad. Sci. USA* 78(10):6376-6380 (1981).

Wang et al., "Bioconjugation by Copper(I)-Catalyzed Azide-Alkyne [3+2] Cycloaddition," *J. Am. Chem. Soc.*, 125(11):3192-3193 (2003).

Ward et al., "Evidence to Support the Cellular Mechanism Involved in Serum IgG Homeostasis in Humans," *Int. Immunol.* 15(2):187-195 (2002).

West et al., "Crystal Structure and Immunoglobulin G Binding Properties of the Human Major Histocompatibility Complex-Related Fc Receptor," *Biochemistry* 39(32):9698-9708 (2000).

Wigler et al., "Biochemical Transfer of Single-Copy Eucaryotic Genes Using Total Cellular DNA as Donor," *Cell* 14:725-731 (1978).

Zobel et al., "Phosphate Ester Serum Albumin Affinity Tags Greatly Improve Peptide Half-Life In Vivo," *Bioorg. Med. Chem. Lett.* 13:1513-1515 (2003).

* cited by examiner

NH2-RF-Pen-TGHFG-Sar-NMeLeu-YPC-rink resin  (protected peptide)

Peptide No. 100

Peptide No. 122

Peptide No. 283

Peptide No. 280

Peptide No. 290: 30 kDa PEG

Peptide No. 291: 20 kDa PEG

Peptide No. 292: 5 kDa PEG

Peptide No. 293: 40 kDa PEG

Lane 1: Molecular Weight Markers
Lane 2: Unconjugated $PEG_{30\,kDa}$ starting material aldehyde
Lane 3: Purified Peptide No. 290
Lane 4: Unconjugated $PEG_{20\,kDa}$ starting material aldehyde
Lane 5: Purified Peptide No. 291
Lane 6: Unconjugated $PEG_{5\,kDa}$ starting material aldehyde
Lane 7: Purified Peptide No. 292

Lane 1: Molecular Weight Markers
Lane 2: Peptide No. 292 (5 kDa linear)
Lane 3: Peptide No. 291 (20 kDa linear)
Lane 4: Peptide No. 290 (30 kDa linear)
Lane 5: Peptide No. 293 (40 kDa linear)
Lane 6: Peptide No. 295 (20 kDa 2-arm)
Lane 7: Peptide No. 296 (40 kDa 2-arm)
Lane 8: Molecular Weight Markers n = 10 kDa Peptide No. 295

Peptide No. 296

FIGURE 16

| Peptide No. | PEG Size | PEG Format | Site of PEG | Relative IC$_{50}$ | In Vivo Transgenic Mouse Efficacy in hIgG Catabolism After 5 mg/kg IV dose |
|---|---|---|---|---|---|
| 283 | n/a | n/a | n/a | 0.10 | Y |
| 304 | n/a | n/a | n/a | 0.11 | Y |
| 305 | n/a | n/a | n/a | 0.20 | Y |
| 306 | n/a | n/a | n/a | 0.13 | Y |
| 292 | 5 kDa | linear | Asp linker | 0.36 | Y |
| 291 | 20 kDa | linear | Asp linker | 0.83 | Y |
| 290 | 30 kDa | linear | Asp linker | 1 | Y |
| 293 | 40 kDa | linear | Asp linker | 0.83 | Y |
| 295 | 20 kDa | 2-arm | Asp linker | 2.7 | Y |
| 296 | 40 kDa | 2-arm | Asp linker | 3.8 | Y |
| 297 | 30 kDa | linear | C-terminus | 1.1 | nd |
| 307 | 30 kDa | linear | Arg2→Lys | 0.91 | N |
| 308 | 30 kDa | linear | Thr4→Lys | 1.4 | N |
| 309 | 30 kDa | linear | Pro12→Lys | 0.96 | N |
| 303 | 30 kDa | linear | modified Asp linker | 1.1 | nd | nd = not determined

FIGURE 19
Peptide No. 307:
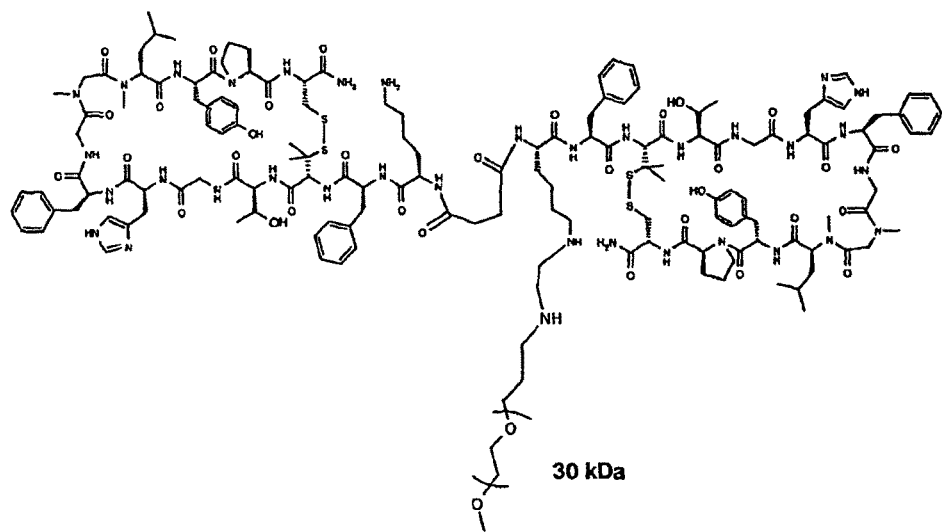
Peptide No. 308:
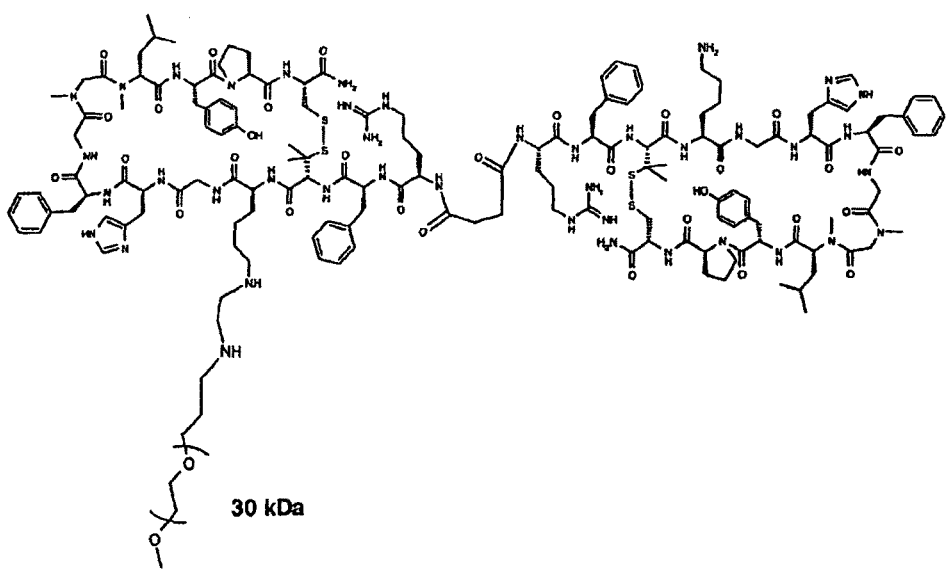

Peptide No. 309:

SEQUENCE LISTING

<160> NUMBER OF SEQ ID NOS: 310

<210> SEQ ID NO 1
<211> LENGTH: 46

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: An optionally derivatized amino acid, an analog
      thereof or not present
<220> FEATURE:
<221> NAME/KEY: MOD_RES
<222> LOCATION: (2)..(15)
<223> OTHER INFORMATION: An optionally derivatized any amino acid, an
      analog thereof, an optionally derivatized peptide of 2 to 15
      amino acids, an analog thereof or not present
<220> FEATURE:
<221> NAME/KEY: MOD_RES
<222> LOCATION: (16)..(16)
<223> OTHER INFORMATION: An optionally derivatized amino acid, an analog
      thereof or not present
<220> FEATURE:
<221> NAME/KEY: MOD_RES
<222> LOCATION: (18)..(18)
<223> OTHER INFORMATION: Any amino acid or analog thereof
<220> FEATURE:
<221> NAME/KEY: MOD_RES
<222> LOCATION: (19)..(19)
<223> OTHER INFORMATION: An optionally derivatized amino acid, an analog
      thereof or not present
<220> FEATURE:
<221> NAME/KEY: MOD_RES
<222> LOCATION: (20)..(22)
<223> OTHER INFORMATION: An optionally derivatized any amino acid, an
      analog thereof, an optionally derivatized peptide of 2 to 4
      amino acids, an analog thereof or not present
<220> FEATURE:
<221> NAME/KEY: MOD_RES
<222> LOCATION: (27)..(27)
<223> OTHER INFORMATION: Sar
<220> FEATURE:
<221> NAME/KEY: MOD_RES
<222> LOCATION: (28)..(28)
<223> OTHER INFORMATION: NMeLeu
<220> FEATURE:
<221> NAME/KEY: MOD_RES
<222> LOCATION: (30)..(30)
<223> OTHER INFORMATION: An optionally derivatized amino acid or analog
      thereof
<220> FEATURE:
<221> NAME/KEY: MOD_RES
<222> LOCATION: (31)..(32)
<223> OTHER INFORMATION: An optionally derivatized amino acid, an analog
      thereof or not present
<220> FEATURE:
<221> NAME/KEY: MOD_RES
<222> LOCATION: (33)..(46)
<223> OTHER INFORMATION: An optionally derivatized any amino acid, an
      analog thereof, an optionally derivatized peptide of 2 to 15
      amino acids, an analog thereof or not present

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Phe Xaa Xaa Xaa Xaa Xaa Gly His Phe Gly Xaa Xaa Tyr Xaa Xaa Xaa
            20                  25                  30

Xaa Xaa Xaa Xaa Xaa Xaa Xaa Xaa Xaa Xaa Xaa Xaa Xaa Xaa
        35                  40                  45

<210> SEQ ID NO 2
<211> LENGTH: 138
<212> TYPE: PRT
<213> ORGANISM: Artificial Sequence
```

-continued

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: An optionally derivatized amino acid, an analog
      thereof or not present
<220> FEATURE:
<221> NAME/KEY: MOD_RES
<222> LOCATION: (2)..(15)
<223> OTHER INFORMATION: Any amino acid, an analog thereof, an
      optionally derivatized peptide of 2 to 15 amino acids, an
      analog thereof or not present
<220> FEATURE:
<221> NAME/KEY: MOD_RES
<222> LOCATION: (16)..(16)
<223> OTHER INFORMATION: An optionally derivatized amino acid, an analog
      thereof or not present
<220> FEATURE:
<221> NAME/KEY: MOD_RES
<222> LOCATION: (18)..(18)
<223> OTHER INFORMATION: Any amino acid or an analog thereof
<220> FEATURE:
<221> NAME/KEY: MOD_RES
<222> LOCATION: (19)..(19)
<223> OTHER INFORMATION: An optionally derivatized amino acid, an analog
      thereof or not present
<220> FEATURE:
<221> NAME/KEY: MOD_RES
<222> LOCATION: (20)..(22)
<223> OTHER INFORMATION: An optionally derivatized any amino acid, an
      analog thereof, an optionally derivatized peptide of 2 to 4
      amino acids, an analog thereof or not present
<220> FEATURE:
<221> NAME/KEY: MOD_RES
<222> LOCATION: (27)..(27)
<223> OTHER INFORMATION: Sar
<220> FEATURE:
<221> NAME/KEY: MOD_RES
<222> LOCATION: (28)..(28)
<223> OTHER INFORMATION: NMeLeu
<220> FEATURE:
<221> NAME/KEY: MOD_RES
<222> LOCATION: (30)..(30)
<223> OTHER INFORMATION: An optionally derivatized amino acid or analog
      thereof
<220> FEATURE:
<221> NAME/KEY: MOD_RES
<222> LOCATION: (31)..(32)
<223> OTHER INFORMATION: An optionally derivatized amino acid, an analog
      thereof or not present
<220> FEATURE:
<221> NAME/KEY: MOD_RES
<222> LOCATION: (33)..(46)
<223> OTHER INFORMATION: Any amino acid, an analog thereof, an
      optionally derivatized peptide of 2 to 15 amino acids, an
      analog thereof or not present
<220> FEATURE:
<221> NAME/KEY: MOD_RES
<222> LOCATION: (47)..(47)
<223> OTHER INFORMATION: An optionally derivatized amino acid, an analog
      thereof or not present
<220> FEATURE:
<221> NAME/KEY: MOD_RES
<222> LOCATION: (48)..(61)
<223> OTHER INFORMATION: Any amino acid, an analog thereof, an
      optionally derivatized peptide of 2 to 15 amino acids, an
      analog thereof or not present
<220> FEATURE:
<221> NAME/KEY: MOD_RES
<222> LOCATION: (62)..(62)
<223> OTHER INFORMATION: An optionally derivatized amino acid, an analog
      thereof or not present
<220> FEATURE:
<221> NAME/KEY: MOD_RES
<222> LOCATION: (64)..(64)
<223> OTHER INFORMATION: Any amino acid or an analog thereof
<220> FEATURE:
```

```
<221> NAME/KEY: MOD_RES
<222> LOCATION: (65)..(65)
<223> OTHER INFORMATION: An optionally derivatized amino acid, an analog
      thereof or not present
<220> FEATURE:
<221> NAME/KEY: MOD_RES
<222> LOCATION: (66)..(68)
<223> OTHER INFORMATION: Any amino acid, an analog thereof, an
      optionally derivatized peptide of 2 or 4 amino acids, an
      analog thereof
<220> FEATURE:
<221> NAME/KEY: MOD_RES
<222> LOCATION: (73)..(73)
<223> OTHER INFORMATION: Sar
<220> FEATURE:
<221> NAME/KEY: MOD_RES
<222> LOCATION: (74)..(74)
<223> OTHER INFORMATION: NMeLeu
<220> FEATURE:
<221> NAME/KEY: MOD_RES
<222> LOCATION: (76)..(76)
<223> OTHER INFORMATION: An optionally derivatized amino acid or analog
      thereof
<220> FEATURE:
<221> NAME/KEY: MOD_RES
<222> LOCATION: (77)..(78)
<223> OTHER INFORMATION: An optionally derivatized amino acid, an analog
      thereof or not present
<220> FEATURE:
<221> NAME/KEY: MOD_RES
<222> LOCATION: (79)..(92)
<223> OTHER INFORMATION: Any amino acid, an analog thereof, an
      optionally derivatized peptide of 2 to 15 amino acids, an
      analog thereof or not present
<220> FEATURE:
<221> NAME/KEY: MISC_FEATURE
<222> LOCATION: (47)..(92)
<223> OTHER INFORMATION: This region may or may not be present
<220> FEATURE:
<221> NAME/KEY: MOD_RES
<222> LOCATION: (93)..(93)
<223> OTHER INFORMATION: An optionally derivatized amino acid, an analog
      thereof or not present
<220> FEATURE:
<221> NAME/KEY: MOD_RES
<222> LOCATION: (94)..(107)
<223> OTHER INFORMATION: Any amino acid, an analog thereof, an
      optionally derivatized peptide of 2 to 15 amino acids, an
      analog thereof or not present
<220> FEATURE:
<221> NAME/KEY: MOD_RES
<222> LOCATION: (108)..(108)
<223> OTHER INFORMATION: An optionally derivatized amino acid, an analog
      thereof or not present
<220> FEATURE:
<221> NAME/KEY: MOD_RES
<222> LOCATION: (110)..(110)
<223> OTHER INFORMATION: Any amino acid or an analog thereof
<220> FEATURE:
<221> NAME/KEY: MOD_RES
<222> LOCATION: (111)..(111)
<223> OTHER INFORMATION: An optionally derivatized amino acid,
      an analog thereof or not present
<220> FEATURE:
<221> NAME/KEY: MOD_RES
<222> LOCATION: (112)..(114)
<223> OTHER INFORMATION: Any amino acid, an analog thereof, an
      optionally derivatized peptide of 2 or 4 amino acids, an
      analog thereof
<220> FEATURE:
<221> NAME/KEY: MOD_RES
<222> LOCATION: (119)..(119)
<223> OTHER INFORMATION: Sar
<220> FEATURE:
<221> NAME/KEY: MOD_RES
<222> LOCATION: (120)..(120)
<223> OTHER INFORMATION: NMeLeu
<220> FEATURE:
<221> NAME/KEY: MOD_RES
```

```
<222> LOCATION: (122)..(122)
<223> OTHER INFORMATION: An optionally derivatized amino acid or analog
      thereof
<220> FEATURE:
<221> NAME/KEY: MOD_RES
<222> LOCATION: (123)..(124)
<223> OTHER INFORMATION: An optionally derivatized amino acid, an analog
      thereof or not present
<220> FEATURE:
<221> NAME/KEY: MOD_RES
<222> LOCATION: (125)..(138)
<223> OTHER INFORMATION: Any amino acid, an analog thereof, an
      optionally derivatized peptide of 2 to 15 amino acids, an
      analog thereof or not present
<220> FEATURE:
<221> NAME/KEY: MISC_FEATURE
<222> LOCATION: (93)..(138)
<223> OTHER INFORMATION: This region may or may not be present

<400> SEQUENCE: 2

Xaa Xaa Xaa Xaa Xaa Xaa Xaa Xaa Xaa Xaa Xaa Xaa Xaa Xaa
1               5                   10                  15

Phe Xaa Xaa Xaa Xaa Xaa Gly His Phe Gly Xaa Xaa Tyr Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Phe Xaa
    50                  55                  60

Xaa Xaa Xaa Xaa Gly His Phe Gly Xaa Xaa Tyr Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Phe Xaa Xaa Xaa
            100                 105                 110

Xaa Xaa Gly His Phe Gly Xaa Xaa Tyr Xaa Xaa Xaa Xaa Xaa Xaa
        115                 120                 125

Xaa Xaa Xaa Xaa Xaa Xaa Xaa Xaa Xaa Xaa
    130                 135

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: An optionally derivatized amino acid, an analog
      thereof or not present
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (4)..(4)
<223> OTHER INFORMATION: An optionally derivatized amino acid or analog
      thereof
<220> FEATURE:
<221> NAME/KEY: MOD_RES
<222> LOCATION: (5)..(7)
<223> OTHER INFORMATION: An optionally derivatized any amino acid, an
      analog thereof, an optionally derivatized peptide of 2 to 4
      amino acids, an analog thereof or not present
<220> FEATURE:
<221> NAME/KEY: MOD_RES
<222> LOCATION: (12)..(12)
```

```
<223> OTHER INFORMATION: Sar
<220> FEATURE:
<221> NAME/KEY: MOD_RES
<222> LOCATION: (13)..(13)
<223> OTHER INFORMATION: NMeLeu
<220> FEATURE:
<221> NAME/KEY: MOD_RES
<222> LOCATION: (15)..(15)
<223> OTHER INFORMATION: An optionally derivatized amino acid or analog
      thereof

<400> SEQUENCE: 3

Xaa Phe Xaa Xaa Xaa Xaa Xaa Gly His Phe Gly Xaa Xaa Tyr Xaa Cys
1               5                   10                  15

<210> SEQ ID NO 4
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: An optionally derivatized amino acid, an analog
      thereof or not present
<220> FEATURE:
<221> NAME/KEY: MOD_RES
<222> LOCATION: (2)..(15)
<223> OTHER INFORMATION: An optionally derivatized any amino acid, an
      analog thereof, an optionally derivatized peptide of 2 to 15
      amino acids, an analog thereof or not present
<220> FEATURE:
<221> NAME/KEY: MOD_RES
<222> LOCATION: (18)..(18)
<223> OTHER INFORMATION: Any amino acid or an analog thereof
<220> FEATURE:
<221> NAME/KEY: MOD_RES
<222> LOCATION: (24)..(24)
<223> OTHER INFORMATION: Sar
<220> FEATURE:
<221> NAME/KEY: MOD_RES
<222> LOCATION: (25)..(25)
<223> OTHER INFORMATION: NMeLeu
<220> FEATURE:
<221> NAME/KEY: MOD_RES
<222> LOCATION: (28)..(29)
<223> OTHER INFORMATION: An optionally derivatized amino acid, an analog
      thereof or not present
<220> FEATURE:
<221> NAME/KEY: MOD_RES
<222> LOCATION: (30)..(43)
<223> OTHER INFORMATION: An optionally derivatized any amino acid, an
      analog thereof, an optionally derivatized peptide of 2 to 15
      amino acids, an analog thereof or not present

<400> SEQUENCE: 4

Xaa Xaa Xaa Xaa Xaa Xaa Xaa Xaa Xaa Xaa Xaa Xaa Xaa Xaa Xaa Arg
1               5                   10                  15

Phe Xaa Thr Gly His Phe Gly Xaa Xaa Tyr Pro Xaa Xaa Xaa Xaa Xaa
            20                  25                  30

Xaa Xaa Xaa Xaa Xaa Xaa Xaa Xaa Xaa Xaa Xaa
            35                  40

<210> SEQ ID NO 5
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (1)..(1)
<223> OTHER INFORMATION: An optionally derivatized amino acid, an analog
      thereof or not present
<220> FEATURE:
<221> NAME/KEY: MOD_RES
<222> LOCATION: (2)..(15)
<223> OTHER INFORMATION: An optionally derivatized any amino acid, an
      analog thereof, an optionally derivatized peptide of 2 to 15
      amino acids, an analog thereof or not present
<220> FEATURE:
<221> NAME/KEY: MOD_RES
<222> LOCATION: (18)..(18)
<223> OTHER INFORMATION: Any amino acid or an analog thereof
<220> FEATURE:
<221> NAME/KEY: MOD_RES
<222> LOCATION: (24)..(24)
<223> OTHER INFORMATION: Sar
<220> FEATURE:
<221> NAME/KEY: MOD_RES
<222> LOCATION: (25)..(25)
<223> OTHER INFORMATION: NMeLeu
<220> FEATURE:
<221> NAME/KEY: MOD_RES
<222> LOCATION: (28)..(29)
<223> OTHER INFORMATION: An optionally derivatized amino acid, an analog
      thereof or not present
<220> FEATURE:
<221> NAME/KEY: MOD_RES
<222> LOCATION: (30)..(43)
<223> OTHER INFORMATION: An optionally derivatized any amino acid, an
      analog thereof, an optionally derivatized peptide of 2 to 15
      amino acids, an analog thereof or not present
<220> FEATURE:
<221> NAME/KEY: MOD_RES
<222> LOCATION: (44)..(44)
<223> OTHER INFORMATION: An optionally derivatized amino acid, an analog
      thereof or not present
<220> FEATURE:
<221> NAME/KEY: MOD_RES
<222> LOCATION: (45)..(58)
<223> OTHER INFORMATION: An optionally derivatized any amino acid, an
      analog thereof, an optionally derivatized peptide of 2 to 15
      amino acids, an analog thereof or not present
<220> FEATURE:
<221> NAME/KEY: MOD_RES
<222> LOCATION: (61)..(61)
<223> OTHER INFORMATION: Any amino acid or an analog thereof
<220> FEATURE:
<221> NAME/KEY: MOD_RES
<222> LOCATION: (67)..(67)
<223> OTHER INFORMATION: Sar
<220> FEATURE:
<221> NAME/KEY: MOD_RES
<222> LOCATION: (68)..(68)
<223> OTHER INFORMATION: NMeLeu
<220> FEATURE:
<221> NAME/KEY: MOD_RES
<222> LOCATION: (71)..(72)
<223> OTHER INFORMATION: An optionally derivatized amino acid, an analog
      thereof or not present
<220> FEATURE:
<221> NAME/KEY: MOD_RES
<222> LOCATION: (73)..(86)
<223> OTHER INFORMATION: An optionally derivatized any amino acid, an
      analog thereof, an optionally derivatized peptide of 2 to 15
      amino acids, an analog thereof or not present
<220> FEATURE:
<221> NAME/KEY: MISC_FEATURE
<222> LOCATION: (44)..(86)
<223> OTHER INFORMATION: This region may or may not be present
<220> FEATURE:
<221> NAME/KEY: MOD_RES
<222> LOCATION: (87)..(87)
<223> OTHER INFORMATION: An optionally derivatized amino acid, an analog
      thereof or not present
<220> FEATURE:
<221> NAME/KEY: MOD_RES
<222> LOCATION: (88)..(101)
```

```
<223> OTHER INFORMATION: An optionally derivatized any amino acid, an
      analog thereof, an optionally derivatized peptide of 2 to 15
      amino acids, an analog thereof or not present
<220> FEATURE:
<221> NAME/KEY: MOD_RES
<222> LOCATION: (104)..(104)
<223> OTHER INFORMATION: Any amino acid or an analog thereof
<220> FEATURE:
<221> NAME/KEY: MOD_RES
<222> LOCATION: (110)..(110)
<223> OTHER INFORMATION: Sar
<220> FEATURE:
<221> NAME/KEY: MOD_RES
<222> LOCATION: (111)..(111)
<223> OTHER INFORMATION: NMeLeu
<220> FEATURE:
<221> NAME/KEY: MOD_RES
<222> LOCATION: (114)..(115)
<223> OTHER INFORMATION: An optionally derivatized amino acid, an analog
      thereof or not present
<220> FEATURE:
<221> NAME/KEY: MOD_RES
<222> LOCATION: (116)..(129)
<223> OTHER INFORMATION: An optionally derivatized any amino acid, an
      analog thereof, an optionally derivatized peptide of 2 to 15
      amino acids, an analog thereof or not present
<220> FEATURE:
<221> NAME/KEY: MISC_FEATURE
<222> LOCATION: (87)..(129)
<223> OTHER INFORMATION: This region may or may not be present

<400> SEQUENCE: 5

Xaa Xaa Xaa Xaa Xaa Xaa Xaa Xaa Xaa Xaa Xaa Xaa Xaa Xaa Xaa Arg
1               5                   10                  15

Phe Xaa Thr Gly His Phe Gly Xaa Xaa Tyr Pro Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Arg Phe Xaa Thr Gly His
    50                  55                  60

Phe Gly Xaa Xaa Tyr Pro Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Arg Phe Xaa Thr Gly His Phe Gly Xaa Xaa Tyr
            100                 105                 110

Pro Xaa Xaa Xaa Xaa Xaa Xaa Xaa Xaa Xaa Xaa Xaa Xaa Xaa Xaa Xaa
        115                 120                 125

Xaa

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: An optionally derivatized amino acid, an analog
      thereof or not present
<220> FEATURE:
<221> NAME/KEY: MOD_RES
<222> LOCATION: (2)..(15)
<223> OTHER INFORMATION: An optionally derivatized any amino acid, an
      analog thereof, an optionally derivatized peptide of 2 to 15
      amino acids, an analog thereof or not present
<220> FEATURE:
```

```
<221> NAME/KEY: MOD_RES
<222> LOCATION: (18)..(18)
<223> OTHER INFORMATION: Pen
<220> FEATURE:
<221> NAME/KEY: MOD_RES
<222> LOCATION: (24)..(24)
<223> OTHER INFORMATION: Sar
<220> FEATURE:
<221> NAME/KEY: MOD_RES
<222> LOCATION: (25)..(25)
<223> OTHER INFORMATION: NMeLeu

<400> SEQUENCE: 6

Xaa Xaa Xaa Xaa Xaa Xaa Xaa Xaa Xaa Xaa Xaa Xaa Xaa Xaa Xaa Arg
1               5                   10                  15

Phe Xaa Thr Gly His Phe Gly Xaa Xaa Tyr Pro Cys
            20                  25

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 7

Arg Phe Xaa Thr Gly His Phe Gly Xaa Xaa Tyr Pro Cys Gly Gly Lys
1               5                   10                  15

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggcgcaact atcggtatca agctg                                         25

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
catgtaccgt aacactgagt ttcgtc                                        26

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 10
gataaaccga tacaattaaa ggctcc                                         26

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid

<400> SEQUENCE: 11

Gly His Phe Gly Gly Xaa Tyr
1               5

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Gly Gln Arg Phe Cys Thr Gly His Phe Gly Gly Leu Tyr Pro Cys
1               5                   10                  15

Asn Gly Pro Gly Thr Gly Gly Gly Lys
            20                  25

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Gly Gly Gly Cys Val Thr Gly His Phe Gly Gly Ile Tyr Cys Asn
1               5                   10                  15

Thr Gln Gly Thr Gly Gly Gly Lys
            20

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Gly Lys Ile Ile Cys Ser Pro Gly His Phe Gly Gly Met Tyr Cys
1               5                   10                  15

Gln Gly Lys Gly Thr Gly Gly Gly Lys
            20                  25

<210> SEQ ID NO 15
<211> LENGTH: 25
<212> TYPE: PRT

-continued

<213> ORGANISM: Artificial Sequence
<220> FEATURE:
<223> OTHER INFORMATION: Description of Artificial Sequence: Synthetic
      peptide

<400> SEQUENCE: 15

Ala Gly Pro Ser Tyr Cys Ile Glu Gly His Ile Asp Gly Ile Tyr Cys
1               5                   10                  15

Phe Asn Ala Gly Thr Gly Gly Gly Lys
            20                  25

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Gly Asn Ser Phe Cys Arg Gly Arg Pro Gly His Phe Gly Gly Cys
1               5                   10                  15

Tyr Leu Phe Gly Thr Gly Gly Gly Lys
            20                  25

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Arg Phe Cys Thr Gly His Phe Gly Gly Leu Tyr Pro Cys Asn Gly
1               5                   10                  15

Pro

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Thr Gly His Phe Gly Gly Leu Tyr Pro Cys Asn Gly Pro
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Arg Phe Cys Thr Gly His Phe Gly Gly Leu Tyr Pro Cys
1               5                   10

<210> SEQ ID NO 20
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 20

Cys Thr Gly His Phe Gly Gly Leu Tyr Pro Cys
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Gly His Phe Gly Gly Leu Tyr Pro
1               5

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Phe Cys Thr Gly His Phe Gly Gly Leu Tyr Pro Cys Asn Gly Pro
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Phe Cys Thr Gly His Phe Gly Gly Leu Tyr Pro Cys Asn Gly Pro
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Arg Phe Cys Thr Gly His Phe Gly Gly Leu Tyr Pro Cys Asn Gly
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Arg Phe Cys Thr Gly His Phe Gly Gly Leu Tyr Pro Cys Asn
1               5                   10                  15
```

```
<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Ala Phe Cys Thr Gly His Phe Gly Gly Leu Tyr Pro Cys Asn Gly
1               5                   10                  15

Pro

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Arg Ala Cys Thr Gly His Phe Gly Gly Leu Tyr Pro Cys Asn Gly
1               5                   10                  15

Pro

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Arg Phe Cys Ala Gly His Phe Gly Gly Leu Tyr Pro Cys Asn Gly
1               5                   10                  15

Pro

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Arg Phe Cys Thr Ala His Phe Gly Gly Leu Tyr Pro Cys Asn Gly
1               5                   10                  15

Pro

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Arg Phe Cys Thr Gly Ala Phe Gly Gly Leu Tyr Pro Cys Asn Gly
1               5                   10                  15

Pro
```

```
<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Arg Phe Cys Thr Gly His Ala Gly Gly Leu Tyr Pro Cys Asn Gly
1               5                   10                  15

Pro

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Arg Phe Cys Thr Gly His Phe Ala Gly Leu Tyr Pro Cys Asn Gly
1               5                   10                  15

Pro

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Arg Phe Cys Thr Gly His Phe Gly Ala Leu Tyr Pro Cys Asn Gly
1               5                   10                  15

Pro

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Arg Phe Cys Thr Gly His Phe Gly Gly Ala Tyr Pro Cys Asn Gly
1               5                   10                  15

Pro

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Arg Phe Cys Thr Gly His Phe Gly Gly Leu Ala Pro Cys Asn Gly
1               5                   10                  15
```

Pro

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Arg Phe Cys Thr Gly His Phe Gly Gly Leu Tyr Ala Cys Asn Gly
1               5                   10                  15

Pro

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Arg Phe Cys Thr Gly His Phe Gly Gly Leu Tyr Pro Cys Ala Gly
1               5                   10                  15

Pro

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: L-homocysteine

<400> SEQUENCE: 38

Gln Arg Phe Cys Thr Gly His Phe Gly Gly Leu Tyr Pro Xaa Asn Gly
1               5                   10                  15

Pro

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: L-homocysteine
<220> FEATURE:
<221> NAME/KEY: MOD_RES
<222> LOCATION: (14)..(14)
<223> OTHER INFORMATION: L-homocysteine

<400> SEQUENCE: 39

Gln Arg Phe Xaa Thr Gly His Phe Gly Gly Leu Tyr Pro Xaa Asn Gly
1               5                   10                  15

Pro

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Cys

<400> SEQUENCE: 40

Gln Arg Phe Xaa Thr Gly His Phe Gly Gly Leu Tyr Pro Cys Asn Gly
1               5                   10                  15

Pro

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: D-Cys

<400> SEQUENCE: 41

Gln Arg Phe Cys Thr Gly His Phe Gly Gly Leu Tyr Pro Xaa Asn Gly
1               5                   10                  15

Pro

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-Cys
<220> FEATURE:
<221> NAME/KEY: MOD_RES
<222> LOCATION: (14)..(14)
<223> OTHER INFORMATION: D-Cys

<400> SEQUENCE: 42

Gln Arg Phe Xaa Thr Gly His Phe Gly Gly Leu Tyr Pro Xaa Asn Gly
1               5                   10                  15

Pro

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 43

Gln Arg Phe Xaa Thr Gly His Phe Gly Gly Leu Tyr Pro Cys Asn Gly

```
1               5                   10                  15
Pro

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Pen

<400> SEQUENCE: 44

Gln Arg Phe Cys Thr Gly His Phe Gly Gly Leu Tyr Pro Xaa Asn Gly
1               5                   10                  15
Pro

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (14)..(14)
<223> OTHER INFORMATION: Pen

<400> SEQUENCE: 45

Gln Arg Phe Xaa Thr Gly His Phe Gly Gly Leu Tyr Pro Xaa Asn Gly
1               5                   10                  15
Pro

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (14)..(14)
<223> OTHER INFORMATION: L-homocysteine

<400> SEQUENCE: 46

Gln Arg Phe Xaa Thr Gly His Phe Gly Gly Leu Tyr Pro Xaa Asn Gly
1               5                   10                  15
Pro

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
```

```
           peptide
<220> FEATURE:
<221> NAME/KEY: MOD_RES
<222> LOCATION: (4)..(4)
<223> OTHER INFORMATION: L-homocysteine
<220> FEATURE:
<221> NAME/KEY: MOD_RES
<222> LOCATION: (14)..(14)
<223> OTHER INFORMATION: Pen

<400> SEQUENCE: 47

Gln Arg Phe Xaa Thr Gly His Phe Gly Gly Leu Tyr Pro Xaa Asn Gly
1               5                   10                  15

Pro

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Pro
<220> FEATURE:
<221> NAME/KEY: MOD_RES
<222> LOCATION: (14)..(14)
<223> OTHER INFORMATION: Pen

<400> SEQUENCE: 48

Gln Arg Phe Xaa Thr Gly His Phe Gly Xaa Leu Tyr Pro Xaa Asn Gly
1               5                   10                  15

Pro

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeAla

<400> SEQUENCE: 49

Gln Arg Phe Cys Xaa Gly His Phe Gly Gly Leu Tyr Pro Cys Asn Gly
1               5                   10                  15

Pro

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
```

```
<222> LOCATION: (6)..(6)
<223> OTHER INFORMATION: Sar

<400> SEQUENCE: 50

Gln Arg Phe Xaa Thr Xaa His Phe Gly Gly Leu Tyr Pro Cys Asn Gly
1               5                   10                  15

Pro

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: NMeHis

<400> SEQUENCE: 51

Arg Phe Xaa Thr Gly Xaa Phe Gly Gly Leu Tyr Pro Cys
1               5                   10

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: NMePhe

<400> SEQUENCE: 52

Gln Arg Phe Xaa Thr Gly His Xaa Gly Gly Leu Tyr Pro Cys Asn Gly
1               5                   10                  15

Pro

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: Sar

<400> SEQUENCE: 53

Gln Arg Phe Xaa Thr Gly His Phe Xaa Gly Leu Tyr Pro Cys Asn Gly
1               5                   10                  15

Pro
```

```
<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: Sar

<400> SEQUENCE: 54

Gln Arg Phe Xaa Thr Gly His Phe Gly Xaa Leu Tyr Pro Cys Asn Gly
1               5                   10                  15

Pro

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (11)..(11)
<223> OTHER INFORMATION: NMeLeu

<400> SEQUENCE: 55

Gln Arg Phe Xaa Thr Gly His Phe Gly Gly Xaa Tyr Pro Cys Asn Gly
1               5                   10                  15

Pro

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: NMeTyr

<400> SEQUENCE: 56

Gln Arg Phe Xaa Thr Gly His Phe Gly Gly Leu Xaa Pro Cys Asn Gly
1               5                   10                  15

Pro

<210> SEQ ID NO 57
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (10)..(10)
<223> OTHER INFORMATION: NMeLeu

<400> SEQUENCE: 57

Arg Phe Xaa Thr Gly His Phe Gly Gly Xaa Tyr Pro Cys Asn Gly Pro
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar

<400> SEQUENCE: 58

Arg Phe Xaa Thr Gly His Phe Gly Xaa Tyr Pro Cys Asn Gly Pro
1               5                   10                  15

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: Sar
<220> FEATURE:
<221> NAME/KEY: MOD_RES
<222> LOCATION: (11)..(11)
<223> OTHER INFORMATION: NMeLeu

<400> SEQUENCE: 59

Gln Arg Phe Xaa Thr Gly His Phe Gly Xaa Xaa Tyr Pro Cys Asn Gly
1               5                   10                  15

Pro

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
```

```
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 60

Arg Phe Xaa Thr Gly His Phe Gly Xaa Xaa Tyr Pro Cys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pen

<400> SEQUENCE: 61

Phe Xaa Thr Gly His Phe Gly Gly Leu Tyr Pro Cys
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen

<400> SEQUENCE: 62

Arg Phe Xaa Thr Gly His Phe Gly Gly Leu Tyr Pro Cys
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Pro

<400> SEQUENCE: 63

Gln Arg Phe Xaa Thr Gly His Phe Gly Xaa Leu Tyr Pro Cys
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: D-Pro

<400> SEQUENCE: 64

Arg Phe Xaa Thr Gly His Phe Gly Xaa Leu Tyr Pro Cys
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (8)..(8)
<223> OTHER INFORMATION: D-Pro

<400> SEQUENCE: 65

Phe Xaa Thr Gly His Phe Gly Xaa Leu Tyr Pro Cys
1               5                   10

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: D-Pro

<400> SEQUENCE: 66

Arg Phe Xaa Thr Gly His Phe Gly Xaa Leu Tyr Pro Cys Asn Gly Pro
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (8)..(8)
<223> OTHER INFORMATION: D-Pro

<400> SEQUENCE: 67

Phe Xaa Thr Gly His Phe Gly Xaa Leu Tyr Pro Cys Asn Gly Pro
1               5                   10                  15
```

```
<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Pro

<400> SEQUENCE: 68

Gln Arg Phe Xaa Thr Gly His Phe Gly Xaa Leu Tyr Pro Cys Asn Gly
1               5                   10                  15

Pro

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Arg

<400> SEQUENCE: 69

Gln Arg Phe Xaa Thr Gly His Phe Gly Xaa Leu Tyr Pro Cys Asn Gly
1               5                   10                  15

Pro

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-His

<400> SEQUENCE: 70

Gln Arg Phe Xaa Thr Gly His Phe Gly Xaa Leu Tyr Pro Cys Asn Gly
1               5                   10                  15

Pro

<210> SEQ ID NO 71
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Ile

<400> SEQUENCE: 71

Gln Arg Phe Xaa Thr Gly His Phe Gly Xaa Leu Tyr Pro Cys Asn Gly
1               5                   10                  15

Pro

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Phe

<400> SEQUENCE: 72

Gln Arg Phe Xaa Thr Gly His Phe Gly Xaa Leu Tyr Pro Cys Asn Gly
1               5                   10                  15

Pro

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Tyr

<400> SEQUENCE: 73

Gln Arg Phe Xaa Thr Gly His Phe Gly Xaa Leu Tyr Pro Cys Asn Gly
1               5                   10                  15

Pro

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
```

```
<221> NAME/KEY: MOD_RES
<222> LOCATION: (10)..(10)
<223> OTHER INFORMATION: Aib

<400> SEQUENCE: 74

Gln Arg Phe Xaa Thr Gly His Phe Gly Xaa Leu Tyr Pro Cys Asn Gly
1               5                   10                  15

Pro

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Asp

<400> SEQUENCE: 75

Gln Arg Phe Xaa Thr Gly His Phe Xaa Gly Leu Tyr Pro Cys Asn Gly
1               5                   10                  15

Pro

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Pro

<400> SEQUENCE: 76

Gln Arg Phe Xaa Thr Gly His Phe Xaa Gly Leu Tyr Pro Cys Asn Gly
1               5                   10                  15

Pro

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Arg

<400> SEQUENCE: 77

Gln Arg Phe Xaa Thr Gly His Phe Xaa Gly Leu Tyr Pro Cys Asn Gly
```

Pro

<210> SEQ ID NO 78
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-His

<400> SEQUENCE: 78

Gln Arg Phe Xaa Thr Gly His Phe Xaa Gly Leu Tyr Pro Cys Asn Gly
1               5                   10                  15
Pro

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Ile

<400> SEQUENCE: 79

Gln Arg Phe Xaa Thr Gly His Phe Xaa Gly Leu Tyr Pro Cys Asn Gly
1               5                   10                  15
Pro

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Phe

<400> SEQUENCE: 80

Gln Arg Phe Xaa Thr Gly His Phe Xaa Gly Leu Tyr Pro Cys Asn Gly
1               5                   10                  15
Pro

<210> SEQ ID NO 81
<211> LENGTH: 17

-continued

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Tyr

<400> SEQUENCE: 81

Gln Arg Phe Xaa Thr Gly His Phe Xaa Gly Leu Tyr Pro Cys Asn Gly
1               5                   10                  15
Pro

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: Aib

<400> SEQUENCE: 82

Gln Arg Phe Xaa Thr Gly His Phe Xaa Gly Leu Tyr Pro Cys Asn Gly
1               5                   10                  15
Pro

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Ala

<400> SEQUENCE: 83

Gln Arg Phe Xaa Thr Gly His Phe Gly Xaa Leu Tyr Pro Cys Asn Gly
1               5                   10                  15
Pro

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Ala

<400> SEQUENCE: 84

Gln Arg Phe Xaa Thr Gly His Phe Xaa Gly Leu Tyr Pro Cys Asn Gly
1               5                   10                  15
Pro

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(10)
<223> OTHER INFORMATION: D-Ala

<400> SEQUENCE: 85

Gln Arg Phe Xaa Thr Gly His Phe Xaa Xaa Leu Tyr Pro Cys Asn Gly
1               5                   10                  15
Pro

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Ala
<220> FEATURE:
<221> NAME/KEY: MOD_RES
<222> LOCATION: (10)..(10)
<223> OTHER INFORMATION: D-Pro

<400> SEQUENCE: 86

Gln Arg Phe Xaa Thr Gly His Phe Xaa Xaa Leu Tyr Pro Cys Asn Gly
1               5                   10                  15
Pro

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
```

```
<221> NAME/KEY: MOD_RES
<222> LOCATION: (9)..(9)
<223> OTHER INFORMATION: D-Phe
<220> FEATURE:
<221> NAME/KEY: MOD_RES
<222> LOCATION: (10)..(10)
<223> OTHER INFORMATION: D-Pro

<400> SEQUENCE: 87

Gln Arg Phe Xaa Thr Gly His Phe Xaa Xaa Leu Tyr Pro Cys Asn Gly
1               5                   10                  15

Pro

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Phe
<220> FEATURE:
<221> NAME/KEY: MOD_RES
<222> LOCATION: (10)..(10)
<223> OTHER INFORMATION: D-Ala

<400> SEQUENCE: 88

Gln Arg Phe Xaa Thr Gly His Phe Xaa Xaa Leu Tyr Pro Cys Asn Gly
1               5                   10                  15

Pro

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(10)
<223> OTHER INFORMATION: D-Pro

<400> SEQUENCE: 89

Gln Arg Phe Xaa Thr Gly His Phe Xaa Xaa Leu Tyr Pro Cys Asn Gly
1               5                   10                  15

Pro

<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
```

```
<220> FEATURE:
<221> NAME/KEY: MOD_RES
<222> LOCATION: (9)..(9)
<223> OTHER INFORMATION: D-Phe
<220> FEATURE:
<221> NAME/KEY: MOD_RES
<222> LOCATION: (11)..(11)
<223> OTHER INFORMATION: NMeLeu

<400> SEQUENCE: 90

Gln Arg Phe Xaa Thr Gly His Phe Xaa Gly Xaa Tyr Pro Cys Asn Gly
1               5                   10                  15
Pro

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Ala
<220> FEATURE:
<221> NAME/KEY: MOD_RES
<222> LOCATION: (11)..(11)
<223> OTHER INFORMATION: NMeLeu

<400> SEQUENCE: 91

Gln Arg Phe Xaa Thr Gly His Phe Xaa Gly Xaa Tyr Pro Cys Asn Gly
1               5                   10                  15
Pro

<210> SEQ ID NO 92
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Phe

<400> SEQUENCE: 92

Gln Arg Phe Xaa Thr Gly His Phe Xaa Gly Pro Tyr Pro Cys Asn Gly
1               5                   10                  15
Pro

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
```

```
<223> OTHER INFORMATION: Pen
<220> FEATURE:
<221> NAME/KEY: MOD_RES
<222> LOCATION: (9)..(9)
<223> OTHER INFORMATION: D-Pro

<400> SEQUENCE: 93

Gln Arg Phe Xaa Thr Gly His Phe Xaa Pro Leu Tyr Pro Cys Asn Gly
1               5                   10                  15

Pro

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Phe

<400> SEQUENCE: 94

Gln Arg Phe Xaa Thr Gly His Phe Xaa Pro Leu Tyr Pro Cys Asn Gly
1               5                   10                  15

Pro

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Ala
<220> FEATURE:
<221> NAME/KEY: MOD_RES
<222> LOCATION: (10)..(10)
<223> OTHER INFORMATION: Sar

<400> SEQUENCE: 95

Gln Arg Phe Xaa Thr Gly His Phe Xaa Xaa Leu Tyr Pro Cys Asn Gly
1               5                   10                  15

Pro

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Phe
<220> FEATURE:
<221> NAME/KEY: MOD_RES
```

```
<222> LOCATION: (4)..(4)
<223> OTHER INFORMATION: Pen

<400> SEQUENCE: 96

Gln Arg Xaa Xaa Thr Gly His Phe Gly Gly Leu Tyr Pro Cys Asn Gly
1               5                   10                  15

Pro

<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 97

Gln Arg Tyr Xaa Thr Gly His Phe Gly Gly Leu Tyr Pro Cys Asn Gly
1               5                   10                  15

Pro

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 98

Gln Arg Trp Xaa Thr Gly His Phe Gly Gly Leu Tyr Pro Cys Asn Gly
1               5                   10                  15

Pro

<210> SEQ ID NO 99
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 99

Gln Arg Phe Xaa His Gly His Phe Gly Gly Leu Tyr Pro Cys Asn Gly
1               5                   10                  15

Pro

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (4)..(4)
<223> OTHER INFORMATION: Pen

<400> SEQUENCE: 100

Gln Arg Phe Xaa Gly Gly His Phe Gly Gly Leu Tyr Pro Cys Asn Gly
1               5                   10                  15

Pro

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (5)..(5)
<223> OTHER INFORMATION: NMeAla

<400> SEQUENCE: 101

Gln Arg Phe Xaa Xaa Gly His Phe Gly Gly Leu Tyr Pro Cys Asn Gly
1               5                   10                  15

Pro

<210> SEQ ID NO 102
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (9)..(9)
<223> OTHER INFORMATION: D-Ala
<220> FEATURE:
<221> NAME/KEY: MOD_RES
<222> LOCATION: (10)..(10)
<223> OTHER INFORMATION: Sar
<220> FEATURE:
<221> NAME/KEY: MOD_RES
<222> LOCATION: (11)..(11)
<223> OTHER INFORMATION: NMeLeu

<400> SEQUENCE: 102

Gln Arg Phe Xaa Thr Gly His Phe Xaa Xaa Xaa Tyr Pro Cys Asn Gly
1               5                   10                  15

Pro

<210> SEQ ID NO 103
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
```

```
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 103

Arg Phe Xaa Thr Gly His Phe Gly Xaa Xaa Tyr Pro Cys
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Phe
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 104

Arg Phe Xaa Thr Gly His Phe Xaa Xaa Xaa Tyr Pro Cys
1               5                   10

<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Val
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 105

Arg Phe Xaa Thr Gly His Phe Xaa Xaa Xaa Tyr Pro Cys
1               5                   10

<210> SEQ ID NO 106
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Leu
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 106

Arg Phe Xaa Thr Gly His Phe Xaa Xaa Xaa Tyr Pro Cys
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Trp
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 107

Arg Phe Xaa Thr Gly His Phe Xaa Xaa Xaa Tyr Pro Cys
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Thr
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu
```

<400> SEQUENCE: 108

Arg Phe Xaa Thr Gly His Phe Xaa Xaa Xaa Tyr Pro Cys
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Ser
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 109

Arg Phe Xaa Thr Gly His Phe Xaa Xaa Xaa Tyr Pro Cys
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Asp
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 110

Arg Phe Xaa Thr Gly His Phe Xaa Xaa Xaa Tyr Pro Cys
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:

```
<221> NAME/KEY: MOD_RES
<222> LOCATION: (8)..(8)
<223> OTHER INFORMATION: D-Asn
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 111

Arg Phe Xaa Thr Gly His Phe Xaa Xaa Xaa Tyr Pro Cys
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Glu
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 112

Arg Phe Xaa Thr Gly His Phe Xaa Xaa Xaa Tyr Pro Cys
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: D-Gln
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 113

Arg Phe Xaa Thr Gly His Phe Xaa Xaa Xaa Tyr Pro Cys
1               5                   10

<210> SEQ ID NO 114
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 4-amino-Phe

<400> SEQUENCE: 114

Gln Arg Phe Xaa Thr Gly His Xaa Gly Gly Leu Tyr Pro Cys Asn Gly
1               5                   10                  15

Pro

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 4-methyoxy-Phe

<400> SEQUENCE: 115

Gln Arg Phe Xaa Thr Gly His Xaa Gly Gly Leu Tyr Pro Cys Asn Gly
1               5                   10                  15

Pro

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: pentafluoro-Phe

<400> SEQUENCE: 116

Gln Arg Phe Xaa Thr Gly His Xaa Gly Gly Leu Tyr Pro Cys Asn Gly
1               5                   10                  15

Pro

<210> SEQ ID NO 117
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

```
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 2-pyridylalanine

<400> SEQUENCE: 117

Gln Arg Phe Xaa Thr Gly His Xaa Gly Gly Leu Tyr Pro Cys Asn Gly
1               5                   10                  15
Pro

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 3-PyridylAla

<400> SEQUENCE: 118

Gln Arg Phe Xaa Thr Gly His Xaa Gly Gly Leu Tyr Pro Cys Asn Gly
1               5                   10                  15
Pro

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 4-nitro-Phe

<400> SEQUENCE: 119

Gln Arg Phe Xaa Thr Gly His Xaa Gly Gly Leu Tyr Pro Cys Asn Gly
1               5                   10                  15
Pro

<210> SEQ ID NO 120
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 1-napthylalanine
```

<400> SEQUENCE: 120

Gln Arg Phe Xaa Thr Gly His Xaa Gly Gly Leu Tyr Pro Cys Asn Gly
1               5                   10                  15

Pro

<210> SEQ ID NO 121
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 2-napthylalanine

<400> SEQUENCE: 121

Gln Arg Phe Xaa Thr Gly His Xaa Gly Gly Leu Tyr Pro Cys Asn Gly
1               5                   10                  15

Pro

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 2-MePhe

<400> SEQUENCE: 122

Gln Arg Phe Xaa Thr Gly His Xaa Gly Gly Leu Tyr Pro Cys Asn Gly
1               5                   10                  15

Pro

<210> SEQ ID NO 123
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 3-MePhe

<400> SEQUENCE: 123

Gln Arg Phe Xaa Thr Gly His Xaa Gly Gly Leu Tyr Pro Cys Asn Gly
1               5                   10                  15

Pro

```
<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: 4-MePhe

<400> SEQUENCE: 124

Gln Arg Phe Xaa Thr Gly His Xaa Gly Gly Leu Tyr Pro Cys Asn Gly
1               5                   10                  15

Pro

<210> SEQ ID NO 125
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: homoPhe

<400> SEQUENCE: 125

Gln Arg Phe Xaa Thr Gly His Xaa Gly Gly Leu Tyr Pro Cys Asn Gly
1               5                   10                  15

Pro

<210> SEQ ID NO 126
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: Cha

<400> SEQUENCE: 126

Gln Arg Phe Xaa Thr Gly His Xaa Gly Gly Leu Tyr Pro Cys Asn Gly
1               5                   10                  15

Pro

<210> SEQ ID NO 127
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: PheNHAc

<400> SEQUENCE: 127

Gln Arg Phe Xaa Thr Gly His Xaa Gly Gly Leu Tyr Pro Cys Asn Gly
 1               5                  10                  15

Pro

<210> SEQ ID NO 128
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 128

Gln Arg Phe Xaa Thr Gly His Trp Gly Gly Leu Tyr Pro Cys Asn Gly
 1               5                  10                  15

Pro

<210> SEQ ID NO 129
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: phenylGly

<400> SEQUENCE: 129

Gln Arg Phe Xaa Thr Gly His Xaa Gly Gly Leu Tyr Pro Cys Asn Gly
 1               5                  10                  15

Pro

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (8)..(8)
<223> OTHER INFORMATION: Tic
```

```
<400> SEQUENCE: 130

Gln Arg Phe Xaa Thr Gly His Xaa Gly Gly Leu Tyr Pro Cys Asn Gly
1               5                   10                  15

Pro

<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 2MePhe

<400> SEQUENCE: 131

Gln Arg Phe Asp Thr Gly His Xaa Gly Gly Leu Tyr Pro Lys Asn Gly
1               5                   10                  15

Pro

<210> SEQ ID NO 132
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (7)..(7)
<223> OTHER INFORMATION: 2-Cl-Phe

<400> SEQUENCE: 132

Arg Phe Xaa Thr Gly His Xaa Gly Gly Leu Tyr Pro Cys
1               5                   10

<210> SEQ ID NO 133
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (7)..(7)
<223> OTHER INFORMATION: 3-Cl-Phe

<400> SEQUENCE: 133

Arg Phe Xaa Thr Gly His Xaa Gly Gly Leu Tyr Pro Cys
1               5                   10

<210> SEQ ID NO 134
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (7)..(7)
<223> OTHER INFORMATION: 4-Cl-Phe

<400> SEQUENCE: 134

Arg Phe Xaa Thr Gly His Xaa Gly Gly Leu Tyr Pro Cys
1               5                   10

<210> SEQ ID NO 135
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (7)..(7)
<223> OTHER INFORMATION: 3,3-Di-Phe

<400> SEQUENCE: 135

Arg Phe Xaa Thr Gly His Xaa Gly Gly Leu Tyr Pro Cys
1               5                   10

<210> SEQ ID NO 136
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (7)..(7)
<223> OTHER INFORMATION: 4,4-Bi-Phe

<400> SEQUENCE: 136

Arg Phe Xaa Thr Gly His Xaa Gly Gly Leu Tyr Pro Cys
1               5                   10

<210> SEQ ID NO 137
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (7)..(7)
<223> OTHER INFORMATION: 4-t-Butyl-Phe

<400> SEQUENCE: 137

Arg Phe Xaa Thr Gly His Xaa Gly Gly Leu Tyr Pro Cys
1               5                   10
```

```
<210> SEQ ID NO 138
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (7)..(7)
<223> OTHER INFORMATION: (D/L)-betamethylPhe
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 138

Arg Phe Xaa Thr Gly His Xaa Gly Xaa Xaa Tyr Pro Cys
1               5                   10

<210> SEQ ID NO 139
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gln Arg Phe Cys Thr Gly His Phe Gly Gly Leu Phe Pro Cys Asn Gly
1               5                   10                  15

Pro

<210> SEQ ID NO 140
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: 4-amino-Phe

<400> SEQUENCE: 140

Gln Arg Phe Xaa Thr Gly His Phe Gly Gly Leu Xaa Pro Cys Asn Gly
1               5                   10                  15

Pro

<210> SEQ ID NO 141
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: 4-methoxyPhe

<400> SEQUENCE: 141

Gln Arg Phe Xaa Thr Gly His Phe Gly Gly Leu Xaa Pro Cys Asn Gly
1               5                   10                  15

Pro

<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: pentafluoroPhe

<400> SEQUENCE: 142

Gln Arg Phe Xaa Thr Gly His Phe Gly Gly Leu Xaa Pro Cys Asn Gly
1               5                   10                  15

Pro

<210> SEQ ID NO 143
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: 2-pyridylAla

<400> SEQUENCE: 143

Gln Arg Phe Xaa Thr Gly His Phe Gly Gly Leu Xaa Pro Cys Asn Gly
1               5                   10                  15

Pro

<210> SEQ ID NO 144
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)

<223> OTHER INFORMATION: 3-pyridylAla

<400> SEQUENCE: 144

Gln Arg Phe Xaa Thr Gly His Phe Gly Gly Leu Xaa Pro Cys Asn Gly
1               5                   10                  15

Pro

<210> SEQ ID NO 145
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: 4-nitro-Phe

<400> SEQUENCE: 145

Gln Arg Phe Xaa Thr Gly His Phe Gly Gly Leu Xaa Pro Cys Asn Gly
1               5                   10                  15

Pro

<210> SEQ ID NO 146
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: 2-nitro-Tyr

<400> SEQUENCE: 146

Gln Arg Phe Xaa Thr Gly His Phe Gly Gly Leu Xaa Pro Cys Asn Gly
1               5                   10                  15

Pro

<210> SEQ ID NO 147
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (12)..(12)
<223> OTHER INFORMATION: 4-fluoro-Phe

<400> SEQUENCE: 147

Gln Arg Phe Xaa Thr Gly His Phe Gly Gly Leu Xaa Pro Cys Asn Gly
1               5                   10                  15

Pro

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 148

Gln Arg Phe Xaa Thr Gly His Phe Gly Gly His Tyr Pro Cys Asn Gly
1               5                   10                  15

Pro

<210> SEQ ID NO 149
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 149

Gln Arg Phe Xaa Thr Gly His Phe Gly Gly Ile Tyr Pro Cys Asn Gly
1               5                   10                  15

Pro

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 150

Gln Arg Phe Xaa Thr Gly His Phe Gly Gly Phe Tyr Pro Cys Asn Gly
1               5                   10                  15

Pro

<210> SEQ ID NO 151
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 151

Gln Arg Phe Xaa Thr Gly His Phe Gly Gly Trp Tyr Pro Cys Asn Gly
1               5                   10                  15

Pro

<210> SEQ ID NO 152
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 152

Gln Arg Phe Xaa Thr Gly His Phe Gly Gly Met Tyr Pro Cys Asn Gly
1               5                   10                  15
Pro

<210> SEQ ID NO 153
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 153

Gln Arg Phe Xaa Thr Gly His Phe Gly Gly Leu Tyr Pro Cys Asn Gly
1               5                   10                  15
Pro

<210> SEQ ID NO 154
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen

<400> SEQUENCE: 154

Arg Phe Xaa Thr Gly His Phe Gly Gly Trp Tyr Pro Cys
1               5                   10

<210> SEQ ID NO 155
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: Sar

<400> SEQUENCE: 155

-continued

Gln Arg Phe Xaa Thr Gly His Phe Gly Xaa Trp Tyr Pro Cys Asn Gly
1               5                   10                  15
Pro

<210> SEQ ID NO 156
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 156

Gln Arg Phe Xaa Thr Gly His Phe Gly Gly Gly Leu Tyr Pro Cys Asn
1               5                   10                  15
Gly Pro

<210> SEQ ID NO 157
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(11)
<223> OTHER INFORMATION: L, L-Friedinger's lactam

<400> SEQUENCE: 157

Gln Arg Phe Xaa Thr Gly His Phe Gly Xaa Xaa Tyr Pro Cys Asn Gly
1               5                   10                  15
Pro

<210> SEQ ID NO 158
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(11)
<223> OTHER INFORMATION: D, L-Friedinger's lactam

<400> SEQUENCE: 158

Gln Arg Phe Xaa Thr Gly His Phe Gly Xaa Xaa Tyr Pro Cys Asn Gly
1               5                   10                  15
Pro

<210> SEQ ID NO 159
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Dab

<400> SEQUENCE: 159

Gln Arg Phe Cys Thr Gly Xaa Phe Gly Gly Leu Tyr Pro Cys Asn Gly
1               5                   10                  15

Pro

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (7)..(7)
<223> OTHER INFORMATION: Thz

<400> SEQUENCE: 160

Gln Arg Phe Xaa Thr Gly Xaa Phe Gly Gly Leu Tyr Pro Cys Asn Gly
1               5                   10                  15

Pro

<210> SEQ ID NO 161
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (7)..(7)
<223> OTHER INFORMATION: Dap

<400> SEQUENCE: 161

Gln Arg Phe Xaa Thr Gly Xaa Phe Gly Gly Leu Tyr Pro Cys Asn Gly
1               5                   10                  15

Pro

<210> SEQ ID NO 162
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (7)..(7)
<223> OTHER INFORMATION: Dap(Guanyl)
```

```
<400> SEQUENCE: 162

Gln Arg Phe Xaa Thr Gly Xaa Phe Gly Gly Leu Tyr Pro Cys Asn Gly
1               5                   10                  15

Pro

<210> SEQ ID NO 163
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (7)..(7)
<223> OTHER INFORMATION: (1Me)His

<400> SEQUENCE: 163

Gln Arg Phe Xaa Thr Gly Xaa Phe Gly Gly Leu Tyr Pro Cys Asn Gly
1               5                   10                  15

Pro

<210> SEQ ID NO 164
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (7)..(7)
<223> OTHER INFORMATION: Dab

<400> SEQUENCE: 164

Gln Arg Phe Xaa Thr Gly Xaa Phe Gly Gly Leu Tyr Pro Cys Asn Gly
1               5                   10                  15

Pro

<210> SEQ ID NO 165
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: NMeHis

<400> SEQUENCE: 165

Arg Phe Xaa Thr Gly Xaa Phe Gly Gly Leu Tyr Pro Cys
1               5                   10
```

-continued

```
<210> SEQ ID NO 166
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: Thz
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 166

Arg Phe Xaa Thr Gly Xaa Phe Gly Xaa Xaa Tyr Pro Cys
1               5                   10

<210> SEQ ID NO 167
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 2PyridylAla
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 167

Arg Phe Xaa Thr Gly Xaa Phe Gly Xaa Xaa Tyr Pro Cys
1               5                   10

<210> SEQ ID NO 168
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 3PyridylAla
<220> FEATURE:
<221> NAME/KEY: MOD_RES
<222> LOCATION: (9)..(9)
<223> OTHER INFORMATION: Sar
```

```
<220> FEATURE:
<221> NAME/KEY: MOD_RES
<222> LOCATION: (10)..(10)
<223> OTHER INFORMATION: NMeLeu

<400> SEQUENCE: 168

Arg Phe Xaa Thr Gly Xaa Phe Gly Xaa Xaa Tyr Pro Cys
1               5                   10

<210> SEQ ID NO 169
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: ThienylAla
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 169

Arg Phe Xaa Thr Gly Xaa Phe Gly Xaa Xaa Tyr Pro Cys
1               5                   10

<210> SEQ ID NO 170
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: Dab
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 170

Arg Phe Xaa Thr Gly Xaa Phe Gly Xaa Xaa Tyr Pro Cys
1               5                   10

<210> SEQ ID NO 171
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: Orn
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 171

Arg Phe Xaa Thr Gly Xaa Phe Gly Xaa Xaa Tyr Pro Cys
1               5                   10

<210> SEQ ID NO 172
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 172

Arg Phe Xaa Thr Gly Lys Phe Gly Xaa Xaa Tyr Pro Cys
1               5                   10

<210> SEQ ID NO 173
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 173

Arg Phe Xaa Thr Gly Arg Phe Gly Xaa Xaa Tyr Pro Cys
1               5                   10

<210> SEQ ID NO 174
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 4GuanylPhe
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 174

Arg Phe Xaa Thr Gly Xaa Phe Gly Xaa Xaa Tyr Pro Cys
1               5                   10

<210> SEQ ID NO 175
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 4aminoPhe
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 175

Arg Phe Xaa Thr Gly Xaa Phe Gly Xaa Xaa Tyr Pro Cys
1               5                   10

<210> SEQ ID NO 176
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: His(Me)

<400> SEQUENCE: 176

Arg Phe Xaa Thr Gly Xaa Phe Gly Gly Leu Tyr Pro Cys
1               5                   10

<210> SEQ ID NO 177
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: His(Me)2

<400> SEQUENCE: 177

Arg Phe Xaa Thr Gly Xaa Phe Gly Gly Leu Tyr Pro Cys
1               5                   10

<210> SEQ ID NO 178
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: PropargylGly
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 178

Arg Phe Xaa Thr Gly Xaa Phe Gly Xaa Xaa Tyr Pro Cys
1               5                   10

<210> SEQ ID NO 179
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 2-PyrrolidinylAla
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 179

Arg Phe Xaa Thr Gly Xaa Phe Gly Xaa Xaa Tyr Pro Cys
1               5                   10
```

```
<210> SEQ ID NO 180
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 3-PiperdyalAla
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 180

Arg Phe Xaa Thr Gly Xaa Phe Gly Xaa Xaa Tyr Pro Cys
1               5                   10

<210> SEQ ID NO 181
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 4-PiperdylAla
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 181

Arg Phe Xaa Thr Gly Xaa Phe Gly Xaa Xaa Tyr Pro Cys
1               5                   10

<210> SEQ ID NO 182
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
```

```
<223> OTHER INFORMATION: NMeLeu

<400> SEQUENCE: 182

Arg Phe Xaa Thr Gly Phe Phe Gly Xaa Xaa Tyr Pro Cys
1               5                   10

<210> SEQ ID NO 183
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 183

Arg Phe Xaa Thr Gly Ala Phe Gly Xaa Xaa Tyr Pro Cys
1               5                   10

<210> SEQ ID NO 184
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 4-PyridylAla
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 184

Arg Phe Xaa Thr Gly Xaa Phe Gly Xaa Xaa Tyr Pro Cys
1               5                   10

<210> SEQ ID NO 185
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: Thz(Me)
```

```
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 185

Arg Phe Xaa Thr Gly Xaa Phe Gly Xaa Xaa Tyr Pro Cys
1               5                   10

<210> SEQ ID NO 186
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: triazolylAla
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 186

Arg Phe Xaa Thr Gly Xaa Phe Gly Xaa Xaa Tyr Pro Cys
1               5                   10

<210> SEQ ID NO 187
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Ala

<400> SEQUENCE: 187

Gln Arg Phe Cys Thr Gly His Phe Xaa Gly Leu Tyr Pro Cys Asn Gly
1               5                   10                  15
Pro

<210> SEQ ID NO 188
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Ala

<400> SEQUENCE: 188
```

```
Gln Arg Phe Cys Thr Gly His Phe Gly Xaa Leu Tyr Pro Cys Asn Gly
1               5                   10                  15

Pro

<210> SEQ ID NO 189
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(10)
<223> OTHER INFORMATION: D-Ala

<400> SEQUENCE: 189

Gln Arg Phe Cys Thr Gly His Phe Xaa Xaa Leu Tyr Pro Cys Asn Gly
1               5                   10                  15

Pro

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: betaAla

<400> SEQUENCE: 190

Gln Arg Phe Cys Gly His Phe Xaa Leu Tyr Pro Cys Asn Gly Pro
1               5                   10                  15

<210> SEQ ID NO 191
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Apa

<400> SEQUENCE: 191

Gln Arg Phe Cys Thr Gly His Phe Xaa Leu Tyr Pro Cys Asn Gly Pro
1               5                   10                  15

<210> SEQ ID NO 192
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen

<400> SEQUENCE: 192

Arg Phe Xaa Thr Gly His Phe Gly Gly Leu Tyr Pro Cys
1               5                   10
```

```
<210> SEQ ID NO 193
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 4-aminomethyl benzoic acid

<400> SEQUENCE: 193

Arg Phe Xaa Thr Gly His Phe Xaa Leu Tyr Pro Cys
1               5                   10

<210> SEQ ID NO 194
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: (3-aminomethyl) benzoic acid

<400> SEQUENCE: 194

Arg Phe Xaa Thr Gly His Phe Xaa Leu Tyr Pro Cys
1               5                   10

<210> SEQ ID NO 195
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 4-aminophenyl acetic acid

<400> SEQUENCE: 195

Arg Phe Xaa Thr Gly His Phe Xaa Leu Tyr Pro Cys
1               5                   10

<210> SEQ ID NO 196
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
```

<221> NAME/KEY: MOD_RES
<222> LOCATION: (8)..(8)
<223> OTHER INFORMATION: 3-aminophenyl acetic acid

<400> SEQUENCE: 196

Arg Phe Xaa Thr Gly His Phe Xaa Leu Tyr Pro Cys
1               5                   10

<210> SEQ ID NO 197
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3-amino-2-oxo-1-piperidine-acetic acid

<400> SEQUENCE: 197

Arg Phe Xaa Thr Gly His Phe Xaa Leu Tyr Pro Cys
1               5                   10

<210> SEQ ID NO 198
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3-amino-2-oxo-1-piperidine-acetic acid

<400> SEQUENCE: 198

Arg Phe Xaa Thr Gly His Phe Xaa Leu Tyr Pro Cys
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3(S)-amino-2-oxo-1-piperidine-acetic acid

<400> SEQUENCE: 199

Arg Phe Xaa Thr Gly His Phe Xaa Leu Tyr Pro Cys
1               5                   10

<210> SEQ ID NO 200
<211> LENGTH: 12
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3-amino-N-1-carboxymethyl-2,3,4,5-tetrahydro-
      1H-[1]-benzazepine-2-one

<400> SEQUENCE: 200

Arg Phe Xaa Thr Gly His Phe Xaa Leu Tyr Pro Cys
1               5                   10

<210> SEQ ID NO 201
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3-amino-N-1-carboxymethyl-2,3,4,5-tetrahydro-
      1H-[1]-benzazepine-2-one

<400> SEQUENCE: 201

Arg Phe Xaa Thr Gly His Phe Xaa Leu Tyr Pro Cys
1               5                   10

<210> SEQ ID NO 202
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(9)
<223> OTHER INFORMATION: 5,5-bicyclic dipeptide mimic

<400> SEQUENCE: 202

Arg Phe Xaa Thr Gly His Phe Xaa Xaa Leu Tyr Pro Cys
1               5                   10

<210> SEQ ID NO 203
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(9)
```

<223> OTHER INFORMATION: 5,5-bicyclic dipeptide mimic

<400> SEQUENCE: 203

Arg Phe Xaa Thr Gly His Phe Xaa Xaa Leu Tyr Pro Cys
1               5                   10

<210> SEQ ID NO 204
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(9)
<223> OTHER INFORMATION: 6,5-bicyclic dipeptide mimic

<400> SEQUENCE: 204

Arg Phe Xaa Thr Gly His Phe Xaa Xaa Leu Tyr Pro Cys
1               5                   10

<210> SEQ ID NO 205
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3(R)-amino-2-oxo-1-azepine acetic acid

<400> SEQUENCE: 205

Arg Phe Xaa Thr Gly His Phe Xaa Leu Tyr Pro Cys
1               5                   10

<210> SEQ ID NO 206
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3(R)-amino-2-oxo-1-pyrrolidine acetic acid

<400> SEQUENCE: 206

Arg Phe Xaa Thr Gly His Phe Xaa Leu Tyr Pro Cys
1               5                   10

<210> SEQ ID NO 207
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3(R)-amino-2-oxo-1-piperidine-acetic acid
<220> FEATURE:
<221> NAME/KEY: MOD_RES
<222> LOCATION: (9)..(9)
<223> OTHER INFORMATION: NMeLeu

<400> SEQUENCE: 207

Arg Phe Xaa Thr Gly His Phe Xaa Xaa Tyr Pro Cys
1               5                   10

<210> SEQ ID NO 208
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (4)..(4)
<223> OTHER INFORMATION: NMeAla
<220> FEATURE:
<221> NAME/KEY: MOD_RES
<222> LOCATION: (8)..(8)
<223> OTHER INFORMATION: 3(R)-3-amino-2-oxo-1-piperidine-acetic acid
<220> FEATURE:
<221> NAME/KEY: MOD_RES
<222> LOCATION: (9)..(9)
<223> OTHER INFORMATION: NMeLeu

<400> SEQUENCE: 208

Arg Phe Xaa Xaa Gly His Phe Xaa Xaa Tyr Pro Cys
1               5                   10

<210> SEQ ID NO 209
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3(R)-amino-2-oxo-1-azepine acetic acid
<220> FEATURE:
<221> NAME/KEY: MOD_RES
<222> LOCATION: (9)..(9)
<223> OTHER INFORMATION: NMeLeu

<400> SEQUENCE: 209

Arg Phe Xaa Thr Gly His Phe Xaa Xaa Tyr Pro Cys
1               5                   10

<210> SEQ ID NO 210
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Dab

<400> SEQUENCE: 210

Gln Arg Phe Asp Thr Gly His Phe Gly Gly Leu Tyr Pro Xaa Asn Gly
1               5                   10                  15

Pro

<210> SEQ ID NO 211
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gln Arg Phe Asp Thr Gly His Phe Gly Gly Leu Tyr Pro Lys Asn Gly
1               5                   10                  15

Pro

<210> SEQ ID NO 212
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab

<400> SEQUENCE: 212

Gln Arg Phe Xaa Thr Gly His Phe Gly Gly Leu Tyr Pro Glu Asn Gly
1               5                   10                  15

Pro

<210> SEQ ID NO 213
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gln Arg Phe Lys Thr Gly His Phe Gly Gly Leu Tyr Pro Glu Asn Gly
1               5                   10                  15

Pro

<210> SEQ ID NO 214
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214
```

Gln Arg Phe Glu Thr Gly His Phe Gly Gly Leu Tyr Pro Lys Asn Gly
1               5                   10                  15

Pro

<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Dab

<400> SEQUENCE: 215

Gln Arg Phe Glu Thr Gly His Phe Gly Gly Leu Tyr Pro Xaa Asn Gly
1               5                   10                  15

Pro

<210> SEQ ID NO 216
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Dap

<400> SEQUENCE: 216

Gln Arg Phe Glu Thr Gly His Phe Gly Gly Leu Tyr Pro Xaa Asn Gly
1               5                   10                  15

Pro

<210> SEQ ID NO 217
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Dap

<400> SEQUENCE: 217

Gln Arg Phe Asp Thr Gly His Phe Gly Gly Leu Tyr Pro Xaa Asn Gly
1               5                   10                  15

Pro

<210> SEQ ID NO 218
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gln Arg Phe Lys Thr Gly His Phe Gly Gly Leu Tyr Pro Asp Asn Gly
1               5                   10                  15

Pro

<210> SEQ ID NO 219
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dab

<400> SEQUENCE: 219

Gln Arg Phe Xaa Thr Gly His Phe Gly Gly Leu Tyr Pro Asp Asn Gly
1               5                   10                  15

Pro

<210> SEQ ID NO 220
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Orn

<400> SEQUENCE: 220

Gln Arg Phe Asp Thr Gly His Phe Gly Gly Leu Tyr Pro Xaa Asn Gly
1               5                   10                  15

Pro

<210> SEQ ID NO 221
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Orn

<400> SEQUENCE: 221

Gln Arg Phe Glu Thr Gly His Phe Gly Gly Leu Tyr Pro Xaa Asn Gly
1               5                   10                  15

Pro

<210> SEQ ID NO 222
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gln Arg Phe Asp Thr Gly His Phe Gly Gly Leu Tyr Lys Asn Gly Pro
1               5                   10                  15

<210> SEQ ID NO 223

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Ala

<400> SEQUENCE: 223

Gln Arg Phe Asp Thr Gly His Phe Gly Xaa Leu Tyr Pro Lys Asn Gly
1               5                   10                  15

Pro

<210> SEQ ID NO 224
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Ala

<400> SEQUENCE: 224

Gln Arg Phe Asp Thr Gly His Phe Xaa Gly Leu Tyr Pro Lys Asn Gly
1               5                   10                  15

Pro

<210> SEQ ID NO 225
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Asp Thr Gly His Phe Gly Gly Leu Tyr Pro Lys Asn Gly Pro
1               5                   10

<210> SEQ ID NO 226
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Phe Asp Thr Gly His Phe Gly Gly Leu Tyr Pro Lys Asn Gly Pro
1               5                   10                  15

<210> SEQ ID NO 227
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Arg Phe Asp Thr Gly His Phe Gly Gly Leu Tyr Pro Lys Asn Gly Pro
1               5                   10                  15
```

```
<210> SEQ ID NO 228
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gln Arg Phe Asp Thr Gly His Phe Gly Gly Leu Tyr Pro Lys Asn Gly
1               5                   10                  15

Pro

<210> SEQ ID NO 229
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gln Arg Phe Asp Thr Gly His Phe Gly Gly Leu Tyr Pro Lys Asn
1               5                   10                  15

<210> SEQ ID NO 230
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dap

<400> SEQUENCE: 230

Gln Arg Phe Xaa Thr Gly His Phe Gly Gly Leu Tyr Pro Asp Asn Gly
1               5                   10                  15

Pro

<210> SEQ ID NO 231
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dap

<400> SEQUENCE: 231

Gln Arg Phe Xaa Thr Gly His Phe Gly Gly Leu Tyr Pro Glu Asn Gly
1               5                   10                  15

Pro

<210> SEQ ID NO 232
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)..(4)
<223> OTHER INFORMATION: Orn

<400> SEQUENCE: 232

Gln Arg Phe Xaa Thr Gly His Phe Gly Gly Leu Tyr Pro Asp Asn Gly
1               5                   10                  15

Pro

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Orn

<400> SEQUENCE: 233

Gln Arg Phe Xaa Thr Gly His Phe Gly Gly Leu Tyr Pro Glu Asn Gly
1               5                   10                  15

Pro

<210> SEQ ID NO 234
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Arg Phe Asp Thr Gly His Phe Gly Gly Leu Tyr Pro Lys
1               5                   10

<210> SEQ ID NO 235
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gln Arg Phe Asp Thr Gly His Phe Gly Gly Leu Tyr Pro Lys
1               5                   10

<210> SEQ ID NO 236
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 236

Gln Arg Phe Asp Thr Gly His Phe Gly Xaa Leu Tyr Pro Lys Asn Gly
1               5                   10                  15

Pro
```

<210> SEQ ID NO 237
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gln Arg Phe Ser Thr Gly His Phe Gly Gly Leu Tyr Pro Ser Asn Gly
1               5                   10                  15

Pro

<210> SEQ ID NO 238
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(10)
<223> OTHER INFORMATION: D-Pro

<400> SEQUENCE: 238

Gln Arg Phe Val Thr Gly His Phe Xaa Xaa Leu Tyr Pro Ala Asn Gly
1               5                   10                  15

Pro

<210> SEQ ID NO 239
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 239

Gln Arg Phe Val Thr Gly His Phe Gly Xaa Leu Tyr Pro Ala Asn Gly
1               5                   10                  15

Pro

<210> SEQ ID NO 240
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Pro

<400> SEQUENCE: 240

Gln Arg Phe Val Thr Gly His Phe Xaa Gly Leu Tyr Pro Ala Asn Gly
1               5                   10                  15

Pro

<210> SEQ ID NO 241

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 241

Gln Arg Phe Leu Thr Gly His Phe Gly Xaa Leu Tyr Pro Ala Asn Gly
1               5                   10                  15

Pro

<210> SEQ ID NO 242
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 242

Gln Arg Phe Ile Thr Gly His Phe Gly Xaa Leu Tyr Pro Ala Asn Gly
1               5                   10                  15

Pro

<210> SEQ ID NO 243
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 243

Gln Arg Phe Phe Thr Gly His Phe Gly Xaa Leu Tyr Pro Ala Asn Gly
1               5                   10                  15

Pro

<210> SEQ ID NO 244
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 244

Gln Arg Phe Tyr Thr Gly His Phe Gly Xaa Leu Tyr Pro Ala Asn Gly
1               5                   10                  15

Pro
```

<210> SEQ ID NO 245
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 245

Gln Arg Phe Trp Thr Gly His Phe Gly Xaa Leu Tyr Pro Ala Asn Gly
1               5                   10                  15

Pro

<210> SEQ ID NO 246
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 246

Gln Arg Phe Val Thr Gly His Phe Gly Xaa Leu Tyr Pro Val Asn Gly
1               5                   10                  15

Pro

<210> SEQ ID NO 247
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 247

Gln Arg Phe Val Thr Gly His Phe Gly Xaa Leu Tyr Pro Leu Asn Gly
1               5                   10                  15

Pro

<210> SEQ ID NO 248
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 248

Gln Arg Phe Val Thr Gly His Phe Gly Xaa Leu Tyr Pro Ile Asn Gly
1               5                   10                  15

Pro

```
<210> SEQ ID NO 249
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 249

Gln Arg Phe Val Thr Gly His Phe Gly Xaa Leu Tyr Pro Phe Asn Gly
1               5                   10                  15

Pro

<210> SEQ ID NO 250
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 250

Gln Arg Phe Val Thr Gly His Phe Gly Xaa Leu Tyr Pro Tyr Asn Gly
1               5                   10                  15

Pro

<210> SEQ ID NO 251
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 251

Gln Arg Phe Val Thr Gly His Phe Gly Xaa Leu Tyr Pro Trp Asn Gly
1               5                   10                  15

Pro

<210> SEQ ID NO 252
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 252

Gln Arg Phe Val Thr Gly His Phe Gly Xaa Val Tyr Pro Ala Asn Gly
1               5                   10                  15

Pro
```

<210> SEQ ID NO 253
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 253

Gln Arg Phe Val Thr Gly His Phe Gly Xaa Ile Tyr Pro Ala Asn Gly
1               5                   10                  15

Pro

<210> SEQ ID NO 254
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 254

Gln Arg Phe Val Thr Gly His Phe Gly Xaa Phe Tyr Pro Ala Asn Gly
1               5                   10                  15

Pro

<210> SEQ ID NO 255
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 255

Gln Arg Phe Val Thr Gly His Phe Gly Xaa Tyr Tyr Pro Ala Asn Gly
1               5                   10                  15

Pro

<210> SEQ ID NO 256
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 256

Gln Arg Phe Val Thr Gly His Phe Gly Xaa Trp Tyr Pro Ala Asn Gly
1               5                   10                  15

Pro

```
<210> SEQ ID NO 257
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 257

Gln Arg Phe Val Thr Gly His Phe Gly Xaa Trp Tyr Pro Ile Asn Gly
1               5                   10                  15

Pro

<210> SEQ ID NO 258
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Pro

<400> SEQUENCE: 258

Arg Phe Val Thr Gly His Phe Gly Xaa Trp Tyr Pro
1               5                   10

<210> SEQ ID NO 259
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Pro

<400> SEQUENCE: 259

Arg Phe Val Thr Gly His Phe Gly Xaa Trp Tyr Pro Ala Asn Gly Pro
1               5                   10                  15

<210> SEQ ID NO 260
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: D-Pro

<400> SEQUENCE: 260

Phe Val Thr Gly His Phe Gly Xaa Trp Tyr Pro Ala
1               5                   10

<210> SEQ ID NO 261
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Pro

<400> SEQUENCE: 261

Val Thr Gly His Phe Gly Xaa Trp Tyr Pro Ala
1               5                   10

<210> SEQ ID NO 262
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 262

Arg Phe Val Thr Gly His Phe Gly Xaa Xaa Tyr Pro Ala
1               5                   10

<210> SEQ ID NO 263
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Pro

<400> SEQUENCE: 263

Arg Phe Val Thr Gly His Phe Gly Xaa Trp Tyr Pro Ala
1               5                   10

<210> SEQ ID NO 264
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 3-amino-2-oxo-1-piperidine-acetic acid

<400> SEQUENCE: 264

Arg Phe Val Thr Gly His Phe Xaa Leu Tyr Pro Ala
1               5                   10

<210> SEQ ID NO 265
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 3-amino-2-oxo-1-piperidine-acetic acid

<400> SEQUENCE: 265

Arg Phe Val Thr Gly His Phe Xaa Leu Tyr Pro Ala
1               5                   10

<210> SEQ ID NO 266
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 3-amino-N-1-carboxymethyl-2,3,4,5-tetrahydro-
      1H-[1]-benzazepine-2-one

<400> SEQUENCE: 266

Arg Phe Val Thr Gly His Phe Xaa Leu Tyr Pro Ala
1               5                   10

<210> SEQ ID NO 267
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 3-amino-N-1-carboxymethyl-2,3,4,5-tetrahydro-
      1H-[1]-benzazepine-2-one

<400> SEQUENCE: 267

Arg Phe Val Thr Gly His Phe Xaa Leu Tyr Pro Ala
1               5                   10

<210> SEQ ID NO 268
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 3-aminophenyl acetic acid

<400> SEQUENCE: 268

Arg Phe Val Thr Gly His Phe Xaa Leu Tyr Pro Ala
1               5                   10

<210> SEQ ID NO 269
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
```

```
<223> OTHER INFORMATION: 3-amino-2-oxo-1-piperidine-acetic acid

<400> SEQUENCE: 269

Gln Arg Phe Val Thr Gly His Phe Xaa Trp Tyr Pro Ile Asn Gly Pro
1               5                   10                  15

<210> SEQ ID NO 270
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: 5,5-bicyclic dipeptide mimic

<400> SEQUENCE: 270

Arg Phe Val Thr Gly His Phe Xaa Xaa Leu Tyr Pro Ala
1               5                   10

<210> SEQ ID NO 271
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: 6,5-bicyclic dipeptide mimic

<400> SEQUENCE: 271

Arg Phe Val Thr Gly His Phe Xaa Xaa Leu Tyr Pro Ala
1               5                   10

<210> SEQ ID NO 272
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: 3(R)-amino-2-oxo-1-azepine acetic acid

<400> SEQUENCE: 272

Arg Phe Val Thr Gly His Phe Xaa Leu Tyr Pro Ala
1               5                   10

<210> SEQ ID NO 273
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Arg Phe Cys Thr Gly His Phe Gly Gly Leu Tyr Pro Cys
1               5                   10

<210> SEQ ID NO 274
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen
<220> FEATURE:
<221> NAME/KEY: MOD_RES
<222> LOCATION: (10)..(10)
<223> OTHER INFORMATION: D-Pro

<400> SEQUENCE: 274

Gln Arg Phe Xaa Thr Gly His Phe Gly Xaa Leu Tyr Pro Cys Asn Gly
1               5                   10                  15

Pro

<210> SEQ ID NO 275
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3(r)-3-amino-1-carboxymethyl-valerolactam
<220> FEATURE:
<221> NAME/KEY: MOD_RES
<222> LOCATION: (9)..(9)
<223> OTHER INFORMATION: NMeLeu

<400> SEQUENCE: 275

Arg Phe Xaa Thr Gly His Phe Xaa Xaa Tyr Pro Cys
1               5                   10

<210> SEQ ID NO 276
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (4)..(4)
<223> OTHER INFORMATION: NMeAla
<220> FEATURE:
<221> NAME/KEY: MOD_RES
<222> LOCATION: (8)..(8)
<223> OTHER INFORMATION: 3(r)-3-amino-1-carboxymethyl-valerolactam
<220> FEATURE:
<221> NAME/KEY: MOD_RES
<222> LOCATION: (9)..(9)
<223> OTHER INFORMATION: NMeLeu

<400> SEQUENCE: 276

Arg Phe Xaa Xaa Gly His Phe Xaa Xaa Tyr Pro Cys
1               5                   10

<210> SEQ ID NO 277
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 277

Arg Phe Xaa Thr Gly His Phe Gly Xaa Xaa Tyr Pro Cys
1               5                   10

<210> SEQ ID NO 278
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 278

Arg Phe Xaa Thr Gly His Phe Gly Xaa Xaa Tyr Pro Cys
1               5                   10

<210> SEQ ID NO 279
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 279

Arg Phe Xaa Thr Gly His Phe Gly Xaa Xaa Tyr Pro Cys
1               5                   10

<210> SEQ ID NO 280
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 280

Arg Phe Xaa Thr Gly His Phe Gly Xaa Xaa Tyr Pro Cys
1               5                   10

<210> SEQ ID NO 281
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (6)..(6)
<223> OTHER INFORMATION: 4GuPhe
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 281

Arg Phe Xaa Thr Gly Xaa Phe Gly Xaa Xaa Tyr Pro Cys
1               5                   10

<210> SEQ ID NO 282
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 282

Arg Phe Xaa Thr Gly His Phe Gly Xaa Xaa Tyr Pro Cys Gly
1               5                   10
```

```
<210> SEQ ID NO 283
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 283

Arg Phe Xaa Thr Gly His Phe Gly Xaa Xaa Tyr Pro Cys Gly
1               5                   10

<210> SEQ ID NO 284
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 284

Arg Phe Asp Thr Gly His Phe Gly Xaa Xaa Tyr Pro Lys
1               5                   10

<210> SEQ ID NO 285
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Gln Arg Phe Asp Thr Gly His Phe Gly Gly Leu Tyr Pro Lys Asn Gly
1               5                   10                  15

Pro

<210> SEQ ID NO 286
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Gln Arg Phe Asp Thr Gly His Phe Gly Gly Leu Tyr Pro Lys Asn Gly
1               5                   10                  15

Pro
```

<210> SEQ ID NO 287
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Gln Arg Phe Asp Thr Gly His Phe Gly Gly Leu Tyr Pro Lys Asn Gly
1               5                   10                  15

Pro

<210> SEQ ID NO 288
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Gln Arg Phe Asp Thr Gly His Phe Gly Gly Leu Tyr Pro Lys Asn Gly
1               5                   10                  15

Pro

<210> SEQ ID NO 289
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Gln Arg Phe Asp Thr Gly His Phe Gly Gly Leu Tyr Pro Lys Asn Gly
1               5                   10                  15

Pro

<210> SEQ ID NO 290
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen

<400> SEQUENCE: 290

Arg Phe Xaa Thr Gly His Phe Gly Gly Leu Tyr Pro Cys
1               5                   10

<210> SEQ ID NO 291
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 291

Gln Arg Phe Xaa Thr Gly His Phe Gly Gly Leu Tyr Pro Cys Asn Gly
1               5                   10                  15

Pro

<210> SEQ ID NO 292
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D-Pro

<400> SEQUENCE: 292

Gln Arg Phe Asp Thr Gly His Phe Gly Xaa Leu Tyr Pro Lys Asn Gly
1               5                   10                  15

Pro

<210> SEQ ID NO 293
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Ala
<220> FEATURE:
<221> NAME/KEY: MOD_RES
<222> LOCATION: (11)..(11)
<223> OTHER INFORMATION: NMeLeu

<400> SEQUENCE: 293

Gln Arg Phe Asp Thr Gly His Phe Xaa Gly Xaa Tyr Pro Lys Asn Gly
1               5                   10                  15

Pro

<210> SEQ ID NO 294
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 294

Phe Phe Xaa Thr Gly His Phe Gly Xaa Xaa Tyr Pro Cys
1               5                   10

```
<210> SEQ ID NO 295
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Pen

<400> SEQUENCE: 295

Gln Arg Phe Xaa Thr Gly His Phe Gly Gly Leu Tyr Pro Cys Asn Gly
1               5                   10                  15

Pro

<210> SEQ ID NO 296
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 296

Arg Phe Xaa Thr Gly His Phe Gly Xaa Xaa Tyr Pro Cys
1               5                   10

<210> SEQ ID NO 297
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 297

Arg Phe Xaa Thr Gly His Phe Gly Xaa Xaa Tyr Pro Cys
1               5                   10

<210> SEQ ID NO 298
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 298

Arg Phe Xaa Thr Gly His Phe Gly Xaa Xaa Tyr Pro Cys
1               5                   10

<210> SEQ ID NO 299
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 299

Arg Phe Xaa Thr Gly His Phe Gly Xaa Xaa Tyr Pro Cys
1               5                   10

<210> SEQ ID NO 300
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 300

Arg Phe Xaa Thr Gly His Phe Gly Xaa Xaa Tyr Pro Cys
1               5                   10

<210> SEQ ID NO 301
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

-continued

```
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 301

Arg Phe Xaa Thr Gly His Phe Gly Xaa Xaa Tyr Pro Cys
1               5                   10

<210> SEQ ID NO 302
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 302

Arg Phe Xaa Thr Gly His Phe Gly Xaa Xaa Tyr Pro Cys
1               5                   10

<210> SEQ ID NO 303
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 303

Arg Phe Xaa Thr Gly His Phe Gly Xaa Xaa Tyr Pro Cys
1               5                   10

<210> SEQ ID NO 304
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 304

Arg Phe Xaa Thr Gly His Phe Gly Xaa Xaa Tyr Pro Cys Gly
1               5                   10

<210> SEQ ID NO 305
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 305

Arg Phe Xaa Thr Gly His Phe Gly Xaa Xaa Tyr Pro Cys Gly Gly
1               5                   10                  15

<210> SEQ ID NO 306
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (8)..(8)
<223> OTHER INFORMATION: 3(R)-3-amino-2-oxo-1-piperidine-acetic acid
<220> FEATURE:
<221> NAME/KEY: MOD_RES
<222> LOCATION: (9)..(9)
<223> OTHER INFORMATION: NMeLeu

<400> SEQUENCE: 306

Arg Phe Xaa Thr Gly His Phe Xaa Xaa Tyr Pro Cys
1               5                   10

<210> SEQ ID NO 307
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 307

Arg Phe Xaa Thr Gly His Phe Gly Xaa Xaa Tyr Pro Cys
1               5                   10

<210> SEQ ID NO 308
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Arg Phe Cys Thr Gly His Phe Gly Gly Leu Tyr Pro Cys
1               5                   10

<210> SEQ ID NO 309
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu

<400> SEQUENCE: 309

Arg Phe Xaa Thr Gly His Phe Gly Xaa Xaa Tyr Pro Cys Gly Gly Lys
1               5                   10                  15

<210> SEQ ID NO 310
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pen
<220> FEATURE:
<221> NAME/KEY: MOD_RES
<222> LOCATION: (9)..(9)
<223> OTHER INFORMATION: Sar
<220> FEATURE:
<221> NAME/KEY: MOD_RES
<222> LOCATION: (10)..(10)
<223> OTHER INFORMATION: NMeLeu
```

-continued

```
<400> SEQUENCE: 310

Arg Phe Xaa Thr Gly His Phe Gly Xaa Xaa Tyr Pro Cys Gly Gly Lys
1               5                   10                  15
```

IMMUNOMODULATORY PEPTIDES

This application is a national stage entry under 35 U.S.C. §371 of International Application No. PCT/US2008/071960, filed Aug. 1, 2008, which claims priority to U.S. Provisional Application No. 60/954,968, filed Aug. 9, 2007, both of which are incorporated herein by reference in their entirety.

IgG plays a critical role in mediating protection against pathogens and in mediating allergic and inflammatory responses that hasten recruitment of immune system components to the tissues, mucosae, and dermal surfaces. Junghans, *Immunol. Res.* 16(1):29 (1997). However, IgG also plays a key role in a variety of autoimmune diseases.

SEQUENCE LISTING

The instant application contains a Sequence Listing which has been submitted in ASCII format via EFS-Web and is hereby incorporated by reference in its entirety. Said ASCII copy, created on May 23, 2012, is named 89452734.txt and is 131,354 bytes in size.

The serum half-life of IgG is longer than the serum half-lives of other plasma proteins. For example, the serum half-life of IgG is 5 to 7 days in mice and 22 to 23 days in humans. Roopenian et al., *J. Immunol.* 170:3528 (2003); Junghans and Anderson, *Proc. Natl. Acad. Sci. USA* 93:5512 (1996). That extended serum half-life is at least partly due to the neonatal Fc receptor, FcRn, which binds to the Fc portion of pinocytosed IgG (in both adults and neonates) to protect it from lysosomal degradation. The pinocytosed IgG is then recycled back to the extracellular compartment. See, e.g., Junghans and Anderson, *Proc. Natl. Acad. Sci. USA* 93:5512 (1996), Roopenian et al., *J. Immunol.* 170:3528 (2003). Indeed, the serum half-life of IgG is reduced in knockout mouse models that do not express at least part of the genes encoding $\beta_2$m and FcRn heavy chain. See WO 02/43658 and Junghans and Anderson, *Proc. Natl. Acad. Sci. USA* 93:5512 (1996).

When the concentration of IgG reaches a level that exceeds available FcRn, unbound IgG is not protected from degradative mechanisms and consequently has a shorter serum half-life. See, e.g., Brambell et al., *Nature* 203:1352 (1964). Analogously, IgG serum half-life is reduced when IgG binding to FcRn is inhibited, thereby preventing IgG recycling. Therefore, agents that inhibit or antagonize the binding of IgG to FcRn may be used to regulating, treating or preventing disorders characterized by the presence of inappropriately expressed IgG antibodies (such as, e.g., autoimmune and inflammatory diseases and disorders). For example, antibodies capable of inhibiting the binding of FcRn with IgG have been generated using a FcRn heavy chain knockout mouse line (WO 02/43658). In another example, peptides have been identified that bind to FcRn complexes. Kolonin et al., *Proc. Natl. Acad. Sci. USA* 99(20):13055-60 (2002); U.S. Pat. No. 6,212,022. The contents of U.S. application Ser. No. 11/676,148, filed Feb. 16, 2007, and U.S. Provisional Application Nos. 60/774,853, filed Feb. 17, 2006, and 60/805,634, filed Jun. 23, 2006, describing further such peptides, their synthesis, and their uses are herein incorporated by reference in their entirety. However, at this time additional agents are needed to regulate, treat, or prevent conditions, diseases, and disorders characterized by immune reactions.

Accordingly, peptides which specifically bind to FcRn and inhibit IgG Fc from binding to FcRn, thereby preventing IgG from recycling by preventing FcRn from functioning in its role of protecting IgG from degradation by the lysosomes are disclosed. In exemplary embodiments, the peptides bind to FcRn and inhibit the IgG1, IgG2, IgG3, or IgG4 subclasses of IgG from binding to FcRn.

Peptides of the invention may exist as monomers or alternatively, as a multimers, such as, e.g., dimers, trimers, or tetramers. In some embodiments, the peptides of the invention may be more susceptible to pinocytosis, which enables more rapid binding of the peptide and consequently, less excretion by the kidney.

In some embodiments, the invention provides pharmaceutical compositions comprising a therapeutically effective amount of one or more peptides of the invention.

In other embodiments, the invention provides methods of regulating a disease state comprising contacting a cell with the peptide of a therapeutically effective amount of one or more peptides of the invention. Further embodiments include methods of regulating IgG levels in the serum of a subject comprising administering to the subject a therapeutically effective amount of a composition comprising one or more peptides of the invention capable of binding to and inhibiting the FcRn from binding to the Fc portion of an IgG molecule. In certain embodiments, the methods of the invention may be employed to reduce the half-life of soluble IgG in the serum of a subject. In some embodiments, the result of administering a composition of the invention is that the half-life of soluble IgG in the serum of the subject is reduced compared to the half-life of IgG in the serum of the subject prior to administration of the peptide.

In other embodiments, the invention provides methods for inhibiting binding of the Fc portion of a human IgG to FcRn to effect a decrease in the serum concentration of IgG as compared to the serum concentration of IgG before treatment. The method of decreasing serum concentration of IgG comprises administering to the subject a therapeutically effective amount of a composition comprising one or more peptides of the invention that inhibit binding of the Fc portion of an IgG molecule to FcRn. In some embodiments, the decrease in the serum concentration of human IgG is at least 5%, such as a decrease of at least 15%, or a decrease in the serum concentration of human IgG of at least 25%.

Some embodiments of the invention provide methods of treating a subject suffering from a disease characterised by increased or inappropriate expression of IgG, such as, e.g., an an autoimmune disease, an inflammatory disease, or an immune system cancer, comprising administering to the subject a therapeutically effective amount of a composition comprising one or more peptides of the invention capable of preventing the FcRn from binding to the Fc portion of an IgG molecule. In some embodiments, methods of the invention may be used to prevent, treat, or regulate an immune response to a therapeutic protein or a gene therapy vector.

In other embodiments, methods of detecting FcRn are provided, comprising labeling a peptide described herein with at least one detectable label chosen from, e.g., a radioisotope, an enzyme (e.g., an enzyme that catalyzes a reaction producing a detectable, including, e.g., a colored, luminescent, or fluorescent, product), a fluorophore, a chromophore, a chemiluminescent compound, a magnetic particle, a microsphere, a nanosphere, biotin, streptavidin, and digoxin.

Other embodiments of the invention include methods of purifying FcRn, comprising immobilizing a peptide described herein to a solid support, contacting a solution containing FcRn with the immobilized peptide on a solid support; and purifying FcRn by separating the solution from said solid support.

Additional embodiments, objects, and advantages of the invention are set forth in part in the description which follows and, in part, will be obvious from the description, or may be learned by practice of the invention. These embodiments, objects, and advantages of the invention may be realized and attained by means of the elements and combinations particularly pointed out in the appended claims.

It is to be understood that both the foregoing general description and the following detailed description are only exemplary and explanatory and are not restrictive of the invention as claimed.

BRIEF DESCRIPTION OF THE DRAWINGS

FIG. 16 is a table comparing the in vitro and in vivo activity of various peptides using the IgG competition ELISA assay as described in Example 4 and the human IgG catabolism of Example 18.

I. DEFINITIONS

Figure 1:
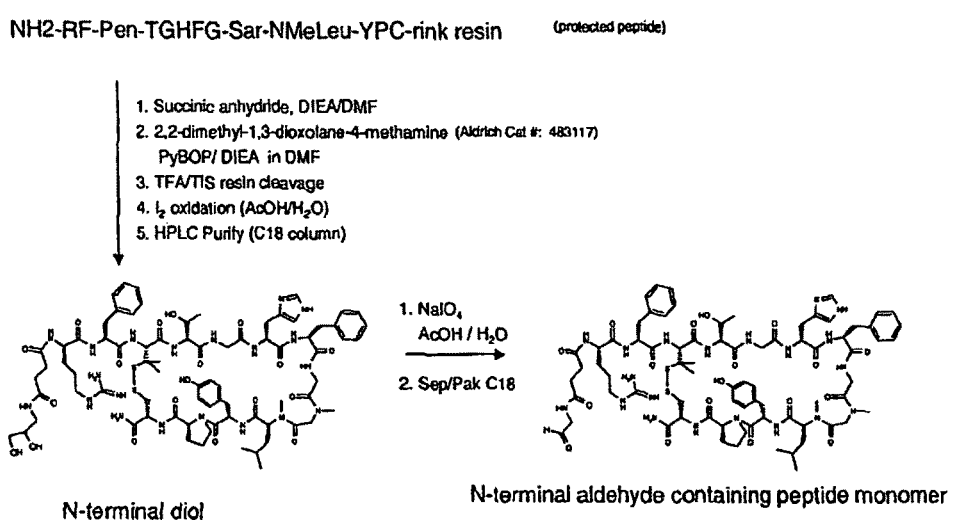
FIG. 1 shows an overview of the synthesis of an illustrative N-terminal aldehyde peptide monomer (SEQ ID NO: 60) as described in Example 12.

The term "amino acid," as used herein, encompasses encoded and non-encoded amino acids. Standard 1- and 3-letter abbreviations are used herein for the encoded amino acids (alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine).

Non-encoded amino acids include, e.g., α-amino acids, β-amino acids, γ-amino acids, δ-amino acids, and ω-amino acids, and may have R or S chirality at any chiral atom. Non-encoded amino acids include isomers of the encoded amino acids such as, e.g., stereoisomers (including, e.g., D-amino acids and allo-amino acids such as, e.g., allo-threonine and allo-isoleucine) and structural isomers (including, e.g., β-alanine) of the encoded amino acids. Lower case single-letter codes are used herein to indicate stereoisomers of the encoded amino acids having D-chirality (e.g., a=D-alanine, y=D-tyrosine). Non-encoded amino acids also include N-methylated amino acids. Conventional 3-letter abbreviations are used herein for certain common non-encoded amino acids (e.g., Aib=aminoisobutyric acid, Apa=5-aminopentanoic acid, Dab=1,3-diaminobutyric acid, Dap=1,2-diaminopropionic acid, Orn=ornithine, Pen=penicillamine, Sar=sarcosine). In general, where no specific configuration is indicated for an α-amino acid, one skilled in the art would understand that amino acid to be an L-amino acid. However, in particular embodiments, non-encoded amino acids may also be in the form of racemic, non-racemic, and diastereomeric mixtures.

Non-encoded amino acids are well known in the peptide art and include, e.g., N-acetylserine, allo-isoleucine, allo-threonine, β-alanine (3-aminopropionic acid), α-aminoadipic acid, 2-aminobutanoic acid, 4-aminobutanoic acid, 3-amino-1-carboxymethylvalerolactam, 1-aminocyclopentanecarboxylic acid, 6-aminohexanoic acid, 2-aminoheptanedioic acid, 7-aminoheptanoic acid, 2-aminoisobutyric acid, aminomethylpyrrole carboxylic acid, 8-amino-3,6-dioxa-octanoic acid, aminopiperidinecarboxylic acid, aminoserine, aminotetrahydropyran-4-carboxylic acid, azetidine carboxylic acid, benzothiazolylalanine, butylglycine, carnitine, 4-chlorophenylalanine, citrulline, cyclohexylalanine, cyclohexylstatine, 2,4-diaminobutanoic acid, 2,3-diaminopropionic acid, dihydroxyphenylalanine, dimethylthiazolidine carboxylic acid, 4-guanyl-phenylalanine, homoarginine, homocitrulline, homocysteine, homophenylalanine, homoproline, homoserine, 4-hydrazinobenzoic acid, 4-hydroxyproline, isonipecotic acid, methanoproline, norleucine, norvaline, ornithine, p-aminobenzoic acid, penicillamine, phenylglycine, O-phosphoserine, piperidinylalanine, piperidinylglycine, pyrrolidinylalanine, sarcosine, statin, tetrahydropyranglycine, thienylalanine, ε-N,N,N-trimethyllysine.

An "analog" of an amino acid is a molecule that is not an amino acid, but that resembles an amino acid with regard to at least one property such as, e.g., size, charge, hydrophilicity, hydrophobicity, polarity, hydrogen bonding capability, or rigidity. For example, lactic acid may be an amino acid analog. Similarly, an analog of a dipeptide is a molecule that is not a dipeptide, but that resembles a dipeptide with regard to at least one property such as, e.g., size, charge, hydrophilicity, hydrophobicity, polarity, hydrogen bonding capability, or rigidity. Further, a peptide analog is a molecule that is not a peptide but that resembles a peptide with regard to at least one property such as, e.g., size, charge, hydrophilicity, hydrophobicity, polarity, hydrogen bonding capability, or rigidity. In some embodiments, a dipeptide analog or peptide analog may differ from a dipeptide or peptide in that one or more peptide linkages are replaced by a linkage selected from, e.g., —CH₂NH—, —CH₂S—, —CH₂—CH₂—, —CH=CH-(cis and trans), —C(O)CH₂—, —CH(OH)CH₂—, or —CH₂SO—, by methods well known in the art. See, e.g., Fauchere, *J. Adv. Drug Res.* 15:29 (1986); Evans et al., *J. Med. Chem.* 30:1229 (1987). Dipeptide analogs also include, e.g., β-turn analogs. See, e.g., Friedinger, *J. Med. Chem.* 46:5553-5566 (2003), and Hanessian, *Tetrahedron* 53:12789-12854 (1997).

Nonlimiting examples of dipeptide analogs include, e.g., β-alanine, 4-aminobutanoic acid, 5-aminobutanoic acid, 3-(aminomethyl)benzoic acid, 4-(aminomethylbenzoic acid), 3-(aminophenyl)acetic acid, 4-(aminophenyl)acetic acid, and:

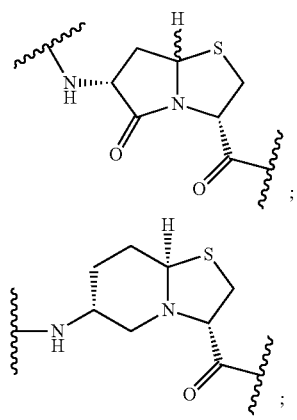

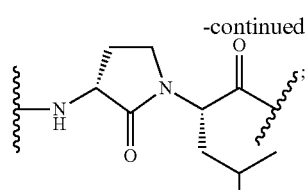

(D,L-Friedinger's lactam)

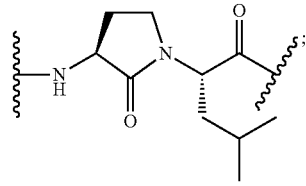

(L,L-Friedinger's lactam)

3(S)-amino-2-oxo-1-piperidine-acetic acid and 3(R)-3-amino-2-oxo-1-piperidine-acetic acid;
3(S)-amino-2-oxo-1-azepine acetic acid and 3(R)-3-amino-2-oxo-1-azepine acetic acid;
3(S)-amino-2-oxo-1-pyrrolidine acetic acid and 3(R)-3-amino-2-oxo-1-pyrrolidine acetic acid; and
3-amino-N-1-carboxymethyl-2,3,4,5-tetrahydro-1H-[1]-benzazepine-2-one.

An amino acid sequence that is "substantially identical" to a given sequence may be, e.g., at least 70%, 75%, 80%, 85%, 90%, 95%, 97%, 98%, or 99% identical to the given sequence. A substantially identical sequence may vary from the given sequence by truncation, deletion, substitution, addition, or modification of one or more amino acids, including, e.g., replacing one or more amino acids with one or more non-encoded amino acid(s) (such as, e.g., D-amino acids or N-methylated amino acids) or amino acid analogs. Alternatively, a substantially identical sequence may differ from a given sequence only by conservative amino acid substitutions.

A conservative substitution is a substitution in which a first amino acid is replaced by a second amino acid that approximates at least one property of the first amino acid, such as, e.g., size, charge, hydrophilicity, hydrophobicity, polarity, hydrogen bonding capability, or rigidity. Conservative substitutions encompass both encoded and non-encoded amino acids, as well as amino acid analogs.

For example, in some embodiments, alanine may be conservatively substituted by another hydrophobic amino acid such as, e.g., methionine, valine, leucine, or isoleucine, or by an analog of the any of the above-mentioned amino acids. In other embodiments, alanine may be conservatively substituted by an amino acid that is approximately isosteric such as, e.g., β-alanine, ethylglycine, α-aminoisobutryic acid, or D-alanine, or by an analog of the any of the above-mentioned amino acids. In some embodiments, cysteine may be conservatively substituted by another thiol-containing amino acid such as, e.g., homocysteine, D-cysteine, or penicillamine, or by an analog of the any of the above-mentioned amino acids. In other embodiments, cysteine may be conservatively substituted by an approximately isosteric amino acid such as, e.g., serine, threonine, or 2,3-diaminopropionic acid, or by an analog of the any of the above-mentioned amino acids. In other embodiments, phenylalanine may be conservatively substituted by, e.g., 3-fluorophenylalanine, 4-methylphenylalanine, phenylglycine, 1-naphthylalanine, and 3,3-diphenylalanine, 4-aminophenylalanine, pentafluorophenylalanine, 2-pyridylalanine, 3-pyridylalanine, 4-nitrophenylalanine, 2-pyrrolidinylalanine, 3-piperidylalanine, or 4-piperidylalanine, or by an analog of the any of the above-mentioned amino acids. As another example, histidine may be conservatively substituted by a basic amino acid such as, e.g., lysine, ornithine, 2,4-diaminobutyric acid, 2,3-diaminopropionic acid, arginine, or guanylalanine, or by an analog of the any of the above-mentioned amino acids. In other embodiments, histidine may be conservatively substituted by an aromatic amino acid such as, e.g., thienylalanine; tyrosine, tryptophan, or phenylalanine, or by an analog of the any of the above-mentioned amino acids. In yet other embodiments, histidine may be conservatively substituted by a basic, aromatic amino acid such as, e.g., 1-methylhistidine, 2-pyridylalanine, 3-pyridylalanine, 4-pyridylalanine, 4-aminophenylalanine, 4-guanylphenylalanine, thiazolylalanine, and analogs thereof.

In certain embodiments, a conservative substitution may be a substitution that replaces a first amino acid with a second amino acid having a similar hydropathic index, such as a value that varies by, e.g., ±0.5, ±1, or ±2. In other embodiments, a conservative substitution may be a substitution that replaces a first amino acid with a second amino acid having a similar hydrophilicity value, such as a value that varies by, e.g., ±0.5, ±1, or ±2.

In some embodiments, non-conservative substitutions may be introduced. A non-conservative substitution may be, e.g., a substitution that replaces a charged amino acid with a neutral amino acid; a substitution that replaces a basic amino acid with an acidic amino acid; a substitution that replaces a polar amino acid with a nonpolar amino acid; a substitution that replaces a hydrophilic amino acid with a hydrophobic amino acid; a substitution that replaces a an amino acid with a sterically dissimilar amino acid; or an amino acid with differing hydrogen bonding capabilities. Non-conservative substitutions may be made where appropriate. For example, a skilled artisan may be able to identify one or more amino acids of a peptide that may be non-conservatively substituted without significant alteration of the biological activities (such as, e.g., FcRn binding affinity or reduction of IgG concentration in vivo) or structure of the peptide. See, e.g., Example 7.

II. PEPTIDES DERIVATIZED WITH A HYDROPHILIC POLYMER

In general, the disclosure provides peptides derivatized with a hydrophilic polymer. For example, any of the peptides disclosed in the Examples may be derivatized with a hydrophilic polymer or may be modified (e.g., as described below) so that they can be derivatized with a hydrophilic polymer. The term "derivatized," as used in connection with the peptides of the invention, refers to amino acids or peptides, or analogs of amino acids or peptides, comprising a hydrophilic polymer.

The hydrophilic polymer may be chosen from, e.g., polyethylene glycol including, e.g., monoalkyl-polyethylene glycol; polypropylene glycol; polysaccharides such as, e.g., dextran and cellulose; methylcellulose; hydroxycellulose; hydroxymethylcellulose; hydroxypropylcellulose; hydroxypropylmethyl cellulose; hydroxyalkyl starch including, e.g., hydroxyethyl starch; polyvinyl alcohol; poly(N-vinyl pyrrolidone); and poloxamers. In other embodiments, the hydrophilic polymer may be chosen from, e.g., polyethylene glycol copolymers such as, e.g., polyethylene glycol-polypropylene glycol copolymers and polyethylene glycol-poly(N-vinyl pyrrolidone) copolymers. In some embodiments, the hydrophilic polymer is a non-peptide polymer. In some embodiments, the hydrophilic polymer is readily hydrated. In some embodiments, the hydrophilic polymer has a large hydrodynamic radius when hydrated. In illustrative embodiments, the hydrophilic polymer is polyethylene glycol.

In some embodiments, a peptide of the invention (monomer or multimer) may contain one molecule of hydrophilic polymer per peptide monomer. In other embodiments, a peptide of the invention may contain multiple molecules of hydrophilic polymer per peptide monomer. For example, the anti-FcRn peptides disclosed herein may have 1, 2, 3, 4, 5, 6, 7, 8, or 1-4,1-8, 2-3, 2-4, 2-6, 3-6, or 2-6 molecules of hydrophilic polymer per peptide monomer.

In some embodiments, the hydrophilic polymer may be linear. In other embodiments, the hydrophilic polymer may be branched. A branched hydrophilic polymer may have, e.g., 2, 3, 4, 5, 6, 7, or 8 branches. In some embodiments, the hydrophilic polymer may have an average molecular weight of, e.g., about 5, 10, 15, 20, 25, 30, 35, 40, 45, 50, 55, or 60 kDa, or may have an average molecular weight ranging from, e.g., about 10-60, 10-40, 10-30, 20-30, 20-40, 20-50, 30-60, 15-25, 25-35, 35-45, or 45-55 kDa.

In some embodiments, the derivatized peptides described herein exhibit enhanced pharmaceutical properties relative to the corresponding underivatized peptides. For example, the derivatized peptides may have extended serum half-lives in animals. In some embodiments, the derivatized peptides may have serum half-lives that are at least 10, 20, 30, 40, 50, 60, 70, 80, 90, 100, 110, 120, 150, 175, 200, or 300% greater than the corresponding underivatized peptides in any of humans, mice, rats, and cynomolgus monkeys. In other embodiments, the derivatized peptides may have serum half-lives that are at least 2, 3, 4, 5, 10, 15, 20, 25, 50, 75, 100, 200, 500, 1,000, 5,000, or 10,000-fold greater than the corresponding underivatized peptides in any of humans, mice, rats, and cynomolgus monkeys. Serum half-life may be determined by, e.g., LC-MS or an ELISA assay using appropriate antibodies. In certain embodiments, derivatization does not result in a significant reduction in potency. For example, in some embodiments, derivatization does not result in a significant reduction in, e.g., binding affinity. In other embodiments, derivatization does not result in a significant reduction in inhibitory activity towards the IgG-FcRn interaction. For example, in some embodiments, derivatization does not result in a significant reduction in potency, as measured by, e.g., the IgG-peptide competition assay as described in Example 4, Biacore, or KinExA (Kinetic Exclusion Assay), and the derivatized peptides may have at least 1, 2, 3, 4, 5, 6, 7, 8, 9, 10, 15, 20, 30, 40, 50, 60, 70, 75, 80, 85, 90, 95, 97, 98, or 99% of the potency of the corresponding, underivatized peptides.

In some embodiments, monomeric peptides, such as, e.g., Peptide Nos. 227, 235, and 239, may be derivatized or may be modified (e.g., by conservative or non-conservative substitutions) so that they can be derivatized. In other embodiments, multimeric peptides such as, e.g., Peptide Nos. 119, 247, 278, 285, 286, 287, may be derivatized or may be modified so that they can be derivatized.

Derivatized peptides of the invention may be chosen from, e.g., Peptide Nos. 290, 291, 292, 293, 294, 295, and 296. In illustrative embodiments, the derivatized anti-FcRn peptide may be Peptide No. 285, pegylated with linear PEG chains as described in Examples 24, 27-29 and 31 or with branched PEG chains as described in Examples 33-34. In some embodiments, branched PEG chains may provide more favorable in vitro and in vivo characteristics than the linear PEGs. In illustrative embodiments, the branched pegylated peptides may be the product of the reductive alkyation of Peptide No. 285 with a 20 kDa, two-branch PEG or a two-branch, 40 kDa PEG.

The derivatized peptides may be monomeric or multimeric (including e.g., dimeric, trimeric, and tetrameric peptides). In the case of multimeric peptides, each of the individual peptide monomers from which the multimer is composed may be the same as or different from any other peptide monomer in the multimer. In some embodiments, peptide multimers may be synthesized by reacting individual peptide monomers with a multivalent linker. See, e.g., Rose, *J. Am. Chem. Soc.* 116:30 (1994). For example, peptide multimers may be synthesized by reacting individual peptide monomers, while on resin, with a multivalent linker. In other embodiments, peptide multimers may be synthesized by incorporating branched linker groups prior to the synthesis of the peptide sequence as in, e.g., Posnett et al., *J. Biol. Chem.* 263:1719 (1988).

Any suitable linker known to one of skill in the art may be used. In general, linkers that do not interfere with binding to FcRn are chosen. For example, the linker may be one of the linkers disclosed in, e.g., the Examples; U.S. Pat. Nos. 4,671,958; 4,867,973; 5,691,154; 5,846,728; 6,472,506; 6,541,669; 7,141,676; 7,176,185; and 7,232,805 and in U.S. Patent Application Pub. No. 2006/0228348.

In general, the linker may be of a suitable length such that it avoids steric hindrance between the peptide monomers of the multimer, and does not interfere with the binding of the peptide monomers to FcRn. In some embodiments, the linker may be a covalent bond. In other embodiments, the linker may comprise 1-100, 1-60, 5-60, 5-40, 2-50, 2-20, 5-10, or 5-20 linear atoms, where the linker is attached to a peptide monomer by means of, e.g., an ester, amide, hydrazone, oxime, semicarbazone, ether, thioether, phosphorothioate, phosphonate, thioester, and/or disulfide linkage. The remaining linear atoms in the linker are preferably selected from the group consisting of carbon, oxygen, nitrogen and sulfur, any of which atoms optionally may be included in a carbocyclic, heterocyclic, aryl, or heteroaryl ring. The linear carbon atoms in the linker optionally can be substituted with a substituent selected from the group consisting of halo, hydroxy, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido. A linear nitrogen atom in the linker optionally can be substituted with acyl, sulfonyl, alkyl, alkaryl, aryl, aralkyl, alkoxycarbonyl. A linear sulfur atom in the linker optionally can be oxidized. In certain embodiments, the linker may be cleavable, as disclosed in, e.g., U.S. Patent Application Pub. No. 2006/0228348 and U.S. Pat. Nos. 4,867,973; 7,176,185; 7,232,805.

In some embodiments, the derivatized peptides may comprise further modifications, such as, e.g., glycosylation, acetylation, phosphorylation, or lipidation.

The derivatized peptides, in certain embodiments, have some affinity for FcRn. For example, in some embodiments, the $K_D$ for the peptide-FcRn interaction may range from 50 fM to 1 mM. In other embodiments, the $K_D$ may range from 50 fM to 100 µM, 50 fM to 1 nM, or 1 pM to 1 nM.

In some embodiments, the peptides inhibit the Fc portion of IgG from binding to FcRn. For example, in certain embodiments, the peptides can inhibit the Fc portion of IgG from binding to FcRn with an $IC_{50}$ of, e.g., 50 fM to 100 µM, 50 fM to 1 µM, 1 pM to 100 nM, or 10 pM to 10 nM.

A. Exemplary Derivatized Peptides

In some embodiments, the disclosure provides the following exemplary derivatized peptides.

Exemplary Embodiment 1

A derivatized peptide having the sequence:

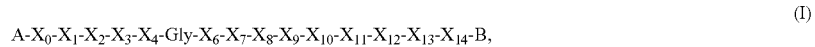

(I) $A-X_0-X_1-X_2-X_3-X_4-Gly-X_6-X_7-X_8-X_9-X_{10}-X_{11}-X_{12}-X_{13}-X_{14}-B$,

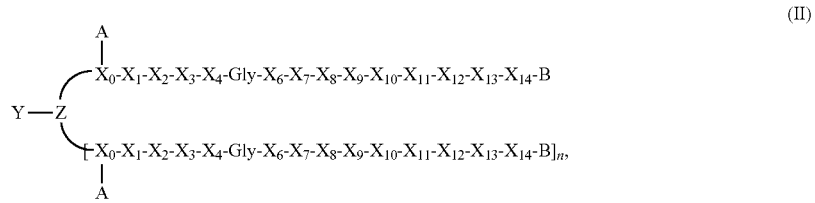

(II)

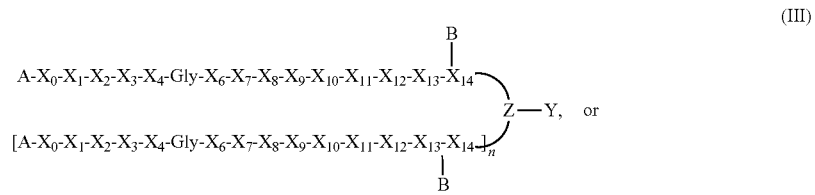

(III)

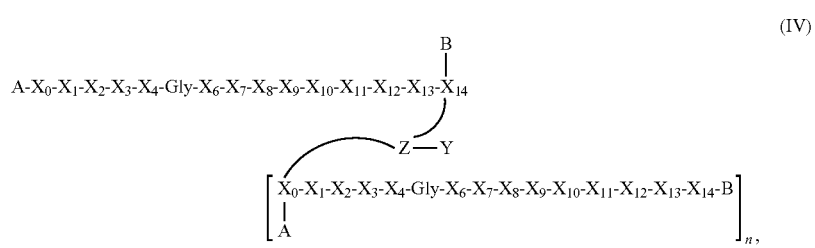

(IV)

wherein:
- A, if present, comprises a hydrophilic polymer or is hydrogen, acyl, or an amino protecting group;
- B, if present, comprises a hydrophilic polymer or is Q, an amino group, a hydroxyl group, or a carboxy protecting group;
- Q, if present, comprises an amine group (which may be neutral or positively charged), wherein the amine group is attached to a peptide by an alkylene group, where the alkylene groups include but are not limited to ethylene, n-propylene, n-butylene, n-pentylene, and n-hexylene; or by a combination of alkylene groups and alkylene oxide subunits, where the alkylene oxide subunits include but are not limited to $—(CH_2—CH_2—O)_p—$, where p is 1, 2, 3, 4, or 5. Non-limiting examples of Q include
  $—CH_2—CH_2—NH_2$,
  $—CH_2—CH_2—CH_2—CH_2—NH_2$,
  $CH_2—CH_2—CH_2—CH_2—CH_2—CH_2—NH_2$,
  $—CH_2—CH_2—O—CH_2—CH_2—NH_2$,
  $—(CH_2—CH_2—O)_2—CH_2—CH_2—NH_2$, and
  $—(CH_2—CH_2—O)_3—CH_2—CH_2—NH_2$;
- $X_0$, if present, is an optionally derivatized amino acid or an analog thereof or is an optionally derivatized peptide of 2-15 amino acids or an analog thereof;
- $X_1$, if present, is an optionally derivatized amino acid or an analog thereof;
- $X_2$, if present, is an amino acid or an analog thereof;
- $X_3$ is an amino acid or analog thereof that is capable of forming a bridge with $X_{10}$, $X_{12}$ or $X_{13}$;
- $X_4$ is an optionally derivatized amino acid or an analog thereof or an optionally derivatized peptide of 2 or 4 amino acids or an analog thereof;
- $X_6$ is a basic amino acid or an analog thereof, an aromatic amino acid or an analog thereof, or a basic aromatic amino acid or an analog thereof;
- $X_7$ is phenylalanine or an analog thereof;
- $X_8$ and $X_9$ are each independently chosen from glycine or an analog thereof, sarcosine or an analog thereof, aspartic acid or an analog thereof, a D-amino acid or an analog thereof, and α-aminoisobutyric acid or an analog thereof, or
- $X_8$, when taken together with $X_9$, forms a dipeptide analog;
- $X_{10}$ is an amino acid or an analog thereof, or
- $X_{10}$, when taken together with $X_9$, forms a dipeptide analog;
- $X_{11}$ is tyrosine or an analog thereof;
- $X_{12}$ is an optionally derivatized amino acid or an analog thereof;
- $X_{13}$, if present, is an amino acid or an analog thereof;
- $X_{14}$, if present, is an optionally derivatized amino acid or an analog thereof or is an optionally derivatized peptide of 2-15 amino acids or an analog thereof;
- Y comprises a hydrophilic polymer;
- Z is a linker that attaches to each peptide monomer through
  - A;
  - B;
  - the amino terminus or a side chain of $X_0$, if $X_0$ is present; to the amino terminus or side chain of $X_1$, if $X_0$ is absent; to the amino terminus or side chain of $X_2$, if both $X_0$ and $X_1$ are absent; or to the amino terminus or side chain of $X_3$, if $X_0$, $X_1$ and $X_2$ are absent; or
  - the carboxy terminus or a side chain of $X_{14}$, if $X_{14}$ is present; to the carboxy terminus or a side chain of $X_{13}$, if $X_{14}$ is absent; or to the carboxy terminus or a side chain of $X_{12}$ if both $X_{13}$ and $X_{14}$ are absent;
- m is an integer chosen from 1, 2, and 3; and
- n is an integer chosen from 1, 2, and 3;

wherein:
- each A, B, $X_0$, $X_1$, $X_2$, $X_3$, $X_4$, $X_6$, $X_7$, $X_8$, $X_9$, $X_{10}$, $X_{11}$, $X_{12}$, $X_{13}$, and $X_{14}$ is chosen independently; and
- each monomer of the peptide ranges from 10 to 50 amino acids in length.

It will be appreciated by the skilled artisan that if Z is attached to the peptide through a side chain of $X_0$, then A is necessarily present. Similarly, if Z is attached to a side chain of $X_{14}$, then B is necessarily present.

In some embodiments, A comprises a hydrophilic polymer. For example, A may comprise a hydrophilic polymer and a linker (such as, e.g., any linker described herein) connecting the hydrophilic polymer and $X_0$ (or $X_1$, if $X_0$ is absent; or $X_2$, if $X_0$ and $X_1$ are absent; or $X_3$ if $X_0$, $X_1$, and $X_2$ are absent). In other embodiments, A is hydrogen, acyl, or an amino protecting group. In some embodiments B comprises a hydrophilic polymer. For example, B may comprise a hydrophilic polymer and a linker (such as, e.g., any linker described herein, including, e.g., that found in FIG. 18) connecting the hydrophilic polymer and $X_{14}$ (or $X_{13}$, if $X_{14}$ is absent; or $X_{12}$, if $X_{13}$ and $X_{14}$ are absent). In other embodiments, B is an amino group, a hydroxyl group, or a carboxy protecting group.

The charge of an ionizable group such as an amino group or carboxyl group may be charged or neutral, depending on the environment.

Exemplary Embodiment 2

The peptide of embodiment 1 having the sequence:

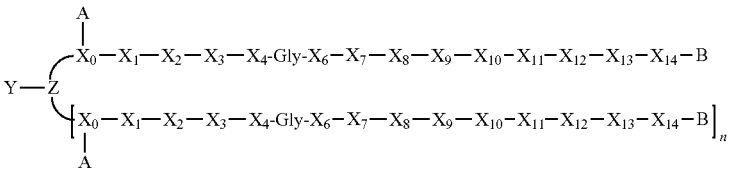

wherein:
- $X_1$ is an underivatized amino acid or an analog thereof;
- $X_4$ is an underivatized amino acid or an analog thereof or an underivatized peptide of 2 or 4 amino acids or an analog thereof; and
- $X_{12}$ is an underivatized amino acid or an analog thereof.

Exemplary Embodiment 3

The peptide of embodiment 1, wherein $X_0$ is absent.

Exemplary Embodiment 4

The peptide of embodiment 1, wherein $X_1$ is arginine or an analog thereof.

Exemplary Embodiment 5

The peptide of embodiment 1, wherein $X_2$ is an aromatic amino acid or an analog thereof.

Exemplary Embodiment 6

The peptide of embodiment 5, wherein $X_2$ is phenylalanine or an analog thereof, tyrosine or an analog thereof, or tryptophan or an analog thereof.

Exemplary Embodiment 7

The peptide of embodiment 6, wherein $X_2$ is phenylalanine or an analog thereof.

Exemplary Embodiment 8

The peptide of embodiment 1, wherein the peptide is unbridged.

Exemplary Embodiment 9

The peptide of embodiment 1, wherein at least one of $X_{10}$, $X_{12}$, or $X_{13}$ is an amino acid or analog thereof that is capable of forming a bridge with $X_3$.

Exemplary Embodiment 10

The peptide of embodiment 9, wherein $X_3$ forms a bridge with $X_{10}$, $X_{12}$, or $X_{13}$. The bridge between $X_3$ and $X_{10}$, $X_{12}$, or $X_{13}$ may be a side chain to side chain bridge or a side chain to carboxy terminus bridge (e.g., in embodiments wherein $X_{13}$ is at the carboxy terminus of the peptide). A bridge may include, or may result from the formation of, one or more functional groups such as, e.g., a disulfide (see, e.g., Example 7), an ether, a thioether, an alkene, or an amide (see, e.g., Example 10), in which case the bridge may be referred to as, e.g., a disulfide, ether, thioether, alkene, or amide bridge.

Exemplary Embodiment 11

The peptide of embodiment 10, wherein $X_3$ forms a bridge with $X_{13}$.

Exemplary Embodiment 12

The peptide of embodiment 11, wherein the bridge is a side chain to side chain bridge.

Exemplary Embodiment 13

The peptide of embodiment 12, wherein the side chain to side chain bridge is a disulfide bridge, an ether bridge, a thioether bridge, an alkene bridge, or an amide bridge.

Exemplary Embodiment 14

The peptide of embodiment 13, wherein the side chain to side chain bridge is a disulfide bridge between:
cysteine and cysteine;
cysteine and homocysteine;
cysteine and penicillamine;
homocysteine and homocysteine;
homocysteine and penicillamine; or
penicillamine and penicillamine.

Exemplary Embodiment 15

The peptide of embodiment 13, wherein the side chain to side chain bridge is an amide bridge between:
aspartic acid and lysine;
aspartic acid and ornithine;
aspartic acid and 2,4-diaminobutyric acid;
aspartic acid and 2,3-diaminopropionic acid
glutamic acid and lysine;
glutamic acid and ornithine;
glutamic acid and 2,4-diaminobutyric acid; or
glutamic acid and 2,3-diaminopropionic acid.

Exemplary Embodiment 16

The peptide of embodiment 1, wherein the peptide comprises at least one cysteine.

Exemplary Embodiment 17

The peptide of embodiment 1, wherein the peptide comprises at least one cysteine analog chosen from:
homocysteine;
D-cysteine; and
penicillamine.

Exemplary Embodiment 18

The peptide of embodiment 1, wherein $X_4$ is threonine or an analog thereof.

Exemplary Embodiment 19

The peptide of embodiment 1, wherein $X_6$ is a basic amino acid or analog thereof chosen from:
lysine or an analog thereof;
ornithine or an analog thereof;
2,4-diaminobutyric acid or an analog thereof;
2,3-diaminopropionic acid or an analog thereof;
arginine or an analog thereof; and
guanylalanine or an analog thereof.

Exemplary Embodiment 20

The peptide of embodiment 1, wherein $X_6$ is an aromatic amino acid or analog thereof chosen from
tyrosine or an analog thereof;
tryptophan or an analog thereof; and
phenylalanine or an analog thereof.

Exemplary Embodiment 21

The peptide of embodiment 1, wherein $X_6$ is a basic aromatic amino acid or an analog thereof chosen from:
histidine or an analog thereof;
1-methylhistidine or an analog thereof;
2-pyridylalanine or an analog thereof;
3-pyridylalanine or an analog thereof;
4-pyridylalanine or an analog thereof;
4-aminophenylalanine or an analog thereof;
4-guanylphenylalanine or an analog thereof; and
thiazolylalanine or an analog thereof.

Exemplary Embodiment 22

The peptide of embodiment 21, wherein $X_6$ is histidine or an analog thereof, 3-pyridylalanine or an analog thereof, 4-pyridylalanine or an analog thereof, or 4-guanylphenylalanine or an analog thereof.

Exemplary Embodiment 23

The peptide of embodiment 22, wherein $X_6$ is 4-guanylphenylalanine or an analog thereof.

Exemplary Embodiment 24

The peptide of embodiment 22, wherein $X_6$ is histidine or an analog thereof.

Exemplary Embodiment 25

The peptide of embodiment 1, wherein $X_7$ is phenylalanine.

Exemplary Embodiment 26

The peptide of embodiment 1, wherein at least one of $X_8$ and $X_9$ is chosen from:
glycine;
D-amino acids;
α-aminoisobutyric acid; and
sarcosine.

Exemplary Embodiment 27

The peptide of embodiment 1, wherein $X_8$, taken together with $X_9$, forms a dipeptide analog chosen from:
β-alanine;
4-aminobutanoic acid;
5-aminopentanoic acid;
3-(aminomethyl)benzoic acid;
4-(aminomethyl)benzoic acid;
3-(aminophenyl)acetic acid;
4-(aminophenyl)acetic acid;

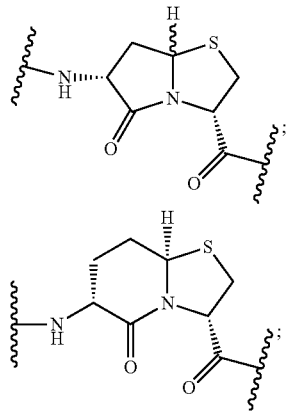

3-amino-2-oxo-1-piperidine-acetic acid;
3(R)-3-amino-2-oxo-1-piperidine-acetic acid;
3(R)-3-amino-2-oxo-1-azepine acetic acid;
3(R)-3-amino-2-oxo-1-pyrrolidine acetic acid; and
3-amino-N-1-carboxymethyl-2,3,4,5-tetrahydro-1H-[1]-benzazepine-2-one.

Exemplary Embodiment 28

The peptide of embodiment 1, wherein the peptide comprises a phenylalanine analog chosen from:
tryptophan;
tyrosine;
2-aminophenylalanine;
3-aminophenylalanine;
4-aminophenylalanine;
pentafluorophenylalanine;
2-pyridylalanine;
3-pyridylalanine;
4-nitrophenylalanine;
1-naphthylalanine;
homophenylalanine;
phenylglycine;
2-methylphenylalanine;
3-methylphenylalanine;
4-methylphenylalanine
2-chlorophenylalanine;
3-chlorophenylalanine;
4-chlorophenylalanine;
3,3-diphenylalanine;
4,4'-biphenylalanine;
4-t-butylphenylalanine;
cyclohexylalanine;
(4-aminoacetyl)phenylalanine;
L-1,2,3,4-tetrahydroisoquinoline-3-carboxylic acid;
D-beta-methylphenylalanine; and
L-beta-methylphenylalanine.

Exemplary Embodiment 29

The peptide of embodiment 1, wherein the peptide comprises at least one tyrosine analog chosen from:
phenylalanine;
4-aminophenylalanine;
4-methoxyphenylalanine;
pentafluorophenylalanine;
2-pyridylalanine;
3-pyridylalanine;
4-pyridylalanine;
4-nitrophenylalanine;
2-nitrotyrosine; and
4-fluorophenylalanine.

Exemplary Embodiment 30

The peptide of embodiment 1, wherein $X_9$ and $X_{10}$, taken together, form a dipeptide analog chosen from:

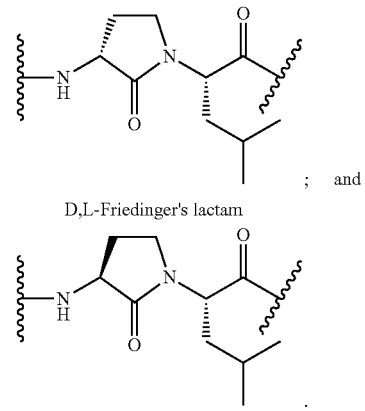

D,L-Friedinger's lactam

L,L-Friedinger's lactam

Exemplary Embodiment 31

The peptide of embodiment 1, wherein the peptide comprises at least one histidine analog chosen from:

2,4-diaminobutyric acid;
thiazolylalanine;
2,3-diaminopropionic acid;
guanylalanine;
2-pyridylalanine;
3-pyridylalanine;
4-pyridylalanine;
thienylalanine;
ornithine;
lysine;
arginine;
4-guanylphenylalanine;
1-methylhistidine;
3-methylhistidine;
1,3-dimethylhistidine;
4-aminophenylalanine;
2-pyrrolidinylalanine;
3-piperdylalanine; and
4-piperidylalanine.

Exemplary Embodiment 32

The peptide of embodiment 1, wherein $X_{10}$ is chosen from neutral hydrophobic amino acids, and analogs thereof. In other embodiments, $X_{10}$ is a neutral amino acid or an analog thereof. In yet other embodiments, $X_{10}$ is a hydrophobic amino acid or an analog thereof. In further embodiments, $X_{10}$ is an N-methylated hydrophobic amino acid or an analog thereof.

Exemplary Embodiment 33

The peptide of embodiment 1, wherein $X_{11}$ is tyrosine or an analog thereof.

Exemplary Embodiment 34

The peptide of embodiment 1, wherein $X_{12}$ is proline or an analog thereof.

Exemplary Embodiment 35

The peptide of embodiment 1, wherein $X_{13}$ is tyrosine or an analog thereof.

Exemplary Embodiment 36

The peptide of embodiment 1, wherein $X_{14}$ is absent.

Exemplary Embodiment 37

The peptide of embodiment 1, wherein $X_{15}$ is an amino group.

Exemplary Embodiment 38

The peptide of embodiment 1, wherein the peptide is a peptide of any of Formulae II, III, and IV and n is 1.

Exemplary Embodiment 39

The peptide of embodiment 1, wherein the peptide is a peptide of any of Formulae II, III, and IV and n is 2.

Exemplary Embodiment 40

The peptide of embodiment 1, wherein the peptide has the sequence:

(SEQ ID NO: 1)

$$A-X_0-X_1-Phe-X_3-X_4-Gly-His-Phe-Gly-Sar-NMeLeu-Tyr-X_{12}-X_{13}-X_{14}-B,$$

(V)

(SEQ ID NOS 1 and 2)

$$Y-Z \begin{cases} X_0-X_1-Phe-X_3-X_4-Gly-His-Phe-Gly-Sar-NMeLeu-Tyr-X_{12}-X_{13}-X_4-B \\ \phantom{X_0-X_1-Phe-X_3-X_4-Gly-His-Phe-Gly-Sar-NMeLeu-Tyr-X_{12}-X_{13}-X_4-B}\overset{|}{A} \\ [X_0-X_1-Phe-X_3-X_4-Gly-His-Phe-Gly-Sar-NMeLeu-Tyr-X_{12}-X_{13}-X_{14}-B]_n, \\ \overset{|}{A} \end{cases}$$

(VI)

(SEQ ID NOS 1 and 2)

$$\begin{array}{c} \overset{B}{|} \\ A-X_0-X_1-Phe-X_3-X_4-Gly-His-Phe-Gly-Sar-NMeLeu-Tyr-X_{12}-X_{13}-X_{14} \\ \phantom{xxxxxxxxxxxxxxxxxxxxxxxxxxxxxxxxxxxxxxxxxxxxxxxxxxxxxxxx} Z-Y, \text{ or} \\ [A-X_0-X_1-Phe-X_3-X_4-Gly-His-Phe-Gly-Sar-NMeLeu-Tyr-X_{12}-X_{13}-X_{14}]_n \\ \phantom{xxxxxxxxxxxxxxxxxxxxxxxxxxxxxxxxxxxxxxxxxxxxxxxxxxxxxxxx} \overset{|}{B} \end{array}$$

(VII)

(SEQ ID NOS 2 and 2)

$$\begin{array}{c} \overset{B}{|} \\ A-X_0-X_1-Phe-X_3-X_4-Gly-His-Phe-Gly-Sar-NMeLeu-Tyr-X_{12}-X_{13}-X_{14}]_m \\ \phantom{xxxxxxxxxxxxx} Z=Y \\ [X_0-X_1-Phe-X_3-X_4-Gly-His-Phe-Gly-Sar-NMeLeu-Tyr-X_{12}-X_{13}-X_{14}-B]_n. \\ \overset{|}{A} \end{array}$$

(VIII)

Exemplary Embodiment 41

The peptide of embodiment 40, wherein $X_0$ is absent.

Exemplary Embodiment 42

The peptide of embodiment 40, wherein $X_1$, $X_4$, and/or $X_{12}$ are derivatized amino acids or analogs thereof.

Exemplary Embodiment 43

The peptide of embodiment 40, wherein the peptide has the sequence:

A-X₁-Phe-Pen-X₄-Gly-His-Phe-Gly-Sar-NMeLeu-Tyr-X₁₂-Cys-B, (IX)

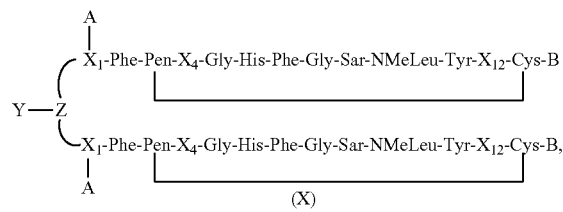

(X)

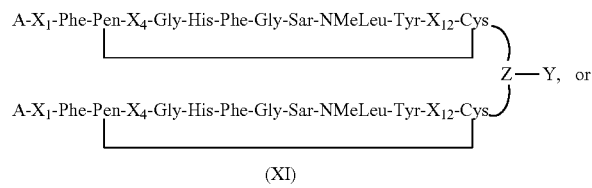

(XI)

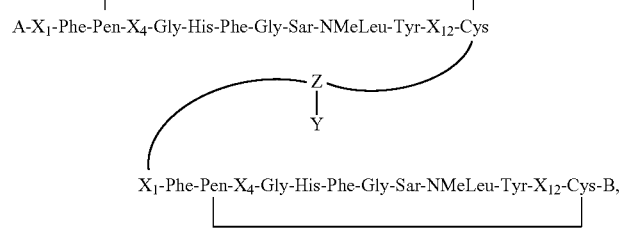

(XII)

wherein horizontal brackets indicate the presence of a bridge. It will be appreciated by the skilled artisan that, in Formula XI, Z attaches to each peptide monomer through the carboxy terminus, as the side chain of the C-terminal cysteine residue ($X_{13}$) forms a bridge with penicillamine ($X_3$). Similarly, it will be appreciated by the skilled artisan that, in Formula XII, Z attaches to one peptide monomer through the carboxy terminus, as the side chain of the C-terminal cysteine residue ($X_{13}$) forms a bridge with penicillamine ($X_3$), and Z attaches to the other peptide monomer through the amino terminus or a side chain of $X_1$.

Exemplary Embodiment 44

The peptide of embodiment 1, wherein the hydrophilic polymer is chosen from polyethylene glycol, polypropylene glycol, dextran; cellulose, methylcellulose, hydroxycellulose, hydroxymethylcellulose, hydroxypropylcellulose, hydroxypropylmethyl cellulose, hydroxyalkyl starch, polyvinyl alcohol, poly(N-vinyl pyrrolidone), poloxamers, and polyethylene glycol copolymers.

Exemplary Embodiment 45

The peptide of embodiment 44, wherein the hydrophilic polymer is polyethylene glycol (PEG).

Exemplary Embodiment 46

The peptide of embodiment 45, wherein the PEG is a linear PEG.

(SEQ ID NO: 3)

(SEQ ID NOS 3 and 3)

(SEQ ID NOS 3 and 3)

(SEQ ID NOS 3 and 3)

Exemplary Embodiment 47

The peptide of embodiment 45, wherein the PEG is a branched PEG.

Exemplary Embodiment 48

The peptide of embodiment 45, wherein the PEG has an average molecular weight ranging from 10-60 kDa.

Exemplary Embodiment 49

The peptide of embodiment 45, wherein the PEG has an average molecular weight ranging from 10-40 kDa.

Exemplary Embodiment 50

The peptide of embodiment 45 wherein the PEG has a molecular weight of about 20 kDa.

Exemplary Embodiment 51

The peptide of embodiment 45, wherein the PEG has a molecular weight of about 30 kDa.

Exemplary Embodiment 52

The peptide of embodiment 1, wherein the peptide binds specifically to human FcRn.

Exemplary Embodiment 53

The peptide of embodiment 52, wherein the affinity of the peptide for human FcRn ranges from 50 fM to 1 mM.

Exemplary Embodiment 54

The peptide of embodiment 53, wherein the affinity of the peptide for human FcRn ranges from 500 fM to 100 μM.

Exemplary Embodiment 55

The peptide of embodiment 54, wherein the affinity of the peptide for human FcRn ranges from 5 pM to 1 μM.

Exemplary Embodiment 56

The peptide of embodiment 52, wherein the peptide inhibits the binding of human FcRn to human IgG, and has an $IC_{50}$ ranging from 50 fM to 1 mM.

Exemplary Embodiment 57

The peptide of embodiment 56, wherein the peptide has an $IC_{50}$ ranging from 1 pM to 100 nM.

Exemplary Embodiment 58

The peptide of embodiment 56, wherein the peptide has an $IC_{50}$ ranging from 10 pM to 10 nM.

Exemplary Embodiment 59

The peptide of embodiment 1, wherein the peptide has the sequence:

(SEQ ID NOS 4 and 5)

$$Y-Z \begin{cases} X_0\text{-Arg-Phe-}X_3\text{-Thr-Gly-His-Phe-Gly-Sar-NMeLeu-Tyr-Pro-}X_{13}\text{-}X_{14}\text{-B} \\ [X_0\text{-Arg-Phe-}X_3\text{-Thr-Gly-His-Phe-Gly-Sar-NMeLeu-Tyr-Pro-}X_{13}\text{-}X_{14}\text{-B}]_n \end{cases}.$$

Exemplary Embodiment 60

The peptide of embodiment 59, wherein the peptide has the sequence:

(SEQ ID NOS 6 and 6)

$$Y-Z \begin{cases} X_0\text{-Arg-Phe-Pen-Thr-Gly-His-Phe-Gly-Sar-NMeLeu-Tyr-Pro-Cys-B} \\ X_0\text{-Arg-Phe-Pen-Thr-Gly-His-Phe-Gly-Sar-NMeLeu-Tyr-Pro-Cys-B} \end{cases},$$

wherein horizontal brackets indicate the presence of a bridge.

Exemplary Embodiment 61

The peptide of embodiment 60, wherein the peptide has the sequence:

(SEQ ID NOS 7 and 7)

Exemplary Embodiment 62

The peptide of embodiment 59, wherein the peptide has the sequence:

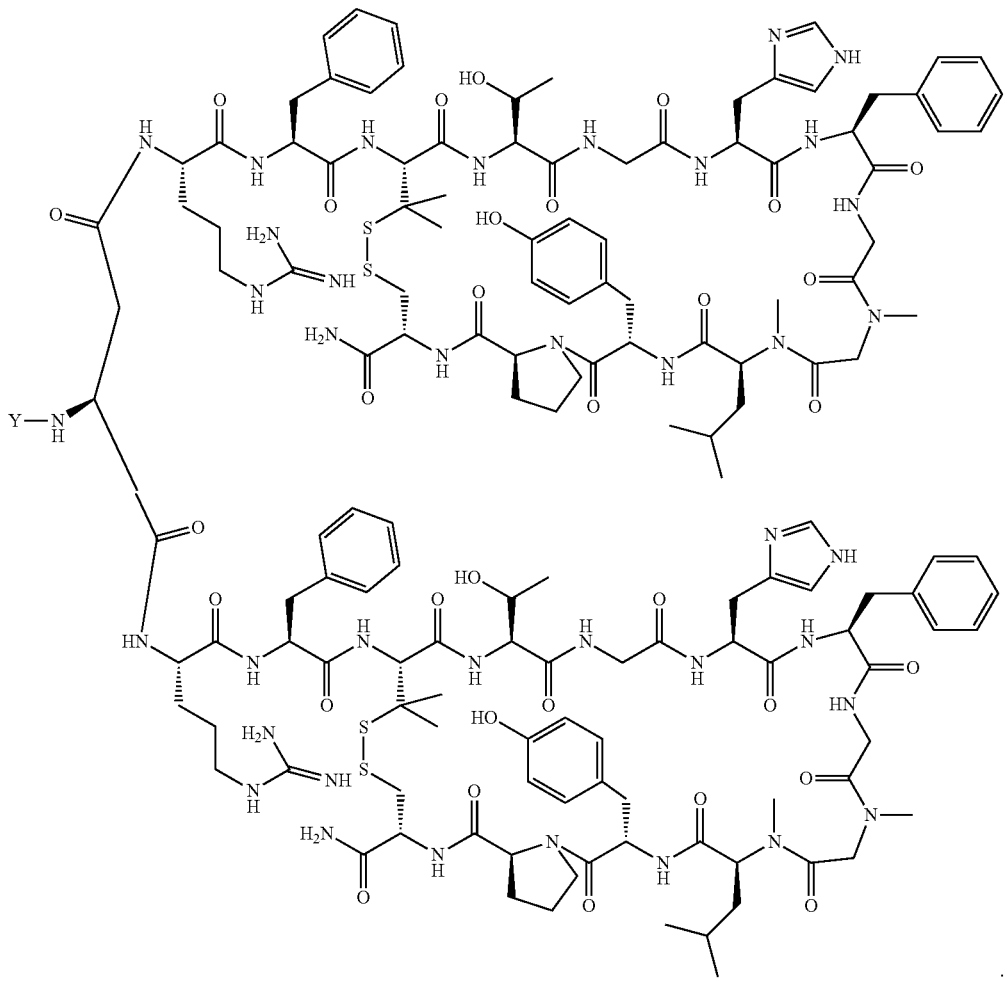

Exemplary Embodiment 63

The peptide of embodiment 1, wherein B is Q.

Exemplary Embodiment 64

The peptide of embodiment 63, wherein B is —(W)$_m$—(CH$_2$)$_n$—NH$_2$, where W, if present, is —(CH$_2$)$_p$, —(CH$_2$—CH$_2$)$_p$, —(CH$_2$—O)$_p$—, or

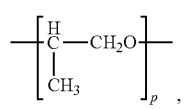

and m is 1, 2, 3, 4, or 5, n is 1, 2, or 3 and p is 1, 2, 3, 4, 5.

Exemplary Embodiment 65

The peptide of embodiment 64, wherein X$_3$ forms a bridge with X$_{13}$.

Exemplary Embodiment 66

The peptide of embodiment 65, wherein the bridge is a side chain to side chain bridge.

Exemplary Embodiment 67

The peptide of embodiment 64, wherein X$_6$ is histidine or an analog thereof.

Exemplary Embodiment 68

The peptide of embodiment 64, wherein at least one of X$_8$ and X$_9$ is chosen from:
glycine;
D-amino acids;
α-aminoisobutyric acid; and
sarcosine.

Exemplary Embodiment 69

The peptide of embodiment 64, wherein X$_{14}$ is absent.

Exemplary Embodiment 70

The peptide of embodiment 64, wherein n is 1.

Exemplary Embodiment 71

The peptide of embodiment 64, wherein the peptide has the sequence:

(SEQ ID NOS 1 and 2)

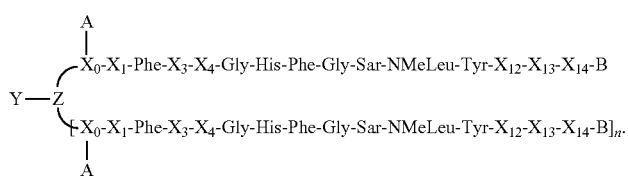

Exemplary Embodiment 72

The peptide of embodiment 71, wherein the peptide has the sequence:

(SEQ ID NOS 3 and 3)

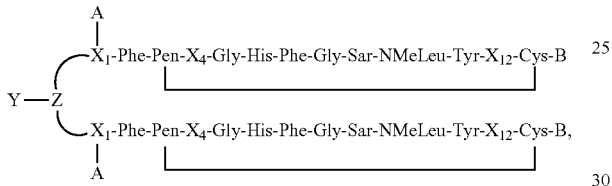

wherein horizontal brackets indicate the presence of a bridge.

Exemplary Embodiment 73

The peptide of embodiment 64, wherein the peptide has the sequence:

(SEQ ID NOS 4 and 5)

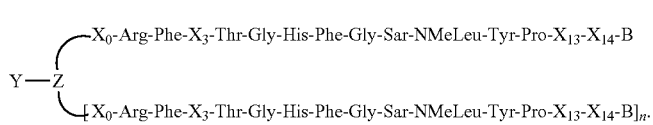

Exemplary Embodiment 74

The peptide of embodiment 73, wherein the peptide has the sequence:

(SEQ ID NOS 6 and 6)

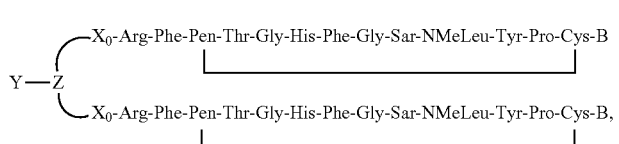

wherein horizontal brackets indicate the presence of a bridge.

Exemplary Embodiment 75

The peptide of embodiment 74, wherein the peptide has the sequence:

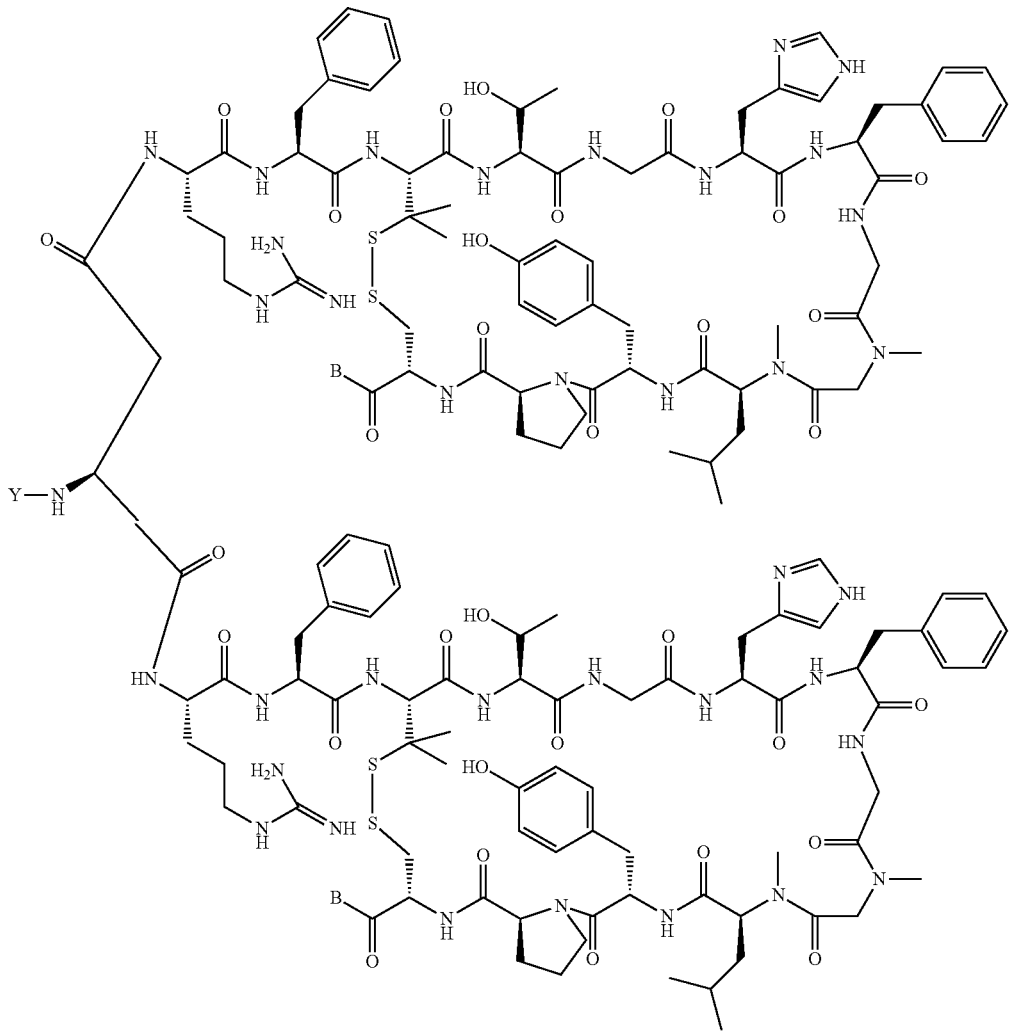

wherein B is $—(W)_n—(CH_2)_r—NH_2$, where W, if present, is $—(CH_2)_p$, $—(CH_2—CH_2)_p$, $—(CH_2—O)_p—$, or

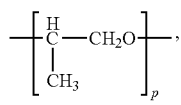

and where m is 1, 2, 3, 4, or 5, r is 1, 2, or 3, and p is 1, 2, 3, 4, 5.

B. Synthesis of Derivatized Peptides

The derivatized peptides may be prepared according to any method known in the art. Exemplary methods of preparing peptides derivatized with polyethylene glycol ("pegylated" peptides) are described infra. Those methods may be used with any of the polymers described herein. Accordingly, it will be appreciated by one of skill in the art that any time the terms "pegylate," "pegylation," or "pegylated" are used throughout the disclosure, any hydrophilic polymer could readily be substituted in place of polyethylene glycol.

(1) Pegylation of Unpegylated Peptides

In some embodiments, the peptides described herein may be synthesized as the corresponding unpegylated peptides and then subsequently pegylated.

a. Synthesis of Unpegylated Peptides

Peptides of the invention may be synthesized following the procedures set forth in the Examples or by other known synthetic methods, such as, e.g., solid phase peptide synthesis. See, e.g., Abelson et al., eds., *Methods in Enzymology, Volume 289: Solid-Phase Peptide Synthesis* (1997); Chan and White, eds., *Fmoc Solid Phase Peptide Synthesis: A Practical Approach* Oxford, University Press Inc., New York (2000); Benoiton, *Chemistry of Peptide Synthesis*, CRC (2005); Bodanszky, *Principles of Peptide Synthesis*, 2nd ed., Springer-Verlag, New York (1993); Stewart and Young, *Solid Phase Peptide Synthesis*, 2nd ed., Pierce Chemical Co., Rockford, Ill. (1984).

Peptides of the invention that are composed entirely of encoded amino acids may be synthesized recombinantly in cells using techniques well known in the art. See, e.g., Sambrook et al., *Molecular Cloning A Laboratory Manual*, Cold Spring Harbor Laboratory, N.Y. (1989) and Ausubel et al., *Current Protocols in Molecular Biology*, Greene Publishing Associates and Wiley Interscience, N.Y. (1989).

Alternatively, peptides of the invention may be synthesized using a combination of synthetic and recombinant methods.

b. Pegylation

Pegylation may be performed according to any of the pegylation reactions known in the art. Methods for preparing a pegylated protein product will generally include (a) reacting a polypeptide with a PEG containing a first reactive group (such as, e.g., an active ester, aldehyde, amine, aminooxy, hydrazine, hydrazide, othiol, maleimide, and α-haloacyl, such as, e.g., iodoacetyl) under conditions whereby the peptide of the invention, which typically contains at least one second reactive group, becomes attached to one or more PEG groups; and (b) obtaining the reaction product(s). Reaction conditions may be selected from any of those known in the pegylation art or those subsequently developed. In general, reaction conditions (including, e.g., temperature, solvent, and pH) that will not degrade the anti-FcRn peptides of the invention are chosen.

In embodiments wherein a peptide to be pegylated contains more than one second reactive group that may be pegylated, some or all of those groups may be pegylated by using an appropriate PEG stoichiometry during the pegylation reaction. In the illustrative example of a peptide dimer containing two C-terminal amines, both amines may be pegylated, or only one amine may be pegylated, depending upon the PEG stoichiometry used.

Acylation.

As used herein, acylation is contemplated to include, without limitation, the following types of linkages between a peptide of the invention and a PEG: amide, carbamate, urethane, and the like. See, e.g., Chamow, *Bioconjugate Chem.*, 5:133-140 (1994).

In a first example, an amine-containing peptide (where the amine group is, e.g., a side chain amine group or an N-terminal amine group) can be selectively reacted with a PEG reagent having an activated ester group (including, e.g., PEG succinimidyl esters and PEG para-nitrophenyl esters; such as, e.g., NOF Corp. (Japan) Cat. Nos. Sunbright MEGC-30TS and Sunbright MENP-30T) to generate an amide bond. Alternatively, the peptide may contain an aminooxy, hydrazine, or hydrazide group.

In a second example, peptide carboxylic acid groups (including, e.g., side chain and C-terminal carboxylic acid groups) can be activated with various reagents (including, e.g., 1-ethyl-3-(3'-dimethylaminopropyl)carbodiimide (EDC) and N-hydroxysuccinimide+EDC). The activated peptides can then be coupled to amine-containing PEG reagents (including, e.g., NOF Corp. (Japan) Cat. No. Sunbright MEPA-30T).

Alkylation and Reductive Alkylation.

Peptide-PEG conjugates may be prepared by alkylation by reacting an amine (or aminooxy, hydrazine, or hydrazide) and an aldehyde. In some embodiments, including, e.g., the reaction of an aminooxy, hydrazine, or hydrazide, the alkylation product is not reduced. In other embodiments, Peptide-PEG conjugates may be prepared by reductive alkylation by reacting an amine (or aminooxy, hydrazine, or hydrazide) and an aldehyde in the presence of a suitable reducing agent, or by reacting an amine (or aminooxy, hydrazine, or hydrazide) and an aldehyde followed by reduction with a suitable reducing agent to generate a stable carbon-nitrogen single bond, e.g., as described in Examples 12, 14, 16, 27-29, and 31-34.

In a first example, a peptide containing a side chain or free N-terminal amine group can be coupled with a PEG containing an aldehyde group. PEG aldehydes are commercially available (including, e.g., NOF Corp. (Japan) Cat. No. Sunbright ME-300AL). Another exemplary PEG aldehyde is polyethylene glycol propionaldehyde, which is water stable, or mono $C_1$-$C_{10}$ alkoxy or aryloxy derivatives thereof. See, for example, U.S. Pat. No. 5,252,714. In general, the PEG containing an aldehyde group may have a single reactive aldehyde group.

In a second example, peptides containing a hydroxylamine, hydrazine, or hydrazide group can be readily reacted with PEG-aldehydes. (Peptides containing an aminooxy, hydrazine, or hydrazide group can be prepared by standard methods known to those skilled in the art such as those described in Example 39.) In some embodiments, the resulting product is reduced. In other embodiments, the resulting product is not reduced.

In a third example, peptide aldehydes are reacted with amine-containing PEG reagents (such as, e.g., NOF Corp. (Japan) Cat. No. MEPA 30T). Peptide aldehydes can be readily generated, for example as described herein in Example 12, or by incorporation of an aldehyde-containing amino acid.

Thioalkylation.

Peptides containing a free thiol functional group (e.g., from a cysteine amino acid residue) can readily react with a PEG functionalized with an electrophile such as, e.g., maleimide (such as, e.g., NOF Corp. (Japan) Cat. No. ME-300MA) or α-haloacyl, including haloacetyl, including iodoacetyl, to form a thioether bond. Alternatively, peptides containing an electrophilic functional group (including, e.g., a maleimide, which can be prepared by standard methods known to those skilled in the art) can be reacted with thiol-containing PEG groups (such as, e.g., NOF Corp. (Japan) Cat. No. ME-300SH). Suitable electrophilic functional groups are known to those of skill in the art.

Other Conjugation Chemistries.

There are a number of PEG attachment methods available to those skilled in the art and described in, for example, EP 0 401 384; Malik et al., *Exp. Hematol.*, 20:1028-1035 (1992); Francis, *Focus on Growth Factors*, 3(2):4-10 (1992); EP 0 154 316; EP 0 401 384; WO 92/16221; and WO 95/34326. Other possible methods for PEG-peptide conjugation include, e.g., the use of azide-alkyne chemistry (e.g., as described in *J. Am. Chem. Soc.* 125:3192-3193 (2003)). In certain embodiments, a PEG thioester may be reacted with a peptide bearing an N-terminal cysteine residue, e.g., as described in Dawson and Kent, *Annu. Rev. Biochem.* 69:923 (2000).

(2) Pegylation Sites

Anti-FcRn peptides described herein may be pegylated at any suitable position of the peptide, as described infra. In some embodiments, the anti-FcRn peptides may be pegylated at multiple positions.

N-Terminus.

Peptides having an amine group at the N-terminus may be pegylated at the N-terminus, e.g., by any suitable conjugation method described supra.

Addition of N-Terminal Reactive Groups.

Figure 18:
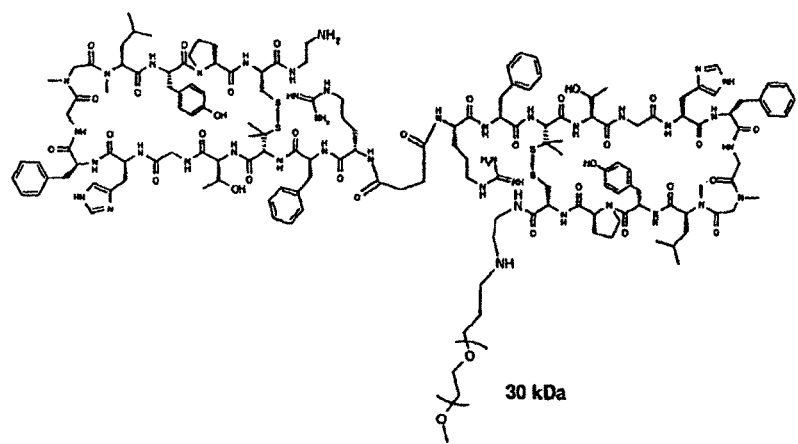
FIG. 18 shows the chemical structures of Peptide No. 297.

In some embodiments, one or more reactive groups may be added to the N-terminus of an anti-FcRn peptide of the invention. In some embodiments, the reactive groups will be amino acid sidechains. For example, an acetyl-capped lysine residue may be added to the N-terminus, resulting in a side chain amine group that may be pegylated. In other embodiments, multiple pegylation sites may be introduced by adding an amino acid having an amine-containing side chain to the N-terminus. For example, a lysine residue may be added to the free amine of Peptide No. 285 to generate two available amine sites for pegylation (the lysine α- and ε-amino groups). Reaction of the lysine-containing product with suitably-activated PEGs (such as, e.g., the aldehyde-containing PEGs described infra) can afford a PEG-peptide conjugate having 2 PEG moieties per peptide, as illustrated in FIG. 18.

N-Terminal Linker.

Monomeric peptides may be multimerized with an N-terminal linker containing a reactive group, e.g., as described in Examples 12, 13, and 15. For example, Peptides Nos. 100, 119, 120, 121, 160, 199 and 200 have an N-terminal linker containing a carboxylic acid group that can be pegylated and Peptide Nos. 285 and 286 have N-terminal linker containing an amine group that can be pegylated.

C-Terminus.

Peptides having a carboxylic acid group at the C-terminus may be pegylated at the C-terminus, e.g., by any suitable conjugation method described supra.

In other embodiments, peptides may be synthesized on an amine-containing resin (such as, e.g., 1,2-diaminoethane trityl PS, Novabiochem Cat. No. 01-64-0081) to yield a C-terminal amine group.

Addition of C-Terminal Reactive Groups.

In some embodiments, one or more reactive groups for pegylation may be added to the C-terminus of an anti-FcRn peptide of the invention. In some embodiments, the reactive groups will be amino acid sidechains. For example, a lysine residue having a C-terminal amide group may be added to the C-terminus, resulting in a side chain amine group that may be pegylated. In other embodiments, multiple pegylation sites may be introduced by adding an amino acid having an amine-containing side chain to the C-terminus. For example, a glutamic acid residue may be added to the C-terminus to generate two available carboxylic acid sites for pegylation (the glutamic acid α- and γ-carboxyl groups). Addition of a reactive group to the C-terminus is not predicted to substantially hinder the activity of the anti-FcRn peptide, based upon the peptide truncation studies described in Example 7.

C-Terminal Linker.

Monomeric peptides may be multimerized with a C-terminal linker containing a reactive group, e.g., as described in Example 12. For example, Peptide No. 278 has a C-terminal linker containing an amine group that can be pegylated.

Side Chain(s).

In some embodiments, the reactive group may be located in, e.g., an amino acid side chain (including, e.g., amino acids containing a side chain amine such as, e.g., 2,3-diaminopropionic acid, 2,4-diaminobutyric acid, ornithine, and lysine; amino acids containing a side chain carboxylic acid such as, e.g., aspartic acid and glutamic acid; and amino acids containing a side chain thiol group such as, e.g., cysteine and penicillamine).

In certain embodiments, the peptide described herein comprises an amino acid side chain that may be pegylated.

In other embodiments, suitable pegylation sites may be obtained by replacement of one or more amino acids of a given sequence with an amino acid containing a desired reactive group. For example, because the peptide alanine scan studies described in Example 7 indicated that the arginine-2, threonine-5, and proline-13 residues of Peptide No. 501 could be substituted for alanine without significant loss in in vitro potency, it is possible that 1, 2, or all of those amino acids could also be replaced by an amino acid containing a desired reactive group without significant loss in in vitro potency. In some embodiments, the arginine-2, threonine-5, and proline-13 residues of Peptide No. 1 may be replaced by, e.g., amino acids containing a side chain amine such as, e.g., 2,3-diaminopropionic acid, 2,4-diaminobutyric acid, ornithine, and lysine; amino acids containing a side chain carboxylic acid such as, e.g., aspartic acid and glutamic acid; and amino acids containing a side chain thiol group such as, e.g., cysteine). In some embodiments, such a substitution may result in a peptide with no loss in in vitro potency, as compared to the original peptide, or in at least 1, 2, 3, 4, 5, 6, 7, 8, 9, 10, 15, 20, 30, 40, 50, 60, 70, 75, 80, 85, 90, 95, 97, 98, or 99% of the in vitro potency of the original peptide, as measured by, e.g., the IgG-peptide competition assay as described in Example 4, Biacore, or KinExA (Kinetic Exclusion Assay).

(3) Incorporation of Pegylated Building Blocks

In other embodiments, the peptides described herein may be synthesized by incorporation of amino acid building blocks comprising PEG moieties.

C. Peptide Conjugates

In some embodiments, peptides of the invention are provided as conjugates, including, e.g., covalent and non-covalent conjugates, comprising a peptide and a second molecule, which may be, e.g., a protein, a peptide, a small molecule, a polymer, or a nucleic acid. In some embodiments, the second molecule may confer a desired property to a peptide described herein, such as, e.g., extended half-life, stability, and/or enhanced transport. In some embodiments, the second molecule may enhance the efficacy of a peptide of the invention, as measured by, e.g., the IgG competition ELISA as shown in Example 4. In some embodiments, the second molecule may enhance the efficacy of a peptide of the invention, as measured by, e.g., overall reduction in serum IgG levels in cynomolgus monkeys or by comparison of the frequency of administration of conjugated peptide needed to obtain a particular therapeutic effect, as compared to the unconjugated peptide. In further embodiments, for example, the second molecule may result in targeting of the peptide to a particular cell, tissue, and/or organ.

In some embodiments, the conjugates may have an increased ability to block the IgG-FcRn. In other embodiments, the conjugates may protect the peptide from degradation and thus enhance the in vivo efficacy of the peptide. In some embodiments, the conjugates may have increased circulation half-lives. In further embodiments, such conjugates may be more efficient in binding and neutralizing other molecules than a peptide of the invention. In other embodiments, conjugates may facilitate purification.

In some embodiments, the second molecule of a conjugated peptide of the invention may be an Fc domain of IgG or a fragment thereof. The IgG may be, e.g., human IgG, such as, e.g., human IgG1, IgG2, or IgG4. In some embodiments, the IgG is an altered or mutated IgG, such as, e.g., a Pro331Ser $Fc_{\gamma 2}$ variant, Leu235Ala $Fc_{\gamma 4}$ variant, Leu234Val $Fc_{\gamma 1}$ variant, Leu235Ala $Fc_{\gamma 1}$ variant, or Pro331Ser $Fc_{\gamma 1}$ variant. In some embodiments, the second molecule may be an IgG fragment that comprises, e.g., hinge, CH2, and/or CH3 domains.

In some embodiments, the second molecule of a conjugated peptide of the invention may be albumin, an albumin fragment, or an albumin-binding molecule (such as, e.g., peptides, proteins, and molecules including, e.g., long alkyl chains, that bind non-covalently to albumin). Such conjugates may have longer in vivo half-lives and may thus require a lower peptide doses to achieve the desired therapeutic effect. See, e.g., Chuang et al., *Pharm. Res.* 19:569 (2002); U.S. Pat. No. 6,685,179.

Conjugates of the peptides of the invention with proteins, peptides, small molecules, polymers, or nucleic acids may be prepared according to any of the conjugation chemistries known in the art or described herein. For example, in some embodiments, peptides may be capped by a hydrophobic aromatic capping reagents for non-covalent binding to albumin as in, e.g., Zobel et al., *Bioorg. Med. Chem. Lett.* 13:1513 (2003). In other embodiments, peptides modified with thiol-reactive groups can be used for covalent conjugation to free cysteine residues as in, e.g., Kim et al., *Diabetes* 52:751 (2003). In further embodiments, a peptide of the invention containing an aldehyde may be reacted with a second molecule by reductive alkylation reaction as in, e.g., Kinstler, *Adv. Drug Del. Rev.* 54:477 (2002). Alternatively, where the second molecule is a protein or a peptide having an N-terminal cysteine, a peptide thioester may be reacted with the second molecule to form a covalent conjugate as described in, e.g., Dawson and Kent, *Annu. Rev. Biochem.* 69:923 (2000). Peptide-protein and peptide-peptide conjugates may also, in certain embodiments where all amino acids are encoded amino acids, be prepared by expression in an appropriate host cell.

D. Exemplary Peptide Conjugates

Exemplary Embodiment 76

A conjugate comprising the peptide of any one of embodiments 1 to 75 and a second molecule.

Exemplary Embodiment 77

The conjugate of embodiment 76, wherein the second molecule is chosen from albumin, transferrin, and the Fc portion of an immunoglobulin.

Exemplary Embodiment 78

The conjugate of embodiment 77, wherein the second molecule is the Fc portion of an immunoglobulin.

Exemplary Embodiment 79

The conjugate of embodiment 78, wherein the immunoglobulin is chosen from $IgG_1$, $IgG_2$, $IgG_3$, and $IgG_4$.

III. OTHER PEPTIDES

In some embodiments, the peptides of the invention are not derivatized. Exemplary embodiments of such peptides are set forth below.

Exemplary Embodiment A

A peptide having the sequence:

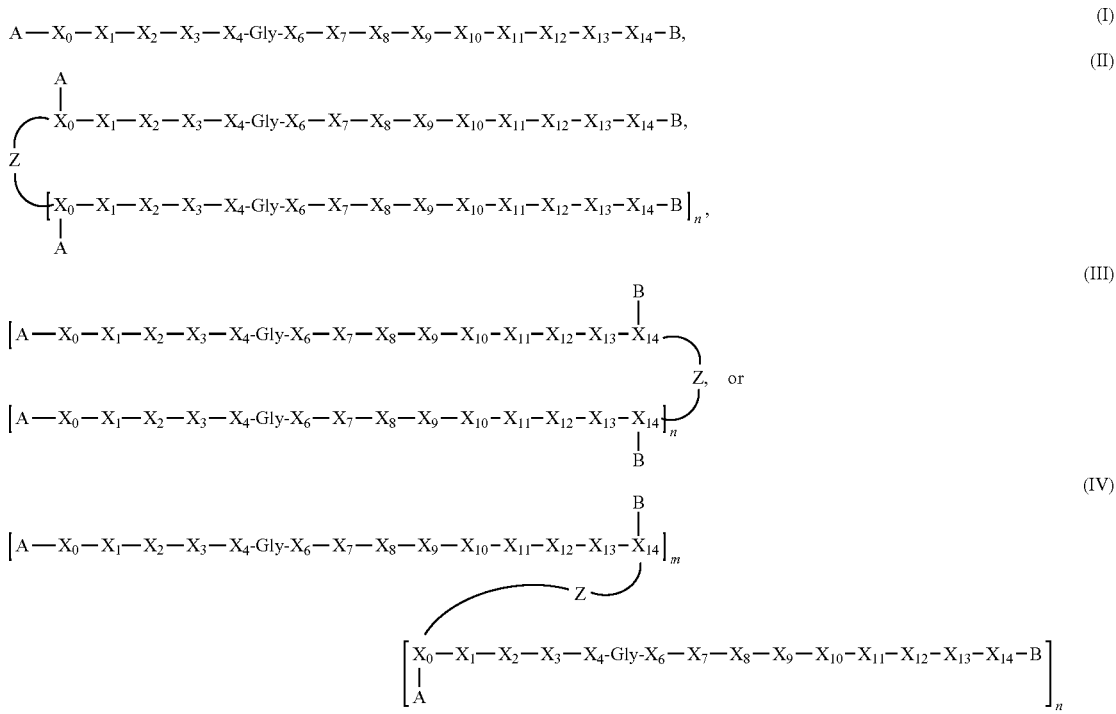

wherein:
A, if present, is hydrogen, acyl, or an amino protecting group;
B, if present, comprises Q or is an amino group, a hydroxyl group, or a carboxy protecting group;
Q, if present, is an amine group (which may be neutral or positively charged), wherein the amine group is attached to a peptide by an alkylene group, where the alkylene groups include but are not limited to ethylene, n-propylene, n-butylene, n-pentylene, and n-hexylene; or by a combination of alkylene groups and alkylene oxide subunits, where the alkylene oxide subunits include but are not limited to —(CH$_2$—CH$_2$—O)$_p$—, where p is 1, 2, 3, 4, or 5. Non-limiting examples of Q include
—CH$_2$—C$_{1-12}$—NH$_2$,
—CH$_2$—CH$_2$—CH$_2$—CH$_2$—NH$_2$,
—CH$_2$—CH$_2$—CH$_2$—CH$_2$—CH$_2$—CH$_2$—NH$_2$,
—CH$_2$—CH$_2$—O—CH$_2$—CH$_2$—NH$_2$,
—(CH$_2$—CH$_2$—O)$_2$—CH$_2$—CH$_2$—NH$_2$, and
—(CH$_2$—CH$_2$—O)$_3$—CH$_2$—CH$_2$—NH$_2$;

$X_0$, if present, is an amino acid or an analog thereof or is an optionally derivatized peptide of 2-15 amino acids or an analog thereof;

$X_1$, if present, is an amino acid or an analog thereof;

$X_2$, if present, is an amino acid or an analog thereof;

$X_3$ is an amino acid or analog thereof that is capable of forming a bridge with $X_{10}$, $X_{12}$ or $X_{13}$;

$X_4$ is an amino acid or an analog thereof or an optionally derivatized peptide of 2 or 4 amino acids or an analog thereof;

$X_6$ is a basic amino acid or an analog thereof, an aromatic amino acid or an analog thereof, or a basic aromatic amino acid or an analog thereof;

$X_7$ is phenylalanine or an analog thereof;

$X_8$ and $X_9$ are each independently chosen from glycine or an analog thereof, sarcosine or an analog thereof, aspartic acid or an analog thereof, a D-amino acid or an analog thereof, and α-aminoisobutyric acid or an analog thereof, or $X_8$, when taken together with $X_9$, forms a dipeptide analog;

$X_{10}$ is an amino acid or an analog thereof, or $X_{10}$, when taken together with $X_9$, forms a dipeptide analog;

$X_{11}$ is tyrosine or an analog thereof;

$X_{12}$ is an amino acid or an analog thereof;

$X_{13}$, if present, is an amino acid or an analog thereof;

$X_{14}$, if present, is an amino acid or an analog thereof or is a peptide of 2-15 amino acids or an analog thereof;

Z is a linker that attaches to each peptide monomer through
A;
B;
the amino terminus or a side chain of $X_0$, if $X_0$ is present; to the amino terminus or side chain of $X_1$, if $X_0$ is absent; to the amino terminus or side chain of $X_2$, if both $X_0$ and $X_1$ are absent; or to the amino terminus or side chain of $X_3$, if $X_0$, $X_1$ and $X_2$ are absent; or
the carboxy terminus or a side chain of $X_{14}$, if $X_{14}$ is present; to the carboxy terminus or a side chain of $X_{13}$, if $X_{14}$ is absent; or to the carboxy terminus or a side chain of $X_{12}$ if both $X_{13}$ and $X_{14}$ are absent;

m is an integer chosen from 1, 2, and 3; and
n is an integer chosen from 1, 2, and 3;
wherein:
each A, B, $X_0$, $X_1$, $X_2$, $X_3$, $X_4$, $X_6$, $X_7$, $X_8$, $X_9$, $X_{10}$, $X_{11}$, $X_{12}$, $X_{13}$, and $X_{14}$ is chosen independently; and
each monomer of the peptide ranges from 10 to 50 amino acids in length.

It will be appreciated by the skilled artisan that if Z is attached to the peptide through a side chain of $X_0$, then A is necessarily present. Similarly, if Z is attached to a side chain of $X_{14}$, then B is necessarily present.

Exemplary Embodiment B

The peptide of embodiment A, wherein B is Q.

Exemplary Embodiment C

The peptide of embodiment B, wherein B is —(W)$_m$—(CH$_2$)$_r$—NH$_2$, where W, if present, is —(CH$_2$)$_p$, —(CH$_2$—CH$_2$)$_p$, —(CH$_2$—O)$_p$—, or

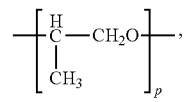

and where m is 1, 2, 3, 4, or 5, r is 1, 2, or 3, and p is 1, 2, 3, 4, 5.

Exemplary Embodiment D

The peptide of embodiment C, wherein $X_3$ forms a bridge with $X_{13}$.

Exemplary Embodiment E

The peptide of embodiment D, wherein the bridge is a side chain to side chain bridge.

Exemplary Embodiment F

The peptide of embodiment B, wherein $X_6$ is histidine or an analog thereof.

Exemplary Embodiment G

The peptide of embodiment B, wherein at least one of $X_8$ and $X_9$ is chosen from:
glycine;
D-amino acids;
α-aminoisobutyric acid; and
sarcosine.

Exemplary Embodiment H

The peptide of embodiment B, wherein $X_{14}$ is absent.

Exemplary Embodiment I

The peptide of embodiment B, wherein n is 1.

Exemplary Embodiment J

The peptide of embodiment B, wherein the peptide has the sequence:

(SEQ ID NOS 1 and 2)

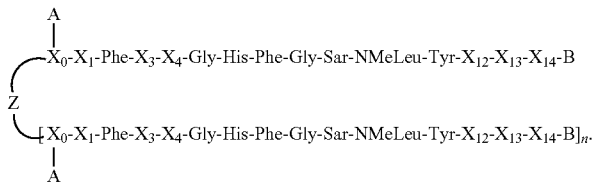

Exemplary Embodiment K

The peptide of embodiment J, wherein the peptide has the sequence:

(SEQ ID NOS 3 and 3)

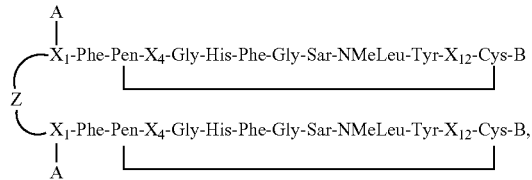

wherein horizontal brackets indicate the presence of a bridge.

Exemplary Embodiment L

The peptide of embodiment B, wherein the peptide has the sequence:

(SEQ ID NOS 4 and 5)

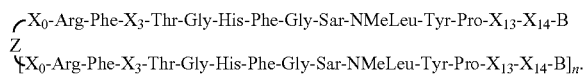

Exemplary Embodiment M

The peptide of embodiment L, wherein the peptide has the sequence:

(SEQ ID NOS 6 and 6)

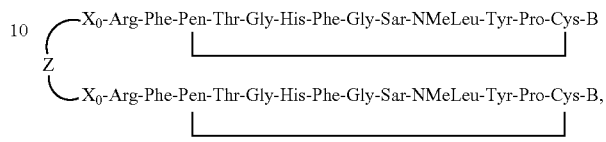

wherein horizontal brackets indicate the presence of a bridge.

Exemplary Embodiment N

The peptide of embodiment M, wherein the peptide has the sequence:

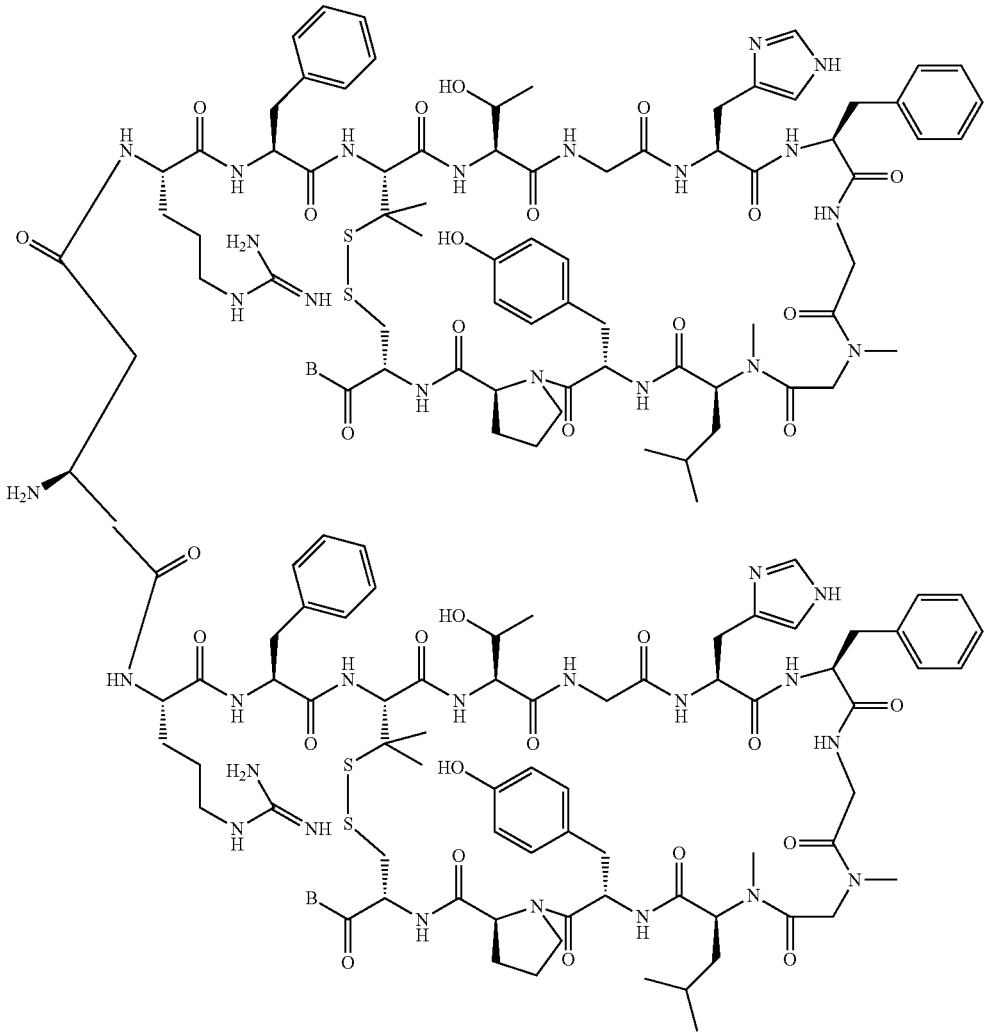

where B is —W—CH$_2$—CH$_2$—NH$_2$, where W, if present, is —(CH$_2$)$_p$, —(CH$_2$—CH$_2$)$_p$, —(CH$_2$—O)$_p$—, or

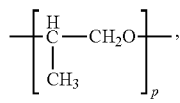

where p is 1, 2, 3, 4, 5.

Exemplary Embodiment O

The peptide of embodiment M, wherein W is absent.

Exemplary Embodiment P

The peptide of embodiment M, wherein W is —(CH$_2$—CH$_2$)—.

Exemplary Embodiment Q

The peptide of embodiment M, wherein W is —(CH$_2$—CH$_2$—O)$_p$— and p is 1.

Exemplary Embodiment R

The peptide of embodiment M, wherein W is —(CH$_2$—CH$_2$—O)$_p$— and p is 2.

IV. METHODS FOR SCREENING AND DISCOVERING PEPTIDES THAT BIND FCRN AND BLOCK THE FCRN-IGG INTERACTION

Peptides binding to FcRn may be identified using phage display libraries. Phage display libraries may be readily generated as described in Smith and Petrenko, *Chem. Rev.* 87:391 (1997). Alternatively, phage display libraries may be acquired from a commercial source, such as, e.g., Dyax Corp. (Cambridge, Mass.). Depending on the screening conditions, phage may be identified with a variety of different properties. To identify peptides that bind to FcRn (and thus compete with IgG for FcRn binding), a phage library may be screened for binding to FcRn and by competition with IgG. Optionally, peptides that bind to alternate receptors may be eliminated from the library by incubating the phage library with one or more alternate receptors. Thus, phage that bound the alternate receptor(s) would be depleted from the desired pool of phage. By sequencing the DNA of phage clones capable of binding to FcRn, peptides capable of binding to FcRn and inhibiting IgG-FcRn binding may be identified.

Examples of other methods to identify FcRn-binding peptides include: mRNA display (Roberts and Szostak, *Proc. Nat. Acad. Sci. USA* 94:12297 (1997), cell-based display (Boder and Wittrup, *Nat. Biotechnol.* 15:553 (1997), and synthetic peptide libraries (Lam, *Nature* 354:82 (1991); Houghten et al., Nature 354:84 (1991)).

V. METHODS FOR ASSAYING PEPTIDES THAT BIND TO FCRN AND BLOCK THE IGG:FCRN INTERACTION

A number of methods may be used to assess the ability of a peptide or peptidomimetic to bind FcRn and block the FcRn:IgG interaction. For example, surface plasmon resonance (SPR) is a method well known in the art to evaluate binding events (Biacore AB, Uppsala, Sweden). Using this method, one of the binding partners (FcRn or IgG) is immobilized on the SPR sensor chip and while the other binding partner is passed over the chip, which is monitored for a resulting signal. In the same experiment, the peptide to be evaluated as a competitor of the interaction between IgG and FcRn is passed over the chip. Any decrease in signal may be interpreted as a measure of the peptide's ability to block the interaction between FcRn and IgG.

Other methods for assaying for possible peptide inhibitors of the IgG:FcRn interaction are also well known in the art. One such method is an IgG competition assay in a 96-well plate format. In this example assay, soluble human FcRn on a 96-well plate is exposed to IgG and a test peptide. Residual bound IgG, as detected by an anti-IgG antibody and standard ELISA visualization reagents, provide a measure of the peptide's ability to block the FcRn-IgG interaction.

The ability of a peptide to block IgG-FcRn binding may also be carried out on cells transfected with DNA encoding a human FcRn to develop a cell line capable of expressing human FcRn on its cell surface. A binding competition assay may be applied where peptide inhibitors of IgG-FcRn binding compete with a fluorescently labeled IgG molecule. The level of residual IgG bound to the cells may be measured using, e.g., a standard fluorescent activated cell sorter (FACS).

VI. PHARMACEUTICAL USES OF IMMUNOMODULATORY PEPTIDES

The peptides of the invention bind FcRn and inhibit the Fc portion of the IgG constant region from binding to FcRn resulting in increased catabolism of IgG in comparison to the catabolism of IgG in the absence of peptides of the invention. In exemplary embodiments, the IgG constant region is from the IgG1, IgG2, IgG3, or IgG4 subclasses.

A. Preparation of Pharmaceutical Compositions

The peptides of the invention may be used in the manufacture of a medicament (pharmaceutical composition) for the treatment of any disease or condition where increased catabolism of IgG may be desired. Accordingly, the invention provides pharmaceutical compositions comprising at least one peptide of the invention. These compositions will typically include a pharmaceutically acceptable carrier or excipient. Examples of suitable pharmaceutical carriers are described in *Remington's Pharmaceutical Sciences* by E. W. Martin. Examples of excipients can include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

The pharmaceutical compositions of the invention may be formulated for administration to a patient in need thereof by any reasonable route of administration, including e.g., intravenously, subcutaneously, intra-muscularly, orally, sublingually, buccally, sublingually, nasally, rectally, vaginally or by inhalation. In some embodiments the peptides of the may be implanted within or linked to a biopolymer solid support that allows for the slow release of the peptide.

For oral administration, the pharmaceutical composition may take the form of tablets or capsules prepared by conventional means. The composition can also be prepared as a liquid, for example as a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal and sublingual administration the composition may take the form of tablets or lozenges according to conventional protocols.

For administration by inhalation, the compounds for use according to the present invention are conveniently delivered in the form of an aerosol spray from a pressurized pack or nebulizer (e.g., in PBS), with a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can be formulated for parenteral administration (including, e.g., intravenous or intramuscular administration) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, such as, e.g., pyrogen free water.

The pharmaceutical composition can also be formulated for rectal administration as a suppository or retention enema, e.g., containing conventional suppository bases such as cocoa butter or other glycerides.

B. Exemplary Pharmaceutical Compositions

Exemplary Embodiment 80

A pharmaceutical composition comprising a therapeutically effective amount of the peptide of any one of embodiments 1 to 75 or A to R or a therapeutically effective amount of the conjugate of any one of embodiments 76 to 79.

Exemplary Embodiment 81

The composition of embodiment 80, wherein the therapeutically effective amount of the peptide is capable of decreasing the serum concentration of human IgG as compared to the serum concentration of human IgG before treatment with the peptide.

Exemplary Embodiment 82

The composition of embodiment 81, wherein the decrease in the serum concentration of human IgG is at least 5%.

Exemplary Embodiment 83

The composition of embodiment 82, wherein the decrease in the serum concentration of human IgG is at least 15%.

Exemplary Embodiment 84

The composition of embodiment 83, wherein the decrease in the serum concentration of human IgG is at least 25%.

C. Methods of Treatment

The pharmaceutical compositions of the invention are useful to treat any disease or condition, where increased catabolism of IgG is desirable. Thus, the invention provides methods of treating diseases characterized by inappropriately expressed IgG antibodies or undesired amounts or levels of IgG, comprising administering a therapeutically effective amount of a peptide of the invention to a patient in need thereof. In some embodiments, the invention provides methods for treating a disease by modulating the serum concentration of IgG with the peptides of the invention. The terms "treat," treatment," and "treating" refer to (1) a reduction in severity or duration of a disease or condition, (2) the amelioration of one or more symptoms associated with a disease or condition without necessarily curing the disease or condition, or (3) the prevention of a disease or condition.

In certain embodiments, the methods of the invention may be employed to treat, prevent, or regulate autoimmune diseases including, but not limited to alopecia greata, ankylosing spondylitis, antiphospholipid syndrome, autoimmune Addison's disease, autoimmune hemolytic anemia, autoimmune hepatitis, autoimmune lymphoproliferative syndrome, autoimmunethrombocytopenic purpura, Behcet's disease, bullous pemphigoid, cardiomyopathy, celiac sprue-dermatitis herpetiformis, chronic fatigue immune dysfunction syndrome, chronic inflammatory demyelinating polyneuropathy, cicatricial pemphigoid, CREST syndrome, cold agglutinin disease, Crohn's disease, Degos' disease, dermatomyositis, dermatomyositis-juvenile, discoid lupus, essential mixed cryoglobulinemia, fibromyalgia-fibromyositis, Graves' disease, Guillain-Barré syndrome, Hashimoto's thyroiditis, idiopathic pulmonary fibrosis, idiopathic thrombocytopenia purpura, IgA nephropathy, insulin dependent diabetes, juvenile arthritis, lichen planus, lupus, Ménière's disease, mixed connective tissue disease, multiple sclerosis, myasthenia gravis, pemphigus (including, e.g., pemphigus vulgaris), pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiffman syndrome, Takayasu arteritis, temporal arteritis/giant cell arteritis, transplant rejection, ulcerative colitis, uveitis, vasculitis, vitiligo, and Wegener's granulomatosis.

In some embodiments, the autoimmune disease is chosen from bullous pemphigoid, idiopathic thrombocytopenia purpura (ITP), myasthenia gravis (MG), pemphigus (including, e.g., pemphigus vulgaris), and transplant rejection.

In certain embodiments, compositions comprising the peptides of the invention may be used in combination with steroids for immunosuppression.

The peptides of the invention may be used to treat inflammatory disorders including, but not limited to, asthma, ulcerative colitis and inflammatory bowel syndrome allergy, including allergic rhinitis/sinusitis, skin allergies (including, e.g., urticaria (i.e., hives), angioedema, atopic dermatitis), food allergies, drug allergies, insect allergies, mastocytosis, arthritis, including osteoarthritis, rheumatoid arthritis, and spondyloarthropathies. In some embodiments, the invention provides methods of treating cardiovascular disease with an inflammation-based etiology (e.g., arterial sclerosis), transplant rejection, and/or graft versus host disease (GVHD).

Other embodiments of the invention include methods of treating cancer by administering a peptide of the invention. The methods of the invention may be employed to treat or help regulate cancers involving overproduction of IgG, such as plasma cell cancers, including multiple myeloma.

Frequently, in diseases or conditions requiring administration of a therapeutic protein, the subject will develop antibodies against the therapeutic protein, which, in turn, prevent the therapeutic protein from be available for its intended therapeutic purpose. Accordingly, the peptides of the invention can be used in combination with the therapeutic protein to enhance the benefit of the therapeutic protein by reducing the levels of IgG; wherein, IgG antibodies are responsible for the decreased bioavailability of a therapeutic protein. Accordingly, some embodiments of the invention provide methods of regulating, treating, or preventing a condition, disease, or disorder resulting from an immune response to a clotting factor comprising contacting a cell with a therapeutically effective amount of any of the peptides disclosed herein, wherein the clotting Factor is chosen from fibrinogen, prothrombin, Factor V, Factor VII, Factor VIII, Factor IX, Factor X, Factor XI, Factor XII, Factor XIII, or von Willebrand's Factor. This method may be used to regulate or treat, or prevent an immune response to a clotting factor in a patient suffering, e.g., from hemophilia A or hemophilia B. In some embodiments, peptides of the present invention block Factor VIII inhibitors. In other embodiments, the method may be used to regulate or treat, or prevent an immune response to, e.g., therapeutic erythropoietin in a patient suffering from pure red cell aplasia (PRCA). The invention further provides methods of regulating, treating, or preventing an immune reaction to a lysosomal hydrolase, the absence of which results in a lysosomal storage disorder, such as, e.g., α-galactosidase A, acid ceramidase, acid α-L-fucosidase, acid β-glucosidase (glucocerebrosidase) acid β-galactosidase, iduronate-2-sulfatase, α-L-iduronidase, galactocerebrosidase, Acid α-mannosidase, acid β-mannosidase, arylsulfatase B, arylsulfatase A, N-acetylgalactosamine-6-sulfate sulfatase, acid β-galactosidase, Acid sphingomyelinase, acid α-glucosidase, β-hexosaminidase B, heparan N-sulfatase, α-N-acetylglucosaminidase, acetyl-CoA:α-glucosaminide, N-acetyltransferase, N-acetylglucosamine-6-sulfate sulfatase, α-N-acetylgalactosaminidase, sialidase, β-glucuronidase, and β-hexosaminidase A.

In other embodiments, the methods of the invention may be employed to treat, prevent, or regulate an immune reaction to a gene therapy vector. Obstacles to the successful implementation of gene therapy for the treatment of a disease or condition also include the development of antibodies specific to the therapeutic protein encoded by the transgene as well as possibly to the vector used to deliver the transgene. Accordingly, in some embodiments, the peptides described herein can be administered in combination with gene therapy to enhance the benefit of the encoded therapeutic protein by reducing the levels of IgG. These methods are particularly useful in situations where IgG antibodies are responsible for the decreased bioavailability of a gene therapy vector or the encoded therapeutic protein. The gene therapy vector may be, e.g., a viral vector such as adenovirus and adeno associated virus. Diseases that can be treated using gene therapy include, but are not limited to, cystic fibrosis, hemophilia, PRCA, muscular dystrophy, or lysosomal storage diseases, such as, e.g., Gaucher's disease and Fabry's disease.

In the methods of the invention, the compositions described herein can be administered via any suitable route, such as, e.g., intravenously, subcutaneously, intra-muscularly, orally, sublingually, buccally, sublingually, nasally, rectally, vaginally or by inhalation. In general, the appropriate dose of a composition described herein will vary depending on the disease or condition to be treated, the severity of the disease or conditions, the subject, including the gender, age, and weight of the subject, the desired outcome, and the particular route of administration used. For example, dosages can range from 0.1 to 100,000 µg/kg body weight. In some embodiments, the dosing range may be 1-10,000 µg/kg. In other embodiments, the dosing range may be 10-1,000 µg/kg. In yet further embodiments, the dosing range is 100-500 µg/kg.

The compositions of the invention may be administered continuously or at specific timed intervals. In vitro assays may be employed to determine optimal dose ranges and/or schedules for administration. Other effective dosages can be readily determined by one of ordinary skill in the art through routine trials establishing dose response curves, for example, the amount of the peptides of the invention necessary to increase or decrease the level of IgG can be calculated from in vivo experimentation. Those of skill will readily appreciate that dose levels can vary as a function of the specific compound, the severity of the symptoms, and the susceptibility of the subject to side effects, and preferred dosages for a given compound are readily determinable by those of skill in the art by a variety of means. For example, those skilled in the art can calculate an appropriate dose using readily available information with respect to the amount necessary to have the desired effect, depending upon the particular agent used.

D. Exemplary Method of Treatment Embodiments

Exemplary Embodiment 85

A method of treating a disease characterized by inappropriately expressed IgG antibodies or excess IgG, comprising administering the composition of any one of embodiments 80 to 84 to a patient in need thereof.

Exemplary Embodiment 86

The method of embodiment 85, wherein the disease is an immune reaction to a therapeutic protein chosen from erythropoietin, a lysosomal hydrolase, the absence of which results in a lysosomal storage disorder, and a clotting factor.

Exemplary Embodiment 87

The method of embodiment 86, wherein the lysosomal hydrolase is chosen from the group consisting of α-galactosidase A, acid ceramidase, acid α-L-fucosidase, acid β-glucosidase (glucocerebrosidase), acid β-galactosidase, iduronate-2-sulfatase, α-L-iduronidase, galactocerebrosidase, acid α-mannosidase, acid β-mannosidase, arylsulfatase B, arylsulfatase A, N-acetylgalactosamine-6-sulfate sulfatase, acid β-galactosidase, acid sphingomyelinase, acid α-glucosidase, β-hexosaminidase B, heparan N-sulfatase, α-N-acetylglucosaminidase, acetyl-CoA:α-glucosaminide, N-acetyltransferase, N-acetylglucosamine-6-sulfate sulfatase, α-N-acetylgalactosaminidase, sialidase, β-glucuronidase, and β-hexosaminidase A.

Exemplary Embodiment 88

The method of embodiment 86, wherein the clotting factor is selected from fibrinogen, prothrombin, Factor V, Factor VII, Factor VIII, Factor IX, Factor X, Factor XI, Factor XII, Factor XIII, and von Willebrand's Factor.

Exemplary Embodiment 89

The method of embodiment 85, wherein the IgG is specific for a gene therapy vector.

Exemplary Embodiment 90

The method of embodiment 89, wherein the disease is chosen from inflammatory diseases, autoimmune diseases, and cancer.

Exemplary Embodiment 91

The method of embodiment 90, wherein the autoimmune disease is chosen from alopecia greata, ankylosing spondylitis, antiphospholipid syndrome, autoimmune Addison's disease, autoimmune hemolytic anemia, autoimmune hepatitis, autoimmune lymphoproliferative syndrome, autoimmune thrombocytopenic purpura, Behcet's disease, bullous pemphigoid, cardiomyopathy, celiac sprue-dermatitis herpetiformis, chronic fatigue immune dysfunction syndrome, chronic inflammatory demyelinating polyneuropathy, cicatricial pemphigoid, CREST syndrome, cold agglutinin disease, Crohn's disease, Degos' disease, dermatomyositis, dermatomyositis-juvenile, discoid lupus, essential mixed cryoglobulinemia, fibromyalgia-fibromyositis, Graves' disease, Guillain-Barré syndrome, Hashimoto's thyroiditis, idiopathic pulmonary fibrosis, idiopathic thrombocytopenia purpura, IgA nephropathy, insulin dependent diabetes, juvenile arthritis, lichen planus, lupus, Ménière's disease, mixed connective tissue disease, multiple sclerosis, myasthenia gravis, pemphigus, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiffman syndrome, Takayasu arteritis, temporal arteritis/giant cell arteritis, transplant rejection, ulcerative colitis, uveitis, vasculitis, vitiligo, and Wegener's granulomatosis.

Exemplary Embodiment 92

The method of embodiment 91, wherein the autoimmune disease is chosen from bullous pemphigoid, idiopathic thrombocytopenia purpura, myasthenia gravis, pemphigus, and transplant rejection.

Exemplary Embodiment 93

The method of embodiment 92, wherein the pemphigus is pemphigus vulgaris.

Exemplary Embodiment 94

The method of embodiment 91, wherein the disease is an inflammatory disease.

Exemplary Embodiment 95

The method of embodiment 94, wherein the inflammatory disease is chosen from asthma, ulcerative colitis and inflammatory bowel syndrome allergy, including allergic rhinitis/sinusitis, skin allergies, food allergies, drug allergies, insect allergies, mastocytosis, arthritis, including osteoarthritis, rheumatoid arthritis, and spondyloarthropathies.

Exemplary Embodiment 96

The method of embodiment 95, wherein the skin allergy is chosen from urticaria, angioedema, and atopic dermatitis.

VII. IN VIVO IMAGING AND DETECTION OF FCRN

The peptides of the invention may be used in assays to detect FcRn. In some embodiments, the assay is a binding assay that detects binding of a peptide of the invention with FcRn. In some embodiments, FcRn may be immobilized, and one or more peptides described herein may passed over the immobilized FcRn. In alternative embodiments, one or more peptides may be immobilized, and FcRn may be passed over the immobilized peptide(s). Either FcRn or the peptides of the invention may be detectably labeled. Suitable labels include radioisotopes, including, but not limited to $^{64}$Cu, $^{67}$Cu, $^{90}$Y, $^{111}$In, $^{124}$I, $^{125}$I, $^{131}$I, $^{137}$Cs, $^{186}$Re, $^{211}$At, $^{212}$Bi, $^{213}$Ra, $^{223}$Ra, $^{241}$Am, $^{2144}$Cm, and $^{99m}$Tc-MDP; enzymes having detectable products (for example, luciferase, peroxidase, alkaline phosphatase, β-galactosidase, and the like); fluorophores (including, e.g., fluorescein (which may be attached as, e.g., fluorescein isothiocyanate), rhodamine, phycoerythrin, phycocyanin, allophycocyanin, o-phthaldehyde and fluorescamine); fluorescence emitting metals, for example, $^{152}$Eu, or others of the lanthanide series, attached to the peptides of the invention through metal chelating groups such as EDTA; chemiluminescent compounds, for example, luminol, isoluminol, theromatic acridinium ester, acridinium salts, imidazole, and oxalate esteror; and bioluminescent compounds, for example, luciferin, or aequorin (green fluorescent protein), specific binding molecules, for example, magnetic particles, microspheres, nanospheres, luminescent quantum dot nanocrystals, and the like.

Alternatively, specific-binding pairs may be used in assays to detect FcRn, involving, for example, a second stage antibody or reagent that is detectably labeled and that can amplify the signal. For example, the peptides of the invention can be conjugated to biotin, and horseradish peroxidase-conjugated streptavidin added as a second stage reagent. Digoxin and antidigoxin provide another suitable binding pair. In other embodiments, a second stage antibody can be conjugated to an enzyme such as peroxidase in combination with a substrate that undergoes a color change in the presence of the peroxidase. The absence or presence of binding between peptides of the invention and FcRn can be determined by various methods, including flow cytometry of dissociated cells, microscopy, radiography, fluorimetry, chromogenic detection, phosphor imaging, detection of chemiluminescence on film and scintillation counting. Such reagents and their methods of use are well known in the art.

For in vivo diagnostic applications, specific tissues or even specific cellular disorders that may be characterized, at least in part, by expression of FcRn, may be imaged by administration of a sufficient amount of a labeled peptide of the invention.

A wide variety of metal ions suitable for in vivo tissue imaging have been tested and utilized clinically. For imaging with radioisotopes, the following characteristics are generally desirable: (a) low radiation dose to the patient; (b) high photon yield which permits a nuclear medicine procedure to be performed in a short time period; (c) ability to be produced in sufficient quantities; (d) acceptable cost; (e) simple preparation for administration; and (f) no requirement that the patient be sequestered subsequently. These characteristics generally translate into the following: (a) the radiation exposure to the most critical organ is less than 5 rad; (b) a single image can be obtained within several hours after infusion; (c) the radioisotope does not decay by emission of a particle; (d) the isotope can be readily detected; and (e) the half-life is less than four days (Lamb and Kramer, "Commercial Production of Radioisotopes for Nuclear Medicine," *In Radiotracers For Medical Applications*, Vol. 1, Rayudu (Ed.), CRC Press, Inc., Boca Raton, pp. 17-62). In some embodiments, the metal is technetium-99m ($^{99m}$Tc).

Accordingly, the invention provides a method of obtaining an image of an internal region of a subject which comprises administering to a subject an effective amount of a composition comprising at least one of the peptides of the invention containing a metal in which the metal is radioactive, and recording the scintigraphic image obtained from the decay of the radioactive metal. Likewise, the invention provides methods for enhancing an magnetic resonance (MR) image of an internal region of a subject which comprises administering to a subject an effective amount of a composition comprising at least one of the peptides of the invention containing a metal in which the metal is paramagnetic, and recording the MR image of an internal region of the subject.

In some embodiments, other methods provided herein include a method of enhancing a sonographic image of an internal region of a subject comprising administering to a subject an effective amount of a composition comprising at least one of the peptides of the invention containing a metal and recording the sonographic image of an internal region of the subject. In general, the metal may be any non-toxic heavy metal ion. In certain embodiments, a method of enhancing an X-ray image of an internal region of a subject is also provided which comprises administering to a subject a peptide composition containing a metal, and recording the X-ray image of an internal region of the subject. In general, a radioactive, non-toxic heavy metal ion may be used.

Peptides of the invention may be linked to chelators such as those described in, e.g., U.S. Pat. No. 5,326,856. The peptide-chelator complex may then be radiolabeled to provide an imaging agent for diagnosis or treatment of diseases or conditions involving the regulation of IgG levels. The peptides of the invention may also be used in the methods that are disclosed in U.S. Pat. No. 5,449,761 for creating a radiolabeled peptide for use in imaging or radiotherapy.

A. Exemplary Methods of Detecting FcRn

Exemplary Embodiment 97

A method of detecting FcRn, comprising:
labeling the peptide of any one of embodiments 1 to 75 or the conjugate of any one of embodiments 76 to 79 with a detectable label chosen from radioisotopes, enzymes having detectable products, fluorophores, chemiluminescent compounds, magnetic particles, microspheres, nanospheres, biotin, streptavidin, and digoxin.

Exemplary Embodiment 98

The method of embodiment 97, wherein the peptide or conjugate labeled with a detectable label is included in a diagnostic kit.

VIII. PURIFICATION OF FcRn

The peptides of the invention may also be used to purify FcRn. In some embodiments, the peptide is covalently attached to an appropriate chromatographic matrix to form an efficient FcRn separation media. A solution containing FcRn is then passed over the chromatographic matrix resulting in the non-covalent binding of FcRn to the immobilized binding partner. Solutions containing FcRn may be from biological samples such as a bodily fluid, a tissue or cell sample, cell culture supernatant. The FcRn is purified by washing the immobilized peptide:FcRn complex with a suitable solution to remove impurities and then releasing the FcRn from the chromatographic matrix with a suitable elution solution.

Peptides of the invention can be attached to suitable chromatographic matrices using a number of chemical approaches well known to those skilled in the art. For example, peptides of the invention can be attached to matrices containing suitably reactive groups, such as thiols, amines, carboxylic acids, alcohols, aldehydes, alkyl halides, N-alkylmaleimides, N-hydroxysuccinimidyl esters, epoxides, aminooxys, and hydrazides.

In other embodiments, the peptides of the invention can be modified to contain chemical moieties or peptide sequences that bind non-covalently to an appropriate chromatographic matrix. For example, the peptides could be modified with a biotin moiety and could be non-covalently bound to a chromatographic matrix containing an avidin protein. Alternatively, the modified peptide could be incubated with the FcRn solution and the resulting mixture passed over the appropriate chromatographic matrix to isolate the FcRn:peptide complex.

Examples of similar uses of peptides for affinity purification can be found in Kelley et al, "Development and Validation of an Affinity Chromatography Step Using a Peptide Ligand for cGMP Production of Factor VIII," In Biotechnology and Bioengineering, Vol. 87, No. 3, Wiley InterScience, 2004, pp. 400-412 and in U.S. Pat. No. 6,197,526.

A. Exemplary Methods of Purifying FcRn

Exemplary Embodiment 99

A method of purifying FcRn, comprising:
(a) immobilizing the peptide of any one of embodiments 1 to 75 or A to R or the conjugate of any one of embodiments 76 to 79 to a solid support,
(b) contacting a solution containing FcRn with the immobilized peptide or conjugate on a solid support; and
(c) purifying FcRn by separating the solution from said solid support.

EXAMPLES

The Examples, which are intended to be purely exemplary of the invention and should therefore not be considered to limit the invention in any way, also describe and detail aspects and embodiments of the invention discussed above. The Examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric pressure.

Example 1

Expression of Soluble Human FcRn (shFcRn)

Soluble human FcRn cDNA was cloned, expressed and purified as described in the literature using the glutamine synthetase expression system in Chinese hamster ovary (CHO) cells. See, e.g., U.S. Pat. No. 5,623,053. A stop codon was placed after amino acid position 274 in the protein sequence of human FcRn in order to remove the transmembrane region.

Example 2

Transfection of HEK 293 Cells with Human FcRn

Human embryonic kidney (HEK) 293 cells (ATCC, Manassas, Va.) were transfected using the SuperFect Transfection Reagent (Qiagen, Valencia, Calif.) according to the manufacturer's recommended protocol. The full length FcRn cDNA construct (Story et al., *J. Exp. Med.* 180:2377-2381 (1994), Simister et al., *Eur. J. Immunol.* 26:1527-1531 (1996)) was originally cloned into pcDNA6 (Invitrogen, Carlsbad, Calif.) as the plasmid vector in order to generate the FcRn expression vector, FcRn:pCDNA6. The Human $\beta_2$m cDNA construct was originally cloned into pcDNA3 (Invitrogen) as the plasmid vector to generate the human $\beta_2$m expression vector, $\beta_2$m:pcDNA3 (Gussow et al., *J. Immunol.* 139:3132-3138 (1987)).

The day before transfection, HEK293 cells were seeded at $0.5$-$2.5 \times 10^6$ cells per 100 mm dish and incubated at 37° C. and 5% $CO_2$ for 16 hours in cDMEM. The composition of cDMEM contains: 1 L DMEM (Invitrogen #11995-065); 10 ml of 1 M HEPES, pH 7.55; 10 ml MEM amino acid solution (Invitrogen #11130-051); 10 ml MEM non-essential amino acid solution (Invitrogen #11140-050); 10 ml of 100 mM sodium pyruvate (Invitrogen #11360-070); 10 ml of Penicillin Streptomycin liquid (Invitrogen #15140-148); 10 ml L-glutamine solution (Invitrogen #25030-081); 1 ml 2-mercaptoethanol solution in 55 mM Dulbecco phosphate buffered saline (DPBS) (Invitrogen #21985-023); 100 ml heat-inactivated fetal bovine serum (FBS) (Invitrogen). On the day of the transfection, 5 µg of the FcRn:pCDNA6 construct and 5 µg of $\beta_2$m:pCDNA3 DNA were added to 290 µL of DMEM (Invitrogen). The solution was mixed for a few seconds and then centrifuged. Then, 60 µL of SuperFect Transfection Reagent (Qiagen) was added to the DNA solution and vortexed for 10 seconds. The DNA/SuperFect solution was incubated for 5 to 10 minutes at room temperature, during which time the media from the cell-containing dish was aspirated and the cells washed once with 4 ml of PBS. After the 5 to 10 minute incubation of the DNA/SuperFect, 3 ml of complete growth medium (cDMEM) was added to the DNA/SuperFect solution; the solution was mixed, and immediately added to the cells in the 100 mm dish.

The cells were incubated with the DNA/SuperFect solution for 2 to 3 hours at 37° C. and 5% $CO_2$. The media containing the DNA/SuperFect solution was removed from the cells the cells were washed 3 times with PBS and fresh cDMEM was added to the cells. After a 48 hour incubation, the medium was assessed by immunoblot analysis to determine if transient expression of the FcRn/$\beta_2$m complex had occurred. In addition, the cells were passaged at a ratio of 1:4 into cDMEM containing 250 µg/L Geneticin (Invitrogen) as an antibiotic and 5 µg/L Blasticidin to select for Blasticidin resistant stable transfectants. After 4 weeks of antibiotic selection, surviving cells were seeded into 96-well tissue culture plates at a density of 1 cell per well. Ultimately 12 clones were selected and each expanded and checked for expression by immunoblot analysis for FcRn and $\beta_2$m. The FcRn and $\beta_2$m-expressing 293 identified as possessing the highest level of expression was then used in subsequent assays.

Example 3

Screening of Phage Libraries for FcRn-IgG Inhibitors

Peptides capable of inhibiting the binding of the IgG Fc portion to FcRn were identified by screening filamentous phage display libraries licensed from Dyax Corp. (Cambridge, Mass.). More specifically, libraries TN-9-IV, TN10-X, TN-11-I and TN-12-I were used in combination in the screen. The total number of individual viable phage contained in each library was reflected by the number of transformants established for each library when the libraries were expressed in *E. coli* and plated at a clonal dilution as described by the Dyax protocol. The number of transformants for TN-9-IV, TN10-X, TN-11-I and TN-12-I was $3.2 \times 10^9$, $2 \times 10^9$, $2.7 \times 10^9$ and $1.4 \times 10^9$, respectively. The absolute number of viable phages in a given volume may be reported in plaque forming units (pfu) per unit volume.

A. Buffers Used in Phage Screening

The following buffers were used for the screening of FcRn-binding peptides.

1. NZCYM Broth: 10 g NZ Amine-A; 5 g sodium chloride; 5 g Bacto Yeast Extract (Difco); 1 g Casamino acids; 1 g magnesium sulfate anhydrous powder: ingredients were dissolved in 800 ml of water, adjusted to pH 7.5 with 1 N sodium hydroxide and then brought up to a total volume of 1 L with water and autoclaved for 20 min.
2. Binding buffer (BB): PBS, pH 6 plus 10 mM EDTA.C. NZCYM-T: NZCYM broth plus 12.5 µg/ml Tetracycline.
3. HBSS-E: Hank's Balanced Saline Solution (Invitrogen) plus 10 mM EDTA (Invitrogen).
4. Min A Salts: 10.5 g $K_2HPO_4$ (potassium phosphate dibasic); 4.5 g $KH_2PO_4$ (potassium phosphate monobasic); 1.0 g $(NH_4)_2SO_4$ (ammonium sulfate) and 0.5 g sodium citrate dissolved in 1 L water.
5. LB Broth: 10 g Bacto Tryptone; 5 g Bacto yeast extract; 10 g sodium chloride dissolved in 1 L water and autoclaved for 20 min.
6. CBS pH 2: 50 mM sodium citrate; 150 mM sodium chloride: buffer was brought to pH 2 with HCl and filter sterilized.
7. LB Agar: 30 g Bacto Tryptone; 15 g Bacto yeast extract; 30 g sodium chloride dissolved in 3 L water and autoclaved for 20 minutes.
8. LB Soft Agar: 20 g Bacto Tryptone; 10 g Bacto yeast extract; 20 g sodium chloride; 14 g Bacto agar dissolved in 2 L water using mild heat without boiling.
9. TE buffer: 10 mM Tris, 1 mM EDTA, pH 7.

B. Screening Protocol: Round 1

Approximately 100 random library equivalents of each library were pooled according to their titer, which meant that 24 µL of TN9-IV ($1.3 \times 10^{10-}$ pfu/µL), 12.5 µL of TN10-X ($1.6 \times 10^{10}$ pfu/µL), 225 µL of TN11-I ($1.2 \times 10^9$ pfu/µL), and 48.7 µL of TN12-I ($2.9 \times 10^9$ pfu/µL) were mixed with 189 µL PBS, 75 µl, of ice-cold 17% polyethylene glycol (PEG) (average molecular weight: 8000 Da, Sigma-Aldrich, St. Louis, Mo.) and 75 µL of 3 M sodium chloride and incubated on ice for 30 minutes. One T75 flask of 293 clone 11 cells (Example 2) was split at a ratio of 1:3 with HBSS-E. The cells were transferred to a 1 ml microcentrifuge tube, washed once with cold binding buffer and the supernatant removed. The cells were incubated with the phage for 1.5 hours at 4° C. on a rotator. After the incubation, the cells were washed five times with 1 ml of ice-cold BB followed each time by centrifugation at 1400 rpm for 2 minutes. The strongly bound phage were eluted by adding 66 μM human IgG (Calbiochem, San Diego, Calif.) that had been dialyzed into BB. The phage-IgG mix was incubated with the cells for 1 hour at 4° C. Following a centrifugation step (1400 rpm spin for 2 min.), the cell pellet was washed first with 200 μL of 66 μM IgG, centrifuged (1400 rpm spin for 2 min.) and washed a final time with 100 μl IgG. The IgG washes were combined with the IgG elution for final volume of 500 μl. The phage in the eluent were titered and amplified as described below.

C. Phage Titer

Phage solutions were diluted in 100-fold steps. Typically 2 μl of phage solution was added to 198 μL of NZCYM broth in a serial manner to achieve dilutions of up to $10^{-10}$. Diluted phage were added to a culture of XL1 Blue MRF' *E. coli* cells when the XL1 Blue MRF' *E. coli* cells were being grown in log phase and reached an optical density of 0.5 at A600 (UV absorbance at 600 nm). The culture was incubated at room temperature for 10 minutes. Afterwards, 0.5 ml of the infected cells were added to 3.5 ml of molten top agar (a 50/50 mix of LB broth and LB agar) at approximately 55° C. and spread onto a standard agar plate and incubated overnight at 37 degrees. The titer was calculated from a plate containing 30 to 300 plaques. For a plate containing 50 plaques, plated from a $10^{-8}$ phage dilution, the calculations would be performed as follows: 50 plaques/500 μL infected cells×10-fold dilution during infection×$10^8$ phage dilution=$10^8$ plaque-forming units per μL.

When necessary for subsequent phage ELISA and sequencing analysis, individual agar plugs containing phage plaques were picked with autoclaved Pasteur pipets. Plugs were deposited in 96-well sterile round-bottom tissue culture plates (Greiner), to which 100 μL per well TE were added. Phage were eluted from the plaques for 2 hours at 37° C. or overnight at 4° C.

D. Phage Amplification

A culture of XL1 blue MRF' *E. coli* cells were grown in NZCYM broth-T, from a 1/100 dilution of a saturated overnight culture until the culture reached an optical density of 0.5 at A600. The cells were concentrated by centrifuging them for 15 minutes at 3500 rpm, followed by resuspension in Min A salts to 1/20 of the original volume. The phage eluted from cells after a round of selection were diluted to a 1 ml final volume in Min A salts and added to 1 ml of the concentrated bacterial culture. After a 15 minute incubation in a 37° C. water bath, the phage-cell mix was added to 2 ml 2×NZCYM broth and spread on a large NUNC plate with NZCYM plus 50 μg/ml Ampicillin until dry. Plates were incubated for 14 to 18 hours at 37° C. Colonies that formed overnight were scraped gently with a spreading bar in the presence of 20 ml of PBS. PBS-containing bacteria and phage were collected in a centrifuge tube. Bacteria remaining on the plate were scraped again in the presence of 10 ml PBS and collected. A final 10 ml PBS rinse was applied to the plate, and pooled together with all scraped material. The bacterial cells were pelleted by centrifugation (15 minutes at 3500 rpm), and the clear supernatant was decanted into another centrifuge tube, clarified again, and finally decanted again. Then, a 0.15 mL volume of 17% PEG+3M NaCl was added to the supernatant, which was mixed and stored overnight at 4° C. The precipitated phage collected by centrifugation (8500×g for 30 minutes), after which, the supernatant was discarded. The phage pellet was resuspended in a small volume of PBS, clarified with a brief spin, and precipitated again with a 0.15 volume of 17% PEG+ 3M NaCl. The final phage pellet was resuspended in PBS and titered in preparation for the next round of selection.

E. Round 2

The amplified phage library was diluted such that only 10 random library equivalents were diluted into 1 ml of binding buffer. One third of a T75 flask of untransfected 293 cells was washed once with cold binding buffer. A subtraction step included to remove phage from the library that expressed peptides capable of binding to cells that did not express FcRn was performed twice by incubating the phage with the untransfected cells for 15 minutes. The supernatant was recovered. Then, one third of a T75 flask of 293 clone 11 cells was washed once with cold binding buffer and incubated with the phage for 1.5 hours at 4° C. in a rotator. The cells were washed and centrifuged (1400 rpm spin for 2 min.) five times with 1 ml cold binding buffer and the strongly bound phage were eluted with 200 μL of 66 μM human IgG (dialyzed in binding buffer) by incubating the phage-cell-IgG mixture for 1 hour at 4° C. After centrifugation (1400 rpm spin for 2 min.), the supernatant was collected and the pellet was washed with 200 μL of 66 uM IgG, followed by a 100 μL wash of 66 uM IgG. The phage in the eluent were titered and amplified as described below in the sections labeled phage titer and phage amplification.

F. Round 3

This round was performed as described above for Round 2. At the completion of Round 3, the phage in the eluent were titered and assayed for IgG-FcRn inhibitors using the phage ELISA.

G. Phage ELISA

The following steps were carried out to identify, by enzyme linked immunosorbent assay (ELISA), phages encoding peptides that were able to bind FcRn. First, the following solutions were prepared:

Buffer A: PBS+0.1% Tween+0.5% BSA.

Buffer B: 100 mM MES, pH 5.5+150 mM NaCl+0.1% Tween.

Buffer C: 50 mM MES, pH 6.0+150 mM NaCl+0.1% Tween

An XL1 blue MRF' *E. coli* culture for the propagation of a phage that demonstrated the ability to bind FcRn was grown to an optical density of 0.5 at A600 from a 1:100 dilution of an overnight culture. Then, 10 μl of each phage plaque eluate that was prepared as described above were added to 30 μl of the XL1 blue MRF' *E. coli* cells into wells of a 96-well plate and incubated for 15 minutes at room temperature. Then, 130 μl of NZCYM broth containing 50 μg/ml of Ampicillin were added to each well and the plates were incubated overnight at 37° C.

A Streptavidin-coated, BSA-blocked microtiter plate (Pierce) was prepared by rinsing it with 200 μl per well of buffer A, and coating it overnight at 4° C. with 1 mg/ml of biotinylated soluble human FcRn (Example 4, section A), in buffer A. The FcRn-containing buffer was discarded and the plate was rinsed twice with buffer C. Then, 70 μl of buffer B was added to each well of the plate, followed by the addition of 30 μl of a bacterial culture containing phage. After 1 hour at room temperature, the plate was washed five times with 200 μl of buffer C. Then, 100 μl of buffer C containing a 1:10000 dilution of an HRP-conjugated anti-M13 antibody (Amersham Pharmacia) was added to each well. The plate was incubated at room temperature for one hour. Then, the plates were washed 9 times with buffer C, developed with 1 step TMB (KPL), stopped after 5-15 minutes with 2M sulfuric acid and read at 450 nm with a Spectra Max Plus plate reader (Molecular Devices).

H. PCR Amplification of Phage DNA

Phage eluted from plaques in TE were amplified for sequencing by using the PCR Core System II kit per the manufacturer's instructions (Promega). Then, 5 ml of eluted phage was added to a reaction mix containing 200 μM each dNTP, 500 nM of primer 3PCRUP (5'-CGGCGCAAC-TATCGGTATCAAGCTG-3 (SEQ ID NO: 8)), 500 nM of primer 3PCRDN (5'-CATGTACCGTAACACT-GAGTTTCGTC-3' (SEQ ID NO: 9)), 1×Taq DNA Polymerase Buffer (10×: 500 mM KCl, 100 mM Tris-HCl pH 9.0 at 25° C., 1% Triton X-100, 15 mM $MgCl_2$), and 1.25 units Taq DNA Polymerase enzyme. The reactions were subjected to the following program on a MJ Research PCT-200 thermal cycler: 5 minutes at 94 °C; 30 cycles consisting of 15 seconds at 94° C., 30 seconds at 55° C., and 60 seconds at 72° C., followed by 7 minutes at 72° C. The resulting product was purified using the QiaQuick PCR Prep kit (Qiagen) according to manufacturer's instructions, quantified by absorbance at A260, and sequenced using primer 3SEQ-80 (5'-GATAAAC-CGATACAATTAAAGGCTCC-3' (SEQ ID NO: 10)).

Sequencing of phage that was amplified following the 3 rounds of screening revealed the DNA sequences that encoded the amino acid sequences of full length human FcRn and human beta-2 microglobulin1. These "phage hits" were used collectively to identify a consensus peptide sequence, defined by the amino acid sequence: G-H-F-G-G-X-Y (SEQ ID NO: 11).

Example 4

Peptide-IgG Competition ELISA

In order to determine whether the peptides of the invention that were derived from the screening of the filamentous phage display libraries were also able to block the binding of IgG to FcRn, the following ELISA assay was devised and performed.

A. Biotinylation of shFcRn

A solution of soluble human FcRn (shFcRn) in Tris buffer was dialyzed twice, each time for 3 hours in 2 liters of PBS, pH 8.0. The quantity of recovered shFcRn was determined by measuring the absorbance at 280 nm. The concentration of shFcRn was obtained by multiplying the absorbance reading by the extinction coefficient for shFcRn, which is: $\epsilon$=85880 $M^{-1}$ $cm^{-1}$. Biotinylation of shFcRn was accomplished by treating the dialyzed shFcRn with a 2-fold-molar excess of Sulfo-NHS-LC-Biotin (Invitrogen, Carlsbad, Calif.) for 2 hours at 4° C. Afterwards, the shFcRn-Sulfo-NHS-LC-Biotin reaction mixture was dialyzed twice in 2 L of cold PBS, followed by another absorbance reading to determine the concentration of the remaining protein. The biotinylated shFcRn was stored at 4° C. with 0.1% sodium azide until needed.

B. Peptide-IgG Competition ELISA assay 96-well ReactiBind Neutravidin-coated plates blocked with BSA (Pierce, Rockford, Ill.) were washed twice with 200 μl/well of Buffer A (Buffer A: PBS pH 7.4 (Gibco, 14040), 0.5% BSA IgG-free, 0.05% Tween-20). The wells were coated with 100 μl/well of 1 μg/ml biotinylated-shFcRn in Buffer A. The plate was sealed and incubated at 37° C. for 2 hours. Afterwards, the plate was washed with 200 μl/well of Buffer B (Buffer B: 100 mM MES pH 6, 150 mM NaCl, 0.5% BSA IgG-free (Jackson ImmunoResearch, West Grove, Pa.), 0.05% Tween-20). Then, 50 μl/well of 6 nM human IgG (Calbiochem, San Diego, Calif.) in Buffer B as well as 50 μl/well of the various peptide competitors (at various concentration) were added, so that the final concentration of IgG in the well was 3 nM. To allow for mixing, the plate was rocked for 2 minutes, sealed and incubated at 37° C. for 2 hours. Following the incubation, the liquid was aspirated from the plate and 100 μl/well of a 1:10 000 dilution of Peroxidase-conjugated goat anti-human IgG F(ab') fragment-specific F(ab')$_2$ fragment (Jackson ImmunoResearch, West Grove, Pa.) in Buffer B was added. The plate was covered, incubated for 30 minutes at room temperature and washed 4 times with 200 μl/well of ice-cold buffer B. SureBlue TMB substrate solution (100 μl/well, KPL, Gaithersburg, Md.) was added and the plate was allowed to incubate at room temperature until color developed, which took 5 to 10 minutes. Once color developed, 100 μl/well of TMB stop solution (KPL, Gaithersburg, Md.) was added and the absorbance was measured at 450 nm. The data was plotted as absorbance vs. peptide concentration to derive the inhibitory concentration 50% ($IC_{50}$) values.

Example 5

Peptide-IgG Competition FACS Assay

In addition to using the ELISA approach described in Example 4 to determine whether the peptides of the invention that were derived from the screening of the filamentous phage display libraries were also able to block the binding of IgG to FcRn on cells, the following fluorescence activated cell sorting (FACS) assay was devised and performed.

A. Labeling of Synagis® with Alexa-Fluor-488

Humanized IgG1 (Synagis®, MedImmune, Gaithersburg, Md.) was labeled with the Alexa Fluor 488 Protein Labeling Kit (Molecular Probes/Invitrogen, Carlsbad, Calif.) according to the manufacturer's suggested protocol. Briefly, 50 μl of 1 M sodium bicarbonate, pH 9.0 was added to 500 of a 2 mg/ml solution of IgG in PBS. This protein solution was added to the Alexa Fluor 488 succinimidyl ester (dry powder) and incubated at room temperature for 1 hour. The protein was purified by size-exclusion chromatography using the kit component column (Bio-Rad BioGel P-30 Fine size exclusion purification resin). The sample was loaded onto the column and eluted with PBS. The first colored band contained the labeled protein. The degree of labeling was determined by measuring the absorbance of the eluted IgG at 280 nm and 494 nm. The protein molar concentration was determined using the formula: protein concentration (M)=[$A_{280}$−($A_{494}$× 0.11)×dilution factor]/203,000. In addition, the formula used to derive the moles of dye per mole of protein was: =$A_{494}$× dilution factor/71,000×protein concentration (M). Typically, 4-7 moles of Alexa-Fluor 488 were incorporated per mole of IgG.

B. IgG-Peptide Competition FACS Assay Using 293 Clone 11 Cells

In preparation for the assay, HEK 293 clone 11 cells (Example 2) in complete DMEM media (Gibco, Carlsbad, Calif.) containing 5 μg/ml Blasticidin and 250 μg/ml G418 (Gibco, Carlsbad, Calif.) were spun down and resuspended in Buffer C (Buffer C: Dulbecco's PBS (Gibco, Carlsbad, Calif.) containing 10 mM EDTA (Gibco)) at a concentration of 3×10$^6$ cells/ml. Cells (0.1 ml) were pipetted into each well of a 96-well assay plate and the plates were centrifuged at 2600 RPM for 5 min using a Sorvall RT7 benchtop centrifuge. The supernatants were gently decanted and the plate was blotted on a paper towel. Peptide competitors (90 μl) solubilized in Buffer C at various concentrations were added to the plate and mixed with a multi-channel pipette. 10 μl of Alexa 488-labeled Synagis® was added to each well on the plate, such that the final concentration of Alexa 488-labeled Synagis® was 100 nM. The plate was wrapped in foil, placed on ice for one hour and subsequently centrifuged at 2600 rpm for 5 minutes in a Sorvall RT7 benchtop centrifuge followed by a single wash with 100 µl of Buffer C and a second centrifugation step. The cells were resuspended in 200 µl of Buffer C and analyzed on a Beckman Coulter EPICS XL flow cytometer.

Example 6

Methods for the Determination of Equilibrium Binding Constants ($K_D$) for Peptides Using Surface Plasmon Resonance (SPR)

The following steps were performed to cross-link soluble human or cynomolgus FcRn to the dextran surface of a CM5 sensor chip (Biacore AB, Uppsala, Sweden) by an amine coupling reaction involving 1-ethyl-(3-dimethylaminopropyl)-carbodiimide hydrochloride (EDC) (Biacore AB, Uppsala, Sweden) and N-hydroxysuccinimide (NHS) (Biacore AB, Uppsala, Sweden) as recommended by Biacore (BIAapplications Handbook, version AB, section 4.2, Biacore AB, Uppsala, Sweden). The FcRn protein was diluted in 50 mM sodium acetate, pH 4.5 (Biacore AB, Uppsala, Sweden) to a concentration of 10 to 30 µg/ml and used to coat one flow cell on the sensor chip. Residual sites on the FcRn flow cell were blocked with 1 M ethanolamine hydrochloride pH 8.5 (Biacore AB, Uppsala, Sweden). A control flow cell was blocked with ethanolamine for reference subtraction. For analysis of the monomeric peptides, FcRn was coated to a final density of 4000-5000 response units (RU). For analysis of the peptide dimers, FcRn was coated to a density of 2000-2500 RU. All SPR measurements were performed using a BIACORE 3000 Instrument (Biacore AB Uppsala, Sweden). For measurements done at either pH 6 or pH 7.4, experiments were performed in 50 mM phosphate, 100 mM sodium chloride, 0.01% surfactant P20 (Biacore AB, Uppsala, Sweden).

A. Representative Procedure for the Determination of Binding Constant of Monomeric Peptides Ten 2-fold dilutions of the peptide were injected over the FcRn-CM5 chip at a rate of 20 µl/min for 2 min. The peptide was dissociated from the chip for 2.5 minutes with buffer. Any remaining peptide was removed from the chip with a 30 second injection of HBS-P buffer (Biacore AB, Uppsala, Sweden) at a rate of 30 µl/min. Sensorgrams were generated and analyzed using BiaEval software version 3.1 (Biacore AB, Uppsala, Sweden). The equilibrium RU observed for each injection was plotted against concentration. The equilibrium $K_D$ values were derived by analysis of the plots using the steady state affinity model included in the BiaEval software.

B. Representative Procedure for Determination of Binding Constant of Dimeric Peptides Ten, 2-fold dilutions of the peptide were injected over the FcRn-CM5 chip at a rate of 30 µl/min for 10 min. Peptides were dissociated from the chip for 10 minutes with buffer. Any remaining peptide was removed from the chip with two, 60 second injections of a solution containing 50 mM Tris-hydrochloride, 100 mM NaCl, 0.01% surfactant P20 pH 9.0 at 100 µl/min.

Sensorgrams were generated and analyzed using BiaEval software version 3.1 (Biacore AB, Uppsala, Sweden). The equilibrium RU observed for each injection was plotted against concentration. The equilibrium $K_D$ values were derived by analysis of the plots using the steady state affinity model included in the BiaEval software.

Example 7

Synthesis of Monomeric Peptides Containing Disulfide Bonds

Synthesis of monomeric peptides was performed using solid-phase peptide synthesis either manually with a flitted round bottom flask or by using an Advanced Chemtech 396-omega synthesizer (Advanced Chemtech, Louisville, Ky.). Standard Fmoc/tBu protocols were used (W. C. Chan and P. D. White eds., *Fmoc Solid Phase Peptide Synthesis: A Practical Approach* Oxford University Press Inc. New York (2000)), in combination with a Rink amide resin (Novabiochem, San Diego, Calif.) or PAL-PEG-PS (Applied Biosystems, Foster City, Calif.) to yield C-terminal amides upon cleavage. The coupling reagents were 2-(1H-Benzotriazole-1-yl)-1,1,3,3,-tetramethyluronium hexafluorophosphate (HBTU) and N-hydroxybenzotriazole (HOBt) (Novabiochem, San Diego, Calif.). The base was diisopropylethylamine (DIEA) (Sigma-Aldrich, St. Louis, Mo.), and N,N-dimethylformamide (DMF) was the solvent (EM Science, Kansas City, Mo.). The typical synthesis cycle involved 2×10 minute deprotection steps with 20% piperidine in DMF, 2×30 minute amino acid couplings with HOBt/HBTU and a 10 minute capping step with acetic anhydride/HOBt. Peptides were cleaved from the resin by treatment for 2 hours with 95% trifluoroacetic acid; 2.5% ethanedithiol; 1.5% triisopropylsilane and 1% water and precipitated with ice-cold ether, centrifuged and triturated three times with ether.

Crude cysteine-containing peptides were oxidized to their corresponding disulfides by dissolving the peptides to a concentration of 1 mg/ml in a 4:1 mixture of acetic acid and water (EM Science, Kansas City, Mo.). Ten molar equivalents of iodine (1M solution in water, Sigma-Aldrich, St. Louis, Mo.) were added to the solution and the reaction mixture was mixed for one hour at room temperature. The reaction was stopped by the progressive addition of 1 M sodium thiosulfate (Sigma-Aldrich, St. Louis, Mo.) until a clear solution was obtained. The reaction mixture was concentrated in vacuo and subsequently purified using a Waters Prep600 reversed phase HPLC system (Millford, Mass.) equipped with a 250 mm×21.2 mm Phenomenex (Torrence Calif.) C18 column. The eluent chosen for the HPLC purification step was a gradient of acetonitrile in water containing 0.1% (w/v) TFA. Appropriate fractions were collected, pooled and lyophilized. Peptide identity and purity was confirmed by reversed phase analytical HPLC in combination with a 250 mm×2 mm column (Phenomenex, Torrence, Calif.) coupled with electrospray mass spectrometry (Mariner ES-MS) (Applied Biosystems, Foster City, Calif.).

Table 2 provides a listing of the original phage peptide sequences derived from the screen of the peptide expression library used to identify peptides with a high affinity for human FcRn and the ability to block the IgG-FcRn interaction. In Table 2 and subsequent tables, Column 1 contains the peptide identifier. Column 2 contains the amino acid sequence of the peptides. Column 3 contains the $IC_{50}$ of each peptide as determined by the IgG competition ELISA outlined in Example 4. Columns 4 and 5 contain the Kr, of each peptide as determined at pH 6 and pH 7.4, respectively, by the Biacore analysis outlined in Example 6.

TABLE 2

Original Phage Peptide Sequences

| | Sequence (SEQ ID NOS 12-16) | IC$_{50}$ µM | K$_D$ (pH 6) µM | K$_D$ pH 7.4 µM |
|---|---|---|---|---|
| Peptide No. 506 | AGQRFCTGHFGGLYPCNGPGTGGGK | 36 | 5.7 | 45 |
| Peptide No. 507 | AGGGCVTGHFGGIYCNTQGTGGGK | 33 | 5.2 | 34.7 |
| Peptide No. 508 | AGKIICSPGHFGGMYCQGKGTGGGK | 64 | 22 | 78 |
| Peptide No. 509 | AGPSYCIEGHIDGIYCFNAGTGGGK | 49 | 8.8 | 76 |
| Peptide No. 510 | AGNSFCRGRPGHFGGCYLFGTGGGK | 33 | 9.4 | 93 |

Table 3 provides a listing of truncations of Peptide No. 506 and shows the effect of the truncations on the binding parameters of these peptides with human FcRn. Column 1 contains the peptide identifier. Column 2 contains the amino acid sequence of the peptides. Column 3 contains the IC$_{50}$ of each peptide as determined by the IgG competition ELISA outlined in Example 4. Columns 4 and 5 contain the K$_D$ of each peptide as determined at pH 6 and pH 7.4, respectively, by the Biacore analysis outlined in Example 6.

TABLE 3

Truncations of Peptide No. 506

| | Sequence (SEQ ID NOS 12 and 17-25) | IC$_{50}$ µM | K$_D$ (pH 6) µM | K$_D$ pH 7.4 µM |
|---|---|---|---|---|
| Peptide No. 506 | AGQRFCTGHFGGLYPCNGPGTGGGK | 36 | 5.7 | 45 |
| Peptide No. 501 | QRFCTGHFGGLYPCNGP | 26 | 5.1 | 30 |
| Peptide No. 517 | CTGHFGGLYPCNGP | 239 | 34 | nd |
| Peptide No. 518 | QRFCTGHFGGLYPC | 27 | 4.2 | 26 |
| Peptide No. 519 | CTGHFGGLYPC | 110 | 20 | 320 |
| Peptide No. 520 | TGHFGGLYP | >250 | >250 | nd |
| Peptide No. 521 | RFCTGHFGGLYPCNGP | 24 | 2.9 | 78 |
| Peptide No. 522 | FCTGHFGGLYPCNGP | 67 | 11 | 120 |
| Peptide No. 523 | QRFCTGHFGGLYPCNG | 34 | 4.6 | 69 |
| Peptide No. 524 | QRFCTGHFGGLYPCN | 31 | 6.1 | 73 |

Table 4 provides a listing of peptides and peptide analogs derived from Peptide No, 501, in which single amino acids have been substituted with alanine (an alanine scan). Table 4 shows the effect of the substitutions on the binding parameters of these peptides with human FcRn.

TABLE 4

Alanine Scan of Peptide No. 501

| | Sequence (SEQ ID NOS 17 and 26-37) | IC$_{50}$ µM | K$_D$ (pH 6) µM | K$_D$ pH 7.4 µM |
|---|---|---|---|---|
| Peptide No. 501 | QRFCTGHFGGLYPCNGP | 26 | 5.1 | 30 |
| Peptide No. 525 | QAFCTGHFGGLYPCNGP | 23 | 7.7 | nd |
| Peptide No. 526 | QRACTGHFGGLYPCNGP | 95 | 28 | nd |

TABLE 4-continued

Alanine Scan of Peptide No. 501

| | Sequence (SEQ ID NOS 17 and 26-37) | IC$_{50}$ μM | K$_D$ (pH 6) μM | K$_D$ pH 7.4 μM |
|---|---|---|---|---|
| Peptide No. 527 | QRFCAGHFGGLYPCNGP | 30 | 4.9 | nd |
| Peptide No. 528 | QRFCTAHFGGLYPCNGP | >125 | >250 | nd |
| Peptide No. 529 | QRFCTGAFGGLYPCNGP | >125 | >250 | nd |
| Peptide No. 530 | QRFCTGHAGGLYPCNGP | >125 | >250 | nd |
| Peptide No. 531 | QRFCTGHFAGLYPCNGP | >125 | 230 | 200 |
| Peptide No. 532 | QRFCTGHFGALYPCNGP | >125 | 120 | 110 |
| Peptide No. 533 | QRFCTGHFGGAYPCNGP | 107 | 26 | 81 |
| Peptide No. 534 | QRFCTGHFGGLAPCNGP | >125 | >250 | nd |
| Peptide No. 535 | QRFCTGHFGGLYACNGP | 96 | 14 | 100 |
| Peptide No. 536 | QRFCTGHFGGLYPCAGP | 30 | 8 | nd |

Table 5 provides a listing of peptide and peptide analogs derived from Peptide No. 501 in which substitutions of cysteines with cysteine analogs have been performed. Table 5 shows the effect of the substitutions on the binding parameters of these peptides with human FcRn.

TABLE 5

Cysteine Analogs of Peptide No. 501

| | Sequence* (SEQ ID NOS 17 and 38-48) | IC$_{50}$ μM | K$_D$ (pH 6) μM | K$_D$ pH 7.4 μM |
|---|---|---|---|---|
| Peptide No. 501 | QRF-C-TGHFGGLYP-C-NGP | 26 | 5.1 | 30 |
| Peptide No. 27 | QRFCTGHFGGINP-hC-NGP | 21 | 3.9 | |
| Peptide No. 28 | QRF-hC-TGHFGGLYP-hC-NGP | 20 | 3.8 | |
| Peptide No. 29 | QRF-c-TGHFGGLYP-C-NGP | >125 | 150 | |
| Peptide No. 30 | QRF-C-TGHFGGLYP-c-NGP | 125 | 31 | |
| Peptide No. 31 | QRF-c-TGHFGGLYP-c-NGP | >500 | 200 | |
| Peptide No. 32 | QRF-Pen-TGHFGGLYP-C-NGP | 2 | 0.25 | |
| Peptide No. 33 | QRF-C-TGHFGGLYP-Pen-NGP | 18 | 2.7 | |
| Peptide No. 34 | QRF-Pen-TGHFGGLYP-Pen-NGP | 2 | 0.37 | |
| Peptide No. 69 | QRF-Pen-TGHFGGLYP-hC-NGP | 2 | 0.31 | |
| Peptide No. 70 | QRF-hC-TGHFGGLYP-Pen-NGP | 16 | 2.1 | |
| Peptide No. 295 | QRF-Pen-TGHFG-p-LYP-Pen-NGP | 1.6 | 0.28 | |

*"Pen" = L-penicillamine; "hC" = L-homocysteine

Table 6 provides a listing of peptides derived from Peptide No. 501 and Peptide No. 32 in which single amino acids have been substituted for N-methyl amino acids. Table 6 shows the effect of the substitutions on the binding parameters of these peptides with human FcRn.

TABLE 6

N-METHYL SCAN OF PEPTIDE NO. 501 AND PEPTIDE NO. 32

| | Sequence* (SEQ ID NOS 17, 49, 43 and 50-60) | $IC_{50}$ µM | $K_D$ (pH 6) µM | $K_D$ pH 7.4 µM |
|---|---|---|---|---|
| Peptide No. 501 | QRFCTGHFGGLYPCNGP | 26 | 5.1 | 30 |
| Peptide No. 196 | QRFC-<u>NMeAla</u>-GHFGGLYPCNGP | 169 | 18 | |
| Peptide No. 32 | QRF-Pen-TGHFGGLYP-C-NGP | 2 | 0.25 | |
| Peptide No. 108 | QRF-Pen-T-<u>Sar</u>-HFGGLYP-C-NGP | >125 | 88 | |
| Peptide No. 192 | RF-Pen-TG-<u>NMeHis</u>-FGGLYPC | >250 | nd | |
| Peptide No. 110 | QRF-Pen-TGH-<u>NMePhe</u>-GGLYPCNGP | >125 | >250 | |
| Peptide No. 111 | QRF-Pen-TGHF-<u>Sar</u>-GLYPCNGP | 27 | 2 | |
| Peptide No. 112 | QRF-Pen-TGHFG-<u>Sar</u>-LYPCNGP | 0.9 | 0.11 | |
| Peptide No. 113 | QRF-Pen-TGHFGG-<u>NMeLeu</u>-YPCNGP | 1.6 | 0.086 | |
| Peptide No. 114 | QRF-Pen-TGHFGGL-<u>NMeTyr</u>-PCNGP | >125 | 92 | |
| Peptide No. 146 | RF-Pen-TGHFGG-<u>NMeLeu</u>-YPCNGP | 2.1 | 0.059 | 0.28 |
| Peptide No. 147 | RF-Pen-TGHFG-<u>Sar</u>-YPCNGP | 1.0 | 0.058 | 0.35 |
| Peptide No. 187 | QRF-Pen-TGHFG-<u>Sar</u>-<u>NMeLeu</u>-YPCNGP | 0.42 | 0.046 | 0.23 |
| Peptide No. 235 | RF-Pen-TGHFG-<u>Sar</u>-<u>NMeLeu</u>-YPC | 0.49 | 0.031 | 0.17 |

*"Pen" = L-penicillamine; Sar = sarcosine (N-methylglycine); "NMe" prefix denotes N-methyl amino acid Table 7 provides a listing of truncations of Peptide No. 32-derived peptide analogs. Table 7 shows the effect of the truncations on the binding parameters of these peptides with human FcRn.

TABLE 7

TRUNCATIONS OF PEPTIDE NO. 32

| | Sequence (SEQ ID NOS 43, 61 and 61-67) | $IC_{50}$ µM | $K_D$ (pH 6) µM | $K_D$ pH 7.4 µM |
|---|---|---|---|---|
| Peptide No. 32 | QRF-Pen-TGHFGGLYPCNGP | 2 | 0.25 | 1.2 |
| Peptide No. 82 | F-Pen-TGHFGGLYPC | 1.7 | 0.31 | 5 |
| Peptide No. 83 | NH$_2$-F-Pen-TGHFGGLYPC | 3.1 | 0.29 | 12 |
| Peptide No. 99 | RF-Pen-TGHFGGLYPC | 2.0 | 0.17 | 3.4 |
| Peptide No. 141 | QRF-Pen-TGHFGpLYPC | 1.5 | 0.19 | |
| Peptide No. 142 | RF-Pen-TGHFGpLYPC | 1.5 | 0.14 | |
| Peptide No. 143 | F-Pen-TGHFGpLYPC | 1.7 | | |
| Peptide No. 144 | RF-Pen-TGHFGpLYPCNGP | 1.5 | | |
| Peptide No. 145 | F-Pen-TGHFGpLYPCNGP | 3.1 | | |

* "Pen" = L-penicillamine

Table 8 provides a listing of peptides and peptide analogs derived from Peptide No, 32, in which substitutions with various amino acid and amino acid analogs have been generated where there is normally the sequence: Gly-Gly-Leu.

TABLE 8

ANALOGS OF PEPTIDE NO. 32 MODIFIED AT GLY-GLY-LEU

|  | Sequence* (SEQ ID NOS 43 and 68-95) | IC$_{50}$ µM | K$_D$ (pH 6) µM | K$_D$ pH 7.4 µM |
| --- | --- | --- | --- | --- |
| Peptide No. 32 | QRF-Pen-TGHF-GG-LYP-C-NGP | 2 | 0.25 | 1.2 |
| Peptide No. 40 | QRF-Pen-TGHF-G-p-LYPCNGP | 1.4 | 0.23 | 1.1 |
| Peptide No. 41 | QRF-Pen-TGHF-G-r-LYPCNGP | 8.1 | 0.83 | 8.8 |
| Peptide No. 42 | QRF-Pen-TGHF-G-h-LYPCNGP | 12 | 2 | 20 |
| Peptide No. 43 | QRF-Pen-TGHF-G-i-LYPCNGP | 18 | 2.2 | 41 |
| Peptide No. 44 | QRF-Pen-TGHF-G-f-LYPCNGP | 13 | 1.7 | 100 |
| Peptide No. 45 | QRF-Pen-TGHF-G-y-LYPCNGP | 13 | 1.5 | 31 |
| Peptide No. 46 | QRF-Pen-TGHF-G-Aib-LYPCNGP | 2.4 | 0.48 | 5.3 |
| Peptide No. 47 | QRF-Pen-TGHF-d-G-LYPCNGP | 3.1 | 0.58 | 4.9 |
| Peptide No. 48 | QRF-Pen-TGHF-p-G-LYPCNGP | 5 | 0.79 | 21 |
| Peptide No. 49 | QRF-Pen-TGHF-r-G-LYPCNGP | 4.1 | 0.31 |  |
| Peptide No. 50 | QRF-Pen-TGHF-h-G-LYPCNGP | 3.6 | 0.41 |  |
| Peptide No. 51 | QRF-Pen-TGHF-i-G-LYPCNGP | 9.4 | 2.6 |  |
| Peptide No. 52 | QRF-Pen-TGHF-f-G-LYPCNGP | 2.8 | 0.51 |  |
| Peptide No. 53 | QRF-Pen-TGHF-y-G-LYPCNGP | 3.2 | 0.32 |  |
| Peptide No. 54 | QRF-Pen-TGHF-Aib-G-LYPCNGP | 17 | 5.2 |  |
| Peptide No. 74 | QRF-Pen-TGHF-G-a-LYPCNGP | 2 | 0.48 | 12 |
| Peptide No. 75 | QRF-Pen-TGHF-a-G-LYPCNGP | 4.5 | 0.49 | 4.5 |
| Peptide No. 148 | QRF-Pen-TGHF-a-a-LYPCNGP | 4.5 | 0.45 |  |
| Peptide No. 149 | QRF-Pen-TGHF-a-p-LYPCNGP | 3.7 | 0.43 |  |
| Peptide No. 150 | QRF-Pen-TGHF-f-p-LYPCNGP | 5.9 | 0.72 |  |
| Peptide No. 151 | QRF-Pen-TGHF-f-a-LYPCNGP | 4.3 | 0.41 |  |
| Peptide No. 152 | QRF-Pen-TGHF-p-p-LYPCNGP | 21 | 3.3 |  |
| Peptide No. 153 | QRF-Pen-TGHF-f-G-NMeLeu-YPCNGP | 1.3 | 0.24 |  |
| Peptide No. 154 | QRF-Pen-TGHF-a-G-NMeLeu-YPCNGP | 3.2 | 0.23 |  |
| Peptide No. 155 | QRF-Pen-TGHF-f-G-P-YPCNGP | 39 | 18.3 |  |
| Peptide No. 202 | QRF-Pen-TGHF-p-P-LYPCNGP | >250 | >100 |  |
| Peptide No. 203 | QRF-Pen-TGHF-f-P-LYPCNGP | 22 | 3.8 |  |
| Peptide No. 189 | QRF-Pen-TGHF-a-Sar-LYPCNGP | 1.7 | 0.19 |  |

*"Pen" = L-penicillamine; "NMeLeu" = N-methylleucine; "Sar" = sarcosine; "Aib" = aminoisobutyric acid Table 9 provides a listing of peptides and peptide analogs derived from Peptide No. 32, in which substitutions with various amino acid and amino acid analogs have been generated where there is normally the sequence: Arg-Phe-Penicillamine.

TABLE 9

ANALOGS OF PEPTIDE NO. 32 MODIFIED AT ARG-PHE-PEN

| | Sequence*<br>(SEQ ID NOS 43 and 96-98) | IC$_{50}$ µM | K$_D$ (pH 6) µM | K$_D$ pH 7.4 µM |
|---|---|---|---|---|
| Peptide No. 32 | QR-F-Pen-TGHFGGLYPCNGP | 2 | 0.25 | 1.2 |
| Peptide No. 96 | QR-f-Pen-TGHFGGLYPCNGP | 11.4 | 1.8 | |
| Peptide No. 97 | QR-Y-Pen-TGHFGGLYPCNGP | 2.4 | 0.31 | |
| Peptide No. 98 | QR-W-Pen-TGHFGGLYPCNGP | 1.5 | 0.29 | |

*"Pen" = L-penicillamine; "NMeLeu" = N-methylleucine; "Sar" = sarcosine; "Aib" = aminoisobutyric acid Table 10 provides a listing of peptides and peptide analogs derived from Peptide No. 32, in which substitutions with various amino acid and amino acid analogs have been generated where there is normally the sequence: Penicillamine-Thr-Gly.

TABLE 10

Analogs of Peptide No. 32 Modified at Pen-Thr-Gly

| | Sequence*<br>(SEQ ID NOS 43 and 99-101) | IC$_{50}$ µM | K$_D$ (pH 6) µM | K$_D$ pH 7.4 µM |
|---|---|---|---|---|
| Peptide No. 32 | QRF-Pen-T-GHFGGLYPCNGP | 2 | 0.25 | 1.2 |
| Peptide No. 296 | QRF-Pen-H-GHFGGLYPCNGP | 3 | 0.15 | 0.96 |
| Peptide No. 195 | QRF-Pen-G-GHFGGLYPCNGP | 7.7 | 0.76 | |
| Peptide No. 213 | QRF-Pen-(NMeAla)-GHFGGLYPCNGP | 5.5 | 1.0 | |

*"Pen" = L-penicillamine; "NMeAla" = N-methylalanine

Table 11 provides a listing of peptides and peptide analogs derived from Peptide No. 187, in which substitutions with various amino acid and amino acid analogs have been generated where there is normally the sequence: Phe-Gly-Sarcosine.

TABLE 11

Analogs of Peptide No. 187 Modified at Phe-Gly-Sar

| | Sequence*<br>(SEQ ID NOS 59 and 102-113) | IC$_{50}$ µM | K$_D$ (pH 6) µM | K$_D$ pH 7.4 µM |
|---|---|---|---|---|
| Peptide No. 187 | QRF-Pen-TGHF-G-Sar-NMeLeu-YPCNGP | 0.42 | 0.046 | 0.23 |
| Peptide No. 188 | QRF-Pen-TGHF-a-Sar-NMeLeu-YPCNGP | 6.5 | 0.73 | |
| Peptide No. 235 | RF-Pen-TGHF-G-Sar-NMeLeu-YPC | 0.49 | 0.031 | 0.17 |
| Peptide No. 217 | RF-Pen-TGHF-f-Sar-NMeLeu-YPC | 11 | 1.4 | |
| Peptide No. 218 | RF-Pen-TGHF-v-Sar-NMeLeu-YPC | >50 | 13 | |
| Peptide No. 219 | RF-Pen-TGHF-l-Sar-NMeLeu-YPC | 4 | 0.47 | |
| Peptide No. 220 | RF-Pen-TGHF-w-Sar-NMeLeu-YPC | 11 | 2.7 | |
| Peptide No. 240 | RF-Pen-TGHF-t-Sar-NMeLeu-YPC | 71 | 4.8 | |
| Peptide No. 241 | RF-Pen-TGHF-s-Sar-NMeLeu-YPC | 23 | 1.1 | |
| Peptide No. 242 | RF-Pen-TGHF-d-Sar-NMeLeu-YPC | 33 | 2.6 | |
| Peptide No. 243 | RF-Pen-TGHF-n-Sar-NMeLeu-YPC | 29 | 2.1 | |

TABLE 11-continued

Analogs of Peptide No. 187 Modified at Phe-Gly-Sar

| Sequence* (SEQ ID NOS 59 and 102-113) | IC$_{50}$ µM | K$_D$ (pH 6) µM | K$_D$ pH 7.4 µM |
|---|---|---|---|
| Peptide No. 244 RF-Pen-TGHF-e-Sar-NMeLeu-YPC | 6.4 | 0.58 | |
| Peptide No. 245 RF-Pen-TGHF-q-Sar-NMeLeu-YPC | 4.5 | 0.36 | |

*"Pen" = L-penicillamine; "Sar" = sarcosine; "NMeLeu" = N-methylleucine

Table 12 provides a listing of peptides and peptide analogs derived from Peptide No. 32, in which substitutions with various amino acid and amino acid analogs have been generated where there is normally the sequence: His-Phe-Gly.

TABLE 12

Analogs of Peptide No. 32 Modified at His-Phe-Gly

| | Sequence | Phe Analog Side-Chain | IC$_{50}$ µM | K$_D$ (pH 6) µM |
|---|---|---|---|---|
| Peptide No. 32 | QRF-Pen-TGH-F-GGLYPCNGP | 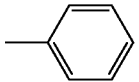 | 2 | 0.25 |
| Peptide No. 55 | QRF-Pen-TGH-(4-amino-Phe)-GGLYPCNGP | 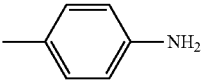 | 13 | 1 |
| Peptide No. 56 | QRF-Pen-TGH-(4-methoxy-Phe)-GGLYPCNGP | 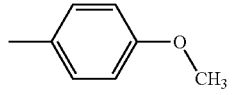 | 100 | 18 |
| Peptide No. 57 | QRF-Pen-TGH-(pentafluoro-Phe)-GGLYPCNGP | 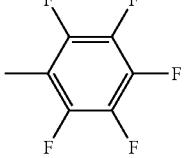 | 120 | 70 |
| Peptide No. 58 | QRF-Pen-TGH-(2-pyridylalanine)-GGLYPCNGP | 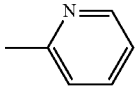 | 90 | 1.2 |
| Peptide No. 59 | QRF-Pen-TGH-(3-PyridylAla)-GGLYPCNGP | 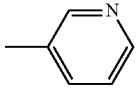 | 60 | 19 |
| Peptide No. 60 | QRF-Pen-TGH-(4-nitro-Phe)-GGLYPCNGP | 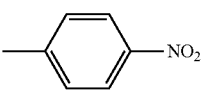 | >125 | 84 |
| Peptide No. 61 | QRF-Pen-TGH-(1-napthylalanine)-GGLYPCNGP | 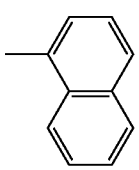 | 13 | 2.2 |
| Peptide No. 62 | QRF-Pen-TGH-(2-napthylalanine)-GGLYPCNGP | 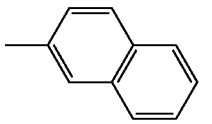 | 90 | 11 |

TABLE 12-continued

Analogs of Peptide No. 32 Modified at His-Phe-Gly

| | Sequence | Phe Analog Side-Chain | IC$_{50}$ μM | K$_D$ (pH 6) μM |
|---|---|---|---|---|
| Peptide No. 88 | QRF-Pen-TGH-(2-MePhe)-GGLYPCNGP | | 1 | 0.20 |
| Peptide No. 89 | QRF-Pen-TGH-(3-MePhe)-GGLYPCNGP | | 4.1 | 0.67 |
| Peptide No. 90 | QRF-Pen-TGH-(4-MePhe)-GGLYPCNGP | | 1.7 | 0.20 |
| Peptide No. 92 | QRF-Pen-TGH-(homoPhe)-GGLYPCNGP | | 80 | 7.8 |
| Peptide No. 93 | QRF-Pen-TGH-(Cha)-GGLYPCNGP | | 31 | 4.5 |
| Peptide No. 94 | QRF-Pen-TGH-(PheNHAc)-GGLYPCNGP | | >125 | 270 |
| Peptide No. 95 | QRF-Pen-TGH-W-GGLYPCNGP | | 26 | 2.7 |
| Peptide No. 102 | QRF-Pen-TGH-(phenylGly)-GGLYPCNGP | | >125 | >250 |
| Peptide No. 103 | QRF-Pen-TGH-(Tic)-GGLYPCNGP | X = backbone nitrogen of amino acid | >125 | >250 |
| Peptide No. 104 | QRF-Asp-TGH-(2MePhe)-GGLYP-Lys-NGP[1] | | 11 | |
| Peptide No. 221 | RF-Pen-TGH-(2-Cl-Phe)-GGLYPC | | 4 | |

TABLE 12-continued

Analogs of Peptide No. 32 Modified at His-Phe-Gly

| | Sequence | Phe Analog Side-Chain | IC$_{50}$ μM | K$_D$ (pH 6) μM |
|---|---|---|---|---|
| Peptide No. 222 | RF-Pen-TGH-(3-Cl-Phe)-GGLYPC | | 3.7 | |
| Peptide No. 223 | RF-Pen-TGH-(4-Cl-Phe)-GGLYPC | | 43 | |
| Peptide No. 224 | RF-Pen-TGH-(3,3-Di-Phe)-GGLYPC | | 32 | |
| Peptide No. 225 | RF-Pen-TGH-(4,4-Bi-Phe)-GGLYPC | | >125 | |
| Peptide No. 226 | RF-Pen-TGH-(4-t-Butyl-Phe)-GGLYPC | | >125 | |
| Peptide No. 267 | RF-Pen-TGH-((D/L)-betamethylPhe)-G-Sar-NMeLeu-YPC | | 16 | |

*"Sar" = sarcosine; "NMeLeu" = N-methylleucine
[1]Peptide No. 104 is cyclized via an amide bond between the Asp and Lys side chains Table 13 provides a listing of peptides and peptide analogs derived from Peptide No. 32, in which substitutions of tyrosine with various amino acid and amino acid analogs have been generated.

TABLE 13

Tyrosine Substitutions

| | Sequence* | Tyr Analog Side Chain | IC$_{50}$ μM | K$_D$ (pH 6) μM | K$_D$ pH 7.4 μM |
|---|---|---|---|---|---|
| Peptide No. 501 | QRFCTGHFGGL-Y-PCNGP | | 26 | 5.1 | 30 |
| Peptide No. 26 | QRFCTGHFGGL-F-PCNGP | | >125 | 230 | |
| Peptide No. 32 | QRF-Pen-TGHFGGL-Y-PCNGP | | 2 | 0.25 | 1.2 |
| Peptide No. 63 | QRF-Pen-TGHFGGL-(4-amino-Phe)-PCNGP | | 110 | 34 | |

TABLE 13-continued

| | | Tyrosine Substitutions | | | |
|---|---|---|---|---|---|
| | Sequence* | Tyr Analog Side Chain | IC$_{50}$ µM | K$_D$ (pH 6) µM | K$_D$ pH 7.4 µM |
| Peptide No. 64 | QRF-Pen-TGHFGGL-(4-methoxyPhe)-PCNGP | | 120 | 31 | |
| Peptide No. 65 | QRF-Pen-TGHFGGL-(pentafluoroPhe)-PCNGP | | >125 | 72 | |
| Peptide No. 66 | QRF-Pen-TGHFGGL-(2-pyridylAla)-PCNGP | | >125 | 120 | |
| Peptide No. 67 | QRF-Pen-TGHFGGL-(3-pyridylAla)-PCNGP | | 92 | 34 | |
| Peptide No. 68 | QRF-Pen-TGHFGGL-(4-nitro-Phe)-PCNGP | | 122 | 180 | |
| Peptide No. 87 | QRF-Pen-TGHFGGL-(2-nitro-Tyr)-PCNGP | | >125 | 290 | |
| Peptide No. 140 | QRF-Pen-TGHFGGL-(4-fluoro-Phe)-PCNGP | | 26 | 2.2 | 24 |

*"Pen" = L-penicillamine

Table 14 provides a listing of peptides and peptide analogs derived from Peptide No. 32, in which substitutions with various amino acid and amino acid analogs have been generated where there is normally the sequence: Gly-Leu.

TABLE 14

| ANALOGS OF PEPTIDE NO. 32 MODIFIED AT GLY-LEU | | | | |
|---|---|---|---|---|
| | Sequence* (SEQ ID NOS 43 and 148-155) | IC$_{50}$ µM | K$_D$ (pH 6) µM | K$_D$ pH 7.4 µM |
| Peptide No. 32 | QRF-Pen-TGHFGG-L-YPCNGP | 2 | 0.25 | 1.2 |
| Peptide No. 84 | QRF-Pen-TGHFGG-H-YPCNGP | 6.5 | 0.38 | 2.5 |
| Peptide No. 101 | QRF-Pen-TGHFGG-I-YPCNGP | 3.4 | 0.34 | |
| Peptide No. 115 | QRF-Pen-TGHFGG-F-YPCNGP | 4.1 | 0.40 | |
| Peptide No. 116 | QRF-Pen-TGHFGG-W-YPCNGP | 1.7 | 0.17 | |
| Peptide No. 117 | QRF-Pen-TGHFGG-M-YPCNGP | 7.7 | 0.44 | |
| Peptide No. 118 | QRF-Pen-TGHFGG-L-YPCNGP | 8.6 | 0.80 | |

TABLE 14-continued

ANALOGS OF PEPTIDE NO. 32 MODIFIED AT GLY-LEU

| | Sequence*<br>(SEQ ID NOS 43 and 148-155) | $IC_{50}$<br>µM | $K_D$<br>(pH 6)<br>µM | $K_D$<br>pH 7.4<br>µM |
|---|---|---|---|---|
| Peptide No. 237 | RF-Pen-TGHFGG-W-YPC | 2.8 | 0.14 | |
| Peptide No. 238 | QRF-Pen-TGHFG-Sar-W-YPCNGP | 1.0 | 0.068 | |

*"Pen" = L-penicillamine; "Sar" = sarcosine

Table 15 provides a listing of peptides and peptide analogs derived from Peptide No. 32, with a substitution of a glycine and a leucine taken together for a dipeptide mimetic where there is normally the sequence: Gly-Leu.

TABLE 15

Peptidomimetic Analogs of Peptide No. 32 Modified at Gly-Leu

| | Sequence | X<br>Description | X<br>Structure | $IC_{50}$<br>µM | $K_D^1$<br>(pH 6)<br>µM |
|---|---|---|---|---|---|
| Peptide No. 32 | QRF-Pen-TGHFG-X-YPCNGP | Gly-Gly-Leu | | 2.0 | 0.25 |
| Peptide No. 216 | QRF-Pen-TGHFG-X-YPCNGP | L,L-Friedinger's lactam | | 19 | |
| Peptide No. 194 | QRF-Pen-TGHFG-X-YPCNGP | D,L-Friedinger's lactam | | 4.9 | |

*"Pen" = L-penicillamine

Example 8

Synthesis of Peptides Containing Histidine Analogs

Modified histidine analogs (Table 16) were synthesized as described in Example 7 for the synthesis of monomeric peptide disulfides except for the following modified histidine analogs. Peptide No. 259 was synthesized by suspending the resin containing the fully protected peptide analogous to Peptide No. 99 in neat methyl iodide for 15 hours. The resin was washed with dichloromethane and the peptide was cleaved from the resin, oxidized and purified by HPLC as described above to yield the mono-methylated histidine peptide Peptide No. 259.

Peptide No. 260 was synthesized by suspending the resin containing the fully protected peptide analogous to Peptide No. 99 in neat methyl iodide for 72 hours. The resin was washed with dichloromethane and the peptide was cleaved from the resin, oxidized and purified by HPLC as described above to yield the di-methylated histidine peptide Peptide No. 260.

Peptide No. 269 was synthesized by suspending the resin containing the fully protected peptide analogous to Peptide No. 248 in dichloromethane under nitrogen. Ten molar equivalents of 2,4,6-tri-tert-butylpyridine (Sigma-Aldrich, St. Louis, Mo.) were added to the suspension followed by five molar equivalents of methyl-trifluoromethane-sulfonate (Sigma-Aldrich, St. Louis, Mo.). The reaction was allowed to proceed for 4 hours while rocking and rinsed first with dichloromethane, followed by a rinse with dimethylformamide and finally with dichloromethane again. The peptide was cleaved from the resin, oxidized and purified by HPLC as described above to yield the N-methyl-thiazolium peptide, Peptide No. 269.

Peptide No. 271 was synthesized by treating the peptide Peptide No. 261 with 30 equivalents of copper sulfate, 30 equivalents of ascorbic acid and 10 equivalents of sodium azide in a solution of 100 mM sodium phosphate buffer at pH 7.5 with 33% ethanol, 10% acetonitrile, 10% N,N-dimethylformamide. The reaction proceeded for 2 hours and the mixture was purified by HPLC as described above to yield the 1,2,3-triazole side-chain containing peptide Peptide No. 271.

Table 16 provides a listing of various peptides and peptide analogs are compared to the same peptide or peptide analog, in which histidine has been substituted with a single amino acid or amino acid analog. The effect of the substitutions on the binding parameters of these peptides with human FcRn is also provided.

TABLE 16

Histidine Substitutions

| | Sequence | His Analog Side Chain | $IC_{50}$ µM | $K_D$ (pH 6) µM | $K_D$ pH 7.4 µM |
|---|---|---|---|---|---|
| Peptide No. 501 | QRFCTG-H-FGGLYPCNGP | | 26 | 5.1 | 30 |
| Peptide No. 36 | QRFCTG-Dab-FGGLYPCNGP | | >125 | 211 | |
| Peptide No. 32 | QRF-Pen-TG-H-FGGLYP-C-NGP | | 2 | 0.25 | 1.2 |
| Peptide No. 91 | QRF-Pen-TG-Thz-FGGLYPCNGP | | 44 | 7.9 | 21 |
| Peptide No. 109 | QRF-Pen-TG-Dap-FGGLYPCNGP | | >125 | >100 | |
| Peptide No. 297 | QRF-Pen-TG-Dap(Guanyl)-FGGLYPCNGP | | 54 | 13 | 16 |
| Peptide No. 138 | QRF-Pen-TG-(1Me)His-FGGLYPCNGP | | 3.4 | 0.74 | 14 |
| Peptide No. 139 | QRF-Pen-TG-Dab-FGGLYPCNGP | | 64 | 7.3 | 8.4 |
| Peptide No. 192 | RF-Pen-TG-NMeHis-FGGLYPC | | >250 | nd | nd |
| Peptide No. 248 | RF-Pen-TG-Thz-FG-Sar-NMeL-YPC | | 1.6 | .84 | 1.1 |
| Peptide No. 249 | RF-Pen-TG-2PyridylAla-FG-Sar-NMeL-YPC | | 6.2 | .33 | 0.41 |
| Peptide No. 250 | RF-Pen-TG-3PyridylAla-FG-Sar-NMeL-YPC | | 1.2 | .064 | 0.26 |
| Peptide No. 251 | RF-Pen-TG-ThienylAla-FG-Sar-NMeL-YPC | | 45 | 2 | 3 |
| Peptide No. 253 | RF-Pen-TG-Dab-FG-Sar-NMeL-YPC | | 16 | 1.2 | 1.2 |

TABLE 16-continued

Histidine Substitutions

| | Sequence | His Analog Side Chain | IC$_{50}$ μM | K$_D$ (pH 6) μM | K$_D$ pH 7.4 μM |
|---|---|---|---|---|---|
| Peptide No. 254 | RF-Pen-TG-Orn-FG-Sar-NMeL-YPC | –(CH$_2$)$_3$–NH$_2$ | 12 | 1.3 | 1.2 |
| Peptide No. 255 | RF-Pen-TG-Lys-FG-Sar-NMeL-YPC | –(CH$_2$)$_4$–NH$_2$ | 40 | 1.3 | 1.1 |
| Peptide No. 256 | RF-Pen-TG-Arg-FG-Sar-NMeL-YPC | –(CH$_2$)$_3$–NH–C(=NH)NH$_2$ | 5.5 | 0.5 | 0.5 |
| Peptide No. 257 | RF-Pen-TG-4GuanylPhe-FG-Sar-NMeL-YPC | 4-guanidino-phenyl | 1.7 | 0.074 | 0.073 |
| Peptide No. 258 | RF-Pen-TG-4aminoPhe-FG-Sar-NMeL-YPC | 4-amino-phenyl | 4.6 | 0.22 | 1.1 |
| Peptide No. 259 | RF-Pen-TG-His(Me)-FGGLYPC | 2-methyl-imidazolyl | 2.9 | 0.14 | 0.38 |
| Peptide No. 260 | RF-Pen-TG-His(Me)2-FGGLYPC | 1,3-dimethyl-imidazolyl | 4.4 | 0.19 | 0.46 |
| Peptide No. 261 | RF-Pen-TG-PropargylGly-FG-Sar-NMeLeu-YPC | –C≡CH | 160 | 13 | 11 |
| Peptide No. 262 | RF-Pen-TG-(2-PyrrolidinylAla)-FG-Sar-NMeLeu-YPC | 2-pyrrolyl | 150 | 8.4 | 13 |
| Peptide No. 263 | RF-Pen-TG-(3-PiperidyalAla)-FG-Sar-NMeLeu-YPC | 3-piperidyl | 6.3 | 0.66 | 0.86 |
| Peptide No. 264 | RF-Pen-TG-(4-PiperidylAla)-FG-Sar-NMeLeu-YPC | 4-piperidyl | 85 | 5.2 | 6.4 |
| Peptide No. 265 | RF-Pen-TGFFG-Sar-NMeLeu-YPC | phenyl | 27 | 3.3 | 4.2 |
| Peptide No. 266 | RF-Pen-TGAFG-Sar-NMeLeu-YPC | CH$_3$ | >100 | 9.9 | 13 |
| Peptide No. 268 | RF-Pen-TG-(4-PyridylAla)-FG-Sar-NMeLeu-YPC | 4-pyridyl | 1.3 | 0.067 | 0.28 |
| Peptide No. 269 | RF-Pen-TG-Thz(Me)-FG-Sar-NMeL-YPC-CONH$_2$ | N-methyl-thiazolium | 2.4 | 0.11 | 0.11 |

TABLE 16-continued

Histidine Substitutions

| Sequence | | His Analog Side Chain | IC$_{50}$ μM | K$_D$ (pH 6) μM | K$_D$ pH 7.4 μM |
|---|---|---|---|---|---|
| Peptide No. 271 | RF-Pen-TG-triazolylAla-FG-Sar-NMeL-YPC | (triazole structure) | 5.7 | 0.32 | 0.36 |

Example 9

Synthesis of Peptides Containing Peptidomimetic Analogs of Gly-Gly

All of the Gly-Gly amino acid mimetics (Table 17) were incorporated as their Fmoc-amino protected amino acids and were commercially available unless otherwise noted (Chem-Impex, Wood Dale, Ill.). Peptides containing 3(R)-3-amino-2-oxo-1-piperidine-acetic were synthesized by incorporating the N-Fmoc derivative of 3(R)-3-amino-2-oxo-1-piperidine-acetic acid into Peptide No. 227 according to the protocol described by Freidinger et al., *J. Org. Chem.* 47: 104-109 (1982). Peptides containing 3(R)-3-amino-2-oxo-1-pyrrolidine acetic acid were synthesized by incorporating the N-Fmoc derivative of 3(R)-3-amino-2-oxo-1-pyrrolidine acetic acid into Peptide No. 214 according to the protocol described by Freidinger et al., *J. Org. Chem.* 47: 104-109 (1982). Peptides containing the 5,5-bicyclic dipeptide mimic were synthesized by incorporating the 5,5-bicyclic dipeptide mimic into Peptide No. 197 or Peptide No. 198 according to the protocol described by Subasinghe et al., *J. Med. Chem.* 36: 2356-2361 (1993) with the exception that all D-amino acids were used. Peptides containing the 6,5-bicyclic dipeptide mimic were synthesized by incorporating the 6,5-bicyclic dipeptide mimic into Peptide No. 204 according to the protocol described by Etzkorn et al., *J. Am. Chem. Soc.* 116: 10412 (1994) with the exception that all D-amino acids were used. Peptides containing the (D,L)-Freidinger's lactam were synthesized by incorporating the (D,L)-Freidinger's lactam into Peptide No. 216 according to the protocol described by Freidinger et al., *J. Org. Chem.* 47: 104-109 (1982) with the exception that L-methionine was used instead of D-methionine.

Table 17 provides a listing of peptides and peptide analogs derived from Peptide No. 501, in which substitutions with various amino acid and amino acid analogs have been generated where there are normally two adjacent glycines (Gly-Gly).

TABLE 17

Analogs of Peptide No. 501 Modified at Gly-Gly

| | Sequence* (SEQ ID NOS 17 and 187-191) | IC$_{50}$ μM | K$_D$ (pH 6) μM | K$_D$ pH 7.4 μM |
|---|---|---|---|---|
| Peptide No. 501 | QRFCTGHFGGLYPCNGP | 26 | 5.1 | 30 |
| Peptide No. 22 | QRFCTGHF-a-GLYPCNGP | 48 | 10 | 137 |
| Peptide No. 23 | QRFCTGHFG-a-LYPCNGP | 57 | 12 | 184 |
| Peptide No. 24 | QRFCTGHF-a-a-LYPCNGP | 69 | 22 | >250 |
| Peptide No. 25 | QRFCGHF-betaAla-LYPCNGP | >125 | >250 | nd |
| Peptide No. 35 | QRFCTGHF-Apa-LYPCNGP | >125 | 220 | nd |

*"beta-Ala" = beta-alanine; "Apa" = 5-aminopentanoic acid

Table 18 provides a listing of peptides and peptide analogs derived from Peptide No. 99 with a substitution of two glycines taken together for a peptidomimetic analog where there is normally the sequence Gly-Gly.

TABLE 18

Peptidomimetic Analogs of Peptide No. 99 Modified at Gly-Gly

| | Sequence | X Description | X Structure | IC$_{50}$ μM | K$_D$ (pH 6) μM |
|---|---|---|---|---|---|
| Peptide No. 99 | RF-Pen-TGHF-X-LYPC | Gly-Gly | (structure) | 2.0 | 0.17 |

TABLE 18-continued

Peptidomimetic Analogs of Peptide No. 99 Modified at Gly-Gly

| | Sequence | X Description | X Structure | IC$_{50}$ μM | K$_D$ (pH 6) μM |
|---|---|---|---|---|---|
| Peptide No. 134 | RF-Pen-TGHF-X-LYPC | 4-aminomethyl-benzoic acid | | >125 | |
| Peptide No. 135 | RF-Pen-TGHF-X-LYPC | (3-aminomethyl)-benzoic acid | | 57 | |
| Peptide No. 136 | RF-Pen-TGHF-X-LYPC | 4-aminophenyl acetic acid | | >125 | |
| Peptide No. 137 | RF-Pen-TGHF-X-LYPC | 3-aminophenyl acetic acid | | 14 | |
| Peptide No. 178 | RF-Pen-TGHF-X-LYPC | 3-amino-2-oxo-1-piperidine-acetic acid | | 0.66 | 0.16 |
| Peptide No. 179 | RF-Pen-TGHF-X-LYPC | 3-amino-2-oxo-1-piperidine-acetic acid | | 7.2 | 0.67 |
| Peptide No. 193 | RF-Pen-TGHF-X-LYPC | -3(S)-amino-2-oxo-1-piperidine-acetic acid | | 7.3 | |
| Peptide No. 80 | RF-Pen-TGHF-X-LYPC | 3-amino-N-1-carboxymethyl-2,3,4,5-tetrahydro-1H-[1]-benzazepine-2-one | | 159 | |
| Peptide No. 181 | RF-Pen-TGHF-X-LYPC | 3-amino-N-1-carboxymethyl-2,3,4,5-tetrahydro-1H-[1]-benzazepine-2-one | | 1.2 | |

TABLE 18-continued

Peptidomimetic Analogs of Peptide No. 99 Modified at Gly-Gly

| | Sequence | X Description | X Structure | IC$_{50}$ μM | K$_D$ (pH 6) μM |
|---|---|---|---|---|---|
| Peptide No. 197 | RF-Pen-TGHF-X-LYPC | 5,5-bicyclic dipeptide mimic | | 13 | 0.99 |
| Peptide No. 198 | RF-Pen-TGHF-X-LYPC | 5,5-bicyclic dipeptide mimic | | 23 | |
| Peptide No. 204 | RF-Pen-TGHF-X-LYPC | 6,5-bicyclic dipeptide mimic | | 2.2 | 0.32 |
| Peptide No. 205 | RF-Pen-TGHF-X-LYPC | 3(R)-amino-2-oxo-1-azepine acetic acid | | 0.64 | 0.103 |
| Peptide No. 214 | RF-Pen-TGHF-X-LYPC | 3(R)-amino-2-oxo-1-pyrrolidine acetic acid | | 2.3 | 0.28 |
| Peptide No. 227 | RF-Pen-TGHF-X-NMeLeu-YPC | 3(R)-amino-2-oxo-1-piperidine-acetic acid | | 0.53 | 0.043 |
| Peptide No. 228 | RF-Pen-NMeAla-GHF-X-NMeLeu-YPC | 3(R)-3-amino-2-oxo-1-piperidine-acetic acid | | 1.1 | 0.145 |
| Peptide No. 239 | RF-Pen-TGHF-X-NMeLeu-YPC | 3(R)-amino-2-oxo-1-azepine acetic acid | | 0.62 | 0.044 |

*"Pen" = L-penicillamine; "NMeLeu" = N-methylleucine; "NMeAla" = N-methylalanine

Example 10

Synthesis of Peptides Cyclized Via a Lactam Bridge

Lactam cyclized peptides (Table 19) were synthesized by solid-phase peptide synthesis as outlined above in Example 7 with the exception that the following amino acids were used as substitutes for various cysteines: Fmoc-Lys(Aloc)-OH, Fmoc-Orn(Aloc)-OH, Fmoc-Dab(Aloc)-OH and Fmoc-Dap(Aloc)-OH, Fmoc-Glu(OAllyl)-OH and Fmoc-Asp(OAllyl)-OH (Bachem, Torrance, Calif.). Following the completion of the process to generate fully protected peptides on resin, the resin was swollen in dichloromethane, purged with nitrogen and treated with 0.1 molar equivalents of tetrakis-(triphenylphosphine)palladium(0) (Sigma-Aldrich, St. Louis, Mo.) and 30 molar equivalents of phenylsilane (Sigma-Aldrich, St. Louis, Mo.) and the reaction was allowed to proceed for three hours. The resin was washed first with dichloromethane, with DMF and finally five additional times with a solution of 1% (v/v) triethylamine and 1% (w/v) diethyldithiocarbamic acid in DMF. An additional washing step with DMF was followed by treatment of the resin with benzotriazole-1-yl-oxy-tris-pyrrolidino-phosphonium hexafluorophosphate (PyBOP) (Novabiochem, San Diego Calif.) and DIEA for 16 hours. The peptides were cleaved from the resin and purified as described above in Example 7.

Table 19 provides a listing of various peptides of the invention with amino acid substitutions of cysteine residues for amino acids and amino acid analogs that would allow for the cyclization of the respective peptides via a lactam bridge. The impact of the substitutions on the binding parameters of these peptides with human FcRn is also provided.

TABLE 19

Lactam Cyclized Peptides

| | Sequence* (SEQ ID NOS 210-236) | $IC_{50}$ µM | $K_D$ (pH 6) µM | $K_D$ pH 7.4 µM |
|---|---|---|---|---|
| Peptide No. 38 | QRF-Asp-TGHFGGLYP-Dab-NGP | 68 | 17 | 150 |
| Peptide No. 39 | QRF-Asp-TGHFGGLYP-Lys-NGP | 10 | 1.2 | 12 |
| Peptide No. 72 | QRF-Dab-TGHFGGLYP-Glu-NGP | 81 | 4.8 | nd |
| Peptide No. 73 | QRF-Lys-TGHFGGLYP-Glu-NGP | 33 | 1.2 | nd |
| Peptide No. 76 | QRF-Glu-TGHFGGLYP-Lys-NGP | 100 | 27 | 320 |
| Peptide No. 77 | QRF-Glu-TGHFGGLYP-Dab-NGP | 86 | 22 | 210 |
| Peptide No. 78 | QRF-Glu-TGHFGGLYP-Dap-NGP | 71 | 9.6 | 81 |
| Peptide No. 79 | QRF-Asp-TGHFGGLYP-Dap-NGP | 32 | 4.5 | 30 |
| Peptide No. 80 | QRF-Lys-TGHFGGLYP-Asp-NGP | 60 | 10 | 52 |
| Peptide No. 81 | QRF-Dab-TGHFGGLYP-Asp-NGP | 31 | 8.4 | 45 |
| Peptide No. 85 | QRF-Asp-TGHFGGLYP-Orn-NGP | 16 | 2.7 | nd |
| Peptide No. 86 | QRF-Glu-TGHFGGLYP-Orn-NGP | 80 | 15 | nd |
| Peptide No. 107 | QRF-Asp-TGHFGGLY-Lys-NGP | >125 | >250 | nd |
| Peptide No. 105 | QRF-Asp-TGHFG-a-LYP-Lys-NGP | 12 | 2.1 | nd |
| Peptide No. 106 | QRF-Asp-TGHF-a-GLYP-Lys-NGP | 17 | 3.7 | nd |
| Peptide No. 123 | Asp-TGHFGGLYP-Lys-NGP | 47 | | |
| Peptide No. 124 | F-Asp-TGHFGGLYP-Lys-NGP | 22 | | |
| Peptide No. 125 | RF-Asp-TGHFGGLYP-Lys-NGP | 9.4 | | |
| Peptide No. 126 | QRF-Asp-TGHFGGLYP-Lys-NGP | 13 | | |
| Peptide No. 127 | QRF-Asp-TGHFGGLYP-Lys-N | 7.6 | | |
| Peptide No. 128 | QRF-Dap-TGHFGGLYP-Asp-NGP | 120 | | |
| Peptide No. 129 | QRF-Dap-TGHFGGLYP-Glu-NGP | >125 | | |
| Peptide No. 130 | QRF-Orn-TGHFGGLYP-Asp-NGP | 120 | | |
| Peptide No. 131 | QRF-Orn-TGHFGGLYP-Glu-NGP | 30 | | |
| Peptide No. 132 | RF-Asp-TGHFGGLYP-Lys | 11 | 0.90 | |

TABLE 19-continued

Lactam Cyclized Peptides

| | Sequence*<br>(SEQ ID NOS 210-236) | IC$_{50}$<br>µM | K$_D$<br>(pH 6)<br>µM | K$_D$<br>pH 7.4<br>µM |
|---|---|---|---|---|
| Peptide No. 133 | QRF-<u>Asp</u>-TGHFGGLYP-<u>Lys</u> | 13 | 0.90 | |
| Peptide No. 159 | QRF-<u>Asp</u>-TGHFG-p-LYP-<u>Lys</u>-NGP | 15 | 1.2 | |

*There is an amide bond between the side-chains of the underlined amino acids; Dab = 1,3-diaminobutyric acid; Dap = 1,2-diaminoproprionic acid; Orn = ornithine

Example 11

Synthesis of Linear Peptide Analogs

Unbridged ("linear") peptide analogs were synthesized as described above in Example 7, with the exception that disulfide-forming amino acids were substituted as set forth in Tables 20 and 21.

Table 20 provides a listing of Peptide No. 501 derived linear peptides and peptide analogs of the invention. Table 20 also provides the binding parameters of these peptides with human FcRn.

TABLE 20

Linear Analogs of Peptide No. 501

| | Sequence*<br>(SEQ ID NOS 17 and 237-263) | IC$_{50}$<br>µM | K$_D$<br>(pH 6)<br>µM | K$_D$<br>pH 7.4<br>µM |
|---|---|---|---|---|
| Peptide No. 501 | QRFCTGHFGGLYPCNGP | 26 | 5.1 | 30 |
| Peptide No. 71 | QRF-<u>S</u>-TGHFGGLYP-<u>S</u>-NGP | >125 | 230 | |
| Peptide No. 156 | QRF-<u>V</u>-TGHF-<u>p-p</u>-LYP-<u>A</u>-NGP | >250 | | |
| Peptide No. 157 | QRF-<u>V</u>-TGHF-<u>G-p</u>-LYP-<u>A</u>-NGP | 195 | 16 | |
| Peptide No. 58 | QRF-<u>V</u>-TGHF-<u>p-G</u>-LYP-<u>A</u>-NGP | >250 | | |
| Peptide No. 162 | QRF-<u>L</u>-TGHF-<u>G-p</u>-LYP-<u>A</u>-NGP | >250 | | |
| Peptide No. 163 | QRF-<u>I</u>-TGHF-<u>G-p</u>-LYP-<u>A</u>-NGP | >250 | | |
| Peptide No. 164 | QRF-<u>F</u>-TGHF-<u>G-p</u>-LYP-<u>A</u>-NGP | >250 | | |
| Peptide No. 165 | QRF-<u>Y</u>-TGHF-<u>G-p</u>-LYP-<u>A</u>-NGP | >250 | | |
| Peptide No. 166 | QRF-<u>W</u>-TGHF-<u>G-p</u>-LYP-<u>A</u>-NGP | >250 | | |
| Peptide No. 167 | QRF-<u>V</u>-TGHF-<u>G-p</u>-LYP-<u>V</u>-NGP | 93 | | |
| Peptide No. 168 | QRF-<u>V</u>-TGHF-<u>G-p</u>-LYP-<u>L</u>-NGP | 100 | | |
| Peptide No. 169 | QRF-<u>V</u>-TGHF-<u>G-p</u>-LYP-<u>I</u>-NGP | 72 | 15 | |
| Peptide No. 170 | QRF-<u>V</u>-TGHF-<u>G-p</u>-LYP-<u>F</u>-NGP | >250 | | |
| Peptide No. 171 | QRF-<u>V</u>-TGHF-<u>G-p</u>-LYP-<u>Y</u>-NGP | 150 | | |
| Peptide No. 172 | QRF-<u>V</u>-TGHF-<u>G-p</u>-LYP-<u>W</u>-NGP | 150 | | |
| Peptide No. 173 | QRF-<u>V</u>-TGHF-<u>G-p</u>-<u>V</u>-YP-<u>A</u>-NGP | >250 | | |
| Peptide No. 174 | QRF-<u>V</u>-TGHF-<u>G-p</u>-<u>I</u>-YP-<u>A</u>-NGP | 94 | | |
| Peptide No. 175 | QRF-<u>V</u>-TGHF-<u>G-p</u>-<u>F</u>-YP-<u>A</u>-NGP | 200 | | |
| Peptide No. 176 | QRF-<u>V</u>-TGHF-<u>G-p</u>-<u>Y</u>-YP-<u>A</u>-NGP | 230 | | |
| Peptide No. 177 | QRF-<u>V</u>-TGHF-<u>G-p</u>-<u>W</u>-YP-<u>A</u>-NGP | 52 | 5.8 | 96 |
| Peptide No. 190 | QRF-<u>V</u>-TGHF-<u>G-p</u>-<u>W</u>-YP-<u>I</u>-NGP | 49 | 4.2 | |

TABLE 20-continued

Linear Analogs of Peptide No. 501

| | Sequence*<br>(SEQ ID NOS 17 and 237-263) | IC$_{50}$<br>μM | K$_D$ (pH 6)<br>μM | K$_D$ pH 7.4<br>μM |
|---|---|---|---|---|
| Peptide No. 209 | RF-V-TGHF-G-p-W-YP | >125 | | |
| Peptide No. 210 | RF-V-TGHF-G-p-W-YP-A-NGP | 100 | 10 | |
| Peptide No. 211 | F-V-TGHF-G-p-W-YPA | 100 | 8 | |
| Peptide No. 212 | V-TGHF-G-p-W-YP-A | >250 | | |
| Peptide No. 236 | RF-V-TGHF-G-Sar-NMeLeu-YP-A | 37 | 1.85 | 9 |
| Peptide No. 246 | RF-V-TGHF-G-p-W-YPA | 60 | 3.6 | |

*"Sar" = sarcosine; "NMeLeu" = N-methylleucine

Table 21 provides a listing of Peptide No. 236-derived peptides and peptide analogs where various peptidomimetic analogs have been substituted where there is normally a Glycine-Sarcosine sequence (Gly-Sar).

TABLE 21

Linear Analogs of Peptide No. 236 with Gly-Gly peptidomimetics

| | Sequence* | X Description | X Structure | IC$_{50}$ μM | K$_D$ (pH 6) μM |
|---|---|---|---|---|---|
| Peptide No. 236 | RF-V-TGHF-X-NMeLeu-YPA | Gly-Sar | | 37 | 1.85 |
| Peptide No. 182 | RF-V-TGHF-X-LYPA | 3-amino-2-oxo-1-piperidine-acetic acid | | 38 | 3.3 |
| Peptide No. 183 | RF-V-TGHF-X-LYPA | 3-amino-2-oxo-1-piperidine-acetic acid | | >250 | |
| Peptide No. 184 | RF-V-TGHF-X-LYPA | 3-amino-N-1-carboxymethyl-2,3,4,5-tetrahydro-1H-[1]-benzazepine-2-one | | >250 | |
| Peptide No. 185 | RF-V-TGHF-X-LYPA | 3-amino-N-1-carboxymethyl-2,3,4,5-tetrahydro-1H-[1]-benzazepine-2-one | | 57 | 3.1 |

TABLE 21-continued

Linear Analogs of Peptide No. 236 with Gly-Gly peptidomimetics

| | Sequence* | X Description | X Structure | IC$_{50}$ µM | K$_D$ (pH 6) µM |
|---|---|---|---|---|---|
| Peptide No. 186 | RF-V-TGHF-X-LYPA | 3-aminophenyl acetic acid | | >250 | |
| Peptide No. 191 | QRF-V-TGHF-X-WYPINGP | 3-amino-2-oxo-1-piperidine-acetic acid | | nd | 333 |
| Peptide No. 206 | RF-V-TGHF-X-LYPA | 5,5 bicyclic dipeptide mimic | | >250 | |
| Peptide No. 207 | RF-V-TGHF-X-LYPA | 6,5-bicyclic dipeptide mimic | | >125 | 20 |
| Peptide No. 208 | RF-V-TGHF-X-LYPA | 3(R)-amino-2-oxo-1-azepine acetic acid | | 23 | 2.3 |

*"Sar" = sarcosine; "NMeLeu" = N-methylleucine

Example 12

Synthesis of Peptide Dimers Via Reductive Alkylation

Peptide dimers (Table 22) were generated by reductive alkylation of a peptide aldehyde and a peptide amino (N) or carboxy (C) terminal amine.

Peptide N-terminal amines were synthesized as described above in Example 7 for the synthesis of monomeric peptide disulfides.

Peptide C-terminal amines were also synthesized as described above in Example 7 for the synthesis of monomeric peptide disulfides, except that 1,2-diaminoethane resin (Novabiochem, San Diego, Calif.) was used in the synthesis step. Consequently, cleavage from the resin resulted in a C-terminal ethyl amine.

Peptide N-terminal aldehydes (FIG. 1) were synthesized by reacting the unprotected amine of the N-terminal amino acid with 5 equivalents of succinic anhydride (Sigma-Aldrich, St. Louis, Mo.) in the presence of DIEA in DMF for 2 hours. A subsequent reaction with 2,2-dimethyl-1,3-dioxolane methamine (Sigma-Aldrich, St. Louis, Mo.) in the presence of PyBOP and DIEA for 2 hours yielded the protected diol resin. Then, cleavage of the crude peptide from the resin, followed by cysteine oxidation and purification as described above in Example 7 for the synthesis of monomeric peptide disulfides, yielded the peptide diol. The diol was dissolved in 33% acetic acid followed by 2 equivalents of sodium periodate (Sigma-Aldrich, St. Louis, Mo.) was added and the reaction was allowed to proceed for 5 minutes. The reaction mixture was quenched with 20 equivalents (with respect to the diol) of ethylene glycol (Sigma-Aldrich, St. Louis, Mo.) and after ten minutes, the crude reaction mixture was diluted 3-fold with water and purified over a C18 Sep-Pak column (Waters Corp., Milford, Mass.) using an increasing gradient of acetonitrile in water containing 0.1% TFA. The peptide aldehyde was lyophilized and subjected to analysis by mass spectroscopy (Mariner ES-MS) following liquid chromatography (Applied Biosystems, Foster City, Calif.) as described in Example 7.

Peptide C-terminal aldehydes were synthesized as described above in Example 7 for the synthesis of monomeric peptide disulfides, except that Fmoc-1-amino-2,3-propanediol-2'-chlorotrityl resin (Novabiochem, San Diego, Calif.) was used instead of Rink amide resin. Therefore the resulting peptide resin contained a masked C-terminal diol. Upon cleavage from the resin, the diol was oxidized to an aldehyde as described above for N-terminal aldehydes.

To synthesize lactam-cyclized peptides such as Peptide No. 275, peptide monomers were synthesized according to the method described above in Example 10 showing synthesis of peptides cyclized by a lactam bridge, whereby the Asp-Lys cyclization was performed on the resin, prior to cleavage from the resin.

Figure 2:
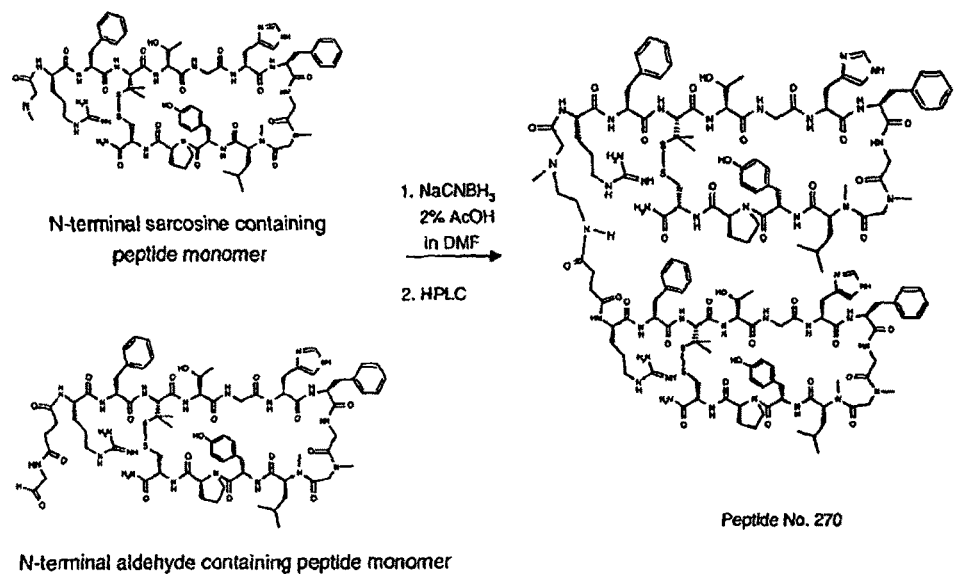
FIG. 2 shows an overview of the synthesis of peptide dimers by reductive alkylation as described in Example 12 using Peptide No. 270 as an illustrative example.

The peptide dimers were synthesized (FIG. 2) by reacting one equivalent of peptide aldehyde with one equivalent of amine-containing peptide at a concentration of 40 mg/ml in DMF containing 2% acetic acid. After 60 min., 2 equivalents of sodium cyanoborohydride (Sigma-Aldrich, St. Louis, Mo.) were added and the reaction was allowed to shake for 1 hour. The reaction mixture was diluted 10-fold with water and purified by HPLC and analyzed by mass spectroscopy (Mariner ES-MS) following liquid chromatography (Applied Biosystems, Foster City, Calif.) as described in Example 7.

Table 22 provides a listing of dimeric peptides of the invention that were synthesized by reductive alkylation. In Table 22 and subsequent tables, Column 1 contains the peptide identifier. Column 2 contains the amino acid sequence of the peptides. Column 3 contains the $IC_{50}$ of each peptide as determined by the IgG competition ELISA outlined in Example 4. Columns 4 and 5 contain the $K_D$ of each peptide as determined at pH 6 and pH 7.4, respectively, by the Biacore analysis outlined in Example 6. Column 6 contains the $IC_{50}$ of each peptide as determined by competitive IgG binding FACS analysis as outlined in Example 5.

TABLE 22

Dimers and Trimers Synthesized by Reductive Alkylation

| Sequence* | $IC_{50}$ nM | $K_D$ pH 6 nM | $K_D$ pH 7.4 nM | $IC_{50}$ nM FACS |
|---|---|---|---|---|
| Peptide No. 276 [RFCTGHFGGLYPC] / [RFCTGHFGGLYPC] | 3700 | 56 | | 12,900 |
| Peptide No. 215 [QRF-Pen-TGHFGpLYPCNGP] / [QRF-Pen-TGHFGpLYPCNGP] | | 30 | | 6.6 |
| Peptide No. 230 [RF-Pen-TGHF-X-NMeLeu-YPC] / [RF-Pen-TGHF-X-NMeLeu-YPC] | 7.2 | <0.5 | | 0.46 |
| Peptide No. 231 [RF-Pen-NMeAla-GHF-X-NMeLeu-YPC] / [RF-Pen-NMeAla-GHF-X-NMeLeu-YPC] | | 30 | | 2.9 |

TABLE 22-continued

Dimers and Trimers Synthesized by Reductive Alkylation

| Sequence* | IC$_{50}$ nM | K$_D$ pH 6 nM | K$_D$ pH 7.4 nM | IC$_{50}$ nM FACS |
|---|---|---|---|---|
| Peptide No. 247 — trimer structure with three R-F-Pen-T-G-H-F-G-Sar-NMeLeu-Y-P-C branches | 6 | | | |
| Peptide No. 270 — dimer structure with two [RF-Pen-TGHFG-Sar-NMeLeu-YPC] branches | 2.6 | <0.5 | <0.8 | 4 |
| Peptide No. 272 — dimer structure with two [RF-Pen-TGHFG-Sar-NMeLeu-YPC] branches | 2.8 | <0.5 | <0.8 | 5 |
| Peptide No. 273 — dimer structure with two [RF-Pen-TGHFG-Sar-NMeLeu-YPC] branches | 2.1 | <0.5 | <0.9 | 4 |
| Peptide No. 274 — dimer structure with two [RF-Pen-TG-4GuPhe-FG-Sar-NMeLeu-YPC] branches | 17 | | | |

TABLE 22-continued

Dimers and Trimers Synthesized by Reductive Alkylation

| Sequence* | $IC_{50}$ nM | $K_D$ pH 6 nM | $K_D$ pH 7.4 nM | $IC_{50}$ nM FACS |
|---|---|---|---|---|
| Peptide No. 277 (structure: [RF-Pen-TGHFG-Sar-NMeLeu-YPCG] linked via ethylene-N-CH₂-C(O)-NH to [RF-Pen-TGHFG-Sar-NMeLeu-?]) | 6.3 | | | |
| Peptide No. 278 (structure: two [RF-Pen-TGHFG-Sar-NMeLeu-YPCG] units linked through ethylenediamine) | 4.4 | | | |
| Peptide No. 275 (structure: two [RF-Asp-TGHFG-Sar-NMeLeu-YP-Lys] units linked via N-methyl-glycyl-amide / ethylenediamine-succinyl bridge) | 44 | 1.6 | | 9.1 |

*X = 3(r)-3-amino-1-carboxymethyl-valerolactam; horizontal brackets placed above or below a peptide sequence indicate the presence of a bridge

Example 13

Synthesis of Peptide Dimers by Thiol Linkers and Bromoacetylated Peptides

Figure 3:
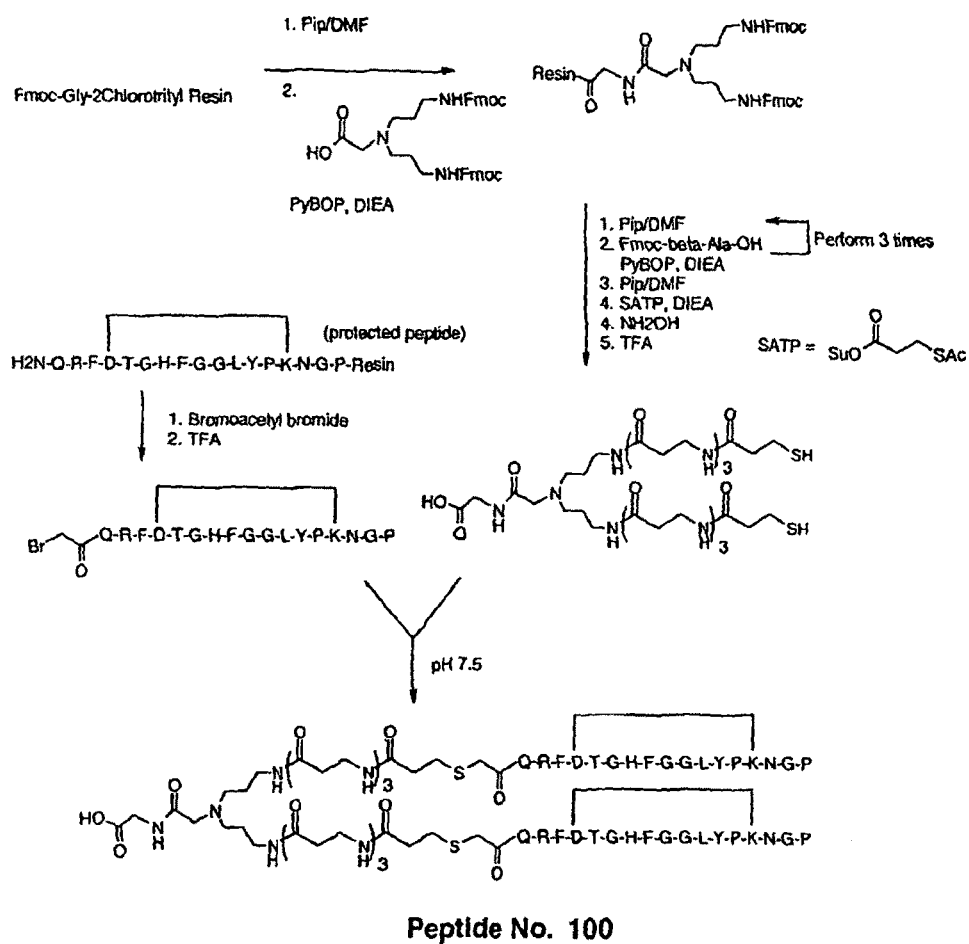
FIG. 3 describes the synthesis of Peptide No. 100 (SEQ ID NO: 285) as an illustrative example of the synthesis of peptide dimers by using a bis-thiol linker containing peptide and a bromoacetylated peptide. Horizontal brackets placed above the peptide sequence indicate the presence of a bridge.

Peptide dimers (Table 23) were also synthesized by reacting bromoacetylated peptides with a thiol linkers. Bromoacetylated peptides were synthesized (FIG. 3) by reacting the free α-amino group of the protected peptide resin with 4 equivalents of bromoacetyl bromide (Sigma-Aldrich, St. Louis, Mo.) and 8 equivalents of DIEA (Sigma-Aldrich, St. Louis, Mo.) in DMF. After 1 hour, the resin was washed with DMF, followed by DCM and cleaved from the resin as described above in Example 7. In the case where lactam-cyclized peptides were dimerized using a bis-thiol linker, the on-resin cyclization step was performed prior to the bromoacetylation step. In the case where disulfide-containing peptides were dimerized using a bis-thiol linker, the iodine oxidation step was performed after cleavage as described above in Example 7.

The bis-thiol linkers were synthesized (FIG. 3) by reacting NH₂-Gly-2-Chlorotrityl resin (Novabiochem, San Diego, Calif.) with 2 equivalents of N,N-bis(N'-Fmoc-3-aminopropyl)glycine potassium hemisulphate (Chem-Impex, Wood Dale, Ill.) in the presence of 2 equivalents of PyBOP (Novabiochem, San Diego, Calif.) and DIEA in DMF for 18 hours. The Fmoc protecting group was removed with two 10 minute treatments of 20% piperidine in DMF. For some of the linker compounds, beta-alanines were also incorporated as spacer units. Fmoc-beta-Ala-OH (Novabiochem) was coupled to the resin as above using PyBOP and DIEA. After the Fmoc protecting group was removed with 20% piperidine in DMF, either another beta-alanine spacer unit was incorporated, or the bis-thiol linker was incorporated by reacting the free N-terminal amine resin with 2 equivalents of N-succinimidyl-5-acetylthiopropionate (SATP; Pierce, Rockford, Ill.) and 4 equivalents of DIEA for 18 hours.

Subsequently, removal of the S-acetyl protecting group was accomplished by reacting 0.05 mmol of the peptide resins with a degassed solution containing 1 ml of DMF and 0.4 ml of buffer A (Buffer A: 1 M hydroxylamine hydrochloride (Sigma-Aldrich, St. Louis, Mo.), 40 mM sodium phosphate pH 7.5, 50 mM EDTA (Sigma-Aldrich, St. Louis, Mo.)) for 18 hours. The resins were washed with DMF, followed by DCM, and cleaved from the resin with a 50% solution of TFA in DCM with 2% triisopropylsilane for 15 min. The crude linkers were processed and purified as described above in Example 7.

The peptide dimers were generated using bis-thiol linkers (FIG. 3) by reacting one equivalent of the purified bis-thiol linker with two equivalents of bromoacetylated N-terminal peptide in DMF with 10% water and 50% 100 mM sodium phosphate, pH 7.5. After 18 hours, the crude reaction mixture was purified by reversed phase HPLC column as described above in Example 7.

Figure 4:
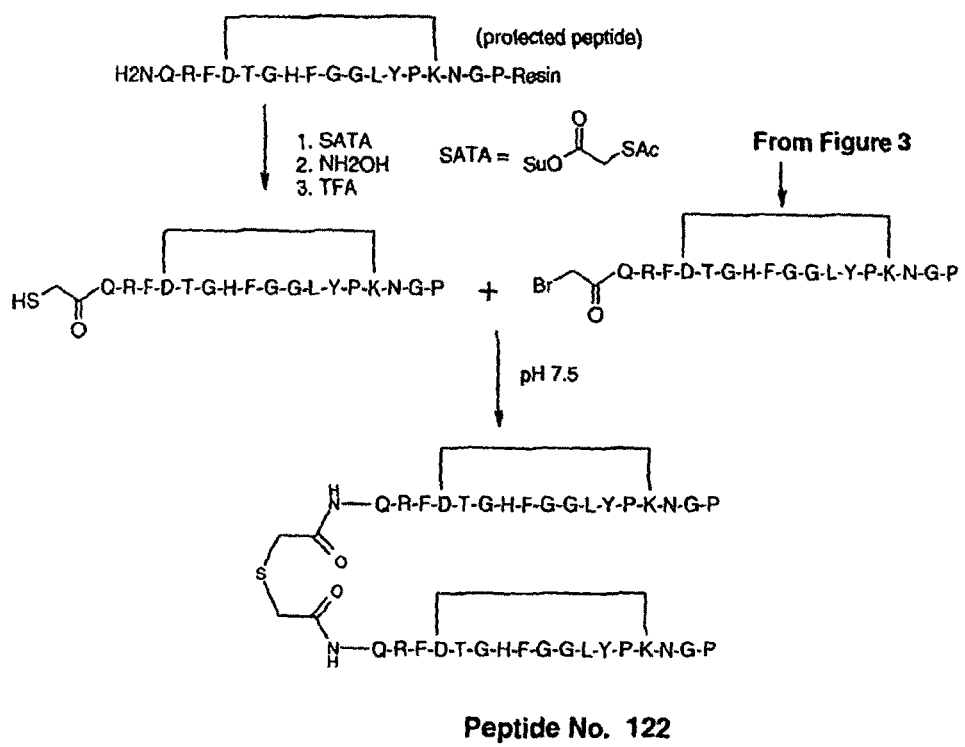
FIG. 4 shows the synthesis of Peptide No. 122 (SEQ ID NO: 289) as an illustrative example of the synthesis of peptide dimers using a thiol linker-containing peptide and a bromoacetylated peptide. Horizontal brackets placed above the peptide sequence indicate the presence of a bridge.

Peptide No. 122 was synthesized (FIG. 4) by reacting a bromoacetylated peptide with a peptide derivatized with SATP. Briefly, the crude peptide resin with a free N-terminal amine was reacted with 2 equivalents of SATP in DMF for 2 hours. The S-acetyl protecting group was removed as described above, followed by cleavage from the resin and subsequent purification as described above.

Table 23 provides a listing of dimeric peptides of the invention that were synthesized by thiol linkers.

TABLE 23
Dimers Synthesized Using Thiol Linkers
| Sequence* | IC$_{50}$ nM | K$_D$ pH 6 nM | K$_D$ pH 7.4 nM | IC$_{50}$ nM FACS |
|---|---|---|---|---|
| Peptide No. 100 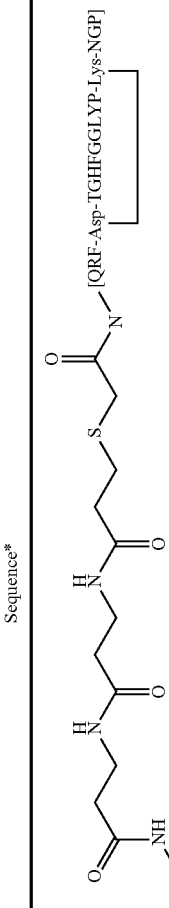 | 760 | 6 | 130 | |
| Peptide No. 119 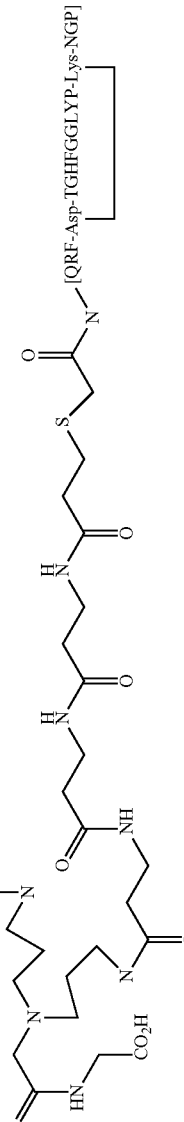 | 900 | 7 | 150 | |

TABLE 23-continued
Dimers Synthesized Using Thiol Linkers
| Sequence* | IC$_{50}$ nM | K$_D$ pH 6 nM | K$_D$ pH 7.4 nM | IC$_{50}$ nM FACS |
|---|---|---|---|---|
| Peptide No. 120 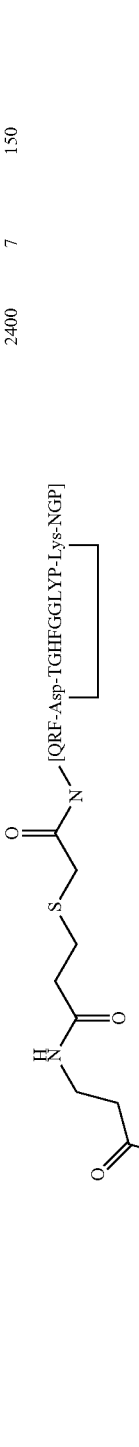 | 2400 | 7 | 150 | |
| Peptide No. 121 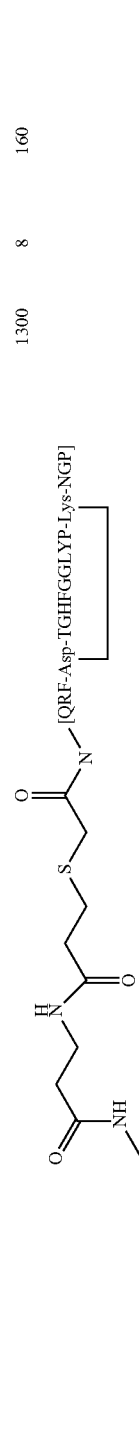 | 1300 | 8 | 160 | |

TABLE 23-continued

Dimers Synthesized Using Thiol Linkers

| Sequence* | IC$_{50}$ nM | K$_D$ pH 6 nM | K$_D$ pH 7.4 nM | IC$_{50}$ nM FACS |
|---|---|---|---|---|
| Peptide No. 122 | 970 | 6 | 120 | |
| Peptide No. 160 | 100 | | | |
| Peptide No. 161 | 90 | | | |

TABLE 23-continued

Dimers Synthesized Using Thiol Linkers

| Peptide No. | Sequence* | IC$_{50}$ nM | K$_D$ pH 6 nM | K$_D$ pH 7.4 nM | IC$_{50}$ nM FACS |
|---|---|---|---|---|---|
| Peptide No. 199 | 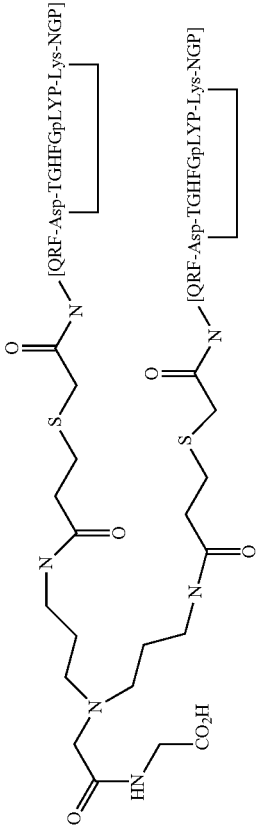 [QRF-Asp-TGHFGpLYP-Lys-NGP] / [QRF-Asp-TGHFGpLYP-Lys-NGP] | 1200 | 7.9 | 190 | |
| Peptide No. 200 | 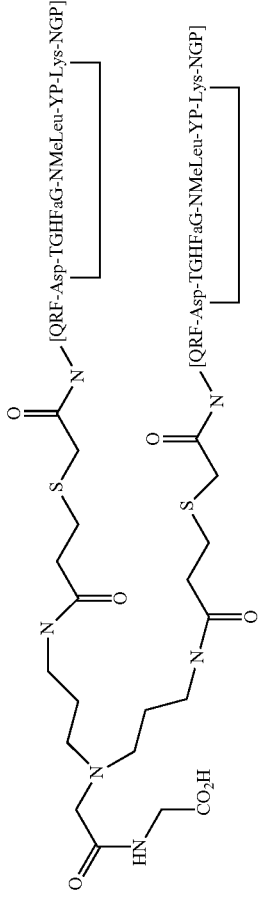 [QRF-Asp-TGHFaG-NMeLeu-YP-Lys-NGP] / [QRF-Asp-TGHFaG-NMeLeu-YP-Lys-NGP] | 1900 | 7.2 | 170 | |

*Pen = penicillamine; Sar = sarcosine; p = D-proline; NMeLeu = N-methylleucine; horizontal brackets placed above or below a peptide sequence indicate the presence of a bridge

Example 14

Synthesis of Peptide Trimers Via Reductive Alkylation: Peptide No. 247

Peptide trimers (Table 22) were generated by reductive alkylation of a peptide aldehyde and a peptide amino N-terminal amine.

Peptide N-terminal amines were synthesized as described above in Example 7 for the synthesis of monomeric peptide disulfides with the exception that the N-terminus was capped with a bifunctional amine linker such as bis-aminipropyl glycine (BAPG; used as Bis-Fmoc-BAPG purchased from Sigma-Aldrich, Stl. Louis, Mo.), followed by coupling sarcosine. Peptide N-terminal aldehydes (FIG. 1) were synthesized as described in Example 12. The peptide trimers were synthesized (as in FIG. 2) by reacting two equivalents of peptide aldehyde with one equivalent of amine-containing peptide at a concentration of 40 mg/ml in DMF containing 2% acetic acid. After 60 min., 4 equivalents of sodium cyanoborohydride (Sigma-Aldrich, St. Louis, Mo.) were added and the reaction was allowed to shake for 1 hour. The reaction mixture was diluted 10-fold with water and purified by HPLC and analyzed by mass spectroscopy (Mariner ES-MS) following liquid chromatography (Applied Biosystems, Foster City, Calif.) as described in Example 7.

Example 15

Synthesis of Peptide Dimers Using Diacid and Amine Linkers

Amide linked peptide dimers (Table 24) were generated either by reacting the N-termini of two on-resin peptide monomers with a bi-functional acid linker or by performing the synthesis of the peptide on resin containing a bi-functional amine linker, thereby tethering the C-termini of two on-resin peptide monomers.

N-terminally linked peptide dimers were synthesized as described above in Example 7 for the synthesis of monomeric peptide disulfides with the following exceptions Before the peptides are cleaved from the resin, the N-termini of two peptide monomers are joined with a bi-functional acid linker. For example, Peptide No. 283 is synthesized by reacting the peptide resin containing the peptide sequence analogous to Peptide No. 235 with an unprotected N-terminus with 0.5 equivalents of succinic acid (Sigma-Aldrich, St. Louis, Mo.) in the presence of 1 equivalent of PyBOP and 2 equivalents of DIEA. This results in adjacent peptides on the resin being covalently attached by amide bonds via their N-termini.

Figure 5:
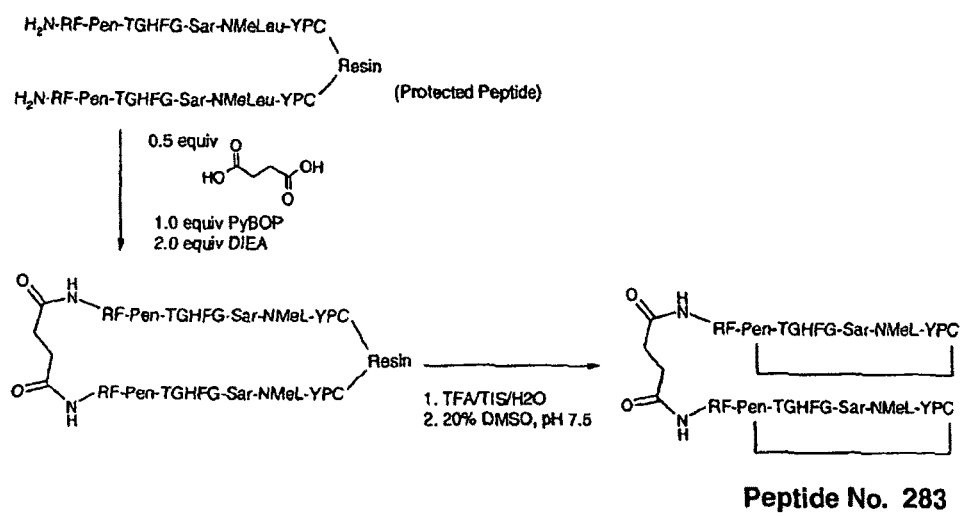
FIG. 5 shows the synthesis of peptide dimers using a diacid containing linker. The synthesis of Peptide No. 283 (SEQ ID NO: 300) is shown as an illustrative example. Horizontal brackets placed below the peptide sequence indicate the presence of a bridge.

The resulting peptide dimer is cleaved from the resin and purified as described in Example 7 with the exception that the peptide disulfides are not oxidized prior to HPLC purification. The purified reduced peptide is dissolved to ca. 0.1 mg/mL in 10 mM sodium phosphate, pH 7.5 with 20% DMSO and mixed for 3 days at room temperature. This oxidation step permits the formation of the disulfide bonds within one peptide monomer of the dimer, as opposed to between two monomers of a dimer. The reaction mixture is diluted with water to peptide concentration of 0.05 mg/mL and purified over a C18 Sep-Pak column (Waters Corp., Milford, Mass.) using an increasing gradient of acetonitrile in water containing 0.1% TFA. The peptide dimer was lyophilized and subjected to analysis by mass spectroscopy (Mariner ES-MS) following liquid chromatography (Applied Biosystems, Foster City, Calif.) as described in Example 7. (See FIG. 5.) In the case of Peptide No. 283, the disulfide linkage pattern was confirmed by digesting the peptide with trypsin for 30 minutes, then analyzing the resulting peptides by LCMS. Trypsin is known to cleave after arginine and lysine residues, and cleaves Peptide No. 283 at the arginine-phenylalanine bond, The major product of LCMS of Peptide No. 283 is $NH_2$-(Phe Phe-Pen-Thr-Gly-His-Phe-Gly-Sar-NMeLeu-Tyr-Pro-Cys]-$CONH_2$(disulfide) (SEQ ID NO:294) (LCMS: M+H=1355.6 Da), which indicates that the disulfide bonds of Peptide No. 283 are formed intramolecularly within each 13 amino acid peptide monomer.

Peptide No. 201 was synthesized as Peptide No: 283 with the exceptions that the peptide sequence was analogous to Peptide No. 32, the diacid linker used was ethylene glycol-bis(succinic acid-N-hydroxysuccinimide ester) (Sigma-Aldrich, St. Louis, Mo.) and that no PyBOP was used for the coupling reaction.

Peptide No. 279 was synthesized as in Peptide No. 283 with the exception that the diacid linker used was Bis-dPEG6-N-hydroxysuccinimide ester (Quanta Biodesigns Ltd.) and that no PyBOP was used for the coupling reaction.

Peptide No. 281 was synthesized as Peptide No. 283 with the exception that the peptide-resin was treated with a large excess of succinic anhydride (Sigma-Aldrich, St. Louis, Mo.), which results in all peptides on the resin containing a succinate capped N-terminus. This resin was treated with 0.5 equivalents of N,N'-dimethylethyl-enediamide (Sigma-Aldrich, St. Louis, Mo.) in the presence of 1 equivalent of PyBOP and 2 equivalents of DIEA. The subsequent cleavage, purification and oxidation steps were performed as with Peptide No. 283.

Peptide No. 282 was synthesized as Peptide No. 283 with the exception that the diacid linker used was N-methyl-iminodiacetic acid (Sigma-Aldrich, St. Louis, Mo.).

Peptide No. 284 was synthesized as Peptide No. 283 with the exception that the diacid linker used was 3,3-dimethyl-glutaric acid (Sigma-Aldrich, St. Louis, Mo.).

Peptide No. 285 was synthesized as Peptide No. 283 with the exception that the diacid linker used was Boc-Asp(OH)—OH (Novabiochem, San Diego, Calif.).

Peptide No. 286 was synthesized as Peptide No. 283 with the exception that the diacid linker used was Boc-Glu(OH)—OH (Novabiochem, San Diego, Calif.).

Figure 6:
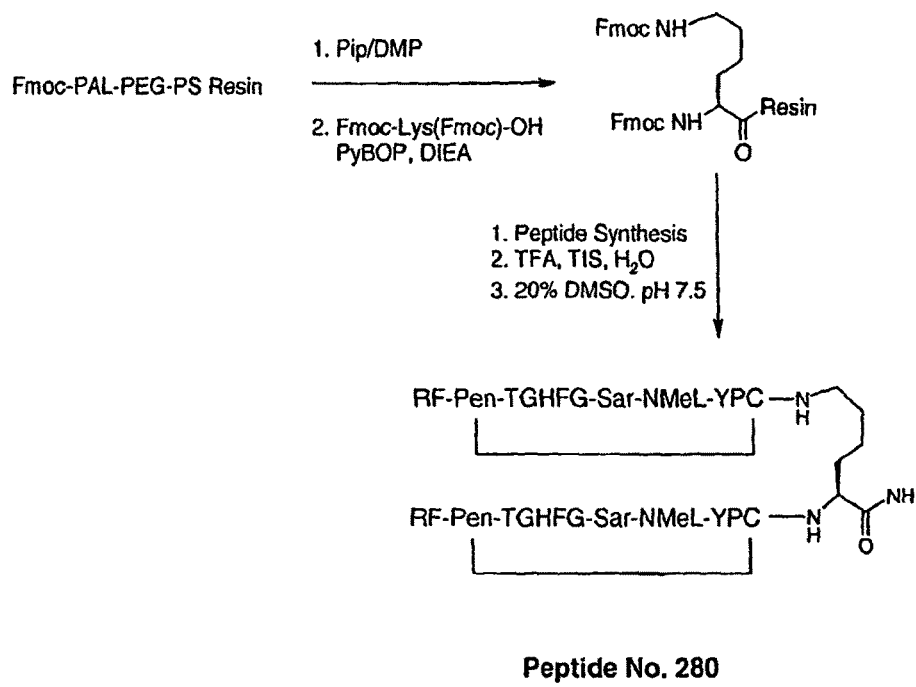
FIG. 6 shows the synthesis of peptide dimers using an amine containing linker. The synthesis of Peptide No. 280 (SEQ ID NO: 297) is shown as an illustrative example. Horizontal brackets placed below the peptide sequence indicate the presence of a bridge.

C-terminally linked peptide dimers were synthesized as described above in Example 7 for the synthesis of monomeric peptide disulfides with the exception that a bifunctional amine linker is coupled to the resin prior to the peptide synthesis. This results in peptide dimers with their C-termini covalently attached by amide bonds. For example, Peptide No. 280 was synthesized by first coupling Fmoc-Lys(Fmoc)-OH (Novabiochem, San Diego, Calif.) to the resin, followed by the coupling of amino acids to give a sequence analogous to Peptide No. 235. This results in the covalent attachment of two peptide chains as they are being synthesized on the resin. The resulting peptide dimer is cleaved from the resin, purified and oxidized as described above for the N-terminally linked dimers (see FIG. 6).

Peptide No. 287 was synthesized as Peptide No. 280 with the exception that a glycine residue (Gly) is inserted between the Peptide No. 235 sequence and the branching Lysine linker.

Peptide No. 288 was synthesized as Peptide No. 280 with the exceptions that two glycine residues (Gly-Gly) are inserted between the Peptide No. 235 sequence and the branching lysine linker.

Table 24 provides a listing of dimeric peptides of the invention that contain amide bonds.

TABLE 24

| | Dimers With Amide Linkers | |
|---|---|---|
| | Sequence* | IC$_{50}$ nM |
| Peptide No. 201 | (structure with two [QRF-Pen-TGHFGGLYPCNGP] peptides linked via succinate-ethylene glycol-succinate diester with amide bonds) | 26 |
| Peptide No. 279 | (structure with two [RF-Pen-TGHFG-Sar-NMeL-YPC] peptides linked via a PEG-based bis-propanamide linker) | 7 |
| Peptide No. 280 | (structure with two [RF-Pen-TGHFG-Sar-NMeL-YPC] peptides linked through a lysine amide) | 25 |
| Peptide No. 281 | (structure with two [RF-Pen-TGHFG-Sar-NMeL-YPC] peptides linked via bis(N-methyl) ethylenediamine bis-succinamide) | 5.2 |
| Peptide No. 282 | (structure with two [RF-Pen-TGHFG-Sar-NMeL-YPC] peptides linked via N-methyl-iminodiacetamide) | 4.7 |

TABLE 24-continued

| | Dimers With Amide Linkers | |
|---|---|---|
| | Sequence* | IC$_{50}$ nM |
| Peptide No. 283 | succinyl-bis[RF-Pen-TGHFG-Sar-NMeL-YPC] | 3.3 |
| Peptide No. 284 | 3,3-dimethylglutaryl-bis[RF-Pen-TGHFG-Sar-NMeL-YPC] | 8.5 |
| Peptide No. 285 | Asn-bis[RF-Pen-TGHFG-Sar-NMeL-YPC] | 4.6 |
| Peptide No. 286 | Gln-bis[RF-Pen-TGHFG-Sar-NMeL-YPC] | 5.6 |
| Peptide No. 287 | Lys-bis[RF-Pen-TGHFG-Sar-NMeL-YPCG] amide | 20 |
| Peptide No. 288 | Lys-bis[RF-Pen-TGHFG-Sar-NMeL-YPCGG] amide | 16 |

*Pen = penicillamine; Sar = sarcosine; NMeLeu = N-methylleucine

Example 16

Synthesis of Peptide-Fc Fusions Via Reductive Alkylation

Peptide N-terminal aldehydes Peptide No. 252, Peptide No. 229 and Peptide No. 232 (Table 25) were synthesized as described in Example 12. All three peptide-Fc fusions were generated using the same protocol: CysFc (Fc domain possessing a N-terminal cysteine) and 4.5 equivalents of peptide aldehyde were incubated on ice in 80 mM sodium acetate pH 5.5 for 1 hour. Sodium cyanoborohydride was added to a final concentration of 20 mM and the reaction was incubated for 16 hours at 4° C. The reaction mixture was analyzed by SDS-PAGE to ensure the addition of predominantly a single peptide to the Fc protein. The protein mixture was dialyzed twice with PBS and assayed for in vitro blocking activity (Table 25). In the case of Peptide No. 252-Fc, the protein was also evaluated in the TG32B mouse IgG catabolism model. The production of CysFc can be performed as described in US Patent Application Publication No. US 2005/0027109, where the disclosure of the production of CysFc is incorporated herein by reference.

Table 25 provides a listing of peptide-Fc fusion proteins of the invention that were synthesized using CysFc and aldehyde-peptides.

TABLE 25

Peptide-Fc Fusions

| | Sequences* | $IC_{50}$ nM |
|---|---|---|
| CysFc | | 210 |
| Peptide No. 229-Fc | 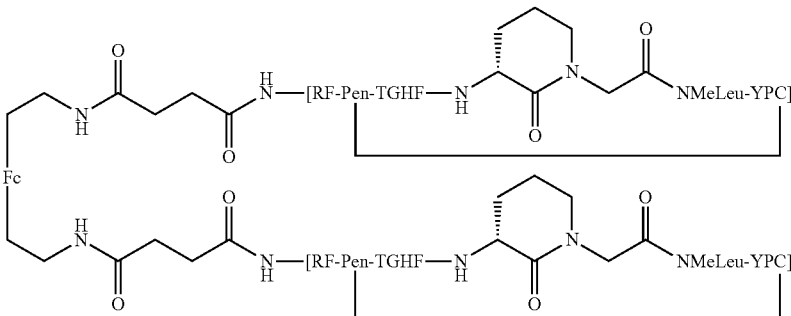 | 2 |
| Peptide No. 232-Fc | 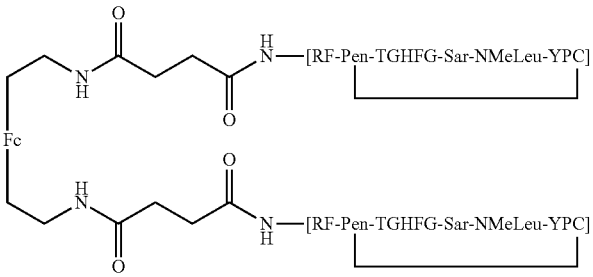 | 3 |
| Peptide No. 252-Fc | 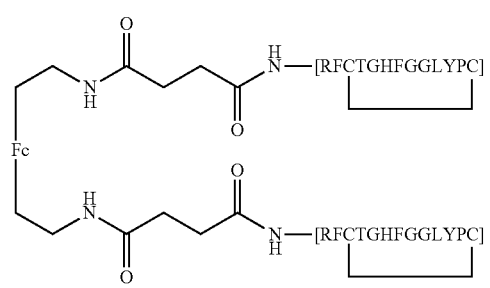 | 39 |

*Pen = penicillamine; Sar = sarcosine; NMeLeu = N-methylleucine

Example 17

Transgenic Mice

Transgenic mice were obtained from Dr. Roopenian of The Jackson Laboratory in Bar Harbor, Me. The endogenous murine FcRn and $\beta_2$m genes were inactivated by insertion of a foreign polynucleotide sequence by homologous recombination and replaced transgenically with the human FcRn and the human $\beta_2$m genes (muFcRn (−/−), mu$\beta_2$m (−/−), +huFcRn, +hu$\beta_2$m). These mice are referred to by the strain name TG32B.

Example 18

Effect of Peptide No. 270 on Human IgG Catabolism in TG32B Mice Using 5 mg/kg and 10 mg/kg Adult TG32B mice were injected intravenously with 500 mg/kg of human IgG (MP Biomedicals, Irvine, Calif.) at t=0 hours ($T_0$). At 24, 48, 72, 96 and 120 hours, the mice were injected intravenously with either 5 mg/kg or 10 mg/kg Peptide No. 270. Control injections were performed at each timepoint using the vehicle PBS with 15 mM sodium acetate, pH 5. Blood samples were taken prior to injections at all timepoints, as well as at 168 hours. Serum was prepared and stored at −20° C. until an ELISA was performed.

An IgG Fc domain-specific ELISA was used to detect the levels of human IgG in the serum at each time point. Briefly, 30 µl of a 10 µg/ml stock solution of goat anti-human IgG (Pierce, Rockford, Ill.) was diluted with 6 ml of 0.05 M sodium bicarbonate, pH 9.6 (Sigma-Aldrich, St. Louis, Mo.). A 96-well plate was coated with 50 µl/well of this solution and incubated for 1 hour at 37° C. The coating solution was removed and washed once with PBST (phosphate buffered saline with 0.05% Tween-20). Then 200 µl/well of a 2% bovine serum albumin (BSA) stock solution in PBS was added and the plate incubated for 1 hour at 37° C. The wells were washed three times with PBST and a standard curve was generated in triplicate by performing 2.5-fold dilutions starting from 50 ng/ml of hIgG1. Then 100 µl of either the standard or sample solutions was added to the wells and the plate was incubated for 1 hour at 37° C. Three more PBST washes were performed followed by the addition of 100 µl of a 1:10,000 dilution of a goat anti-human IgG[Fc]-HRP conjugate (Pierce, Rockford, Ill.) in PBS containing 2% BSA. The plate was allowed to incubate for 1 hour at 37° C. followed by washes with PBST and the addition of a 100 µl of TMB One-Component substrate (BioFX, Owings Mills, Md.) to each well. Color development was halted after 5 minutes by the addition of 100 µl of 0.25 M sulfuric acid to each well. The UV absorbance for each well was measured at 450 nm and a calibration curve was used to derive a plot of serum IgG concentration vs. time for the experiments.

Example 19

Effect of Peptide No. 231, Peptide No. 274 and Peptide No. 252-Fc on Human IgG Catabolism in TG32B mice Adult TG32B mice were injected intravenously with 500 mg/kg of human IgG (MP Biomedicals, Irvine, Calif.) at t=0 hours ($T_0$). At 24, 48 and 72 hours, the mice were injected intravenously with either 1 mg/kg of Peptide No. 231, 1 mg/kg Peptide No. 274 or 20 mg/kg of Peptide No. 252-Fc. Control injections were performed at each timepoint using 15 mM sodium acetate, pH 5 and served as the vehicle for all injections. Blood samples were taken prior to injections at all timepoints, as well as at 30, 96 and 144 hours. Serum was prepared and stored at −20° C. until an ELISA was performed.

The concentration of human IgG in the serum at each time point were determined as described above in Example 18.

Example 20

Effect of Peptide No. 270 on Human IgG Catabolism as Well as Endogenous IgG, IgM and Albumin in Cynomolgus Monkeys Three adult cynomolgus monkeys with an average weight of 4.8 kg were injected intravenously with an IV dose of 5 mg/kg biotinylated human IgG (MP Biomedicals, Irvine, Calif.) at 0 hours. At 24, 48, 72 and 96 hours, the animals were injected intravenously at a rate of 1 ml/min with either 10 mg/kg of Peptide No. 270 or an equal volume of vehicle (30 mM sodium acetate, pH 5). At 120 hours, animal CO6215 was treated with a fifth dose of 10 mg/kg of Peptide No. 270. Blood samples were taken prior to all injections, as well as at 120, 168, 192, and 244 hrs and at 30 days. Serum was prepared and stored at −20° C. until an ELISA was performed.

The biotin-hIgG tracer was detected using a Streptavidin-Fc-specific ELISA. Streptavidin-coated plates (Pierce, Rockford, Ill., cat#15121) were washed three times with PBST (phosphate buffered saline+0.05% Tween-20). Serum samples and standards were diluted with PBSB (PBS+2% BSA). A standard curve was established with a range from 1.56 ng/ml to 200 ng/ml. Diluted samples (100 µl) or standards were added per well and incubated for two hours at room temperature. Afterwards, the wells were washed three times with PBST (300 µl/well). Goat anti-human Fc-HRP (Pierce, Rockford, Ill., Cat#31416) was diluted 1:25,000 with PBSB and 100 µl/well was added and the plates were incubated for 30 minutes at room temperature. The plate was washed three times with PBST (300 µl/well) and developed with 100 µl/well of BioFx Supersensitive TMB substrate (BioFX, Owing Mills, Md.) for approximately five minutes at room temperature. The development of the reaction was stopped by adding 100 µl/well of 0.25 M sulfuric acid and the absorbance of each well was measured at a wavelength of 450 nm.

Endogenous cynomolgus IgG was detected using the following ELISA protocol. First, rabbit anti-monkey IgG was diluted to 2 µg/ml in coating buffer (coating buffer=1 carbonate-bicarbonate capsule, Sigma-Aldrich, St. Louis, Mo. cat#C-3041, dissolved in 100 mL water). Next, a 96-well plate (Costar/Corning) was coated with 100 µl/well of a 2 µg/ml rabbit anti-monkey IgG (Sigma-Aldrich, St. Louis, Mo.) and incubated for one hour at 37° C. The plate was washed four times with PBST (PBS with 0.05% Tween-20) and blocked for one hour at 37° C. with 200 µl/well of PBSB (1% BSA in PBS; diluted from 10% BSA in PBS stock; KPL). The plate was washed again four times with PBST. Serum samples and standards were diluted with PBSB. A standard curve was established with a range of 2000 ng/ml to 1.9 ng/ml of monkey IgG (Antibodies Incorporated, Davis, Calif.). Then 100 µl/well of each sample was incubated for one hour at 37° C. The plate was washed three times with PBST. 100 µl/well of a 1:30,000 dilution of rabbit anti-Monkey IgG-HRP (Sigma-Aldrich, St. Louis, Mo.) in PBSB was added and incubated for one hour at 37° C. The plate was washed three times with PBST and developed with 100 µl/well of SureBlue TMB substrate (KPL, Gaithersburg, Md.) for approximately five minutes at room temperature. The development reaction was stopped with 100 µl/well of TMP stop solution (KPL, Gaithersburg, Md.) and the absorbance of each well was measured at a wavelength of 450 nm.

Endogenous cynomolgus serum albumin was detected using the following ELISA protocol. First, rabbit anti-monkey serum-albumin was diluted to 5 µg/ml in coating buffer (coating buffer=1 carbonate-bicarbonate capsule, Sigma-Aldrich, St. Louis, Mo. cat#C-3041, dissolved in 100 mL water). Next, a 96-well plate (Costar/Corning) was coated with 100 µl/well of the 5 µg/ml rabbit anti-monkey serum-albumin (Nordic Immunology, The Netherlands, cat#RAMon/Alb) and incubated for one hour at 37° C. The plate was washed four times with PBST (PBS with 0.05% Tween-20) and blocked for one hour at 37° C. with 300 µl/well of a 5% fish gelatin (Sigma-Aldrich, St. Louis, Mo.

cat#G-7765) stock solution in PBS. The plate was washed again four times with PBST. Serum samples and standards were diluted with PBSB. A standard curve was established with a range of 200 ng/ml to 0.39 ng/ml of monkey serum albumin (Nordic Immunology, The Netherlands, cat#MonAlb Batch#6082). Then 100 µl/well of each sample was incubated for one hour at 37° C. The plate was washed six times with PBST. 100 µl/well of a 1:30,000 dilution of goat anti-human albumin-HRP conjugate (Academy Bio-Medical, Inc., Houston, Tex., cat#AL10H-G1a) in PBSB was added and incubated for one hour at 37° C. The plate was washed six times with PBST and developed with 100 µl/well of SureBlue TMB substrate (KPL, Gaithersburg, Md.) for approximately five minutes at room temperature. The development reaction was stopped with 100 µl/well of TMP stop solution (KPL, Gaithersburg, Md.) and the absorbance of each well was measured at a wavelength of 450 nm.

Endogenous cynomolgus IgM was detected using the following ELISA protocol. First, goat anti-monkey-IgM antibody was diluted to 5 µg/ml in coating buffer (coating buffer=1 carbonate-bicarbonate capsule, Sigma-Aldrich, St. Louis, Mo. cat#C-3041, dissolved in 100 mL water). Next, a 96-well plate (Costar/Corning) was coated with 100 µl/well of the 5 µg/ml goat anti-monkey IgM (KPL, Gaithersburg, Md., cat#071-11-031) and incubated for one hour at 37° C. The plate was washed four times with PBST (PBS with 0.05% Tween-20) and blocked for one hour at 37° C. with 200 µl/well of PBSB (1% BSA in PBS; diluted from 10% BSA in PBS stock; KPL). The plate was washed again four times with PBST. Serum samples and standards were diluted with PBSB. A standard curve was established with a range of 2000 ng/ml to 15.6 ng/ml of monkey IgM (Alpha Diagnostic International, San Antonio, Tex., cat#2001301). Then 100 µl/well of each sample was incubated for one hour at 37° C. The plate was washed four times with PBST. 100 µl/well of a 1:10,000 dilution of goat anti-monkey IgM-HRP conjugate (RDI, Concord, Mass., cat#617103007) in PBSB was added and incubated for one hour at 37° C. The plate was washed four times with PBST and developed with 100 µl/well of SureBlue TMB substrate (KPL, Gaithersburg, Md.) for approximately five minutes at room temperature. The development reaction was stopped with 100 µl/well of TMP stop solution (KPL, Gaithersburg, Md.) and the absorbance of each well was measured at a wavelength of 450 nm.

Example 21

Effect of Peptide No. 270 on Human IgG Catabolism in TG32B Mice Using Varying Dosing Schedules Adult TG32B mice were injected intravenously with 500 mg/kg of human IgG (MP Biomedicals, Irvine, Calif.) at t=0 hours ($T_0$). Groups of four mice were injected intravenously with 5 mg/kg of Peptide No. 270 at t=24 hours (first group); 5 mg/kg of Peptide No. 270 at t=24 and 72 hours (second group); and 2.5 mg/kg of Peptide No. 270 at t=24, 48, 72, 96 hours (third group). Control injections were performed at each timepoint using the vehicle PBS with 15 mM sodium acetate, pH 5 using an additional group of mice. Blood samples were taken prior to injections at all timepoints, as well as at 168 hours. Serum was prepared and stored at −20° C. until an ELISA was performed as in Example 18.

Example 22

Additional TG32B Mouse Experiments

Additional experiments were performed with Peptide No. 270 in TG32B mice. Using the same experimental design as described in Example 18, Peptide No. 270 was found effective at accelerating the rate of IgG catabolism using subcutaneous (SC) and intraperitoneal (IP) routes of administration. Five daily doses of 5 mg/kg of Peptide No. 270 starting at 24 hours was found to reduce the half-life of IgG to 56 hours following both subcutaneous (SC) and intraperitoneal (IP) injections of Peptide No. 270. These half-lives are significantly shorter than typical control groups which exhibit IgG half-lives of 80 to 100 hours. In addition, the concentration of hIgG was reduced by 56% (SC) and 66% (IP) after 168 hours using Peptide No. 270 as compared to the control group.

Peptide No. 230 was also tested in the TG32B mice using the experimental protocol described in Example 18. Twenty-four hours after the intravenous injection of human IgG, daily intravenous (IV) injections of 5 mg/kg of Peptide No. 230 were administered for a total of five days. The half-life of hIgG was reduced to 39 hr as compared to the control group half-life of 92 hr. In addition, the concentration of hIgG was reduced by 76% after 168 hours as compared to the control group.

Peptide No. 230 was also tested in two experiments designed to evaluate the effect of a single peptide dose as compared to three daily peptide doses. Using the experimental protocol described in Example 18, twenty-four hours after the IV injection of human IgG, one animal group was treated with a single IV dose of 5 mg/kg Peptide No. 230, while a second animal group received three consecutive daily IV doses of 5 mg/kg Peptide No. 230. After 120 hours, the single dose of Peptide No. 230 reduced the concentration of hIgG in the mice by 41%. In the group of mice that received three daily doses of Peptide No. 230 the concentration of hIgG decreased 61% after 120 hours.

Example 23

Effect of Peptide No. 283 on Human IgG Catabolism in TG32B Mice

Adult TG32B mice were injected intravenously with 500 mg/kg of human IgG (MP Biomedicals, Irvine, Calif.) at t=0 hours ($T_0$). At 24, 48, 72 and 96 hours, the mice were injected intravenously with either 0.5, 1, 2.5, 5, or 10 mg/kg of Peptide No. 283. Control injections were performed at each timepoint using 15 mM sodium acetate, pH 5 and served as the vehicle for all injections. Blood samples were taken prior to injections at all timepoints, 120 hours, and 168 hours, as well as at 30 days. Serum was prepared and stored at −20° C. until an ELISA was performed.

The concentration of human IgG in the serum at each, time point were determined as described above in Example 18.

Example 24

Synthesis of Pegylated Peptide No. 289

Figure 7:
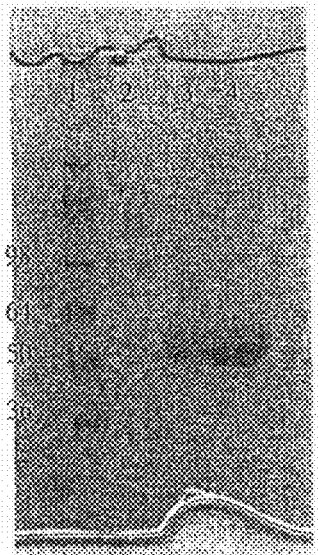
FIG. 7 shows ihc molecular weight of Peptide No. 289 by SDS-PAGE analysis of purified Peptide No. 289 on a 4-20% Tris-Gly gel. Lane 1 contains molecular weight markers. Lane 2 contains unconjugated $PEG_{30\ kDa}$ starting material. Lane 3 contains crude reaction mixture. Lane 4 contains purified Peptide No. 289.

Peptide No. 285 was dissolved in 10 mM phosphate pH 7.4 buffer and treated with one equivalent of $PEG_{30\,kDa}$—succinimidyl ester (NOF Corp. (Japan) Cat. No. Sunbright MEGC-30TS) for 18 h. The crude reaction mixture was purified on a C4 column (Jupiter, Phenomenex) as described in example 7, lyophilized, and purified again with cation exchange chromatography (Fractoprep $SO_3^-$, Cat No. 1.17972, EMD Chemicals Inc, Gibbstown, N.J.) whereby the peptide bound to the resin in 10 mM sodium acetate pH 5, the resin was washed with 10 mM sodium acetate pH 5, and the peptide was eluted with 100 mM sodium chloride in 10 mM sodium acetate pH 5. The peptide solution was dialyzed against 1% acetic acid, and lyophilized. The purified peptide was analyzed by SDS-PAGE demonstrating a peptide staining band at ~50 kDa, and by HPLC demonstrating that there is no residual free peptide. (FIG. 7.)

TABLE 26

Peptide No. 289, a Pegylated Analog of Peptide No. 285

| | Sequence | IC$_{50}$ nM |
|---|---|---|
| Peptide No. 289 | see below | 18 |

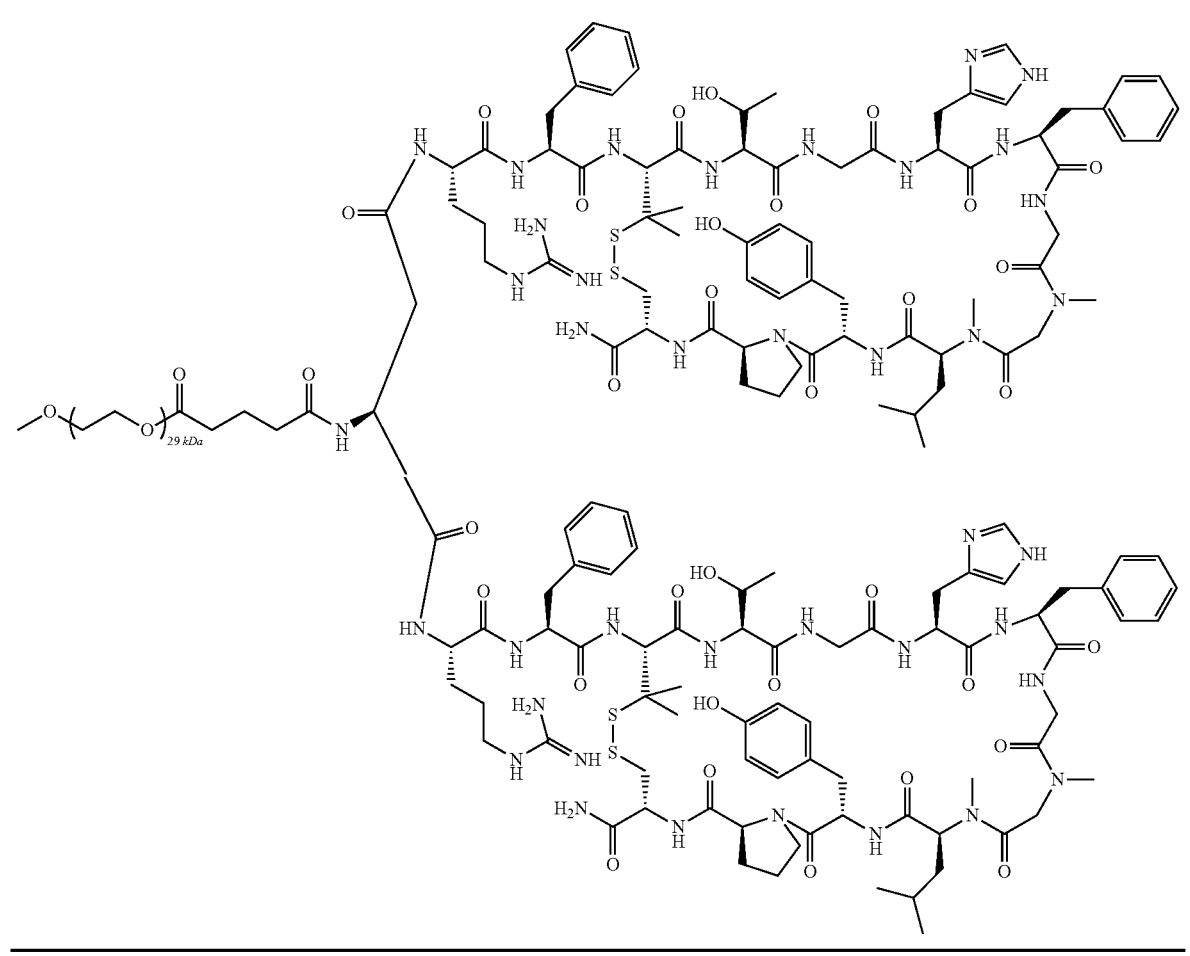

Example 25

Effect of Peptide No. 289 on Human IgG Catabolism in TG32B Mice

Figure 8:
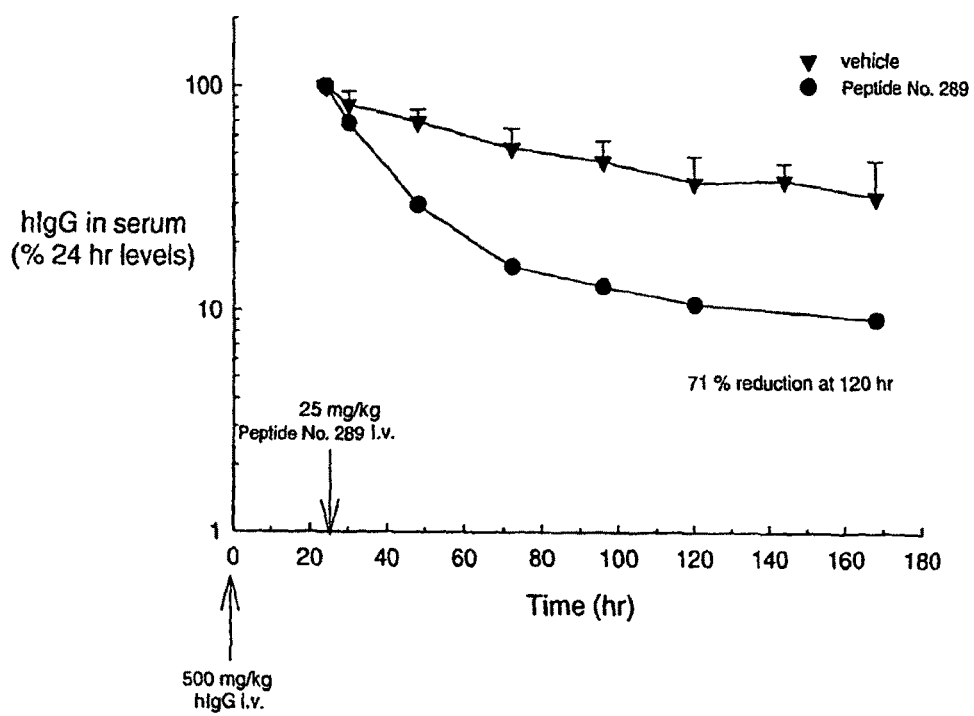
FIG. 8 shows the kinetics of human IgG catabolism in TG32B mice following intravenous injection of Peptide No. 289.

Adult TG32B mice were injected intravenously with 500 mg/kg of human IgG (MP Biomedicals, Irvine, Calif.) at t=0 hours (T$_0$). At 24 hours, the mice were injected intravenously with 25 mg/kg of Peptide No. 289. Blood samples were taken at 24, 48, 72, 96, 120 and 168 hours. Serum was prepared and stored at −20° C. until an ELISA was performed. The concentration of human IgG in the serum at each time point were determined as described above in Example 18. The results are depicted in FIG. 8.

Example 26

Effect of Peptide No. 283 on hIgG Catabolism and Endogenous IgG, IgM, and Albumin Concentrations in Cynomolgus Monkeys Eighteen cynomolgus monkeys were divided into six groups of three animals each and all animals were treated with 5 mg/kg biotinylated human IgG (MP Biomedical) at t=−3 days. Starting at t=0, animals were treated for four weeks with Peptide No. 283 according to the following dosing regimen: 1) 1 mg/kg 3×/week intravenously; 2) 1 mg/kg 1×/week subcutaneously; 3) 1 mg/kg 3×/week subcutaneously; 4) 5 mg/kg 3×/week intravenously; 5) 5 mg/kg 1×/week subcutaneously; 6) 5 mg/kg 3×/week subcutaneously. Note that the last peptide dose for group 4 was at day 16. Serum samples were taken at day −3 d, −15 min, 1 d, 2 d, 3 d, 4 d, 5 d, 7 d, 9 d, 11 d, 14 d, 16 d, 18 d, 21 d, 23 d, 25 d, 28 d, 30 d, 32 d, 35 d, 42 d, 49 d, 77 d. The concentrations of biotinylated human IgG, endogenous IgG, and albumin were determined as described in Example 20.

Example 27

Synthesis of 30 kDa Pegylated Peptide No. 290 Using Reductive Alkylation

Figure 9:
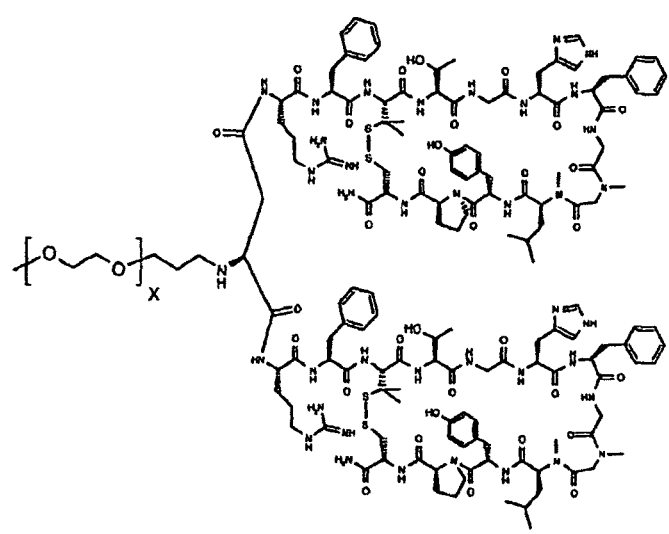
FIG. 9 shows the chemical structures of Peptide Nos. 290, 291, 292, and 293.
Figure 10:
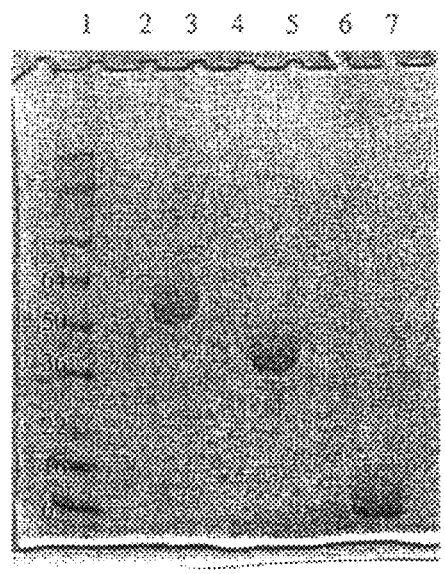
FIG. 10 provides an SDS-PAGE analysis of pegylated peptides synthesized by reductive alkylation using a 4-20% Tris-Gly gel. 10 mg were loaded into all lanes. Lane 1 contains molecular weight markers. Lane 2 contains unconjugated $PEG_{30\ kDa}$ starting material aldehyde. Lane 3 contains purified Peptide No. 290. Lane 4 contains unconjugated $PEG_{20\ kDa}$ starting material aldehyde. Lane 5 contains purified Peptide No. 291. Lane 6 contains unconjugated $PEG_{5\ kDa}$ starting material aldehyde. Lane 7 contains purified Peptide No. 292.
Figure 11:
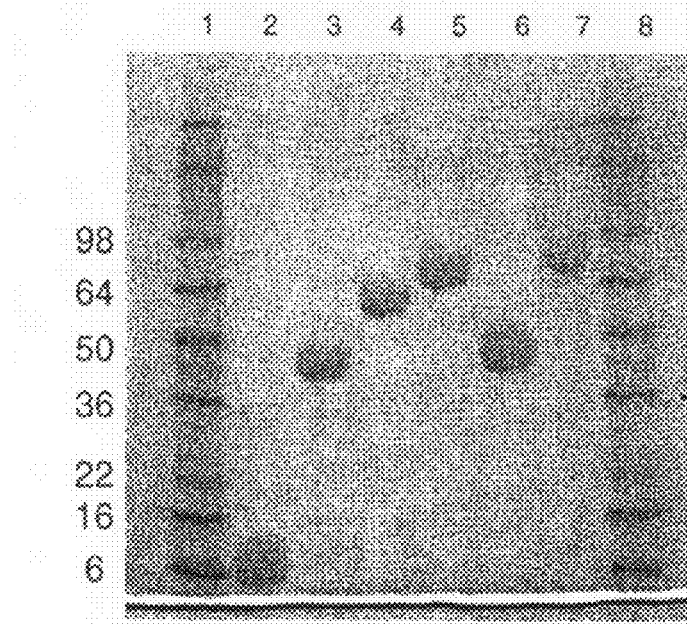
FIG. 11 provides an SDS-PAGE analysis of pegylated peptides synthesized by reductive alkylation using a 4-20% Tris-Gly gel. Lane 1 contains molecular weight markers. Lane 2 contains purified Peptide No. 292. Lane 3 contains purified Peptide No. 291. Lane 4 contains purified Peptide No. 290. Lane 5 contains purified Peptide No. 293. Lane 6 contains purified Peptide No. 295. Lane 7 contains purified Peptide No. 296. Lane 8 contains molecular weight markers.

Peptide No. 285 and 1.25 equivalents of a linear 30 kDa PEG-aldehyde (NOF Corp. (Japan) Cat. No. Sunbright ME-300-AL) were dissolved in 100 mM sodium acetate pH 5.5 at a PEG concentration of 10 mg/mL, and incubated at 4° C. for 30 minutes. Sodium cyanoborohydride was added such that its final concentration was 20 mM. The reaction was rocked for 18 h at 4° C., then purified on a reversed phase C4 column (Jupiter, Phenomenex) to remove free peptide as described in Example 7 and lyophilized. The material was then purified by cation exchange chromatography to remove free PEG as described in Example 24. After dialysis as in Example 24, the peptide solution was analyzed by SDS-PAGE which showed a band at ~50 kDa and by reversed phase HPLC demonstrating that there was no residual free peptide. See FIGS. 9, 10, and 11.

Example 28

Synthesis of 20 kDa Pegylated Peptide No. 291 Using Reductive Alkylation

Peptide No. 285 and 1.25 equivalents of a linear 20 kDa PEG-aldehyde (NOF Corp, Japan, Sunbright ME-200-AL) were dissolved in 100 mM sodium acetate pH 5.5 at a PEG concentration of 10 mg/mL, and incubated at 4° C. for 30 minutes. Sodium cyanoborohydride was added such that its final concentration was 20 mM. The reaction was rocked for 18 h at 4° C., then purified on a reversed phase C4 column (Jupiter, Phenomenex) to remove free peptide as described in Example 7 and lyophilized. The material was then purified by cation exchange chromatography to remove free PEG as described in Example 24. The combined elution fractions containing 100-300 mM sodium acetate were passed over a C18 Sep-Pak (Waters Corp, Milford Mass.) to remove the acetate salts, then lyophilized from 1% acetic acid. The peptide was analyzed by SDS-PAGE which showed a band at ~35 kDa and by reversed phase HPLC demonstrating that there was no residual free peptide. See FIGS. 9, 10, and 11.

Example 29

Synthesis of 5 kDa Pegylated Peptide No. 292 Using Reductive Alkylation

Peptide No. 285 and 1.25 equivalents of a linear 5 kDa PEG-aldehyde (NOF Corp. (Japan) Cat. No. Sunbright ME-050-AL) were dissolved in 100 mM sodium acetate pH 5.5 at a PEG concentration of 10 mg/mL, and incubated at 4° C. for 30 minutes. Sodium cyanoborohydride was added such that its final concentration was 20 mM. The reaction was rocked for 18 h at 4° C., then purified on a reversed phase C4 column (Jupiter, Phenomenex) to remove free peptide as described in Example 7 and lyophilized. The material was then purified by cation exchange chromatography to remove free PEG as described in Example 24. The combined elution fractions containing 100-300 mM sodium acetate were passed over a C18 Sep-Pak (Waters Corp, Milford Mass.) to remove the acetate salts, then lyophilized from 1% acetic acid. The peptide was analyzed by SDS-PAGE which showed a band at ~8 kDa and by reversed phase HPLC demonstrating that there was no residual free peptide. See FIGS. 9, 10, and 11.

Example 30

Effect of Peptide No. 290 on Human IgG Catabolism in TG32B Mice

Figure 12:
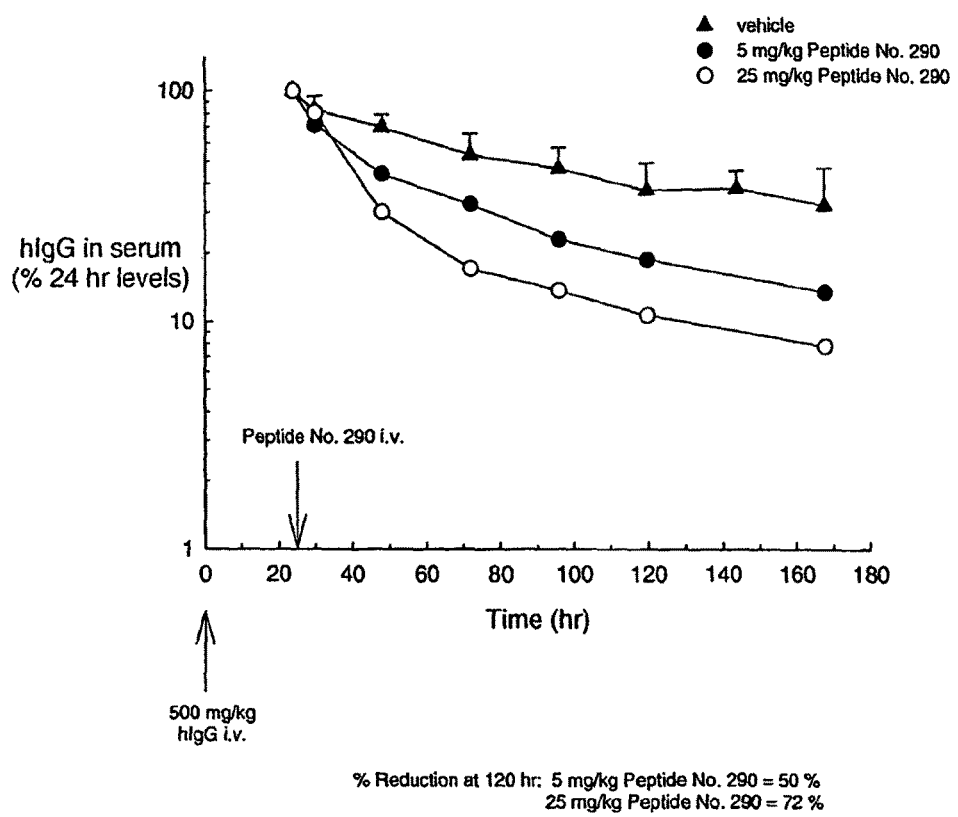
FIG. 12 shows the rate of human IgG catabolism in TG32B mice after a 500 mg/kg IV dose of human IgG at t=0 h followed by intravenous injection of Peptide No. 290 at 5 mg/kg or 25 mg/kg at t=24 hours. The concentration of hIgG was determined by ELISA as in Example 18, normalized to the t=24 h level, and compared with a vehicle control group.

Adult TG32B mice were injected intravenously with 500 mg/kg of human IgG (MP Biomedicals, Irvine, Calif.) at t=0 hours (T0). At 24 hours, the mice were injected intravenously with either 5 mg/kg or 25 mg/kg of Peptide No. 290. Blood samples were taken at 24, 48, 72, 96, 120 and 168 hours. Serum was prepared and stored at −20° C. until an ELISA was performed. The concentration of human IgG in the serum at each time point was determined as described above in Example 18 (FIG. 12).

Example 31

Synthesis of 40 kDa Pegylated Peptide No. 293 Using Reductive Alkylation

Peptide No. 285 and 1.25 equivalents of a linear 40 kDa PEG-aldehyde (Dow Pharma, Cat #008-005) were dissolved in 100 mM sodium acetate pH 5.5 at a PEG concentration of 10 mg/mL, and incubated at 4° C. for 30 minutes. Sodium cyanoborohydride was added such that its final concentration was 20 mM. The reaction was rocked for 18 h at 4° C., then dialyzed across a 10 kDa membrane cutoff into 10 mM sodium acetate pH 5. The material was then purified by cation exchange chromatography to remove free PEG as described in Example 24. After dialysis into 1% acetic acid, the peptide solution was analyzed by SDS-PAGE which showed a band at ~65 kDa (FIG. 11) and by reversed phase HPLC (TSK phenyl 1000A column) demonstrating that there was no residual free peptide.

Example 32

Synthesis of 10 kDa Pegylated Peptide No. 294 Using Reductive Alkylation

Peptide No. 285 and 1.25 equivalents of a linear 10 kDa PEG-aldehyde (NOF Corp, Japan, Sunbright ME-100-AL) will be dissolved in 100 mM sodium acetate pH 5.5 at a PEG concentration of 10 mg/mL, and incubated at 4° C. for 30 minutes. Sodium cyanoborohydride will be added such that its final concentration is 20 mM. The reaction will be rocked for 18 h at 4° C., and then purified on a reversed phase C4 column (Jupiter, Phenomenex) to remove free peptide as described in example 7 and then the liquid will be lyophilized. The material will be purified by cation exchange chromatography to remove free PEG as described in Example 24. The combined elution fractions containing 100-300 mM sodium acetate will be passed over a C18 Sep-Pak (Waters Corp, Milford Mass.) to remove the acetate salts, then lyophilized from 1% acetic acid. The peptide will be analyzed by SDS-PAGE to confirm that conjugation reaction was successful, and by reversed phase HPLC to demonstrate that there is no residual free peptide in the final product.

Example 33

Synthesis of 20 kDa 2-Arm Pegylated Peptide No. 295

Figure 13:
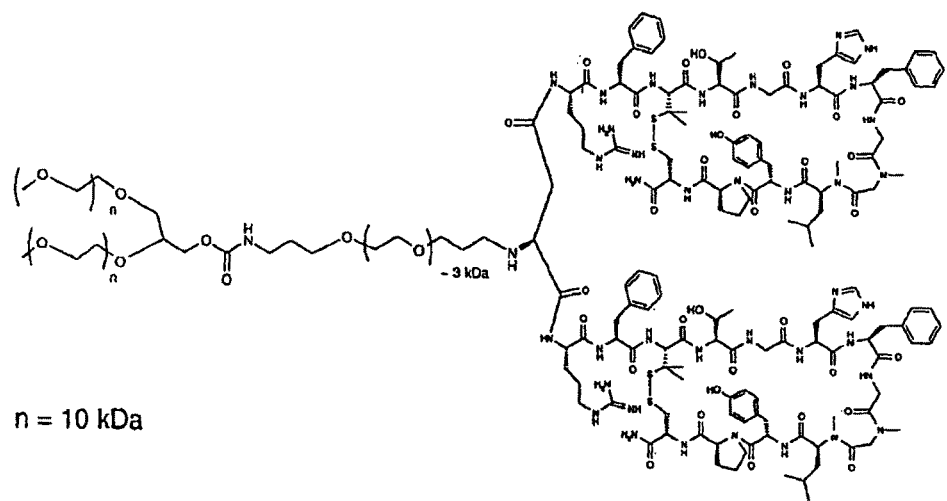
FIG. 13 shows the chemical structure of Peptide No. 295.

Peptide No. 285 and 1.25 equivalents of a 20 kDa branched PEG-aldehyde (NOF Corp. (Japan) Cat. No. Sunbright GL3-200AL020U) were dissolved in 100 mM sodium acetate pH 5.5 at a PEG concentration of 10 mg/mL, and incubated at 4° C. for 30 minutes. Sodium cyanoborohydride was added such that its final concentration was 20 mM. The reaction was rocked for 18 h at 4° C., then dialyzed across a 10 kDa membrane cutoff into 10 mM sodium acetate pH 5. The material was then purified by cation exchange chromatography to remove free PEG as described in Example 24. After dialysis into 1% acetic acid, the peptide solution was analyzed by SDS-PAGE which showed a band at ~44 kDa (FIG. 12) and by reversed phase HPLC (TSK phenyl 1000 A column) demonstrating that there was no residual free peptide. The structure of Peptide No. 295 is depicted in FIG. 13.

Example 34

Synthesis of 40 kDa 2-Arm Pegylated Peptide No. 296

Figure 14:
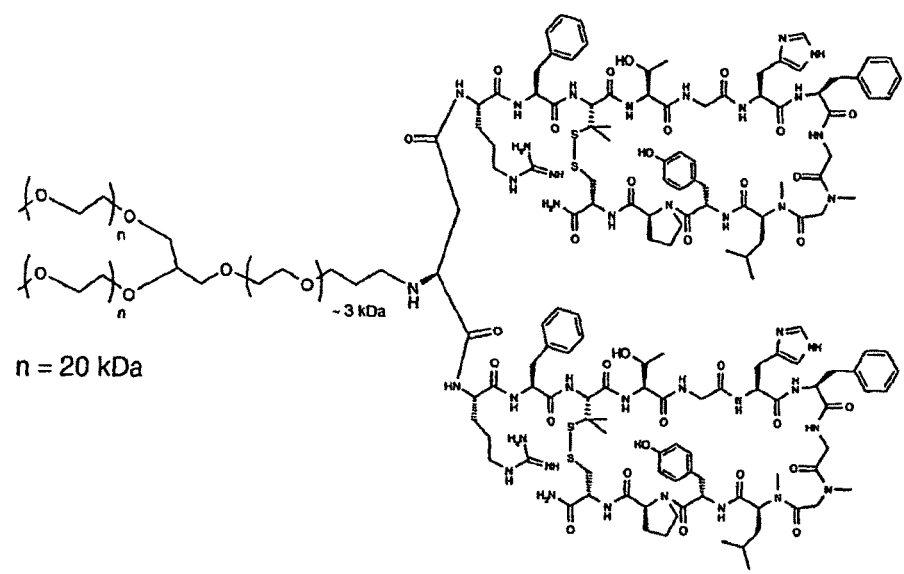
FIG. 14 shows the chemical structure of Peptide No. 296.

Peptide No. 285 and 1.25 equivalents of a 40 kDa branched PEG-aldehyde (NOF Corp. (Japan) Cat. No. Sunbright GL3-400AL2) were dissolved in 100 mM sodium acetate pH 5.5 at a PEG concentration of 10 mg/mL, and incubated at 4° C. for 30 minutes. Sodium cyanoborohydride was added such that its final concentration was 20 mM. The reaction was rocked for 18 h at 4° C., then dialyzed across a 10 kDa membrane cutoff into 10 mM sodium acetate pH 5. The material was then purified by cation exchange chromatography to remove free PEG as described in Example 24. After dialysis into 1% acetic acid, the peptide solution was analyzed by SDS-PAGE which showed a band at ~75 kDa (FIG. 12) and by reversed phase HPLC (TSK phenyl 1000 A column) demonstrating that there was no residual free peptide. The structure of Peptide No. 296 is depicted in FIG. 14.

Example 35

Figure 15:
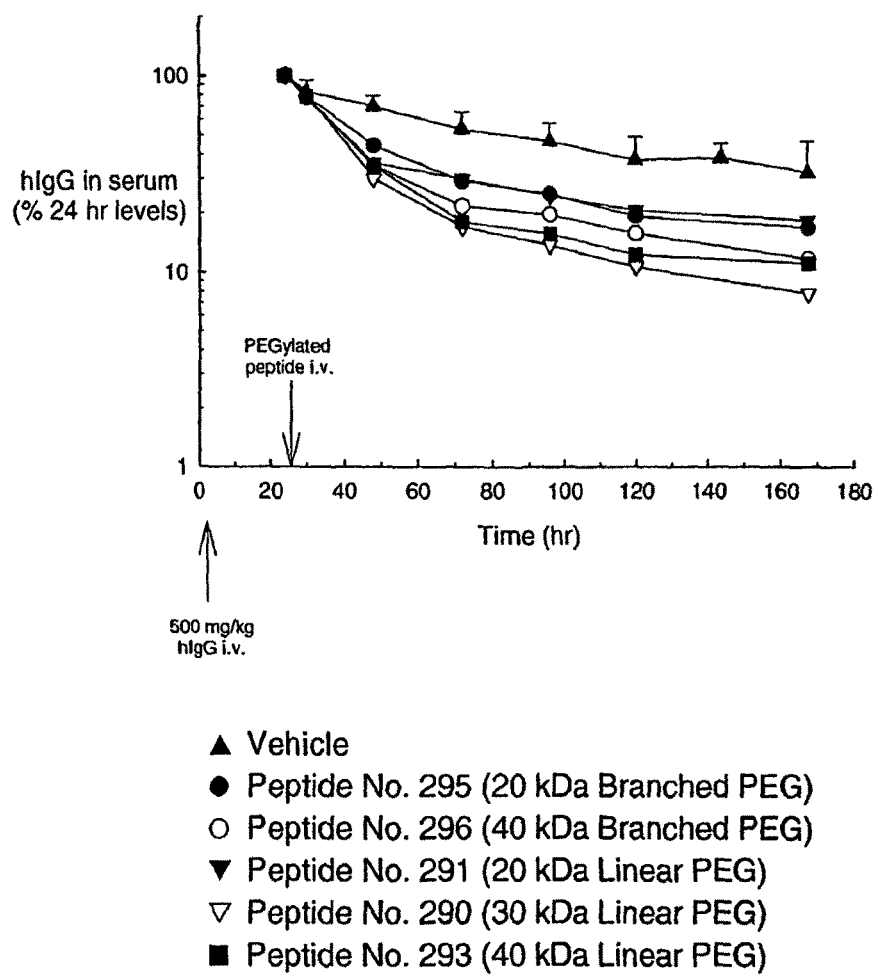
FIG. 15 shows the rate of human IgG catabolism in TG32B mice after a 500 mg/kg IV dose of human IgG at t=0 h followed by intravenous injection of Peptide Nos. 290, 291, 293, 295, and 296 at 25 mg/kg at t=24 hours, as described in Example 35. The concentration of hIgG was determined by ELISA as in Example 18, normalized to the t=24 h level, and compared with a vehicle control group.

Effect of Peptide Nos. 290, 292, 291, 296, 295, and 293 on Human IgG Catabolism in TG32B Mice Adult TG32B mice were injected intravenously with 500 mg/kg of human IgG (MP Biomedicals, Irvine, Calif.) at t=0 hours ($T_0$). At 24 hours, the mice were injected intravenously with 25 mg/kg of pegylated peptide. Blood samples were taken at 24, 48, 72, 96, 120 and 168 hours. Serum was prepared and stored at −20° C. until an ELISA was performed. The concentration of human IgG in the serum at each time point was determined as described above in Example 18. The results are depicted in FIG. 15.

Example 36

In Vitro Activity of Pegylated Peptides

The in vitro activities of various pegylated peptides were assayed using an IgG competition ELISA assay as described in Example 4. The results are depicted in FIG. 16.

Example 37

Synthesis of an Anti-FcRn Peptide with Branched PEG Linkages

Figure 17:
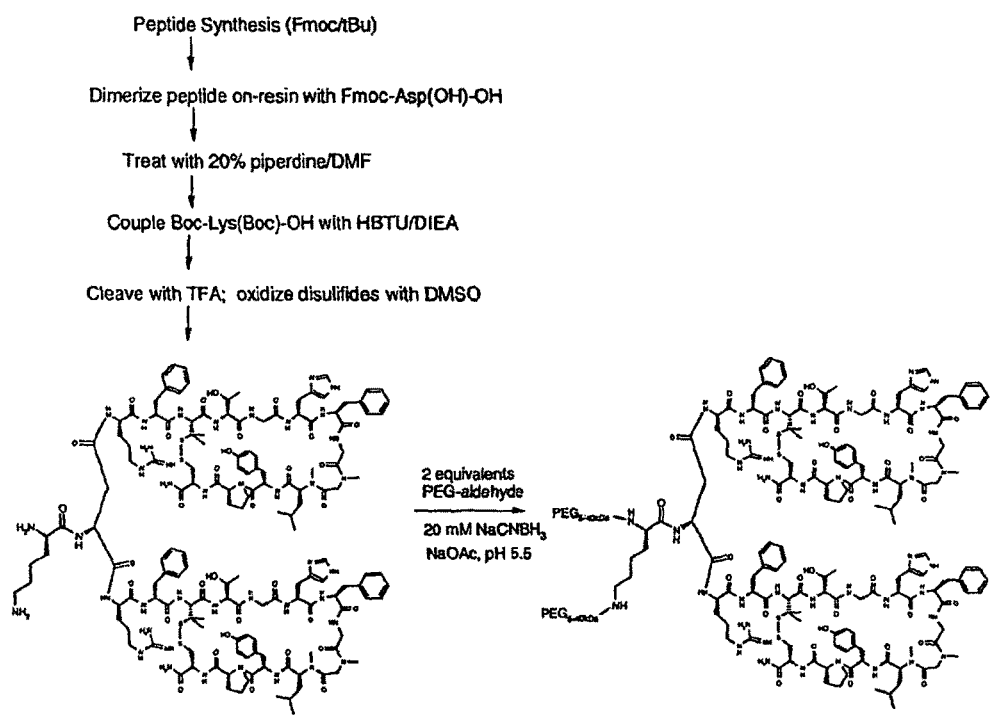
FIG. 17 shows the synthesis of a anti-FcRn peptide with branched PEG linkages.

A bis-amine linker, such as lysine, can be coupled to the free amine of Peptide No. 285 to generate two available amine sites for pegylation. Reaction of such a compound with linear PEGs (such as aldehyde-PEGs) can afford a branched PEG-peptide conjugate, such as the conjugate depicted in FIG. 17.

Example 38

Synthesis of 30 kDa Pegylated Peptide No. 297 Using Reductive Alkylation

Figure 19:
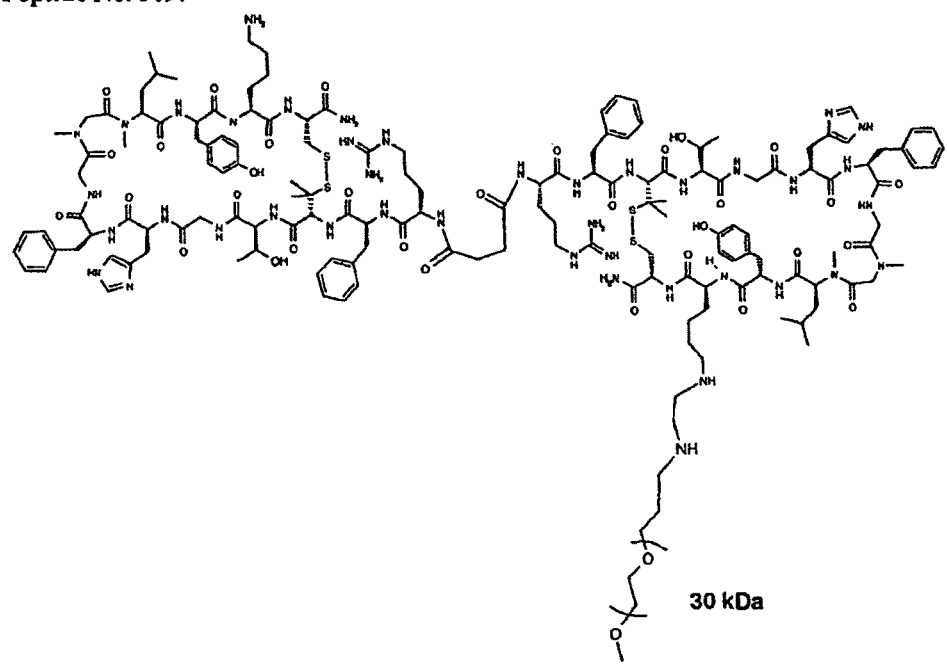
FIG. 19 shows the chemical structures of Peptide Nos. 307, 308, and 309.

Peptide No. 297 with a C-terminal ethyl amine linker (see FIG. 18) was synthesized as described in Example 15 except that the peptide was synthesized on 1,2 diaminoethane trityl resin (Novabiochem, cat#01-64-0081). Peptide No. 297 and 0.75 equivalents of a linear 30 kDa PEG-aldehyde (NOF Corp. (Japan) Cat. No. Sunbright ME-300-AL) was dissolved in 100 mM sodium acetate pH 5.5 at a PEG concentration of 10 mg/mL, and incubated at 4° C. for 30 minutes. Sodium cyanoborohydride was added such that its final concentration was 20 mM. The reaction was rocked for 18 h at 4° C., then dialyzed across a 10 kDa membrane cutoff into 10 mM sodium acetate pH 5. The material was then purified by cation exchange chromatography to remove free PEG as described in Example 24. After dialysis into 1% acetic acid, the peptide solution was analyzed by reversed phase HPLC (TSK phenyl 1000 A column) demonstrating that there was no residual free peptide. The combined elution fractions containing 100-300 mM sodium acetate were dialyzed into 1% acetic acid and lyophilized. Peptide No. 297 was assessed for activity using the IgG competition ELISA assay as described in Example 4. Results of this assay are shown in FIG. 19.

Example 39

Synthesis of Additional Peptide Dimers Using Diacid and Amine Linkers

Additional amide linked peptide dimers (Table 27) were synthesized as described in Example 15, except as follows: Peptide No. 298 was synthesized on 1,2-diaminoethane trityl resin (Novabiochem Cat#01-64-0081); Peptide No. 299 was synthesized on 1,4-diaminobutane trityl resin (Novabiochem Cat#01-64-0082); Peptide No. 300 was synthesized on on O-bis(2-aminoethyl)ethylene glycol trityl resin (Novabiochem Cat#01-64-0235); and Peptide No. 301 was synthesized on Bis-(2-aminoethyl)-ether trityl resin (Novabiochem Cat#01-64-0141).

TABLE 27

Peptide Nos. 298, 299, 300, 301

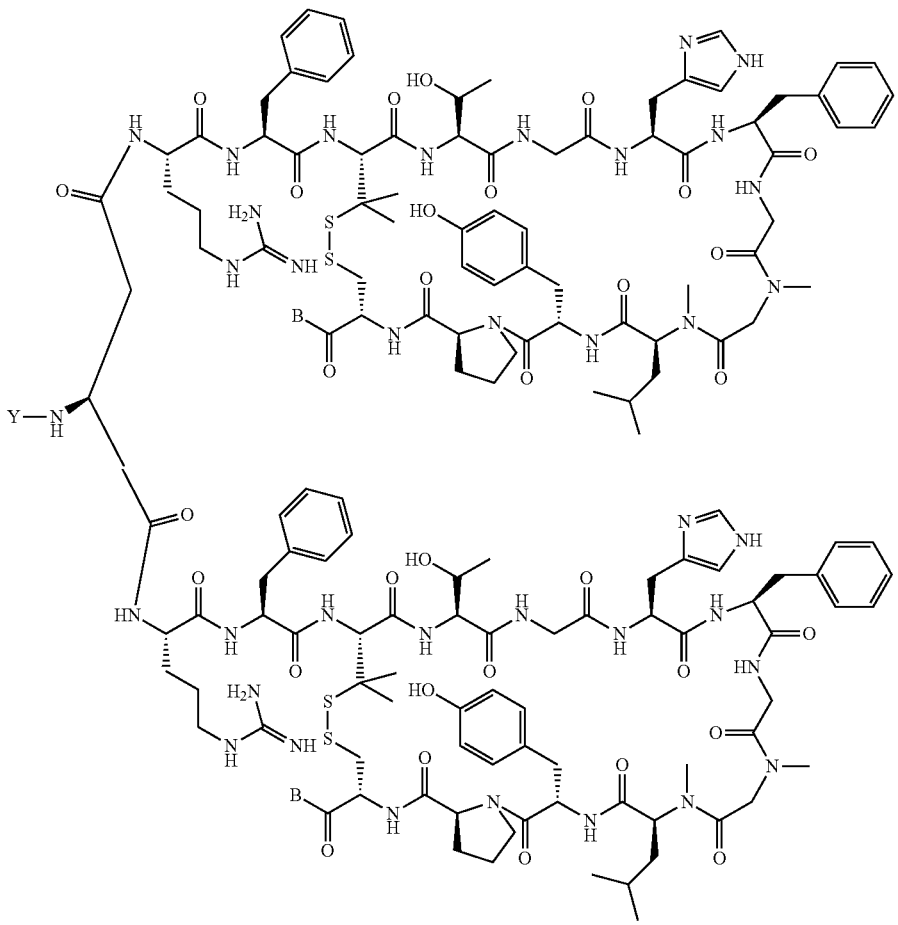

Sequence, where B is —W—CH$_2$—CH$_2$—NH$_2$

| | | IC$_{50}$ nM |
|---|---|---|
| Peptide No. 298 | W is absent | 3.3 ± 2.9 |
| Peptide No. 299 | W is —CH$_2$—CH$_2$— | 1.7 ± 0.8 |
| Peptide No. 300 | W is —(CH$_2$—CH$_2$—O)$_p$— and p is 1 | 1.6 ± 0.6 |
| Peptide No. 301 | W is —(CH$_2$—CH$_2$—O)$_p$— and p is 2 | 1.6 ± 0.6 |

Figure 20:
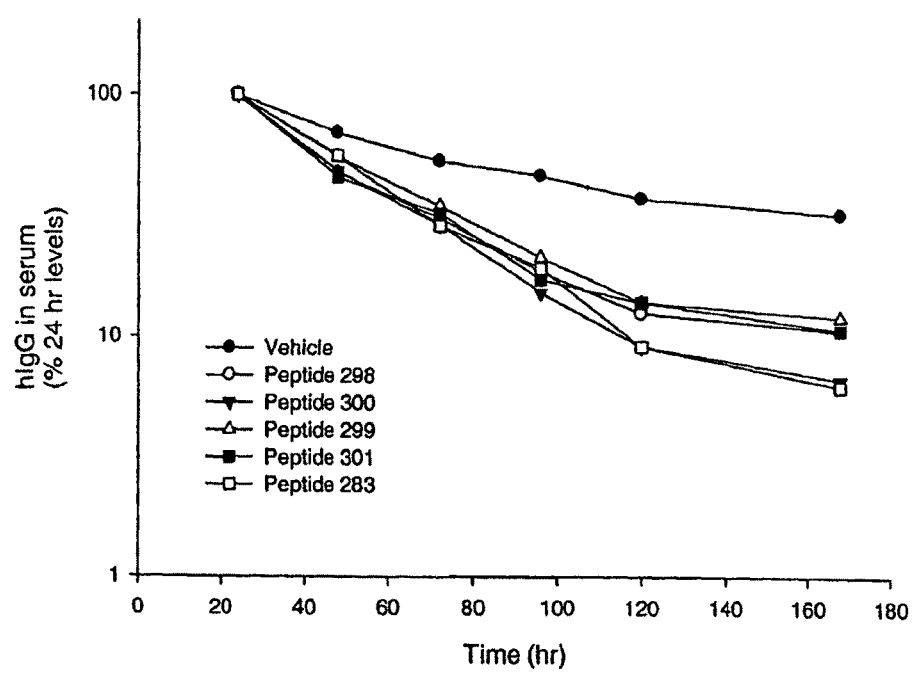
FIG. 20 shows the effect of peptides 283, 298, 299, 300, 301 in the IgG catabolism experiment as described in Example 18 using 2.5 mg/kg subcutaneous dosing.

The rate of human IgG catabolism in TG32B mice after a 500 mg/kg IV dose of human IgG at t=0 h followed by subcutaneous injections of Peptides 299, 300, and 301 at 2.5 mg/kg at t=24 h, 48 h, 72 h, and 96 h, as described in Example 18 is depicted in FIG. 20. The concentration of hIgG was determined by ELISA as in Example 18 normalized to the t=24 h level and compared to the vehicle control group.

Example 40

Synthesis of 30 kDa Pegylated Peptides 307, 308 and 309 Using Reductive Alkylation The peptide components of pegylated peptides 307, 308 and 309 are Peptide Nos 304, 305, and 306, respectively. Peptides 304, 305 and 306 were synthesized as Peptide 283 in Example 15 with the exception that in 304, Arg2 is replaced with Lys, in 305, Thr4 is replaced with Lys and in 306, Pro12 is replaced with Lys. This affords two Lys residues per dimeric peptide. PEGylation is performed to yield one PEG moiety per dimeric peptide.

Peptide 304, 305 or 306 and 2 equivalents of a linear 30 kDa PEG-aldehyde (NOF Corp. (Japan) Cat. No. Sunbright ME-300-AL) were dissolved in 100 mM sodium acetate pH 5.5 at a PEG concentration of 10 mg/mL, and incubated at 4° C. for 30 minutes. Sodium cyanoborohydride was added such that its final concentration was 20 mM. The reaction was rocked for 18 h at 4° C., then dialyzed against 10 mM acetate, pH 5 to remove the free peptide. The dialyzed reaction was then purified by cation exchange chromatography to remove free PEG as described in Example 24. The purified material was dialyzed against 1% acetic acid and lyophilized. The

Example 41

Synthesis of 30 kDa Pegylated Peptide 303

Peptide No. 302 was synthesized on resin as described above, except that Fmoc-Asp(OH)—OH instead of using Boc-Asp(OH)—OH was used in the dimerization reaction. After reaction of the on-resin peptide with Fmoc-Asp(OH)—OH to generate the on-resin dimer, the resin was treated with 20% piperidine/DMF (2×10 min), washed with DMF, and treated with 4 equivalents of Bis-Boc-aminooxyacetic acid, 4 equivalents of PyBOP and 8 equivalents of DIEA in DMF and mixed for 1 hour. The peptide was cleaved from the resin and oxidized as described in Example 15, to provide Peptide No. 302.

Peptide No. 303 (SEQ ID NOS 309 and 309)

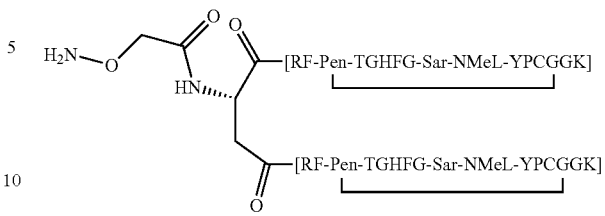

Peptide No. 302 was treated with 1.1 equivalents of 30 kDa PEG-aldehyde (NOF Corp., Japan, Cat#Sunbright ME-300-AL) in water containing 0.1% (v/v) TFA. The reaction mixture was incubated for 30 minutes and purified as in Example 24 to yield Peptide No. 303. In vitro and in vivo activity of this peptide was tested as described in Examples 4 and 18, and the results are provided in FIG. 16.

Peptide No. 303 (SEQ ID NOS 310 and 310)

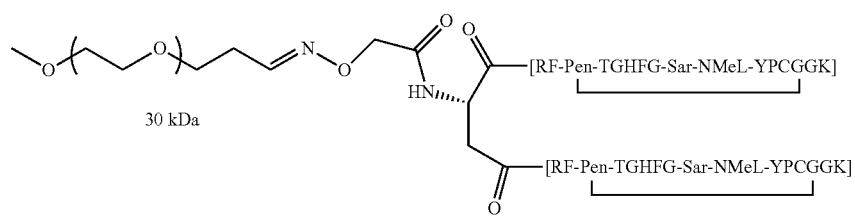

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

---

The invention claimed is:

1. A peptide having the sequence:

$$A\text{-}X_0\text{-}X_1\text{-}X_2\text{-}X_3\text{-}X_4\text{-}Gly\text{-}X_6\text{-}X_7\text{-}X_8\text{-}X_9\text{-}X_{10}\text{-}X_{11}\text{-}X_{12}\text{-}X_{13}\text{-}X_{14}\text{-}B, \quad (I)$$

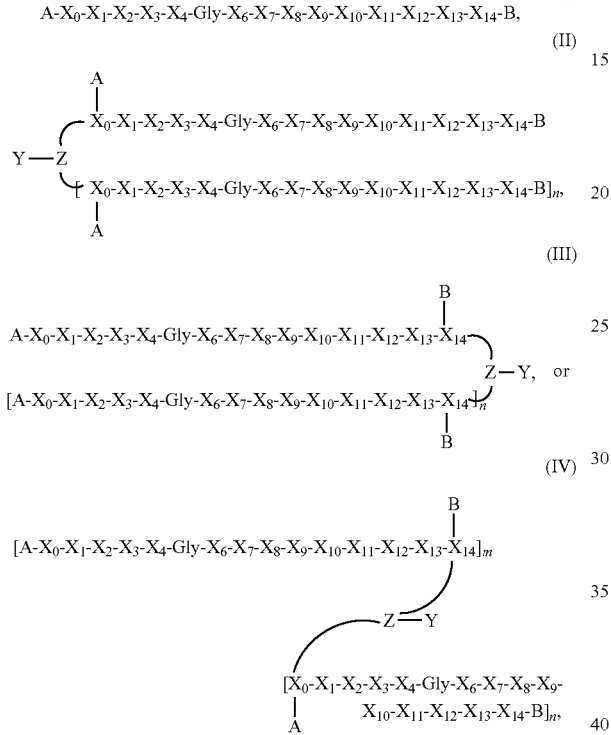

wherein:

at least one of A, B, and Y is present and comprises a hydrophilic polymer; and wherein A, if present, comprises a hydrophilic polymer or is hydrogen, acyl, or an amino protecting group;

B, if present, comprises a hydrophilic polymer or is an amino group, a hydroxyl group, or a carboxy protecting group;

$X_0$, if present, is an optionally derivatized amino acid or an analog thereof or an optionally derivatized peptide of 2-15 amino acids or an analog thereof;

$X_1$, if present, is an optionally derivatized amino acid or an analog thereof;

$X_2$, if present, is an amino acid or an analog thereof;

$X_3$ is an amino acid or analog thereof that is capable of forming a bridge with $X_{10}$, $X_{12}$ or $X_{13}$;

$X_4$ is an optionally derivatized amino acid or an analog thereof or an optionally derivatized peptide of 2 or 4 amino acids or an analog thereof;

$X_6$ is a basic amino acid or an analog thereof, an aromatic amino acid or an analog thereof, or a basic aromatic amino acid or an analog thereof;

$X_7$ is phenylalanine or an analog thereof;

$X_8$ and $X_9$ are each independently chosen from glycine or an analog thereof, sarcosine or an analog thereof, aspartic acid or an analog thereof, a D-amino acid or an analog thereof, and α-aminoisobutyric acid or an analog thereof, or $X_8$, when taken together with $X_9$, forms a dipeptide analog;

$X_{10}$ is an amino acid or an analog thereof, or $X_{10}$, when taken together with $X_9$, forms a dipeptide analog;

$X_{11}$ is tyrosine or an analog thereof;

$X_{12}$ is an optionally derivatized amino acid or an analog thereof;

$X_{13}$, if present, is an amino acid or an analog thereof;

$X_{14}$, if present, is an optionally derivatized amino acid or an analog thereof or an optionally derivatized peptide of 2-15 amino acids or an analog thereof;

Y comprises a hydrophilic polymer;

Z is a linker that attaches to each peptide monomer through
A;
B;
the amino terminus or a side chain of $X_0$, if $X_0$ is present; to the amino terminus or side chain of $X_1$, if $X_0$ is absent; to the amino terminus or side chain of $X_2$, if both $X_0$ and $X_1$ are absent; or to the amino terminus or side chain of $X_3$, if $X_0$, $X_1$ and $X_2$ are absent; or
the carboxy terminus or a side chain of $X_{14}$, if $X_{14}$ is present; to the carboxy terminus or a side chain of $X_{13}$, if $X_{14}$ is absent; or to the carboxy terminus or a side chain of $X_{12}$ if both $X_{13}$ and $X_{14}$ are absent;

m is an integer chosen from 1, 2, and 3; and n is an integer chosen from 1, 2, and 3;

wherein:

each A, B, $X_0$, $X_1$, $X_2$, $X_3$, $X_4$, $X_6$, $X_7$, $X_8$, $X_9$, $X1_0$, $X_{11}$, $X_{12}$, $X_{13}$, and $X_{14}$ is chosen independently; and each monomer of the peptide ranges from 10 to 50 amino acids in length.

2. The peptide of claim 1 having the sequence:

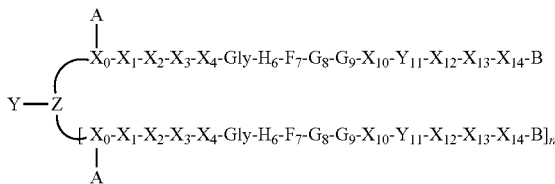

wherein:

$X_1$ is an underivatized amino acid or an underivatized amino acid analog;

$X_4$ is an underivatized peptide of 1, 2, or 4 amino acids or analogs thereof; and $X_{12}$ is an underivatized amino acid or an underivatized amino acid analog.

3. The peptide of claim 1, wherein the peptide is unbridged.

4. The peptide of claim 1, wherein $X_3$ forms a bridge with $X_{13}$.

5. The peptide of claim 4, wherein the bridge is a side chain to side chain bridge.

6. The peptide of claim 1, wherein $X_6$ is histidine or an analog thereof.

7. The peptide of claim 1, wherein at least one of $X_8$ and $X_9$ is chosen from glycine, D-amino acids, α-aminoisobutyric acid, and sarcosine.

8. The peptide of claim 1, wherein the peptide has the sequence:

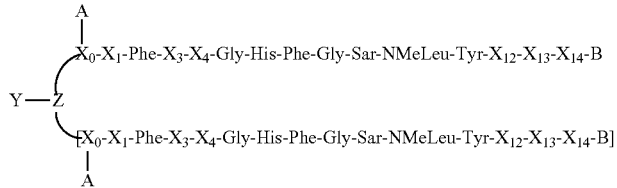

V)

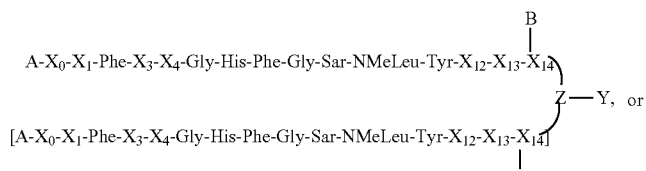

VI)

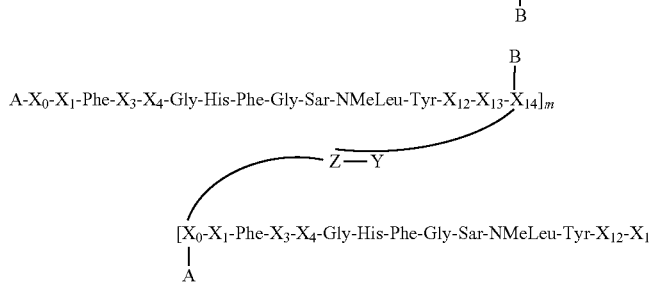

VII)

or (VIII)

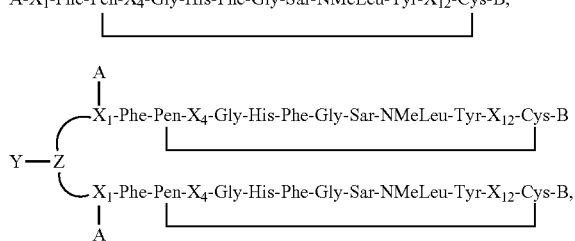

9. The peptide of claim 8, wherein the peptide has the sequence:

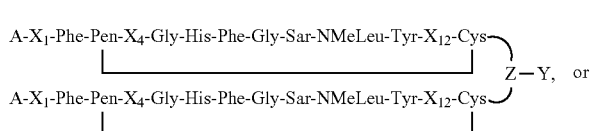

IX)

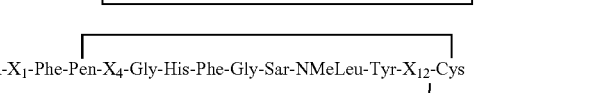

X)

XI)

or

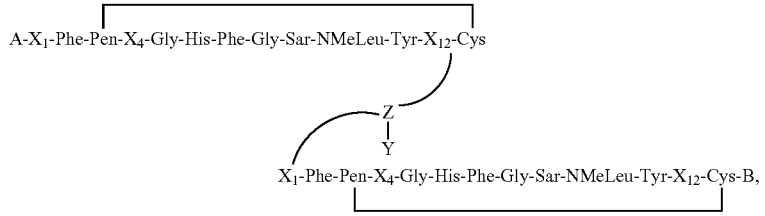

XII)

wherein horizontal brackets indicate the presence of a bridge.

10. The peptide of claim 1, wherein the hydrophilic polymer is chosen from polyethylene glycol, polypropylene glycol, dextran; cellulose, methylcellulose, hydroxycellulose, hydroxymethylcellulose, hydroxypropylcellulose, hydroxypropylmethyl cellulose, hydroxyalkyl starch, polyvinyl alcohol, poly(N-vinyl pyrrolidone), poloxamers, and polyethylene glycol copolymers.

11. The peptide of claim 10, wherein the hydrophilic polymer is polyethylene glycol (PEG).

12. The peptide of claim 11, wherein the PEG is a linear PEG.

13. The peptide of claim 11, wherein the PEG is a branched PEG.

14. The peptide of claim 11, wherein the PEG has an average molecular weight ranging from 10-60 kDa.

15. The peptide of claim 1, wherein the peptide binds specifically to human FcRn.

16. The peptide of claim 15, wherein the affinity of the peptide for human FcRn ranges from 50 fM to 1 mM.

17. The peptide of claim 15, wherein the peptide inhibits the binding of human FcRn to human IgG, and has an $IC_{50}$ ranging from 50 fM to 1 mM.

18. The peptide of claim 1, wherein the peptide has the sequence:

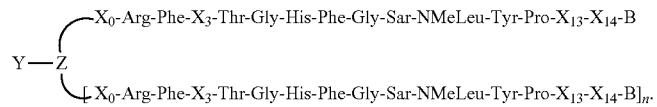

19. The peptide of claim 18, wherein the peptide has the sequence:

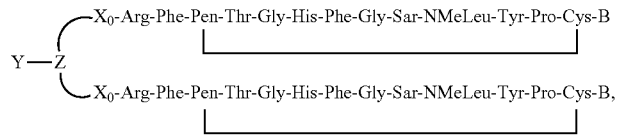

wherein horizontal brackets indicate the presence of a bridge.

20. The peptide of claim 19, wherein the peptide has the sequence:

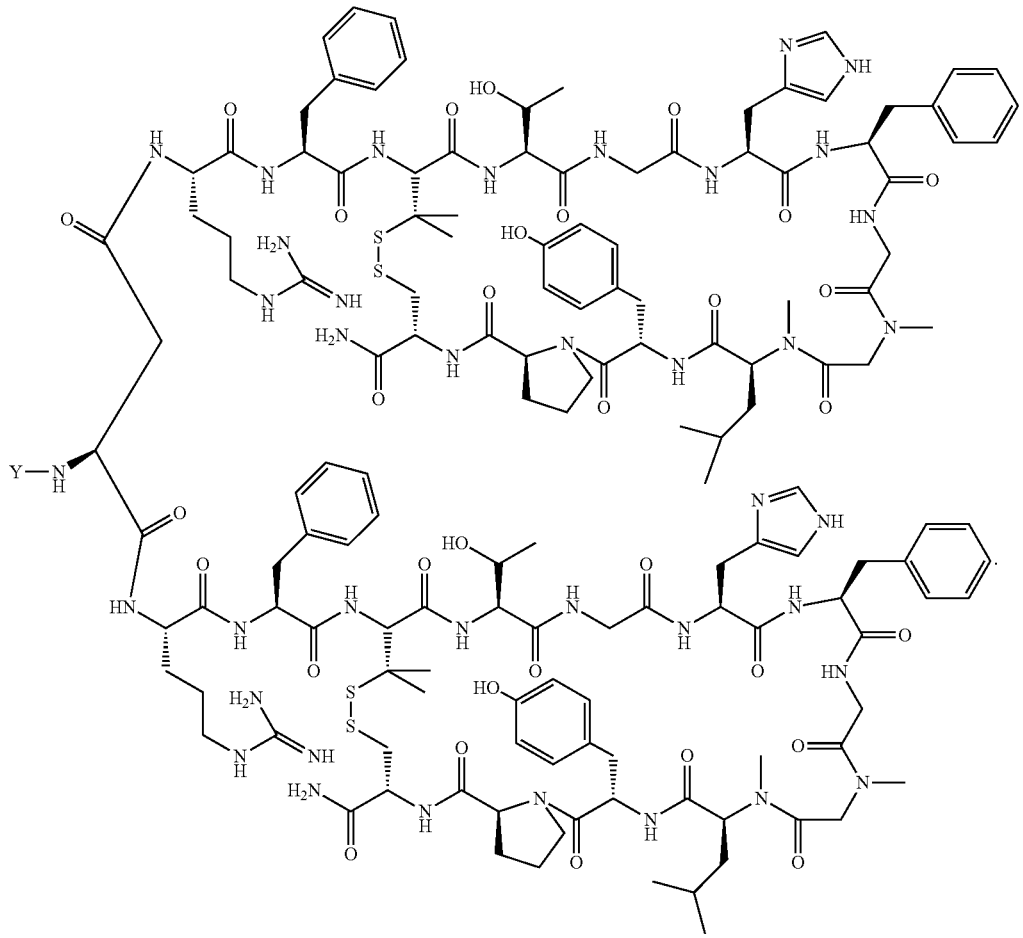

* * * * *